US007652122B2

(12) United States Patent
Miyake et al.

(10) Patent No.: US 7,652,122 B2
(45) Date of Patent: Jan. 26, 2010

(54) METHOD FOR PRODUCING AN AROMATIC CARBONATE

(75) Inventors: Nobuhisa Miyake, Kurashiki (JP); Tomonari Watanabe, Yamato (JP); Kazuhiro Onishi, Kurashiki (JP); Akihiro Sato, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 395 days.

(21) Appl. No.: 10/562,814

(22) PCT Filed: Jun. 25, 2004

(86) PCT No.: PCT/JP2004/009383

§ 371 (c)(1),
(2), (4) Date: Dec. 27, 2005

(87) PCT Pub. No.: WO2005/000783

PCT Pub. Date: Jan. 6, 2005

(65) Prior Publication Data

US 2007/0055042 A1  Mar. 8, 2007

(30) Foreign Application Priority Data

Jun. 27, 2003 (JP) ............................. 2003-185077
Jun. 27, 2003 (JP) ............................. 2003-185078

(51) Int. Cl.
*C08G 64/00* (2006.01)
*C08G 63/18* (2006.01)
(52) U.S. Cl. .................. 528/196; 528/198; 549/228; 558/277
(58) Field of Classification Search ............ 549/228; 558/277; 528/196, 198
See application file for complete search history.

(56) References Cited

U.S. PATENT DOCUMENTS 3,274,214 A * 9/1966 Prochaska .................. 549/228
5,252,771 A * 10/1993 Harley et al. ............... 558/274

FOREIGN PATENT DOCUMENTS

JP            5-331108         * 12/1993
JP         2001-247519           9/2001

OTHER PUBLICATIONS

International Search Report from Japanese Patent Office with a mailing date of Sep. 7, 2004.
Noboru Yamazaki et al.Study on Chemical Reactions of Carbon dioxide (Rep. Asahi Glass Found. Ind. Technol.), vol. 33, pp. 31-45 (1978).
Shizuyoshi Sakai et al., Reaction of Organotin Alkoxides with Carbon Disulfide, Carbonyl Sulfide of Carbon Dioxide, (Journal of the Chemical Society of Japan), 1975, (10), pp. 1789-1794.
Toshiyasu Sakakura et al., Synthesis of dimethyl carbonate from carbon dioxide: catalysis and mechanism, Polyhedron, vol. 19, pp. 573-576 (2000).

* cited by examiner

*Primary Examiner*—Terressa M Boykin
(74) *Attorney, Agent, or Firm*—Staas & Halsey LLP

(57) ABSTRACT

A method for producing an aromatic carbonate, comprising:
(1) performing a reaction between an organometal compound and carbon dioxide to obtain a reaction mixture containing a dialkyl carbonate formed by the reaction,
(2) separating the dialkyl carbonate from the reaction mixture to obtain a residual liquid,
(3) reacting the residual liquid with an alcohol to form at least one organometal compound and form water and removing the water from the organometal compound, and
(4) reacting the dialkyl carbonate separated in step (2) with an aromatic hydroxy compound to obtain an aromatic carbonate.

35 Claims, 12 Drawing Sheets

METHOD FOR PRODUCING AN AROMATIC CARBONATE

BACKGROUND OF THE INVENTION

1. Field of the Invention

The present invention relates to a method for producing an aromatic carbonate. More particularly, the present invention is concerned with a method for producing an aromatic carbonate, comprising: (1) performing a reaction between an organometal compound and carbon dioxide to obtain a reaction mixture containing a dialkyl carbonate formed by the reaction, (2) separating the dialkyl carbonate from the reaction mixture to obtain a residual liquid, and performing the following steps (3) and (4) in either order, or partially or wholly simultaneously: (3) reacting the residual liquid with an alcohol to form at least one organometal compound and form water and removing the water from the organometal compound, and (4) reacting the dialkyl carbonate separated in step (2) with an aromatic hydroxy compound to obtain an aromatic carbonate.

The method of the present invention is advantageous not only in that the method does not require any toxic substances and is free from the generation of any corrosive substances, but also in that the amounts of by-products are very small and the intermediate products generated during the production of the desired aromatic carbonate can be recycled. Thus, the method of the present invention is favorable from the viewpoint of protection of the environment, and enables a simple and efficient production of a high purity aromatic carbonate.

2. Prior Art

An aromatic carbonate is widely used as carbonyl sources, such as raw materials for producing a polycarbonate, an isocyanate and a pharmaceutical, and it has been desired to develop a method for producing an aromatic carbonate at a low cost.

As methods for producing an aromatic polycarbonate on a commercial scale, there can be mentioned the following methods (i) and (ii):

(i) an interfacial polymerization method (method in which phosgene and a bisphenol are polymerized at the interface between a dichloromethane phase and an aqueous phase in the presence of an appropriate chlorine acceptor); and (ii) a melt method (method in which diphenyl carbonate and a bisphenol are polymerized by a transesterification/dephenolation reaction).

The above-mentioned method (i) (i.e., interfacial polymerization method) uses dichloromethane, whereas the above-mentioned method (ii) (i.e., melt method) does not use dichloromethane. Recently, the problem of water pollution due to an alkyl halide has arisen and, hence, the melt method which does not use dichloromethane has been attracting attention.

As well-known methods for producing an aromatic carbonate (e.g., diphenyl carbonate) used as a raw material in the above-mentioned melt method, there can be mentioned the following five methods 1) to 5):

1) a method for producing an aromatic carbonate using phosgene as a carbonyl source (see, e.g., patent document 1 below);

2) a method for producing an aromatic carbonate using carbon monoxide as a carbonyl source;

3) a method for producing an aromatic carbonate from a diaryl oxalate;

4) a method for producing an aromatic carbonate using urea (or a derivative thereof) as a carbonyl source; and 5) a method for producing an aromatic carbonate using carbon dioxide as a carbonyl source.

With respect to method 1), an explanation is given below. Examples of specific modes of method 1) include an aqueous solution mode in which phosgene is introduced into an aqueous solution of a metal phenoxide; an interface mode in which the production of an aromatic carbonate is performed in a two-phase system comprising an organic solvent phase and an aqueous phase; and a gaseous phase mode in which phenol is reacted with phosgene in a gaseous phase. By each of these modes, an aromatic carbonate can be easily produced. However, since method 1) employs phosgene which is extremely toxic and highly corrosive, method 1) is disadvantageous in that the transportation and storage of phosgene needs great care, and the maintenance of production equipment is costly, which maintenance is indispensable for assuring safety. Further, in method 1), hydrochloric acid which is highly corrosive is by-produced in a large amount, thereby causing difficulty in the waste disposal and the like. Moreover, since the aromatic carbonate (e.g., diphenyl carbonate) obtained by method 1) inevitably contains a chlorine-containing compound as an impurity, method 1) also poses the following serious problem. When such an aromatic carbonate containing a chlorine-containing compound is used for producing a polycarbonate by the melt method, the chlorine-containing compound, even if the amount thereof in the aromatic carbonate is very small, causes the deactivation of a catalyst used for producing a polycarbonate and the discoloration of the polycarbonate produced. For removing the chlorine-containing compound which is contained in the aromatic carbonate in a very small amount (generally, a few ppm by weight, based on the weight of the aromatic carbonate), an additional purification step becomes necessary (see, e.g., patent document 2 below).

As seen from the above, method 1) has a number of serious problems, such as the use of a toxic substance as a raw material, the by-production of a corrosive compound, and the impurity (such as a chlorine-containing compound) contained in the aromatic carbonate produced.

With respect to method 2), an explanation is given below. Method 2) is an oxidative carbonylation method in which an aromatic carbonate (e.g., diphenyl carbonate) is produced from oxygen and an aromatic hydroxy compound using carbon monoxide as a carbonyl source. Carbon monoxide used in method 2) is extremely toxic. Therefore, the transportation and handling of carbon monoxide require great care, and the maintenance of the production equipment is costly, which maintenance is indispensable for assuring safety in the production of the aromatic carbonate. Further, method 2) employs a chlorine or a chlorine-containing compound as a part of a catalyst or as a co-catalyst. Therefore, as in the case of the above-mentioned method 1) using phosgene, the aromatic carbonate produced by method 2) inevitably contains a chlorine-containing compound as an impurity. Moreover, method 2) employs, as a catalyst, palladium which is expensive and difficult to recover. Therefore, method 2) inevitably becomes an extremely expensive and complicated method.

Thus, method 2) also has a number of serious problems, such as the use of a toxic compound as a raw material, the corrosion caused by chlorine, the chlorine-containing impurities contained in the aromatic carbonate produced, and a high production cost.

As a conventional method similar to method 2), there can be mentioned a method in which dimethyl carbonate is obtained from carbon monoxide, oxygen and methanol by an oxidative carbonylation reaction, and the obtained dimethyl carbonate is reacted with an aromatic hydroxy compound to obtain an aromatic carbonate. However, this method also poses a problem in that a large amount of a chlorine-containing compound is used in the oxidative carbonylation reaction, so that the chlorine-containing compound is contained in the dimethyl carbonate produced by the oxidative carbonylation reaction or corrodes the production equipment used in this method (see, e.g., patent document 3 below).

With respect to method 3), an explanation is given below. Method 3) is a method in which a diaryl oxalate is produced from carbon monoxide as a raw material, and the produced diaryl oxalate is subjected to a decarbonylation reaction to produce a diaryl carbonate (e.g., diphenyl carbonate). The diaryl carbonate produced by method 3) contains a large amount of impurities, such as a furan-type compound and a chlorine-containing compound derived from a raw material. Therefore, if the produced diaryl carbonate as such is used without purification for producing a polycarbonate, the polycarbonate produced is inevitably discolored to assume a yellow color. For obviating such a problem, it is necessary to perform a number of additional steps for removing impurities from the diaryl carbonate so as to obtain a purified diaryl carbonate (see, e.g., patent document 4 below).

With respect to method 4), an explanation is given below. Method 4) is a method in which urea as a carbonate source is reacted with an alcohol to obtain a dialkyl carbonate, and the obtained dialkyl carbonate is reacted with an aromatic hydroxy compound to obtain an aromatic carbonate (e.g., diphenyl carbonate). When compared with the above-mentioned methods 1) to 3), method 4) is improved in that urea used as a raw material has substantially no toxicity. However, in the reaction for producing the dialkyl carbonate from urea and an alcohol, an allophanic ester is inevitably by-produced, thereby lowering the selectivity for the dialkyl carbonate. Therefore, the production of the aromatic carbonate (e.g., diphenyl carbonate) by method 4) inevitably becomes costly. Further, an alkyl carbamate generated as an intermediate product and the dialkyl carbonate together form an azeotropic mixture and, hence, the isolation of the dialkyl carbonate is very difficult. For obtaining a pure dialkyl carbonate which contains no alkyl carbamate, an additional step involving cumbersome operations is necessary (see, e.g., patent document 5 below). Further, an apparatus for the disposal of by-products, such as the above-mentioned allophanic ester, is also necessary. Therefore, the production of the aromatic carbonate by method 4) inevitably becomes complicated.

With respect to method 5), an explanation is given below. Method 5) is a method in which carbon dioxide as a carbonyl source is reacted with ethylene oxide or the like to obtain a cyclic carbonate, the obtained cyclic carbonate is reacted with an alcohol to obtain a dialkyl carbonate, and the obtained dialkyl carbonate is reacted with an aromatic hydroxy compound to obtain an aromatic carbonate (see, e.g., patent document 6). This method is advantageous in that carbon dioxide which has substantially no toxicity and is inexpensive is used as a raw material. However, in method 5), ethylene glycol is co-produced with a diaryl carbonate (e.g., diphenyl carbonate), and it is very difficult to regenerate ethylene oxide from ethylene glycol. Therefore, it is necessary to produce the above-mentioned ethylene oxide used as a raw material separately from the above-mentioned reactions involved in method 5).

Thus, method 5) has problems, for example, in that the production of ethylene oxide used as a raw material is necessary, and the ethylene glycol co-produced with the diaryl carbonate cannot be recycled in the production of the aromatic carbonate.

As a method similar to the above-mentioned method 5) in which carbon dioxide as a carbonyl source is reacted with ethylene oxide to obtain a cyclic carbonate, the obtained cyclic carbonate is reacted with an alcohol to obtain a dialkyl carbonate, and the obtained dialkyl carbonate is reacted with an aromatic hydroxy compound to obtain an aromatic carbonate, there is known a method in which a dialkyl carbonate is produced directly from carbon dioxide and an alcohol without production of a cyclic carbonate as an intermediate product (see patent documents 7, 8 and 9 below). When the alcohol used in this method is produced using acetal as an organic dehydrating agent, water formed in the reaction of carbon dioxide with an alcohol to produce a dialkyl carbonate is consumed in the reaction to produce alcohol, thereby promoting the above-mentioned reaction to produce a dialkyl carbonate. More specific explanation is given below, referring to formulae (4) and (5) below (in which Me represents a methyl group, which is a representative example of an alkyl group) which represent reactions involved in the above-mentioned method. Water by-produced in the equilibrium reaction represented by formula (4) below (i.e., reaction to produce an alkyl carbonate) is used in the equilibrium reaction represented by formula (5) (i.e., reaction to produce an alcohol). Therefore, the amount of water by-produced in the reaction to produce an alkyl carbonate is reduced, thereby displacing the equilibrium of formula (4) in the direction of the desired product formation. Thus, a dialkyl carbonate (i.e., dimethyl carbonate) can be obtained from carbon dioxide and an alcohol (i.e., methanol). However, in the method involving the reactions of formulae (4) and (5), acetal is consumed in an amount equimolar to the dialkyl carbonate produced and, therefore, acetone (derived from acetal) is co-produced with a dialkyl carbonate. It is difficult to convert the co-produced acetone to acetal because the reaction converting acetone to acetal (organic dehydrating agent) is a dehydrating reaction which is difficult to proceed. Therefore, the use of a large amount of acetal as a raw material is necessary, and the energy efficiency is poor. For this reason, the above-mentioned method has not been commercialized.

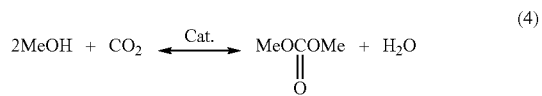

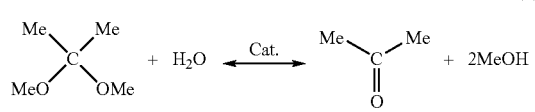

Even when an inorganic dehydrating agent is used in place of an organic dehydrating agent (such as acetal), the same problems as mentioned above arise, i.e., problems that an inorganic compound used as a dehydrating agent absorbs water, and it requires a large amount of energy to dehydrate the water-absorbed inorganic compound so as to regenerate an inorganic compound usable as a dehydrating agent, so that a dialkyl carbonate cannot be produced at a low cost. Therefore, the method using an inorganic dehydrating agent has also not been commercialized.

As mentioned above, a number of methods for producing an aromatic carbonate have been proposed; however, these methods have various problems, such as the use of a toxic substance as a raw material; the corrosion of the production equipment due to a chlorine-containing compound; the cumbersome operation for the removal of a by-product (such as a chlorine-containing compound); and the difficulty in (or impossibility of) the conversion of a co-product to a raw material. Even when carbon dioxide (which has substantially no toxicity and contains no chlorine compound) is used as a carbonyl source, there still are problems, such as the generations of a co-product and a by-product derived from a dehydrating agent used, and the need for regeneration or disposal of a dehydrating agent.

Thus, it has been desired to develop a method for producing an aromatic carbonate, which is advantageous not only in that the method does not need the use of any toxic substance and is free from the generation of any corrosive substances, but also in that the amounts of co-products and by-products are very small, so that the method is favorable from the view point of protection of environment, and enables a simple and efficient production of a high purity aromatic carbonate.

Patent document 1: Japanese Patent No. 3071008

Patent document 2: Unexamined Japanese Patent Application Laid-Open Specification No. Hei 8-198816

Patent document 3: Unexamined Japanese Patent Application Laid-Open Specification No. Hei 7-145109

Patent document 4: Unexamined Japanese Patent Application Laid-Open Specification No. 2002-47251

Patent document 5: Unexamined Japanese Patent Application Laid-Open Specification No. 2000-1461

Patent document 6: Unexamined Japanese Patent Application Laid-Open Specification No. Hei 9-40616

Patent document 7: Unexamined Japanese Patent Application Laid-Open Specification No. 2001-247519

Patent document 8: German Patent No. 4310109

Patent document 9: Unexamined Japanese Patent Application Laid-Open Specification No. 2001-31629

SUMMARY OF THE INVENTION

In this situation, the present inventors have made extensive and intensive studies with a view toward solving the above-mentioned problems accompanying the prior art. In their studies, the present inventors have utilized the techniques of their previous inventions of WO 03/055840 and WO 04/014840, each of which is directed to a method for continuously producing a dialkyl carbonate, which method comprises reacting an organometal compound, carbon dioxide, and optionally an alcohol with each other to obtain a reaction mixture containing a dialkyl carbonate, separating the dialkyl carbonate from the reaction mixture to obtain a residual liquid, regenerating the organometal compound from the residual liquid, and recycling the regenerated organometal compound. As a result, the present inventors have succeeded in improving the above-mentioned previous inventions and arrived at the present invention. That is, it has been found that all of the problems accompanying the prior art can be solved by a method comprising: (1) performing a reaction between an organometal compound and carbon dioxide to obtain a reaction mixture containing a dialkyl carbonate formed by the reaction, (2) separating the dialkyl carbonate from the reaction mixture to obtain a residual liquid, and performing the following steps (3) and (4) in either order, or partially or wholly simultaneously: (3) reacting the residual liquid with an alcohol to form at least one organometal compound and form water and removing the water from the organometal compound, and (4) reacting the dialkyl carbonate separated in step (2) with an aromatic hydroxy compound to obtain an aromatic carbonate. Specifically, the method of the present invention is advantageous not only in that the method does not need the use of any toxic substance and is free from the generation of any corrosive substance, but also in that the amounts of by-products are very small and intermediate products generated during the production of the desired aromatic carbonate can be recycled, so that the method of the present invention is favorable from the view point of protection of environment, and enables a simple and efficient production of a high purity aromatic carbonate. Based on this finding, the present invention has been completed.

More specifically, in the method of the present invention, intermediate products generated during the production of the desired aromatic carbonate can be recycled, and only an aromatic carbonate and water are obtained as products from carbon dioxide and an aromatic hydroxy compound as raw materials, wherein substantially no other raw materials than carbon dioxide and the aromatic hydroxy compound are necessary. Thus, the method of the present invention has solved all of the problems accompanying the prior art, such as the use of a toxic substance as a raw material, the corrosion of the production equipment due to a chlorine-containing compound, the generation of by-products and intermediate products which are difficult to separate, the production of co-products, and the chlorine-containing compound contained in the aromatic carbonate produced.

Accordingly, it is an object of the present invention to provide a method for producing an aromatic carbonate, which is advantageous not only in that the method does not need the use of any toxic substance and is free from the generation of any corrosive substance, but also in that the amounts of by-products are very small and intermediate products generated during the production of the desired aromatic carbonate can be recycled, so that the method is favorable from the view point of protection of environment, and enables a simple and efficient production of a high purity aromatic carbonate.

The foregoing and other objects, features and advantages of the present invention will be apparent from the following detailed description taken in connection with the accompanying drawings and the appended claims.

DESCRIPTION OF REFERENCE NUMERALS

Figure 1:
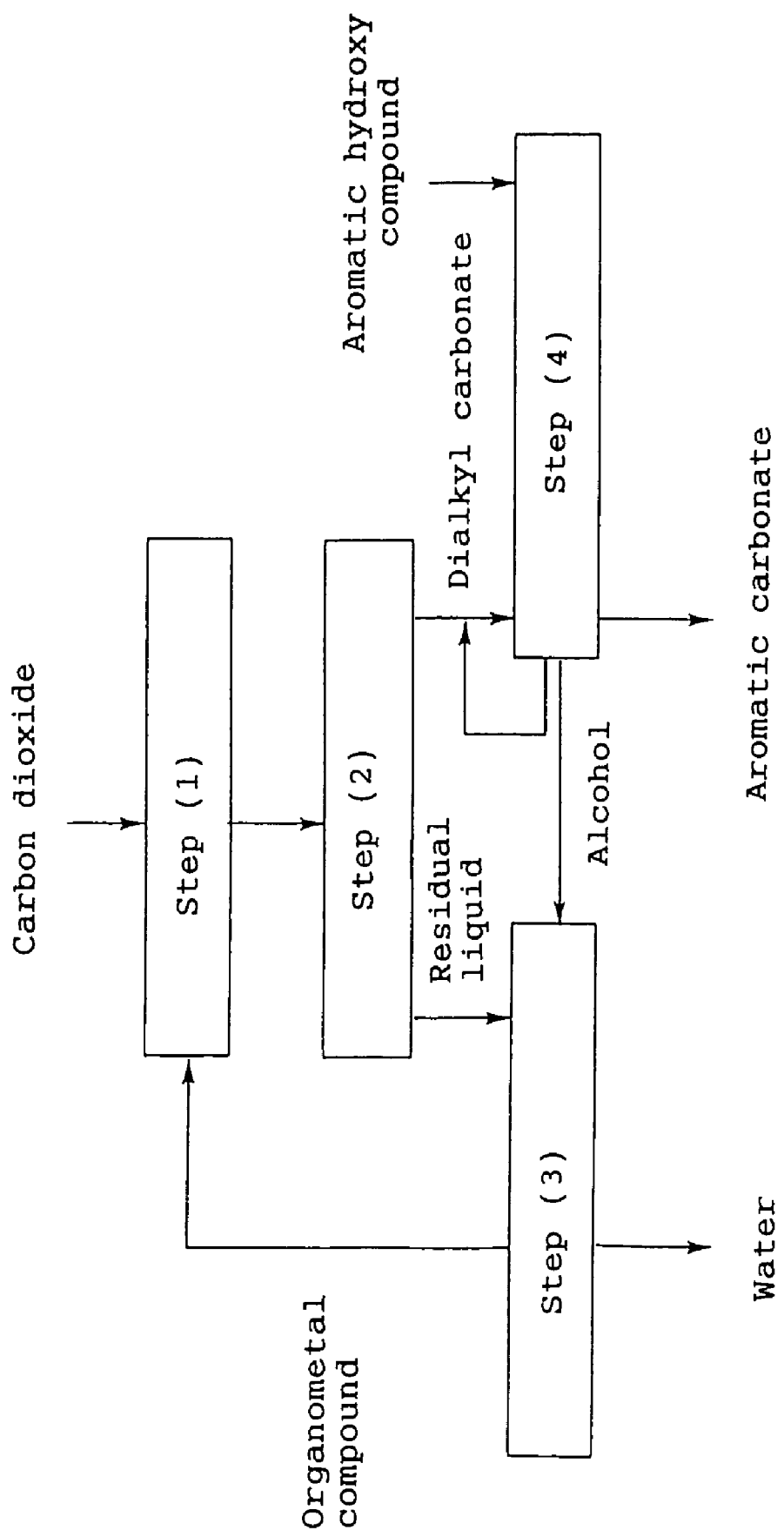
FIG. 1 is a flow chart showing an example of the method of the present invention for producing an aromatic carbonate.

1: reaction vessel
2, 3, 4, 5, 8, 10, 12, 15, 17, 20, 21, 24, 26, 31, 33, 34, 35, 37, 40, 44, 46, 48, 51, 55, 57, 59, 62, 66, 68, 70, 73, 77, 79, 81, 84, 88, 90, 92, 95, 99, 101, 103, 106, 110, 112, 114, 117, 121, 123, 128, 132, 133, 134, 136: conduit
6, 18, 28, 41, 52, 63, 74, 85, 96, 107, 118: condenser
7, 9, 16, 19, 23, 29, 32, 47, 58, 69, 80, 91, 102, 113, 124, 125, 126, 127, 131, 135, 137, 138, 139, 140: reservoir
11: apparatus for removing an alcohol
13, 38, 49, 60, 71, 82, 93, 104, 115: preheater
14, 39, 50, 61, 72, 83, 94, 105, 116: continuous multi-stage distillation column
22, 45, 56, 67, 78, 89, 100, 111, 122: reboiler
25: vessel for removing carbon dioxide
27: multi-stage distillation column
42, 53, 64, 75, 86, 97, 108, 119, 129: vapor-liquid separation apparatus
30: thin film distillation apparatus
36, 43, 54, 65, 76, 87, 98, 109, 120, 130: pressure adjustment valve

DETAILED DESCRIPTION OF THE INVENTION

According to the present invention, there is provided a method for producing an aromatic carbonate, comprising:

(1) performing a reaction between an organometal compound and carbon dioxide to obtain a reaction mixture containing a dialkyl carbonate formed by the reaction, (2) separating the dialkyl carbonate from the reaction mixture to obtain a residual liquid, and performing the following steps (3) and (4) in either order, or partially or wholly simultaneously:

(3) reacting the residual liquid with an alcohol to form at least one organometal compound and form water and removing the water from the organometal compound, and (4) reacting the dialkyl carbonate separated in step (2) with an aromatic hydroxy compound to obtain an aromatic carbonate.

For easy understanding of the present invention, the essential features and various preferred embodiments of the present invention are enumerated below.

1. A method for producing an aromatic carbonate, comprising:

(1) performing a reaction between an organometal compound and carbon dioxide to obtain a reaction mixture containing a dialkyl carbonate formed by the reaction, (2) separating the dialkyl carbonate from the reaction mixture to obtain a residual liquid, and performing the following steps (3) and (4) in either order, or partially or wholly simultaneously:

(3) reacting the residual liquid with an alcohol to form at least one organometal compound and form water and removing the water from the organometal compound, and (4) reacting the dialkyl carbonate separated in step (2) with an aromatic hydroxy compound to obtain an aromatic carbonate.

2. The method according to item 1 above, wherein the aromatic carbonate obtained in step (4) is at least one compound selected from the group consisting of an alkyl aryl carbonate and a diaryl carbonate.

3. The method according to item 1 or 2 above, wherein, in step (3), the organometal compound having the water removed therefrom is recycled to step (1).

4. The method according to any one of items 1 to 3 above, wherein, in step (4), an alcohol which is generated together with the aromatic carbonate is recycled to step (3).

5. The method according to any one of items 1 to 4 above, wherein a dialkyl carbonate recovered in step (4) is recycled to step (4).

6. The method according to any one of items 1 to 5 above, wherein a cycle of steps (1) to (4) is repeated at least one time.

7. The method according to any one of items 2 to 5 above, wherein the aromatic carbonate obtained in step (4) is an alkyl aryl carbonate and which, after step (4), further comprises the following step (5):

(5) subjecting the alkyl aryl carbonate to a disproportionation reaction to obtain a diaryl carbonate.

8. The method according to item 7 above, wherein, in step (5), a dialkyl carbonate which is generated together with the diaryl carbonate is recycled to step (4).

9. The method according to item 7 or 8 above, wherein a cycle of steps (1) to (5) is repeated at least one time.

10. The method according to any one of items 1 to 9 above, wherein, in step (1), the organometal compound is used in an amount which is 1/200 to 1 time the stoichiometric amount relative to the amount of the carbon dioxide.

11. The method according to any one of items 1 to 10 above, wherein the reaction in step (1) is performed at 20° C. or higher.

12. The method according to any one of items 1 to 11 above, wherein the organometal compound used in step (1) is an organometal compound having a metal-oxygen-carbon linkage.

13. The method according to item 12 above, wherein the organometal compound having a metal-oxygen-carbon linkage comprises at least one compound selected from the group consisting of:

an organometal compound represented by the formula (1):

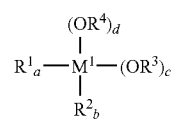

(1)

wherein:

$M^1$ represents a metal atom selected from the group consisting of elements belonging to Groups 4 and 14 of the Periodic Table, exclusive of silicon;

each of $R^1$ and $R^2$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;

each of $R^3$ and $R^4$ independently represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and each of a and b is an integer of from 0 to 2, a+b=0 to 2, each of c and d is an integer of from 0 to 4, and a+b+c+d=4; and an organometal compound represented by the formula (2)

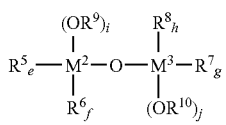

wherein:

each of $M^2$ and $M^3$ independently represents a metal atom selected from the group consisting of elements belonging to Groups 4 and 14 of the Periodic Table, exclusive of silicon;

each of $R^5$, $R^6$, $R^7$ and $R^8$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;

each of $R^9$ and $R^{10}$ independently represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and each of e, f, g and h is an integer of from 0 to 2, e+f=0 to 2, g+h=0 to 2, each of i and j is an integer of from 1 to 3, e+f+i=3, and g+h+j=3.

14. The method according to any one of items 1 to 13 above, wherein the separation of the dialkyl carbonate in step (2) is performed by at least one separation method selected from the group consisting of distillation, extraction and filtration.

15. The method according to item 14 above, wherein the separation of the dialkyl carbonate in step (2) is performed by distillation.

16. The method according to item 15 above, wherein the separation of the dialkyl carbonate in step (2) is performed by thin film distillation.

17. The method according to any one of items 1 to 16 above, wherein the removal of the water in step (3) is performed by membrane separation.

18. The method according to item 17 above, wherein the membrane separation is pervaporation.

19. The method according to any one of items 1 to 16 above, wherein the removal of the water in step (3) is performed by distillation.

20. The method according to any one of items 1 to 19 above, wherein the alcohol used in step (3) is at least one alcohol selected from the group consisting of an alkyl alcohol having a straight chain or branched $C_1$-$C_{12}$ alkyl group, a cycloalkyl alcohol having a $C_5$-$C_{12}$ cycloalkyl group, an alkenyl alcohol having a straight chain or branched $C_2$-$C_{12}$ alkenyl group, and an aralkyl alcohol having a $C_7$-$C_{20}$ aralkyl group comprised of unsubstituted or substituted $C_6$-$C_{19}$ aryl and alkyl selected from the group consisting of a straight chain or branched $C_1$-$C_{14}$ alkyl and $C_5$-$C_{14}$ cycloalkyl.

21. The method according to any one of items 1 to 20 above, wherein the alcohol used in step (3) has a boiling point which is higher than the boiling point of water.

22. The method according to item 21 above, wherein the alcohol used in step (3) is at least one alcohol selected from the group consisting of 1-butanol, 2-methyl-1-propanol, an alkyl alcohol having a straight chain or branched $C_5$-$C_{12}$ alkyl group, and an alkenyl alcohol having a straight chain or branched $C_4$-$C_{12}$ alkenyl group.

23. The method according to item 21 or 22 above, wherein the alcohol used in step (3) has a boiling point which is lower than that of the aromatic hydroxy compound used in step (4).

24. The method according to item 13 above, wherein each of $R^3$ and $R^4$ in formula (1) and $R^9$ and $R^{10}$ in formula (2) independently represents an n-butyl group, a 2-methylpropyl group, a straight chain or branched $C_5$-$C_{12}$ alkyl group, or a branched $C_4$-$C_{12}$ alkenyl group.

25. The method according to any one of items 1 to 24 above, wherein, in step (1), the organometal compound is used in at least one form selected from the group consisting of a monomeric form, an oligomeric form, a polymeric form and an associated form.

26. The method according to any one of items 13, 24 and 25 above, wherein each of $M^1$ in formula (1) and $M^2$ and $M^3$ in formula (2) represents a tin atom.

27. The method according to any one of items 1 to 26 above, wherein the organometal compound used in step (1) is produced from an organotin oxide and an alcohol.

28. The method according to any one of items 1 to 27 above, wherein the amount of the aromatic hydroxy compound used in step (4) is 0.1 to 10,000 times the stoichiometric amount relative to the amount of the dialkyl carbonate used in step (4).

29. The method according to any one of items 1 to 28 above, wherein the reaction in step (4) is performed at a temperature in the range of from 50 to 350° C.

30. The method according to any one of items 1 to 29 above, wherein the reaction in step (4) is performed in the presence of a transesterification reaction catalyst.

31. The method according to any one of items 7 to 30 above, wherein the reaction in step (5) is performed in the presence of a disproportionation reaction catalyst.

32. The method according to any one of items 1 to 31 above, wherein the aromatic hydroxy compound is represented by the following formula (3):

$$ArOH \qquad (3)$$

wherein Ar is a $C_5$-$C_{30}$ aromatic group.

33. The method according to item 32 above, wherein the aromatic hydroxy compound represented by formula (3) is phenol.

34. The method according to any one of items 1 to 33 above, wherein the total content of an aromatic hydroxy compound and a carboxylic acid group-containing compound in the alcohol used in step (3) is 1,000 ppm or less.

35. An aromatic carbonate produced by the method of any one of items 1 to 34 above.

36. A polycarbonate, an isocyanate or a polycarbonate diol produced using the aromatic carbonate of item 35 above.

37. The polycarbonate, isocyanate or polycarbonate diol according to item 36 above, wherein the aromatic carbonate is a diaryl carbonate.

Hereinbelow, the present invention is described in detail.

The method of the present invention comprises the following four steps (1) to (4):

(1) performing a reaction between an organometal compound and carbon dioxide to obtain a reaction mixture containing a dialkyl carbonate formed by the reaction;

(2) separating the dialkyl carbonate from the reaction mixture to obtain a residual liquid;

(3) reacting the residual liquid with an alcohol to form at least one organometal compound and form water and removing the water from the organometal compound; and (4) reacting the dialkyl carbonate separated in step (2) with an aromatic hydroxy compound to obtain an aromatic carbonate.

With respect to steps (3) and (4), these steps are performed after steps (1) and (2) are performed in this order, wherein steps (3) and (4) may be performed in either order, or partially or wholly simultaneously. Further, steps (3) and (4) may be performed in this or another order and partially simultaneously (e.g., step (4) may be started after starting step (3) and, then, performed simultaneously with step (3)). Steps (3) and (4) are performed using different apparatuses, respectively.

With respect to each of steps (1) to (3), an outline thereof is explained below. In step (1), a reaction represented by formula (6) below is performed.

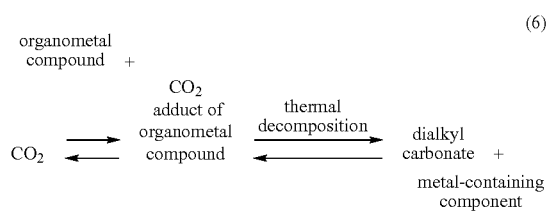

(6)

That is, in step (1), a reaction between an organometal compound and carbon dioxide is performed to form a CO₂ adduct of the organometal compound, followed by a thermal decomposition reaction of the CO₂ adduct, to thereby obtain a reaction mixture containing a dialkyl carbonate. This reaction mixture contains not only a dialkyl carbonate but also a metal-containing component(s) formed from the organometal compound.

In step (2), a reaction and a subsequent separation are performed as shown in formula (7) below.

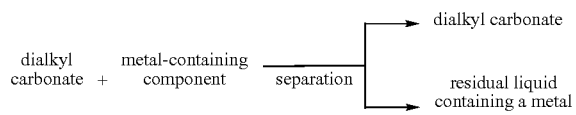

(7)

That is, from the reaction mixture obtained in step (1), the dialkyl carbonate is separated to thereby obtain a residual liquid containing the metal-containing component(s).

In step (3), a reaction represented by formula (8) below (i.e., reaction in which at least one organometal compound and water are formed from the residual liquid (containing the metal-containing component(s)) and an alcohol) is performed, and the water is removed from the organometal compound.

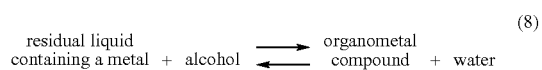

(8)

In step (3), it is preferred that the organometal compound having water removed therefrom is recycled to step (1).

With respect to step (4), an explanation is given below. In step (4), the dialkyl carbonate separated in step (2) is reacted with an aromatic hydroxy compound to obtain an aromatic carbonate. In general, by the reaction of a dialkyl carbonate with an aromatic hydroxy compound, an alkyl aryl carbonate and an alcohol are generated (see formula (9) below).

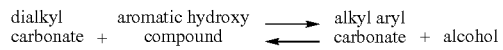

(9)

For example, this reaction can be performed using a catalyst while withdrawing the alcohol from the reaction system. The alkyl aryl carbonate reacts with the aromatic hydroxy compound to generate a diaryl carbonate and an alcohol (see formula (10) below).

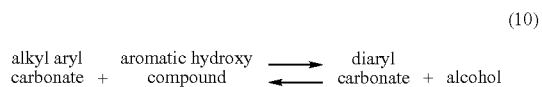

(10)

The alkyl aryl carbonate also undergoes a disproportionation reaction to form a diaryl carbonate and a dialkyl carbonate (see formula (11) below).

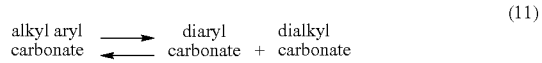

(11)

For example, the disproportionation reaction of the alkyl aryl carbonate can be performed using a catalyst while withdrawing the dialkyl carbonate from the reaction system.

Thus, in step (4), by controlling the reaction conditions, a desired aromatic carbonate(s) can be obtained. That is, for example, it is possible to obtain, as an aromatic carbonate, mainly an alkyl aryl carbonate. Alternatively, it is also possible to obtain, as an aromatic carbonate, mainly a diaryl carbonate. Further, it is also possible to obtain, as an aromatic carbonate, a mixture of an alkyl aryl carbonate and a diaryl carbonate, in which the difference between the amount of the alkyl aryl carbonate and the amount of the diaryl carbonate is relatively small.

As mentioned above, in step (4), by the reaction between a dialkyl carbonate and an aromatic hydroxy compound, an alkyl aryl carbonate and an alcohol are generated. It is preferred that the alcohol generated is recycled to step (3).

Further, as mentioned above, in step (4), it is possible to generate a dialkyl carbonate by the above-mentioned disproportionation reaction of the alkyl aryl carbonate. Further, in step (4), with respect to the dialkyl carbonate (which is separated in step (2)) used for the reaction with an aromatic hydroxy compound, a part thereof remains unreacted. It is preferred that these dialkyl carbonates (i.e., dialkyl carbonate generated by the disproportionation reaction and dialkyl carbonate remaining unreacted) are recycled to step (4).

In the method of the present invention, it is preferred that a cycle of steps (1) to (4) is repeated at least one time.

It is preferred that the aromatic carbonate obtained in step (4) is an alkyl aryl carbonate and that the method of the present invention, after step (4), further comprises the following step (5):

(5) subjecting the alkyl aryl carbonate to a disproportionation reaction to obtain a diaryl carbonate.

The reaction performed in step (5) is a reaction represented by formula (11) above, namely, a reaction in which a diaryl carbonate and a dialkyl carbonate are generated by the disproportionation reaction of the alkyl aryl carbonate. It is preferred that the dialkyl carbonate generated is recycled to step (4).

When the method of the present invention comprises step (5) as well as steps (1) to (4), it is preferred that a cycle of steps (1) to (5) is repeated at least one time.

Thus, in a preferred mode of the method of the present invention, steps (1) to (4) are performed while recycling the organometal compound (which is generated in step (3)) and the alcohol (which is generated in step (4)) to steps (1) and (3), respectively. In this preferred mode of the method of the present invention, only an aromatic carbonate and water are obtained as products from carbon dioxide and an aromatic hydroxy compound as raw materials, wherein substantially no other raw materials than carbon dioxide and the aromatic hydroxy compound are used. That is, an overall reaction scheme of the aromatic carbonate production by this preferred mode of the method of the present invention can be represented by formula (12) below.

(12)

Hereinbelow, comparison is made between the above-mentioned preferred mode of the method of the present invention and conventional methods which, as in the method of the present invention, use carbon dioxide as a carbonyl source.

The preferred mode of the method of the present invention, which involves the reaction represented by formula (12) above, is completely different from any one of the following conventional methods (a), (b) and (c) which use carbon dioxide as a carbonyl source:

a) method for producing an aromatic carbonate from ethylene oxide or the like and carbon dioxide through a cyclic carbonate generated as an intermediate product;

b) method for producing a dialkyl carbonate, in which an organic dehydrating agent is used; and c) method for producing a dialkyl carbonate, in which a solid dehydrating agent (inorganic dehydrating agent) is used.

First, the difference between method a) and the above-mentioned preferred mode of the method of the present invention is explained. It is understood that, in method a), an aromatic carbonate is produced by a sequence of reactions represented by formulae (13) to (17) below (an overall reaction scheme of the aromatic carbonate production involving the reactions of formulae (13) to (17) can be represented by formula (18) below).

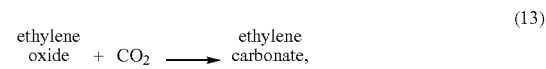
(13)

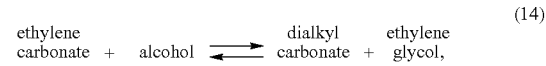
(14)

(15)

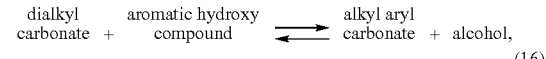
(16)

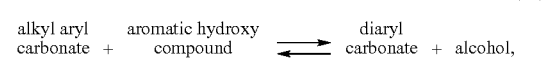
(17)

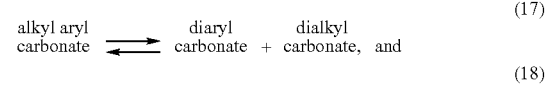
(18)

In the reactions of formulae (15) and (16) above, alcohols are produced. These alcohols are recycled to the reaction system of the reaction of formula (14) for producing a dialkyl carbonate from ethylene carbonate and an alcohol. In this respect, method a) is different from the preferred mode of the present invention, in which the alcohol generated as an intermediate product is recycled for producing an organometal compound. Further, the overall reaction scheme of the aromatic carbonate production by method a) is shown in formula (18) (i.e., reaction scheme in which an aromatic carbonate and ethylene glycol are produced from carbon dioxide, ethylene oxide and an aromatic hydroxy compound), and this reaction scheme is completely different from the reaction of formula (12) above, which is performed in the above-mentioned preferred mode of the method of the present invention. Therefore, method a) is completely different from the preferred mode of the method of the present invention.

With respect to method b), this is a method for producing a dialkyl carbonate, not an aromatic carbonate. However, for information, the difference between method b) and the preferred mode of the method of the present invention is explained below. In method b), a dialkyl carbonate and water are generated by an equilibrium reaction represented by formula (4) below, and the water generated is reacted with an organic dehydrating agent (i.e., acetal) (i.e., reaction of formula (5)), so that the equilibrium of the reaction of formula (4) is displaced in the direction of the desired product formation, thereby increasing the amount of the dialkyl carbonate produced. Therefore, it is understood that, in method b), a dialkyl carbonate is produced by a reaction represented by formula (19) below, in which acetone is co-produced with a dialkyl carbonate wherein the amount of the acetone is equimolar to the dialkyl carbonate.

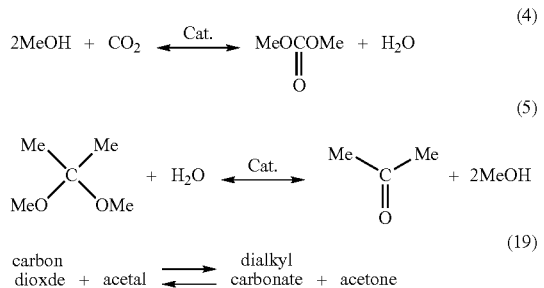

(4)

(5)

(19)

The reaction of formula (19) is completely different from the reaction of formula (12) which is performed in the above-mentioned preferred mode of the method of the present invention. Therefore, method b) is completely different from the preferred mode of the method of the present invention.

It is conceivable to react the dialkyl carbonate obtained by method b) with an aromatic hydroxy compound to produce an aromatic carbonate and an alcohol. In such a case, when it is intended to recycle the alcohol which is co-produced with the aromatic carbonate, the alcohol is presumed to be used for regeneration of the organic dehydrating agent (i.e., acetal). Also in this respect, it is apparent that method b) is completely different from the preferred mode of the method of the present invention, in which the alcohol generated as an intermediate product is recycled for regeneration of an organometal compound.

With respect to the difference between method c) (i.e., method for producing a dialkyl carbonate, in which a solid dehydrating agent is used) and the preferred mode of the method of the present invention, an explanation is given below. (As in the case of method b), method c) is also a method for producing a dialkyl carbonate, not an aromatic carbonate. However, for information, explanation on method c) is given below.) The reaction performed in method c) for producing a dialkyl carbonate is an equilibrium reaction represented by the following formula (20).

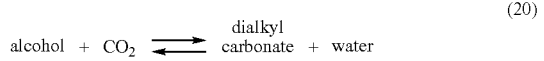

(20)

The water produced by the reaction of formula (20) can be reacted with or adsorbed to a solid dehydrating agent (inorganic dehydrating agent), thereby displacing the equilibrium of the reaction of formula (20) in the direction of the desired product formation, thereby increasing the yield of the dialkyl carbonate. However, the reaction of formula (20) is completely different from the reaction of formula (12) which is performed in the above-mentioned preferred mode of the method of the present invention. Therefore, method c) is completely different from the preferred mode of the method of the present invention.

It is conceivable to react the dialkyl carbonate obtained by method c) with an aromatic hydroxy compound to produce an aromatic carbonate and an alcohol. In such a case, when it is intended to recycle the alcohol which is co-produced with the aromatic carbonate, the alcohol is presumed to be used as a raw material for producing the aromatic carbonate by the reaction of formula (20). Also in this respect, it is apparent that method c) is completely different from the preferred mode of the method of the present invention, in which the alcohol generated as an intermediate product is recycled for regeneration of an organometal compound.

Hereinbelow, explanations are made with respect to the compounds used in the present invention.

With respect to the organometal compound used in step (1) of the method of the present invention, there is no particular limitation so long as it reacts with carbon dioxide to form a dialkyl carbonate. However, it is preferred to use an organometal compound which has a metal-oxygen-carbon linkage, such as an organometal compound having an alkoxy group. With respect to such an organometal compound having a metal-oxygen-carbon linkage, it is preferred that the organometal compound comprises at least one compound selected from the group consisting of:

an organometal compound represented by the formula (1):

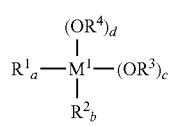

(1)

wherein:

$M^1$ represents a metal atom selected from the group consisting of elements belonging to Groups 4 and 14 of the Periodic Table, exclusive of silicon;

each of $R^1$ and $R^2$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;

each of $R^3$ and $R^4$ independently represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and each of a and b is an integer of from 0 to 2, a+b=0 to 2, each of c and d is an integer of from 0 to 4, and a+b+c+d=4; and an organometal compound represented by the formula (2):

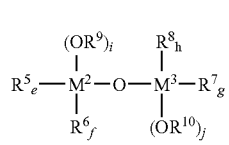

(2)

wherein:

each of $M^2$ and $M^3$ independently represents a metal atom selected from the group consisting of elements belonging to Groups 4 and 14 of the Periodic Table, exclusive of silicon;

each of $R^5$, $R^6$, $R^7$ and $R^8$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;

each of $R^9$ and $R^{10}$ independently represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and each of e, f, g and h is an integer of from 0 to 2, e+f=0 to 2, g+h=0 to 2, each of i and j is an integer of from 1 to 3, e+f+1=3, and g+h+j=3.

The Periodic Table mentioned herein is as prescribed in the IUPAC (International Union of Pure and Applied Chemistry) nomenclature system (1989).

The above-mentioned organometal compound is used in at least one form selected from the group consisting of a monomeric form, an oligomeric form, a polymeric form and an associated form.

As mentioned above, each of $M^1$ in formula (1) and $M^2$ and $M^3$ in formula (2) independently represents a metal atom selected from the group consisting of elements belonging to Groups 4 and 14 of the Periodic Table, exclusive of silicon. It is preferred that each of $M^1$, $M^2$ and $M^3$ is a metal atom selected from the group consisting of a titanium atom, a tin atom, a nickel atom, a cobalt atom and a zirconium atom. From the viewpoint of the solubility in and reactivity with an alcohol, it is more preferred that each of $M^1$, $M^2$ and $M^3$ is a metal selected from the group consisting of a titanium atom and a tin atom, and it is most preferred that each of $M^1$, $M^2$ and $M^3$ is a tin atom.

Examples of $R^1$ and $R^2$ in formula (1) and $R^5$, $R^6$, $R^7$ and $R^8$ in formula (2) include $C_1$-$C_{12}$ alkyl groups and $C_5$-$C_{12}$ cycloalkyl groups, such as a methyl group, an ethyl group, a propyl group (and isomers thereof), a butyl group (and isomers thereof), a pentyl group (and isomers thereof), a hexyl group (and isomers thereof), a heptyl group (and isomers thereof), an octyl group (and isomers thereof), a nonyl group (and isomers thereof), a butenyl group (and isomers thereof), a pentenyl group (and isomers thereof), a cyclobutyl group, a cyclopentyl group, a cyclopentadienyl group and a cyclohexenyl group; $C_7$-$C_{20}$ aralkyl groups, such as a benzyl group and a phenylethyl group; and $C_6$-$C_{20}$ aryl groups, such as a phenyl group, a tolyl group and a naphthyl group. Each of these hydrocarbon groups may be substituted with a group (such as an alkoxy group, a dialkylamino group or an alkoxycarbonyl group) which does not react with carbon dioxide or an alcohol. Further, each of these hydrocarbon groups may have an ether linkage. Moreover, each of these hydrocarbon groups may be a halogenated hydrocarbon group (i.e., hydrocarbon group which has at least one hydrogen atom thereof replaced by a halogen atom), such as a nonafluorobutyl group or a heptafluorobutyl group (and isomers thereof). However, $R^1$, $R^2$, $R^5$, $R^6$, $R^7$ and $R^8$ are not limited to these examples. Of the above-mentioned groups, lower alkyl groups, such as $C_1$-$C_8$ alkyl groups, are preferred, and straight chain or branched $C_1$-$C_4$ alkyl groups are more preferred. Hydrocarbon groups having more carbon atoms than mentioned above can also be used as $R^1$, $R^2$, $R^5$, $R^6$, $R^7$ and $R^8$; however, when such groups having a larger number of carbon atoms are used, there is a danger that the fluidity of the organometal compound and/or the productivity of an aromatic carbonate becomes low.

Examples of $R^3$ and $R^4$ in the formula (1) and $R^9$ and $R^{10}$ in the formula (2) include $C_1$-$C_{12}$ alkyl groups and $C_5$-$C_{12}$ cycloalkyl groups, such as a methyl group, an ethyl group, a propyl group (and isomers thereof), a butyl group (and isomers thereof), a pentyl group (and isomers thereof), a hexyl group (and isomers thereof), a cyclopropyl group, a cyclobutyl group, a cyclopentyl group, a cyclopentadienyl group, a cyclohexyl group, a cyclohexenyl group, a methoxyethyl group and an ethoxymethyl group; and $C_7$-$C_{20}$ aralkyl groups, such as a benzyl group and a phenylethyl group. Of the above-mentioned groups, lower alkyl groups are preferred.

With respect to the alkoxy groups of the organometal compounds represented by formula (1) and (2) above (i.e., —$OR^3$ and —$OR^4$ in formula (1), and —$OR^9$ and —$OR^{10}$ in formula (2)), it is preferred that each of the corresponding alcohols (i.e., $R^3OH$, $R^4OH$, $R^9OH$ and $R^{10}OH$) has a boiling point higher than that of water (wherein the boiling point is measured under atmospheric pressure), and that the alkyl or alkenyl moiety of each of the alkoxy group is n-butyl, 2-methylpropyl, a straight chain or branched $C_5$-$C_{12}$ alkyl or a branched $C_4$-$C_{12}$ alkenyl. Further, from the viewpoint of recycling the organometal compound recovered in step (3) and efficiently performing the reaction in step (4), it is more preferred that each of the above-mentioned corresponding alcohols has a boiling point lower than that of the aromatic hydroxy compound used in step (4) (wherein the boiling point is measured under atmospheric pressure), and that the above-mentioned alkyl moiety of the alkoxy group is n-butyl, 2-methylpropyl or a straight chain or branched $C_5$-$C_8$ alkyl. It is most preferred that the above-mentioned alkyl moiety of the alkoxy group has no branch structure at the α-carbon atom (i.e., carbon atom present in the metal-oxygen-carbon linkage of the organometal compound). Examples of such alkyl moieties include n-butyl, 2-methylpropyl and a straight chain or branched $C_5$-$C_6$ alkyl.

Examples of organometal compounds represented by formula (1) above include alkoxytin compounds, alkoxytitanium compounds and alkylalkoxytin compounds. Specific examples of such organometal compounds include tetramethoxytin, tetraethoxytin, tetrapropyloxytin (and isomers thereof), tetrabutyloxytin (and isomers thereof), tetrapentyloxytin (and isomers thereof), tetrahexyloxytin (and isomers thereof), tetraheptyloxytin (and isomers thereof), tetraoctyloxytin (and isomers thereof), tetranonyloxytin (and isomers thereof), dimethoxydiethoxytin, tetramethoxytitanium, tetraethoxytitanium, tetrapropyloxytitanium, tetraisopropyloxytitanium, tetrakis(2-ethyl-1-hexyloxy)titanium, tetrabenzyloxytin, diethoxydipropyloxytin (and isomers thereof), dimethoxydihexyloxytin (and isomers thereof), dimethyldimethoxytin, dimethyldiethoxytin, dimethyldipropyloxytin (and isomers thereof), dimethyldibutyloxytin (and isomers thereof), dimethyldipentyloxytin (and isomers thereof), dimethyldihexyloxytin (and isomers thereof), dimethyldiheptyloxytin (and isomers thereof), dimethyldioctyloxytin (and isomers thereof), dimethyldinonyloxytin (and isomers thereof), dimethyldidecyloxytin (and isomers thereof), methylbutyltin dimethoxide, methylbutyltin diethoxide, methylbutyltin dipropoxide (and isomers thereof), methylbutyltin dibutoxide (and isomers thereof), methylbutyltin dipentyloxide (and isomers thereof), methylbutyltin dihexyloxide (and isomers thereof), methylbutyltin diheptyloxide (and isomers thereof), metylbutyltin dioctyloxide (and isomers thereof), ethylbutyltin dimethoxide, ethylbutyltin diethoxide, ethylbutyltin dipropoxide (and isomers thereof), ethylbutyltin dibutoxide (and isomers thereof), ethylbutyltin dipentyloxide (and isomers thereof), ethylbutyltin dihexyloxide (and isomers thereof), ethylbutyltin diheptyloxide (and isomers thereof), ethylbutyltin dioctyloxide (and isomers thereof), propylbutyltin dimethoxide, propylbutyltin diethoxide, propylbutyltin propoxide (and isomers thereof), propylbutyltin dibutoxide (and isomers thereof), propylbutyltin dipentyloxide (and isomers thereof), propylbutyltin dihexyloxide (and isomers thereof), propylbutyltin diheptyloxide (and isomers thereof), propylbutyltin dioctyloxide (and isomers thereof), dibutyltin dimethoxide, dibutyltin diethoxide, dibutyltin dipropoxide (and isomers thereof), dibutyltin dibutoxide (and isomers thereof), dibutyltin dipentyloxide (and isomers thereof), dibutyltin dihexyloxide (and isomers thereof), dibutyltin diheptyloxide (and isomers thereof), dibutyltin dioctyloxide (and isomers thereof), dibutyltin dinonyloxide (and isomers thereof), dibutyltin didecyloxide (and isomers thereof), dibutyltin dibenzyloxide, dibutyltin diphenylethoxide, diphenyltin dimethoxide, diphenyltin diethoxide, diphenyltin dipropoxide (and isomers thereof), diphenyltin dibutoxide (and isomers thereof), diphenyltin dipentyloxide (and isomers thereof), diphenyltin dihexyloxide (and isomers thereof), diphenyltin diheptyloxide (and isomers thereof), diphenyltin dioctyloxide (and isomers thereof), diphenyltin dinonyloxide (and isomers thereof), diphenyltin didecyloxide (and isomers thereof), diphenyltin dibenzyloxide, diphenyltin diphenylethoxide, bis(trifluorobutyl)tin dimethoxide, bis(trifluorobutyl)tin diethoxide, bis(trifluorobutyl)tin dipropoxide (and isomers thereof), bis(trifluorobutyl)tin dibutoxide (and isomers thereof), bis(trifluorobutyl)tin dipentyloxide (and isomers thereof), bis(trifluorobutyl)tin dihexyloxide (and isomers thereof), bis(trifluorobutyl)tin diheptyloxide (and isomers thereof), bis(trifluorobutyl)tin dioctyloxide (and isomers thereof), bis(trifluorobutyl)tin dinonyloxide (and isomers thereof), bis(trifluorobutyl)tin didecyloxide (and isomers thereof), bis(trifluorobutyl)tin dibenzyloxide, bis(trifluorobutyl)tin diphenylethoxide, bis(pentafluorobutyl)tin dimethoxide, bis(pentafluorobutyl)tin diethoxide, bis(pentafluorobutyl)tin dipropoxide (and isomers thereof), bis(pentafluorobutyl)tin dibutoxide (and isomers thereof), bis(pentafluorobutyl)tin dipentyloxide (and isomers thereof), bis(pentafluorobutyl)tin dihexyloxide (and isomers thereof), bis(pentafluorobutyl)tin diheptyloxide (and isomers thereof), bis(pentafluorobutyl)tin dioctyloxide (and isomers thereof), bis(pentafluorobutyl)tin dinonyloxide (and isomers thereof), bis(pentafluorobutyl)tin didecyloxide (and isomers thereof), bis(pentafluorobutyl)tin dibenzyloxide, bis(pentafluorobutyl)tin diphenylethoxide, bis(heptafluorobutyl)tin dimethoxide, bis(heptafluorobutyl)tin diethoxide, bis(heptafluorobutyl)tin dipropoxide (and isomers thereof), bis(heptafluorobutyl)tin dibutoxide (and isomers thereof), bis(heptafluorobutyl)tin dipentyloxide (and isomers thereof), bis(heptafluorobutyl)tin dihexyloxide (and isomers thereof), bis(heptafluorobutyl)tin diheptyloxide (and isomers thereof), bis(heptafluorobutyl)tin dioctyloxide (and isomers thereof), bis(heptafluorobutyl)tin dinonyloxide (and isomers thereof), bis(heptafluorobutyl)tin didecyloxide (and isomers thereof), bis(heptafluorobutyl)tin dibenzyloxide, bis(heptafluorobutyl)tin diphenylethoxide, bis(nonafluorobutyl)tin dimethoxide, bis(nonafluorobutyl)tin diethoxide, bis(nonafluorobutyl)tin dipropoxide (and isomers thereof), bis(nonafluorobutyl)tin dibutoxide (and isomers thereof), bis(nonafluorobutyl)tin dipentyloxide (and isomers thereof), bis(nonafluorobutyl)tin dihexyloxide (and isomers thereof), bis(nonafluorobutyl)tin diheptyloxide (and isomers thereof), bis(nonafluorobutyl)tin dioctyloxide (and isomers thereof), bis(nonafluorobutyl)tin dinonyloxide (and isomers thereof), bis(nonafluorobutyl)tin didecyloxide (and isomers thereof), bis(nonafluorobutyl)tin dibenzyloxide, and bis(nonafluorobutyl)tin diphenylethoxide.

Examples of organometal compounds represented by formula (2) above include alkoxydistannoxanes and aralkyloxydistannoxanes. Specific examples of such organometal compounds include
1,1,3,3-tetramethyl-1,3-dimethoxydistannoxane,
1,1,3,3-tetramethyl-1,3-diethoxydistannoxane,
1,1,3,3-tetramethyl-1,3-dipropyloxydistannoxane (and isomers thereof),
1,1,3,3-tetramethyl-1,3-dibutyloxydistannoxane (and isomers thereof),
1,1,3,3-tetramethyl-1,3-dipentyloxydistannoxane (and isomers thereof),
1,1,3,3-tetramethyl-1,3-dihexyloxydistannoxane (and isomers thereof),
1,1,3,3-tetramethyl-1,3-diheptyloxydistannoxane (and isomers thereof),
1,1,3,3-tetramethyl-1,3-dioctyloxydistannoxane (and isomers thereof),
1,1,3,3-tetramethyl-1,3-dinonyloxydistannoxane (and isomers thereof),
1,1,3,3-tetramethyl-1,3-didecyloxydistannoxane (and isomers thereof),
1,1,3,3-tetramethyl-1,3-dibenzyloxydistannoxane,
1,1,3,3-tetramethyl-1,3-diphenylethoxydistannoxane,
1,3-dibutyl-1,3-dimethyl-1,3-dimethoxydistannoxane,
1,3-dibutyl-1,3-dimethyl-1,3-diethoxydistannoxane,
1,3-dibutyl-1,3-dimethyl-1,3-dipropyloxydistannoxane (and isomers thereof),
1,3-dibutyl-1,3-dimethyl-1,3-dibutyloxydistannoxane (and isomers thereof),
1,3-dibutyl-1,3-dimethyl-1,3-dipentyloxydistannoxane (and isomers thereof),
1,3-dibutyl-1,3-dimethyl-1,3-dihexyloxydistannoxane (and isomers thereof),
1,3-dibutyl-1,3-dimethyl-1,3-diheptyloxydistannoxane (and isomers thereof),
1,3-dibutyl-1,3-dimethyl-1,3-dioctyloxydistannoxane (and isomers thereof),
1,3-dibutyl-1,3-dimethyl-1,3-dinonyloxydistannoxane (and isomers thereof),
1,3-dibutyl-1,3-dimethyl-1,3-didecyloxydistannoxane (and isomers thereof),
1,3-dibutyl-1,3-dimethyl-1,3-dibenzyloxydistannoxane,
1,3-dibutyl-1,3-dimethyl-1,3-diphenylethoxydistannoxane,
1,3-dibutyl-1,3-diethyl-1,3-dimethoxydistannoxane,
1,3-dibutyl-1,3-diethyl-1,3-diethoxydistannoxane,
1,3-dibutyl-1,3-diethyl-1,3-dipropyloxydistannoxane (and isomers thereof),
1,3-dibutyl-1,3-diethyl-1,3-dibutyloxydistannoxane (and isomers thereof),
1,3-dibutyl-1,3-diethyl-1,3-dipentyloxydistannoxane (and isomers thereof),
1,3-dibutyl-1,3-diethyl-1,3-dihexyloxydistannoxane (and isomers thereof),
1,3-dibutyl-1,3-diethyl-1,3-diheptyloxydistannoxane (and isomers thereof),
1,3-dibutyl-1,3-diethyl-1,3-dioctyloxydistannoxane (and isomers thereof),
1,3-dibutyl-1,3-diethyl-1,3-dinonyloxydistannoxane (and isomers thereof),
1,3-dibutyl-1,3-diethyl-1,3-didecyloxydistannoxane (and isomers thereof),
1,3-dibutyl-1,3-diethyl-1,3-dibenzyloxydistannoxane,
1,3-dibutyl-1,3-diethyl-1,3-diphenylethoxydistannoxane,
1,3-dibutyl-1,3-dipropyl-1,3-dimethoxydistannoxane,
1,3-dibutyl-1,3-dipropyl-1,3-diethoxydistannoxane, 1,3-dibutyl-1,3-dipropyl-1,3-dipropyloxydistannoxane (and isomers thereof),
1,3-dibutyl-1,3-dipropyl-1,3-dibutyloxydistannoxane (and isomers thereof),
1,3-dibutyl-1,3-dipropyl-1,3-dipentyloxydistannoxane (and isomers thereof),
1,3-dibutyl-1,3-dipropyl-1,3-dihexyloxydistannoxane (and isomers thereof),
1,3-dibutyl-1,3-dipropyl-1,3-diheptyloxydistannoxane (and isomers thereof),
1,3-dibutyl-1,3-dipropyl-1,3-dioctyloxydistannoxane (and isomers thereof),
1,3-dibutyl-1,3-dipropyl-1,3-dinonyloxydistannoxane (and isomers thereof),
1,3-dibutyl-1,3-dipropyl-1,3-didecyloxydistannoxane (and isomers thereof),
1,3-dibutyl-1,3-dipropyl-1,3-dibenzyloxydistannoxane,
1,3-dibutyl-1,3-dipropyl-1,3-diphenylethoxydistannoxane,
1,1,3,3-tetrabutyl-1,3-dimethoxydistannoxane,
1,1,3,3-tetrabutyl-1,3-diethoxydistannoxane,
1,1,3,3-tetrabutyl-1,3-dipropyloxydistannoxane (and isomers thereof),
1,1,3,3-tetrabutyl-1,3-dibutyloxydistannoxane (and isomers thereof),
1,1,3,3-tetrabutyl-1,3-dipentyloxydistannoxane (and isomers thereof),
1,1,3,3-tetrabutyl-1,3-dihexyloxydistannoxane (and isomers thereof),
1,1,3,3-tetrabutyl-1,3-diheptyloxydistannoxane (and isomers thereof),
1,1,3,3-tetrabutyl-1,3-dioctyloxydistannoxane (and isomers thereof),
1,1,3,3-tetrabutyl-1,3-dinonyloxydistannoxane (and isomers thereof),
1,1,3,3-tetrabutyl-1,3-didecyloxydistannoxane (and isomers thereof),
1,1,3,3-tetrabutyl-1,3-dibenzyloxydistannoxane,
1,1,3,3-tetrabutyl-1,3-diphenylethoxydistannoxane,
1,1,3,3-tetraphenyl-1,3-dimethoxydistannoxane,
1,1,3,3-tetraphenyl-1,3-diethoxydistannoxane,
1,1,3,3-tetraphenyl-1,3-dipropyloxydistannoxane (and isomers thereof),
1,1,3,3-tetraphenyl-1,3-dibutyloxydistannoxane (and isomers thereof),
1,1,3,3-tetraphenyl-1,3-dipentyloxydistannoxane (and isomers thereof),
1,1,3,3-tetraphenyl-1,3-dihexyloxydistannoxane (and isomers thereof),
1,1,3,3-tetraphenyl-1,3-diheptyloxydistannoxane (and isomers thereof),
1,1,3,3-tetraphenyl-1,3-dioctyloxydistannoxane (and isomers thereof),
1,1,3,3-tetraphenyl-1,3-dinonyloxydistannoxane (and isomers thereof),
1,1,3,3-tetraphenyl-1,3-didecyloxydistannoxane (and isomers thereof),
1,1,3,3-tetraphenyl-1,3-dibenzyloxydistannoxane,
1,1,3,3-tetraphenyl-1,3-diphenylethoxydistannoxane,
1,1,3,3-tetrakis(trifluorobutyl)-1,3-dimethoxydistannoxane,
1,1,3,3-tetrakis(trifluorobutyl)-1,3-diethoxydistannoxane,
1,1,3,3-tetrakis(trifluorobutyl)-1,3-dipropyloxydistannoxane (and isomers thereof),
1,1,3,3-tetrakis(trifluorobutyl)-1,3-dibutyloxydistannoxane (and isomers thereof),
1,1,3,3-tetrakis(trifluorobutyl)-1,3-dipentyloxydistannoxane (and isomers thereof),
1,1,3,3-tetrakis(trifluorobutyl)-1,3-dihexyloxydistannoxane (and isomers thereof),
1,1,3,3-tetrakis(trifluorobutyl)-1,3-diheptyloxydistannoxane (and isomers thereof),
1,1,3,3-tetrakis(trifluorobutyl)-1,3-dioctyloxydistannoxane (and isomers thereof),
1,1,3,3-tetrakis(trifluorobutyl)-1,3-dinonyloxydistannoxane (and isomers thereof),
1,1,3,3-tetrakis(trifluorobutyl)-1,3-didecyloxydistannoxane (and isomers thereof),
1,1,3,3-tetrakis(trifluorobutyl)-1,3-dibenzoxydistannoxane,
1,1,3,3-tetrakis(trifluorobutyl)-1,3-diphenylethoxydistannoxane,
1,1,3,3-tetrakis(pentafluorobutyl)-1,3-dimethoxydistannoxane,
1,1,3,3-tetrakis(pentafluorobutyl)-1,3-diethoxydistannoxane,
1,1,3,3-tetrakis(pentafluorobutyl)-1,3-dipropyloxydistannoxane (and isomers thereof),
1,1,3,3-tetrakis(pentafluorobutyl)-1,3-dibutyloxydistannoxane (and isomers thereof),
1,1,3,3-tetrakis(pentafluorobutyl)-1,3-dipentyloxydistannoxane (and isomers thereof),
1,1,3,3-tetrakis(pentafluorobutyl)-1,3-dihexyloxydistannoxane (and isomers thereof),
1,1,3,3-tetrakis(pentafluorobutyl)-1,3-diheptyloxydistannoxane (and isomers thereof),
1,1,3,3-tetrakis(pentafluorobutyl)-1,3-dioctyloxydistannoxane (and isomers thereof),
1,1,3,3-tetrakis(pentafluorobutyl)-1,3-dinonyloxydistannoxane (and isomers thereof),
1,1,3,3-tetrakis(pentafluorobutyl)-1,3-didecyloxydistannoxane (and isomers thereof),
1,1,3,3-tetrakis(pentafluorobutyl)-1,3-dibenzyloxydistannoxane,
1,1,3,3-tetrakis(pentafluorobutyl)-1,3-diphenylethoxydistannoxane,
1,1,3,3-tetrakis(heptafluorobutyl)-1,3-dimethoxydistannoxane,
1,1,3,3-tetrakis(heptafluorobutyl)-1,3-diethoxydistannoxane,
1,1,3,3-tetrakis(heptafluorobutyl)-1,3-dipropyloxydistannoxane (and isomers thereof),
1,1,3,3-tetrakis(heptafluorobutyl)-1,3-dibutyloxydistannoxane (and isomers thereof),
1,1,3,3-tetrakis(heptafluorobutyl)-1,3-dipentyloxydistannoxane (and isomers thereof),
1,1,3,3-tetrakis(heptafluorobutyl)-1,3-dihexyloxydistannoxane (and isomers thereof),
1,1,3,3-tetrakis(heptafluorobutyl)-1,3-diheptyloxydistannoxane (and isomers thereof),
1,1,3,3-tetrakis(heptafluorobutyl)-1,3-dioctyloxydistannoxane (and isomers thereof),
1,1,3,3-tetrakis(heptafluorobutyl)-1,3-dinonyloxydistannoxane (and isomers thereof),
1,1,3,3-tetrakis(heptafluorobutyl)-1,3-didecyloxydistannoxane (and isomers thereof),
1,1,3,3-tetrakis(heptafluorobutyl)-1,3-dibenzyloxydistannoxane,
1,1,3,3-tetrakis(heptafluorobutyl)-1,3-diphenylethoxydistannoxane,
1,1,3,3-tetrakis(nonafluorobutyl)-1,3-dimethoxydistannoxane,
1,1,3,3-tetrakis(nonafluorobutyl)-1,3-diethoxydistannoxane,
1,1,3,3-tetrakis(nonafluorobutyl)-1,3-dipropyloxydistannoxane (and isomers thereof), 1,1,3,3-tetrakis(nonafluorobutyl)-1,3-dibutyloxydistannoxane (and isomers thereof),
1,1,3,3-tetrakis(nonafluorobutyl)-1,3-dipentyloxydistannoxane (and isomers thereof),
1,1,3,3-tetrakis(nonafluorobutyl)-1,3-dihexyloxydistannoxane (and isomers thereof),
1,1,3,3-tetrakis(nonafluorobutyl)-1,3-diheptyloxydistannoxane (and isomers thereof),
1,1,3,3-tetrakis(nonafluorobutyl)-1,3-dioctyloxydistannoxane (and isomers thereof),
1,1,3,3-tetrakis(nonafluorobutyl)-1,3-dinonyloxydistannoxane (and isomers thereof),
1,1,3,3-tetrakis(nonafluorobutyl)-1,3-didecyloxydistannoxane (and isomers thereof),
1,1,3,3-tetrakis(nonafluorobutyl)-1,3-dibenzyloxydistannoxane, and
1,1,3,3-tetrakis(nonafluorobutyl)-1,3-diphenylethoxydistannoxane.

The above-mentioned organometal compounds may be used individually or in combination. Further, an orgnometal compound other than mentioned above, and optionally an inorganic metal may be used in combination with any of the above-mentioned organometal compounds. As an organometal compound, those which are commercially available may be used. Alternatively, an organometal compound may be produced by a conventional method. For example, an organometal compound can be produced by a method in which an organotin oxide is reacted with an alcohol to obtain an organometal compound. Specifically, for example, a dibutyltin dialkoxide having a long-chain alkoxy group can be obtained from dibutyltin oxide and a long-chain alcohol by a method described in Dutch Patent No. 6612421. It is also possible to obtain a dialkyltin dialkoxide from a halogenated dialkyltin (e.g., a dichlorodialkyltin) and a sodium alcoholate or the like. Further, a dialkyltin alkoxide can be obtained also from a dialkyltin oxide and a lower alcohol by a method described in the above-mentioned WO03/055840 or WO04/014840. In the method described in WO03/055840 or WO04/014840, when an organometal compound is obtained from dibutyltin oxide and an alcohol having a boiling point lower than that of water, the obtained organometal compound tends to be comprised mainly of an organometal compound represented by formula (2). However, if desired, a large amount of an organometal compound represented by formula (1) can be obtained by subjecting the above-mentioned organometal compound comprised mainly of an organometal compound represented by formula (2) to distillation, thereby obtaining an organometal compound represented by formula (1) as a distillate.

The organometal compounds which are, respectively, represented by formulae (1) and (2) can be identified by tin-119 nuclear magnetic resonance ($^{119}$Sn-NMR) spectroscopy (see, for example, U.S. Pat. No. 5,545,600). However, it is known that, in a $^{119}$Sn-NMR spectrum, the value of a chemical shift ascribed to the structure of the organometal compound represented by formula (1) largely varies depending, for example, on the organometal compound content of the sample used for a $^{119}$Sn-NMR analysis and on the presence or absence of an alcohol in the sample used for a $^{119}$Sn-NMR analysis (this fact is not described in the above-mentioned U.S. Pat. No. 5,545,600). Therefore, it is preferred that the analysis of the organometal compound is performed by a method in which proton nuclear magnetic resonance ($^{1}$H-NMR) spectroscopy and carbon-13 nuclear magnetic resonance ($^{13}$C-NMR) spectroscopy are used in combination with the above-mentioned $^{119}$Sn-NMR spectroscopy.

In the present invention, as mentioned above, it is preferred that the organometal compound comprises at least one compound selected from the group consisting of an organometal compound represented by formula (1) and an organometal compound represented by formula (2). It is possible to obtain a dialkyl carbonate from either of an organometal compound of formula (1) and an organometal compound of formula (2). However, from the viewpoint of the formation rate of the dialkyl carbonate and the amount of the dialkyl carbonate produced, it is preferred to use an organometal compound of formula (1). Specifically, it is preferred to use an organometal compound of formula (1) alone or in combination with other species of the organometal compound such that the amount of an organometal compound of formula (1) is 50 mol % or more, in terms of the mol % of the metal contained in the organometal compound of formula (1), based on the total molar amount of the metals contained in the organometal compounds used in the present invention.

Hereinbelow, explanations are given with respect to the alcohols used in the method of the present invention.

In the method of the present invention, a first alcohol is used in step (3). In addition, a second alcohol may be optionally used in step (1) and a third alcohol may be optionally used in step (2).

The first, second and third alcohols may be the same or different from one another. Examples of such alcohols include alkyl alcohols having a straight chain or branched $C_1$-$C_{12}$ alkyl group, cycloalkyl alcohols having a $C_5$-$C_{12}$ cycloalkyl group, alkenyl alcohols having a straight chain or branched $C_2$-$C_{12}$ alkenyl group, and aralkyl alcohols having a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl.

Specific examples of these alcohols include $C_1$-$C_{12}$ aliphatic alcohols and $C_5$-$C_{12}$ alicyclic alcohols, such as methanol, ethanol, propanol, 2-propanol, 1-butanol, 2-butanol (and isomers thereof), 2-methyl-1-propanol, 2-methyl-2-propanol, cyclobutanol, 1-pentanol, 2-pentanol (and isomers thereof), 3-pentanol, 3-methyl-1-butanol, 2-methyl-1-butanol, 2-methyl-2-butanol (and isomers thereof), 3-methyl-2-butanol (and isomers thereof), cyclopentanol, 2-methyl-1-cyclobutanol (and isomers thereof), 3-methyl-1-cyclobutanol (and isomers thereof), 1-methyl-1-cyclobutanol (and isomers thereof), cyclobutylmethanol (and isomers thereof), 1-hexanol, 2-hexanol (and isomers thereof), 3-hexanol (and isomers thereof), 4-methyl-1-pentanol (and isomers thereof), 3-methyl-1-pentanol (and isomers thereof), 2-methyl-1-pentanol (and isomers thereof), 2-ethyl-1-butanol, 3-methyl-2-pentanol (and isomers thereof), 3-methyl-3-pentanol (and isomers thereof), cyclohexanol, 1-methyl 1-cyclopentanol (and isomers thereof), 2-methyl-1-cyclopentanol (and isomers thereof), 2-cyclobutylethanol (and isomers thereof), 1-cyclobutylethanol (and isomers thereof), (1-methylcyclobutyl)methanol (and isomers thereof), (2-methylcyclobutyl)methanol (and isomers thereof), heptanol (and isomers thereof), cyclohexylmethanol (and isomers thereof), (methylcyclohexyl)methanol (and isomers thereof), cyclohexylethanol (and isomers thereof), (methylcyclobutyl)methanol (and isomers thereof), (methylcyclopropyl)ethanol (and isomers thereof), (methylcyclopropyl)methanol (and isomers thereof), octanol (and isomers thereof), nonanol (and isomers thereof), decanol (and isomers thereof), undecanol (and isomers thereof), dodecanol (and isomers thereof), propenyl alcohol, butenyl alcohol (and isomers thereof), pentenyl alcohol (and isomers thereof), cyclopentenol (and isomers thereof), cyclopentadienyl alcohol, hexenol (and isomers thereof) and cyclohexenol (and isomers thereof); and aralkyl alcohols, such as benzyl alcohol and phenethyl alcohol.

Further, as the first, second and third alcohols, polyhydric alcohols may be used. Examples of polyhydric alcohols include polyhyric $C_1$-$C_{12}$ aliphatic alcohols and polyhydric $C_5$-$C_{12}$ alicyclic alcohols, such as ethylene glycol, 1,3-propanediol, 1,2-propanediol, cyclohexanediol and cyclopentanediol; and aralkyl alcohols, such as benzenedimethanol.

Among the above-mentioned alcohols, preferred are those which have a boiling point higher than that of water (wherein the boiling point is measured under atmospheric pressure). Examples of such alcohols include 1-butanol, 2-methyl-1-propanol, an alkyl alcohol having a straight chain or branched $C_5$-$C_{12}$ alkyl group, an alkenyl alcohol having a straight chain or branched $C_4$-$C_{12}$ alkenyl group, a cycloalkyl alcohol and an aralkyl alcohol. Among these alcohols, more preferred are 1-butanol, 2-methyl-1-propanol and an alkyl alcohol having a straight chain or branched $C_5$-$C_8$ alkyl group.

In the present invention, when an aromatic carbonate is produced by repeatedly performing a cycle of steps (1) to (4), it is preferred to use an alcohol which has a boiling point lower than that of the aromatic hydroxy compound used in step (4) (wherein the boiling point is measured under atmospheric pressure), and it is more preferred to use a primary alcohol selected from the group consisting of 1-butanol, 2-methyl-1-propanol and a primary alcohol which is a straight chain or branched $C_5$-$C_6$ alkyl alcohol.

Hereinbelow, explanations are given with respect to the aromatic hydroxy compound used in step (4) of the method of the present invention.

With respect to the aromatic hydroxy compound, there is no particular limitation. Examples of aromatic hydroxy compounds include aromatic hydroxy compounds represented by the following formula (3):

ArOH (3)

wherein Ar represents a $C_5$-$C_{30}$ aromatic group.

Examples of aromatic hydroxy compounds represented by formula (3) above include phenol; alkylphenols, such as cresol (and isomers thereof), xylenol (and isomers thereof), trimethylphenol (and isomers thereof), tetramethylphenol (and isomers thereof), ethylphenol (and isomers thereof), propylphenol (and isomers thereof), butylphenol (and isomers thereof), diethylphenol (and isomers thereof), methylethylphenol (and isomers thereof), methylpropylphenol (and isomers thereof), dipropylphenol (and isomers thereof), methylbutylphenol (and isomers thereof), pentylphenol (and isomers thereof), hexylphenol (and isomers thereof) and cyclohexylphenol (and isomers thereof); alkoxyphenols, such as methoxyphenol (and isomers thereof) and ethoxyphenol (and isomers thereof); and substituted phenols represented by the below-mentioned formula (21):

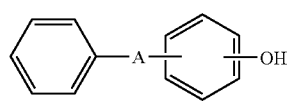

(21)

wherein A represents a single bond; a divalent group, such as —O—, —S—, —CO— or —SO$_2$—; an unsubstituted or substituted alkylene group represented by formula (22) below; or a cycloalkylene group represented by formula (23) below, wherein each of the aromatic rings may independently be substituted with a lower alkyl group, a lower alkoxy group, an ester group, a hydroxy group, a nitro group, a halogen atom, a cyano group or the like.

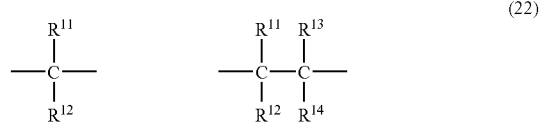

(22)

wherein each of $R^{11}$, $R^{12}$, $R^{13}$ and $R^{14}$ independently represents a hydrogen atom, a lower alkyl group, a cycloalkyl group, an aryl group or an aralkyl group, wherein each of the lower alkyl group, the cycloalkyl group, the aryl group and the aralkyl group is optionally substituted with a halogen atom or an alkoxy group.

(23)

wherein k is an integer of from 3 to 11, and each hydrogen atom (H) may be replaced by a lower alkyl group, an aryl group or a halogen atom.

Specific examples of aromatic hydroxy compounds represented by the above-mentioned formula (21) include naphthol (and isomers thereof); substituted naphthols; and heteroaromatic hydroxy compounds, such as hydroxypyridine (and isomers thereof), hydroxycoumarine (and isomers thereof) and hydroxyquinoline (and isomers thereof).

Among the above-mentioned aromatic hydroxy compounds represented by the above-mentioned formula (3), preferred are aromatic hydroxy compounds having a $C_6$-$C_{10}$ aromatic group as the aromatic group Ar, and most preferred is phenol.

The type of the aromatic hydroxy compound used in the present invention is appropriately selected depending on the type of the desired aromatic carbonate. For example, when it is desired to produce diphenyl carbonate, phenol is used as the aromatic hydroxy compound; when it is desired to obtain ditolyl carbonate, cresol is used as the aromatic hydroxy compound; and when it is desired to produce dinaphthyl carbonate, naphthol is used as the aromatic hydroxy compound.

As mentioned above, the aromatic hydroxy compound may have a substituent, such as an alkyl group or a halogen atom. Further, the aromatic hydroxy compound may be a heterocyclic compound, such as hydroxypyridine.

With respect to each step of the method of the present invention, more detailed explanations are given below.

As mentioned above, in step (1), an organometal compound is reacted with carbon dioxide to form a CO$_2$ adduct of the organometal compound, followed by a thermal decomposition reaction of the CO$_2$ adduct, to thereby obtain a reaction mixture containing a dialkyl carbonate (see formula (6) above).

The temperature for the reaction in step (1) is generally 20° C. (room temperature) or higher, preferably from 20 to 300° C. For completing the reaction in a short period of time, it is more preferred to perform the reaction at 80 to 200° C. The reaction in step (1) is generally performed for 10 minutes to 500 hours.

In step (1), it is preferred that carbon dioxide is used in an amount which is 1 to 200 times the stoichiometric amount relative to the amount of the organometal compound. When an alcohol (second alcohol) is used in step (1) and a largely excess amount of carbon dioxide is present in the reaction system in step (1), the equilibrium of the reaction in step (1) (i.e., reaction of formula (6) above) is further displaced in the direction of the desired product formation; however, the metal-containing component is also produced in a large amount, and the produced metal-containing component reacts with the alcohol, thereby causing the generation of free water which lowers the yield of the desired dialkyl carbonate. Therefore, it is more preferred that carbon dioxide is used in an amount which is 1 to 50 times the stoichiometric amount relative to the amount of the organometal compound. Further, when the amount of carbon dioxide is large, the reaction in step (1) becomes a high pressure reaction so that not only does it become necessary to use a reaction vessel having high pressure resistance, but also a large amount of carbon dioxide is wasted during purging of unreacted carbon dioxide after completion of step (1). Therefore, it is most preferred that carbon dioxide is used in an amount which is 1 to 20 times the stoichiometric amount relative to the amount of the organometal compound. Thus, in step (1), it is preferred that the organometal compound is used in an amount which is $\frac{1}{200}$ to 1 time, more advantageously $\frac{1}{50}$ to 1 time, most advantageously $\frac{1}{20}$ to 1 time, as large as the stoichiometric amount relative to the amount of carbon dioxide.

When the reaction in step (1) is performed at room temperature (20° C.) or higher, the solubility of carbon dioxide in the alcohol is limited and, therefore, there is a danger that the reaction rate becomes extremely low. Accordingly, the pressure employed for the reaction in step (1) is generally from atmospheric pressure to 200 MPa, preferably from atmospheric pressure to 100 MPa, wherein, if desired, the reaction may be performed while introducing additional carbon dioxide into the reaction system. The introduction of additional carbon dioxide into the reaction system may be performed intermittently or continuously.

When it is confirmed by the analysis of the obtained reaction mixture (which is a liquid) that a satisfactory amount of the desired dialkyl carbonate has been obtained, step (1) is stopped. For example, when the dialkyl carbonate is obtained in an amount which is 10% or more, based on the stoichiometric amount relative to the amount of the organometal compound, the reaction mixture may be taken out from the reaction vessel after the pressure in the reaction vessel is reduced to atmospheric pressure or, alternatively, without reducing the pressure in the reaction vessel.

In the method of the present invention, the reaction system in step (1) may contain substances other than mentioned above. Examples of other substances which are useful in step (1) include those which function as a dehydrating agent in the reaction system. By using a dehydrating agent in step (1), the reaction system can be maintained non-aqueous. As a dehydrating agent, any conventional organic dehydrating agent may be used. Examples of dehydrating agents include acetal compounds and orthoesters, such as orthotrimethyl acetate. Further, dicyclohexylcarbodiimide and the like may also be used as an organic dehydrating agent. Alternatively, solid dehydrating agents, such as molecular sieves, may be used as a dehydrating agent. When a solid dehydrating agent is used, it is preferred that the solid dehydrating agent is removed from the reaction system before step (3) is performed.

In step (1) of the method of the present invention, an alcohol (second alcohol) is optionally used. By the use of an alcohol, it sometimes becomes possible to obtain a dialkyl carbonate in high yield. The reason for this is as follows. As shown in formula (6) above, the reaction in step (1) is an equilibrium reaction and, hence, has a reverse reaction. By adding an alcohol to the reaction system, it becomes possible to cause another equilibrium reaction between the alcohol and the above-mentioned metal-containing component formed together with the desired alkyl carbonate, thereby suppressing the advance of the above-mentioned reverse reaction. When the second alcohol added to the reaction system contains a large amount of water, the yield of the dialkyl carbonate is lowered. Therefore, it is preferred that the amount of water contained in the second alcohol is not more than 0.1, more advantageously not more than 0.01, in terms of the ratio of the actual amount of the water to the stoichiometric amount thereof relative to the amount of the organometal compound. As the second alcohol, a part of the alcohol used for producing an organometal compound may be used. More specific explanation is given below. In the production of the organometal compound used in step (1), an alcohol is reacted with a metal to obtain a reaction mixture containing an organometal compound (comprising an organometal compound of formula (1) and/or an organometal compound of (2)) and water, followed by distillation for removing water from the reaction mixture. The distillation is stopped when a part of the alcohol (which remains unreacted in the reaction mixture) still remains unvaporized. The alcohol remaining unvaporized can be used in step (1) as at least a part of the second alcohol. With respect to the impurities (other than water) contained in the second alcohol, the types and amounts thereof vary depending on the conditions for producing the second alcohol and the conditions for the purification of the second alcohol, which purification is optionally performed for recycling the second alcohol. Examples of impurities contained in the alcohol include ethers, aromatic hydroxy compounds and carboxylic acids. With respect to the impurity which adversely affects the reaction in step (1), it is necessary to remove such an impurity from the alcohol before the use thereof in step (1). On the other hand, with respect to the impurity which does not adversely affect the reaction in step (1), it is not necessary to remove such an impurity from the alcohol before the use thereof in step (1).

From the viewpoint of improving the purity of the dialkyl carbonate, as the second alcohol (i.e., alcohol used in step (i)), it is preferred to use an alcohol having an organic group which is the same as the organic group (such as $R^3$ and $R^4$) of the oxy group (e.g., an alkoxy group or an aralkyloxy group) of the organometal compound. When such an alcohol is used as the second alcohol, it is preferred that the amount of the second alcohol is 1 to 100,000 times the stoichiometric amount relative to the amount of the organometal compound. On the other hand, when an alcohol having an organic group different from that of the oxy group (e.g., an alkoxy group or an aralkyloxy group) of the organometal compound is used as the second alcohol or when, as the organometal compound, only an organometal compound of formula (2) is used, the amount of the second alcohol is preferably 2 to 1,000 times, more preferably 10 to 1,000 times, as large as the stoichiometric amount relative to the amount of the organometal compound. When an alcohol having an organic group different from that of the oxy group (e.g., an alkoxy group or an aralkyloxy group) of the organometal compound is used as the second alcohol, an asymmetric dialkyl carbonate is produced in step (1).

When an organometal compound formed in step (3) is recycled to step (1), the organometal compound may be recycled together with the unreacted alcohol as the above-mentioned second alcohol so that the amount of the second alcohol falls within the above-mentioned range. Alternatively, the organometal compound may be separated from the unreacted alcohol and, then, recycled to step (1).

The reaction mixture after completion of step (1) as such may be used in step (2). Alternatively, the reaction mixture after completion of step (1) may be cooled and/or heated prior to the use thereof in step (2). The reaction mixture after completion of step (1) may contain carbon dioxide which may be dissolved in the reaction mixture (which is a liquid) or may be present in the form of a $CO_2$ adduct of the organometal compound. The presence of carbon dioxide in the reaction mixture after completion of step (1) is disadvantageous in the following point. When a distillation is performed in step (2), there is a danger that the reaction mixture suddenly foams due to the presence of carbon dioxide in the reaction mixture. Even when the distillation is performed under reduced pressure, it is difficult to keep the level of reduced pressure constant. For obviating such disadvantage, an additional step for removing carbon dioxide from the reaction mixture may be performed prior to step (2), wherein the carbon dioxide may be dissolved in the reaction mixture (which is a liquid) or may be present in the form of a $CO_2$ adduct of the organometal compound. As preferred methods for removing carbon dioxide from the reaction mixture, there can be mentioned a method in which the reaction mixture is heated, and a method in which the pressure of the reaction vessel (used in step (1)) containing the reaction mixture after completion of step (1) is reduced. Needless to say, carbon dioxide recovered in this carbon dioxide removal step may be recycled to step (1).

In step (2), the dialkyl carbonate formed in step (1) is separated from the reaction mixture obtained in step (1) to obtain a residual liquid. The dialkyl carbonate separated in step (2) (i.e., dialkyl carbonate formed in step (1)) is represented by the following formula (24):

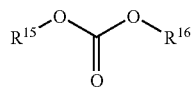

(24)

wherein each of $R^{15}$ and $R^{16}$ independently represents an alkyl group which is the same as the alkyl moiety of the alkoxy group contained in the organometal compound used in step (1), with the proviso that, when a second alcohol is used in step (1) or a third alcohol is used in step (2), each of $R^{15}$ and $R^{16}$ independently represents an alkyl group selected from the group consisting of an alkyl group which is the same as the above-mentioned alkyl moiety of the alkoxy group contained in the organometal compound, an alkyl group contained in the second alcohol, and an alkyl group contained in the third alcohol.

Examples of dialkyl carbonates separated in step (2) include dimethyl carbonate, diethyl carbonate, dipropyl carbonate (and isomers thereof), dibutenyl carbonate (and isomers thereof), dibutyl carbonate (and isomers thereof), dipentyl carbonate (and isomers thereof), dihexyl carbonate (and isomers thereof), diheptyl carbonate (and isomers thereof), dioctyl carbonate (and isomers thereof), dinonyl carbonate (and isomers thereof), didecyl carbonate (and isomers thereof), dicyclopentyl carbonate (and isomers thereof), dicyclohexyl carbonate (and isomers thereof), dicycloheptyl carbonate (and isomers thereof), dibenzyl carbonate (and isomers thereof), diphenetyl carbonate (and isomers thereof), diphenylpropyl carbonate (and isomers thereof), diphenylbutyl carbonate (and isomers thereof), dichlorobenzyl carbonate (and isomers thereof), dimethoxybenzyl carbonate (and isomers thereof), dimethoxymethyl carbonate (and isomers thereof), dimethoxyethyl carbonate (and isomers thereof), dichloroethyl carbonate (and isomers thereof), dicyanoethyl carbonate (and isomers thereof), methyl ethyl carbonate, methyl propyl carbonate (and isomers thereof), methyl butyl carbonate (and isomers thereof), methyl pentyl carbonate (and isomers thereof), ethyl propyl carbonate (and isomers thereof), ethyl butyl carbonate (and isomers thereof), ethyl pentyl carbonate (and isomers thereof), propyl butyl carbonate (and isomers thereof), propyl pentyl carbonate (and isomers thereof), butyl pentyl carbonate (and isomers thereof), butyl hexyl carbonate (and isomers thereof), butyl heptyl carbonate (and isomers thereof) and butyl octyl carbonate (and isomers thereof).

In step (2), a residual liquid containing a metal-containing component is obtained by separating the dialkyl carbonate from the reaction mixture obtained in step (1). The term "residual liquid containing a metal-containing component" means a residual liquid containing a regenerable, active organometal compound which is unmodified or modified.

The separation of the dialkyl carbonate in step (2) can be performed by a conventional separation method. Examples of such separation methods include distillation, extraction, filtration and membrane separation. These separation methods may be used individually or in combination. As a preferred solvent for extraction, there can be mentioned a solvent which does not react with a dialkyl carbonate. Examples of such preferred solvents include aliphatic hydrocarbons, such as hexane and cyclohexane; halogenated hydrocarbons, such as chloroform, dichloromethane and trichloromethylene; aromatic hydrocarbons, such as benzene, toluene and chlorobenzene; and ethers, such as diethyl ether and anisole.

In step (1), when methanol and/or ethanol is used as a second alcohol, or when a second alcohol is not used and the organometal compound has a methoxy group and/or ethoxy group, it is possible to obtain a reaction mixture containing a dialkyl carbonate (such as dimethyl carbonate or diethyl carbonate) having a boiling point of 100° C. or lower (wherein the boiling point is measured under atmospheric pressure). Such a dialkyl carbonate can be separated directly from the reaction mixture by distillation. The distillation can be performed by any of conventionally employed distillation methods, such as a distillation under atmospheric pressure, a distillation under reduced pressure and a distillation under superatmospheric pressure. The temperature for the distillation is generally from −20° C. to the boiling point of the dialkyl carbonate, preferably from 20° C. to the boiling point of the dialkyl carbonate. The distillation may be performed in the presence of a solvent or by extractive distillation. On the other hand, when the dialkyl carbonate has a boiling point higher than 100° C. (wherein the boiling point is measured under atmospheric pressure) or has six or more carbon atoms so that the boiling point of the dialkyl carbonate is high, the separation of the dialkyl carbonate by distillation is sometimes accompanied by the following disadvantage. When the temperature for distillation (i.e., temperature of the reaction mixture to be subjected to distillation) becomes high, the reverse reaction in the equilibrium reaction of the above-mentioned formula (6) is greatly promoted, thereby lowering the yield of the dialkyl carbonate. However, in such a case, the yield of the dialkyl carbonate can be improved by separating the dialkyl carbonate from the reaction mixture at a rate which is higher than the rate of the reverse reaction. For this purpose, it is preferred to employ, for example, a distillation method which is performed under highly reduced pressure, or a thin film distillation method in which the specific surface area of the reaction mixture is increased so as to separate the dialkyl carbonate swiftly in the form of a vapor from the reaction mixture.

As an apparatus for the thin film distillation performed in step (2), any of the conventional apparatus can be used. The thin film distillation apparatus may have attached thereto any conventional supplemental equipment. In the present invention, it is preferred to use a thin film distillation apparatus provided with a distillation column. As the distillation column, a conventional one can be used.

In the case of the thin film distillation, the temperature of the heat transferring surface in the thin film distillation vessel is used as the temperature for separation (separation temperature). Alternatively, the temperature of a jacket or a heating medium (which are used for heating the heat transferring surface) may be used as the separation temperature. The separation temperature varies depending on the types and amounts of the dialkyl carbonate and metal-containing component which are contained in the reaction mixture obtained in step (1); however, the separation temperature is generally from room temperature (20° C.) to 300° C. From the viewpoint of suppressing the displacement of the equilibrium of the reaction of formula (6) above in the direction of the original system (that is, for suppressing the reverse reaction of the equilibrium reaction of formula (6)), and improving not only the fluidity of the reaction mixture obtained in step (1), but also the fluidity of each of the dialkyl carbonate and metal-containing component after the separation of the dialkyl carbonate from the metal-containing component by the thin film distillation, it is preferred that the separation temperature is in the range of from 80 to 180° C.

In the thin film distillation, the heating of the reaction mixture obtained in step (1) can be performed by a conventional method, such as a method using a jacket.

With respect to the pressure for the separation (separation pressure) by the thin film distillation, explanation is given below. When the thin film distillation apparatus is provided with a distillation column, the pressure at the top of the distillation column is used as the separation pressure. On the other hand, when the thin film distillation apparatus is not provided with a distillation column, the internal pressure of the distillation vessel is used as the separation pressure. The separation pressure varies depending, for example, on the types and amounts of the dialkyl carbonate and the metal-containing component which are contained in the reaction mixture obtained in step (1). Generally, the separation pressure may be either reduced pressure or atmospheric pressure. Specifically, the separation pressure is generally from 0.1 to 101.3 kPa (atmospheric pressure), preferably from 0.3 to 30 kPa.

When the separation of the dialkyl carbonate from the reaction mixture obtained in step (1) is performed under 30 KPa or higher, and the dialkyl carbonate has a high boiling point, the vapor pressure of the dialkyl carbonate is low and, therefore, it is necessary to use a high distillation temperature. However, when the distillation temperature is high, there is a danger that the equilibrium of the reaction of formula (6) above is greatly displaced in the direction of the original system (that is, the reverse reaction of the equilibrium reaction of formula (6) vigorously occurs) during the distillation, thereby lowering the yield of the dialkyl carbonate. Therefore, when the distillation separation is performed is under 30 KPa or higher with respect to a reaction mixture containing a dialkyl carbonate having a high boiling temperature, it is necessary to control the temperature, the pressure and the residence time so that the displacement of the equilibrium of the reaction of formula (6) above in the direction of the original system can be satisfactorily suppressed. The residence time of the reaction mixture in the thin film distillation vessel varies depending on the types and amounts of the dialkyl carbonate and the metal-containing component which are contained in the reaction mixture; however, the residence time is generally from 1 second to 1 hour. For suppressing the displacement of the equilibrium of the reaction of formula (6) above in the direction of the original system, it is preferred that the residence time is from 10 seconds to 10 minutes. The area of the heat transferring surface in the thin film distillation vessel varies depending not only on the types and amounts of the dialkyl carbonate and the metal-containing component which are contained in the reaction mixture, but also on the feeding rate of the reaction mixture and the material of the thin film distillation vessel. For example, the area of the heat transferring surface may be adjusted so that the area of the heat transferring surface and the feeding rate of the reaction mixture satisfy the relationship represented by formula (25) below.

$$\text{feeding rate}(g/hr) \times \text{coefficient } k(hr \times m^2/g) = \text{area of heat transferring surface}(m^2) \quad (25)$$

wherein coefficient k is a number in the range of from 1/10,000 to 1/1, preferably from 1/4,000 to 1/100.

Needless to say, the area of the heat transferring surface may be adjusted by a method other than the method using formula (25), based on the conventional knowledge and technique relating to the thin film distillation.

The thickness of the film formed during the thin film distillation of the reaction mixture obtained in step (1) varies depending not only on the types and amounts of the dialkyl carbonate and metal-containing component which are contained in the reaction mixture, but also on the feeding rate of the reaction mixture and the above-mentioned separation temperature; however, the thickness of the film is generally from $1 \times 10^{-8}$ to $1 \times 10^{-1}$ m. For improving the separation efficiency, it is preferred that the thickness of the film is from $1 \times 10^{-6}$ to $1 \times 10^{-2}$ m.

In the present invention, it is not necessary to use a solvent. However, for facilitating the operations using the reaction mixture obtained in step (1) by improving the fluidities of the separated dialkyl carbonate and the separated metal-containing component, a solvent which does not react with the dialkyl carbonate or metal-containing component may be used. Preferred examples of such solvents include aliphatic and alicyclic hydrocarbons, such as hexane and cyclohexane; halogenated hydrocarbons, such as chloroform, dichloromethane and trichloromethylene; aromatic hydrocarbons, such as benzene, toluene and chlorobenzene; and ethers, such as diethyl ether and anisole.

In the thin film distillation apparatus, a fraction (in a gaseous form) comprised mainly of the dialkyl carbonate is withdrawn from the upper portion of the apparatus while withdrawing the residual liquid from the lower portion of the apparatus. The withdrawn fraction comprised mainly of the dialkyl carbonate such may be used in step (4) without purification. Alternatively, the withdrawn fraction may be purified by a conventional method before the fraction is used in step (4).

When the dialkyl carbonate formed in step (1) has so high a boiling point that it is difficult to separate the dialkyl carbonate from the metal-containing component in the reaction mixture obtained in step (1), the separation may be performed by adding an alcohol (third alcohol) to the reaction mixture before performing the separation of the dialkyl carbonate in step (2). As the third alcohol, it is preferred to use an alcohol which has a boiling point lower than the boiling point(s) of the alcohol(s) corresponding to the alkoxy group(s) contained in the dialkyl carbonate, and which is selected from the group consisting of alkyl alcohols wherein the alkyl moiety is a straight or branched $C_1$-$C_6$ alkyl. Specifically, by addition of the third alcohol having such a lower boiling point to the reaction mixture obtained in step (1), a transesterification reaction occurs between the dialkyl carbonate and the third alcohol to exchange the alkyl groups of the dialkyl carbonate with the alkyl groups of the third alcohol, thereby obtaining a dialkyl carbonate having a boiling point lower than that of the dialkyl carbonate obtained in step (1). The obtained dialkyl carbonate having a lower boiling point can be easily separated from the metal-containing component by the distillation separation.

The amount of the third alcohol added in step (2) varies depending on the reaction conditions in step (1); however, it is preferred that the amount of the third alcohol is from 2 to 100, in terms of the molar ratio of the third alcohol to the dialkyl carbonate formed in step (1). The temperature at which the third alcohol is added to the reaction mixture obtained in step (1) is generally in the range of from room temperature (about 20° C.) to the boiling point of the third alcohol. With respect to the addition of the third alcohol and the separation of the dialkyl carbonate produced by the above-mentioned transesterification reaction, the addition and separation can be performed, for example, as follows. The third alcohol is added to the reaction mixture obtained in step (1) in a batchwise or continuous manner to perform a transesterification reaction and, after completion of the transesterification reaction, the dialkyl carbonate produced by the transesterification reaction is separated by distillation. The transesterification reaction of the dialkyl carbonate with the third alcohol and the separation of the dialkyl carbonate can also be performed by a reactive distillation method using a multi-stage distillation column in the following manner. The reaction mixture obtained in step (1) is fed to a multi-stage distillation column from the upper portion thereof while feeding the third alcohol to the multi-stage distillation column from the lower portion thereof, wherein the transesterification reaction and distillation are performed under temperature and pressure conditions wherein the third alcohol has a vapor pressure.

The reaction mixture obtained in step (1) may contain the organometal compound remaining unreacted and a thermal decomposition product of the organometal compound. Step (2) may be performed after or while removing the organometal compound remaining unreacted and the thermal decomposition product from the reaction mixture obtained in step (1).

As mentioned above, in step (1), an organometal compound is reacted with carbon dioxide. Since the organometal compound used in step (1) has a reactivity with carbon dioxide, the organometal compound is, hereinafter, frequently referred to as "reactive organometal compound". As the present inventors proposed in the above-mentioned WO 04/014840, the reaction mixture obtained in step (1) can be caused to contain the following components: a dialkyl carbonate formed by the reaction between the organometal compound and carbon dioxide; a regenerable, active, modified organometal compound; and an unregenerable, inactive organometal compound (i.e., a degraded compound). When such a reaction mixture is obtained, the unregenerable, inactive organometal compound (degraded compound) may be separated from the reaction mixture obtained in step (1). Specifically, for example, the separation of the degraded compound can be performed by a method in which the reaction mixture obtained in step (1) is separated into a first mixture comprising the dialkyl carbonate and the degraded compound and a second mixture comprising a residual liquid comprised of the regenerable, active, modified organometal compound, and the dialkyl carbonate is separated from the first mixture. Alternatively, the separation of the degraded compound can be performed by a method in which the reaction mixture obtained in step (1) is separated into a first mixture comprising the dialkyl carbonate and a second mixture comprising the regenerable, active, modified organometal compound and the degraded compound, and the degraded compound is removed from the second mixture.

In the present invention, the term "regenerable, active, modified organometal compound" is used to indicate compounds derived from the reactive organometal compound, which are comprised mainly of the above-mentioned adduct ($CO_2$ adduct) formed by the reaction of the reactive organometal compound with carbon dioxide, or decomposition products formed by the thermal decomposition of the adduct, wherein the thermal decomposition products are formed simultaneously with the formation of the dialkyl carbonate. It is difficult to specify the detailed structure of the regenerable, active, modified organometal compound. However, as general examples of regenerable, active, modified organometal compounds which may be formed in step (1) of the method of the present invention, there can be mentioned the above-mentioned carbon dioxide adduct of the reactive organometal compound, a hydrolysis product of the reactive organometal compound and a hydrolysis product of the carbon dioxide adduct of the reactive organometal compound.

On the other hand, the term "unregenerable, inactive organometal compound" (or "degraded compound") is used to indicate compounds which are also derived from the reactive organometal compound and which are unregenerable organic compounds (formed by a thermal degradation of the reactive organometal compound or the carbon dioxide adduct thereof) having an extremely low activity. A degraded compound is formed mainly in step (3). However, a degraded compound is sometimes formed in a step for producing the reactive organometal compound. As a representative example of the degraded compound, there can be mentioned a compound having, per metal atom in a molecule thereof, at least three metal-carbon linkages. As an example of such a compound, there can be mentioned a compound represented by the following formula (26):

(26)

wherein:
$M^4$ represents a metal atom selected from the group consisting of elements belonging to Groups 4 and 14 of the Periodic Table, exclusive of silicon;
each of $R^{17}$, $R^{18}$ and $R^{19}$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;
$R^{20}$ represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and each of l, m and n is an integer of from 0 to 4, l+m+n=3 or 4, o is an integer of 0 or 1, and l+m+n+o=4.

Specific examples of degraded compounds of formula (26) above include tetraalkyltin and trialkyltin alkoxide. Further examples of degraded compounds include metal oxides, such as $SnO_2$, $TiO_2$ and $ZrO_2$.

It is known that, in general, an organometal compound undergoes modification in the presence of oxygen. The organometal compound used in the present invention also undergoes modification in the presence of oxygen to form a degraded compound other than the above-mentioned degraded compounds. (The specific structure of the other degraded compound has not yet been elucidated.) Therefore, during the production and storage of the organometal compound and during each step of the method of the present invention, it is necessary to suppress the amount of oxygen which gets in contact with the organometal compound by a conventional method.

It is considered that the degraded compound represented by formula (26) above is formed during the production of the organometal compound of formula (1) or (2) above, or formed by the thermal modification of the organometal compound of formula (1) or (2) above.

It is preferred that each step of the method of the present invention is performed under conditions wherein the amount of a degraded compound formed is as small as possible. In the method of the present invention, degraded compounds other than the compound of formula (26) above may be formed. However, in step (2) of the method of the present invention, the compound of formula (26) is mainly removed as a degraded compound. The reason for this is as follows. The degraded compound of formula (26) (having, per metal atom in a molecule thereof, at least three metal-carbon linkages) has physical and chemical properties different from those of the useful organometal compound (i.e., the reactive organometal compound or the regenerable, active, modified organometal compound) (for example, the degraded compound has a boiling point lower than that of the useful organometal compound and less susceptible to hydrolysis than the useful organometal compound).

Any degraded compound other than the degraded compound represented by formula (26) may also be removed. As preferred methods for removing a degraded compound, there can be mentioned blowdown and filtration, each of which is generally used in the art. A degraded compound (such as the compound of formula (26)) which has been removed may be discarded by a conventional method. For example, the degraded compound may be discarded in the form of a metal oxide thereof which is formed by burning the degraded compound. Needless to say, a useful organometal compound may be regenerated from the removed, degraded compound by a conventional method.

In step (2), even the dialkyl carbonate having a boiling point higher than 100° C. can be easily separated by a method in which water or a water-containing solvent is added to the reaction mixture obtained in step (1) to form a white slurry, solids in the white slurry are removed by filtration to obtain a filtrate, and the obtained filtrate is subjected to distillation. With respect to the water used in this method, there is no particular limitation; however, it is preferred to use a distilled water or a deionized water.

In step (2), the temperature at which water is added to the reaction mixture obtained in step (1) is in the range from a temperature (e.g., −20° C.) at which the water is not frozen in the reaction mixture to 100° C. After completion of step (1), it is preferred that the temperature of the reaction mixture may be adjusted to 10 to 80° C. When the dialkyl carbonate formed in step (1) is susceptible to hydrolysis, for satisfactorily suppressing the occurrence of the hydrolysis of the dialkyl carbonate, it is more preferred to adjust the temperature of the reaction mixture to 10 to 50° C. When water is used in step (2) of the method of the present invention, water may be used alone or in combination with a solvent other than water. As a solvent other than water, any of those which do not react with the dialkyl carbonate can be used. In this case, when water is used in the form of a solution thereof in an alcohol which is the same as used in step (1), the separation of the solvent by the distillation becomes easy.

As a method for distillation, there can be mentioned a distillation method which is conventionally known in the art, such as distillation under atmospheric pressure, distillation under reduced pressure and distillation under superatmospheric pressure. The distillation can be performed at a temperature of from −20° C. to the boiling point of the dialkyl carbonate and/or the alcohol, preferably from 50° C. to the boiling point of the dialkyl carbonate and/or the alcohol. The distillation may be performed in the presence of another solvent or by extractive distillation.

The dialkyl carbonate contained in the reaction mixture obtained in step (1) may be separated also by the following method. Water and/or an extraction solvent is added to the reaction mixture obtained in step (1) to obtain a mixture containing an oil phase containing the dialkyl carbonate, followed by recovery of the dialkyl carbonate from the mixture.

The thus-separated dialkyl carbonate as such may be used in step (4). Alternatively, if desired, the dialkyl carbonate may be purified by a conventional method before the use thereof in step (4).

In step (3), the residual liquid which is obtained in step (2) is reacted with an alcohol (i.e., first alcohol) to form at least one organometal compound and water and, then, the water is removed from the organometal compound. Step (3) can be performed by the method described in the present inventors' previous applications WO 03/055840 or WO 04/014840. The residual liquid obtained in step (2) after the separation of the dialkyl carbonate contains a metal. The residual liquid is generally obtained in the form of a transparent liquid. However, in the residual liquid, the metal is sometimes present in the form of solids. Even in this case, an organometal compound can be synthesized from the residual liquid in step (3).

The water formed in step (3) can be removed from the organometal compound by a method, such as distillation.

The first alcohol used in step (3) may contain an aromatic hydroxy compound and/or a carboxyl group-containing compound. However, the total content of an aromatic hydroxy compound and a carboxyl group-containing compound which are present in the first alcohol used in step (3) is preferably 1,000 ppm or less, more preferably 100 ppm or less. For controlling the amounts of the aromatic hydroxy compound and the carboxyl group-containing compound so as to achieve the above-mentioned specific total content of these compounds, if desired, the first alcohol may be purified by a conventional purification method, such as distillation, before the use thereof in step (3). For achieving such a specific total content of the above-mentioned compounds, it is preferred to use, as the first alcohol, an alcohol having a boiling point (as measured under atmospheric pressure) of 300° C. or lower.

When a polyhydric alcohol is used as the first alcohol in step (3), it is possible that the organometal compound (metal alkoxide or metal aralkoxide) is obtained in the form of a crosslinked product of an organometal compound of formula (1) or (2) in step (3). Even such a crosslinked product can be used in the present invention.

In step (3), the amount of the first alcohol is preferably 1 to 10,000 times, more preferably 2 to 100 times, as large as the stoichiometric amount relative to the amount of the organometal compound used in step (1).

The temperature for the reaction in step (3) varies depending on the type of the alcohol used in step (3); however, the reaction in step (3) is generally performed at room temperature (20° C.) to 300° C.

The removal of water in step (3) can be performed by any conventional dehydration method which is generally employed in the art. The removal of water may be performed by, for example, the use of dehydration column packed with a solid dehydrating agent (e.g., molecular sieves), distillation, or membrane separation. However, when it is intended to obtain a large amount of an organometal compound within a short period of time, it is preferred that the removal of water is performed by distillation (the use of a solid dehydrating agent has a disadvantage in that the regeneration of a solid dehydrating agent is cumbersome). The distillation may be performed by any conventional distillation method, such as a distillation under atmospheric pressure, a distillation under reduced pressure, a distillation under superatmospheric pressure, thin film distillation or extractive distillation. The distillation can be performed at a temperature of from −20° C. to the boiling point of the first alcohol used in step (3), preferably from 50° C. to the boiling point of the first alcohol. Needless to say, when a pressure resistant apparatus is used for the distillation, the distillation can be performed at a high temperature under the vapor pressure of the first alcohol as measured at the high temperature employed or under a superatmospheric pressure which is achieved by the introduction of an inert gas into the pressure resistant apparatus. When the distillation using a pressure resistant apparatus is performed under a superatmospheric pressure as mentioned above, the distillation temperature is from the boiling point of the first alcohol as measured under atmospheric pressure to the boiling point of the first alcohol as measured under the above-mentioned superatmospheric pressure. As mentioned below, for performing the distillation efficiently, a substance (e.g., the below-mentioned solvent forming an azeotropic mixture with water) may be used. When an alcohol having a boiling point higher than that of water is used as the first alcohol, water can be removed by distilling off the water. When the removal of water is performed by membrane separation, for efficiently removing water, it is preferred that the removal of water is performed by pervaporation.

When the removal of water in step (3) is performed by distillation, the distillation temperature is not particularly limited so long as the distillation temperature is equal to or lower than the boiling point of the first alcohol and is a temperature at which water has a vapor pressure. When it is intended to complete the distillation within a short period of time, it is preferred that the distillation is performed at the azeotropic temperature of a mixture of water and the first alcohol. When water and the first alcohol do not form an azeotropic mixture, it is preferred that the distillation is performed at the boiling point of water.

Further, even when the first alcohol does not form an azeotropic mixture with water, water can be removed by an azeotropic distillation in which a solvent forming an azeotropic mixture with water is used. This method is preferred since water can be removed at a relatively low temperature. Examples of solvents which form an azeotropic mixture with water include unsaturated and saturated hydrocarbons, such as hexane, benzene, toluene, xylene and naphthalene; ethers, such as anisole and 1,4-dioxane; hydrogenated hydrocarbons, such as chloroform.

From the viewpoint of facilitating the separation of water from the azeotropic mixture after azeotropic distillation, it is preferred to use, as the above-mentioned solvent used for forming an azeotropic mixture, an unsaturated or saturated hydrocarbon in which water has a low solubility. When such a solvent is used, it is necessary to use the solvent in an amount such that water can be satisfactorily removed by azeotropic distillation. It is preferred to use a distillation column for the azeotropic distillation because the solvent can be recycled to the reaction system after separating the solvent from the azeotropic mixture in the distillation column and, hence, azeotropic distillation can be performed using only a relatively small amount of the solvent.

If desired, the reaction in step (3) may be performed in the presence of an inert gas. By introducing an inert gas to the reaction vessel used in step (3), it becomes possible to remove water present in the vapor phase from the reaction vessel, so that the reaction in step (3) can be sometimes promoted. With respect to the inert gas, there is no particular limitation so long as the inert gas does not adversely affect the reaction in step (3). Examples of such inert gases include nitrogen, argon and helium. Instead of the inert gas, the above-mentioned organic solvent which forms an azeotropic mixture with water may be used in a gaseous form.

Further, instead of the inert gas, carbon dioxide can also be used. Carbon dioxide is not an inert gas. However, carbon doxide can be used in step (3) because carbon dioxide has no adverse effect. In addition, when carbon dioxide is used in step (3), it is sometimes possible that the organometal compound formed by the reaction between the residual liquid and the first alcohol is reacted with the carbon dioxide to form a dialkyl carbonate. Similarly, an alcohol which is the same as the first alcohol used for the reaction in step (3) may be introduced in a gaseous form because the alcohol in a gaseous form does not adversely affect the reaction in step (3). The inert gas may be introduced into the reaction vessel used in step (3) from any portion thereof; however it is preferred that the inert gas is introduced into the liquid phase in the reaction vessel from the lower portion thereof. The amount of the inert gas introduced into the reaction vessel may be appropriately determined, depending on the shape of the reaction vessel and the reaction conditions for the reaction in step (3).

With respect to the type of the reaction vessel used in step (3), there is no particular limitation, and any conventional reaction vessel can be used. It is preferred to use a reaction vessel in which the area of the vapor phase/liquid phase interface of the residual liquid is large. It is also preferred to use, as the reaction vessel, a stirring vessel having a baffle, or a bubble column.

By the reaction in step (3) (i.e., reaction between the first alcohol and the residual liquid which contains a metal-containing component), at least one organometal compound and water are formed. This organometal compound is generally comprised of at least one organometal compound selected from the group consisting of the organometal compounds represented by formulae (1) and (2).

When it is confirmed that the formation of water has almost stopped, step (3) can be stopped. When the reaction mixture (obtained in step (3)) containing an organometal compound and water is recycled to step (1), the presence of a large amount of water in the reaction mixture inevitably causes the lowering of the yield of a dialkyl carbonate in step (1). Therefore, it is preferred that water in the reaction mixture obtained in step (3) is removed as much as possible.

Generally, the amount of water removed in step (3) is in the range of from 0.01 to 1 time the amount of water produced by the reaction in step (3), wherein the amount of the produced water is theoretically calculated on the assumption that only an organometal compound (e.g., a metal alkoxide or a metal aralkoxide) represented by the above-mentioned formula (1) is produced by the reaction in step (3).

After completion of step (3), if desired, an excess amount of the first alcohol may be removed. From the viewpoint of improving the purity of the dialkyl carbonate in the case where the reaction mixture obtained in step (3) is recycled to step (1), it is preferred to remove an excess amount of the first alcohol. However, when the same alcohol as the first alcohol used in step (3) is used as the second alcohol in step (1), it is not necessary to remove an excess amount of the first alcohol and, if desired, an appropriate amount of the alcohol may be added to the reaction mixture after completion of step (3). Further, if desired, the organometal compound contained in the reaction mixture after completion of step (3) is recovered for use in step (1).

When, in step (3), the organometal compound (e.g., a metal alkoxide or a metal aralkoxide) is obtained in a solid form, the removal of an excess amount of the first alcohol can be performed by filtration (wherein the first alcohol is removed as a filtrate). On the other hand, when the organometal compound is obtained in a liquid form, the removal of an excess amount of the first alcohol can be performed by a distillation under reduced pressure, or by a method in which an inert gas, such as nitrogen, is introduced into the reaction vessel used in step (3) to remove at least a part of the first alcohol present in a vapor form. When the removal of an excess amount of the first alcohol is performed by the method using an inert gas, it is necessary to use, as the inert gas, a satisfactorily dried gas. Otherwise, the organometal compound (e.g., a metal alkoxide or a metal aralkoxide) is inevitably hydrolyzed in the presence of water contained in the inert gas to thereby form a metal oxide and an alcohol. Therefore, the amount of the organometal compound which can be recycled to step (1) is inevitably markedly lowered, thereby greatly lowering the yield of a dialkyl obtained in step (1) in the case where the reaction mixture obtained in step (3) is recycled to step (1).

In recycling the organometal compound having water removed therefrom to step (1), the organometal compound may be cooled or heated before the recycling thereof to step (1). Recycling of the organometal compound may be performed in a continuous or batchwise manner. If desired, in addition to the organometal compound recovered in step (3), a fresh organometal compound may be used.

In step (4), the dialkyl carbonate separated in step (2) is reacted with an aromatic hydroxy compound to obtain an aromatic carbonate. Specifically, in step (4), the dialkyl carbonate (represented by formula (24) above) separated in step (2) is used as a starting material, and is reacted with an aromatic hydroxy compound (e.g., an aromatic hydroxy compound represented by formula (3) above) as a reactant to thereby obtain an aromatic carbonate. In general, the aromatic carbonate obtained in step (4) comprises at least one aromatic carbonate selected from the group consisting of an alkyl aryl carbonate represented by formula (27) below and a diaryl carbonate represented by formula (28) below. Each of the alkyl aryl carbonate of formula (27) and the diaryl carbonate of formula (28) may be obtained in the form of a mixture of two or more different aromatic carbonates.

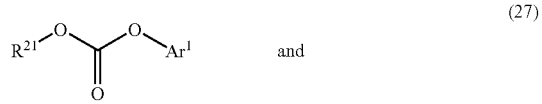 and

wherein $R^{21}$ represents the same alkyl group as alkyl group $R^{15}$ or $R^{16}$ contained in the dialkyl carbonate of formula (24) above used as the starting material, and each of $Ar^1$, $Ar^2$ and $Ar^3$ represents the same aromatic group (such as R group in formula (3) above) contained in the aromatic hydroxy compound used as the reactant.

Examples of alkyl aryl carbonates represented by formula (27) above include methyl phenyl carbonate, ethyl phenyl carbonate, propyl phenyl carbonate (and isomers thereof), allyl phenyl carbonate, butyl phenyl carbonate (and isomers thereof), pentyl phenyl carbonate (and isomers thereof), hexyl phenyl carbonate (and isomers thereof), heptyl phenyl carbonate (and isomers thereof), octyl tolyl carbonate (and isomers thereof), nonyl ethylphenyl carbonate (and isomers thereof), decyl butylphenyl carbonate (and isomers thereof), methyl tolyl carbonate (and isomers thereof), ethyl tolyl carbonate (and isomers thereof), propyl tolyl carbonate (and isomers thereof), butyl tolyl carbonate (and isomers thereof), allyl tolyl carbonate (and isomers thereof), methyl xylyl carbonate (and isomers thereof), methyl trimethylphenyl carbonate (and isomers thereof), methyl chlorophenyl carbonate (and isomers thereof), methyl nitrophenyl carbonate (and isomers thereof), methyl methoxyphenyl carbonate (and isomers thereof), methyl cumyl carbonate (and isomers thereof), methyl naphthyl carbonate (and isomers thereof), methyl pyridyl carbonate (and isomers thereof), ethyl cumyl carbonate (and isomers thereof), methyl benzoylphenyl carbonate (and isomers thereof), ethyl xylyl carbonate (and isomers thereof) and benzyl xylyl carbonate.

Examples of diaryl carbonates represented by formula (28) above include diphenyl carbonate, ditolyl carbonate (and isomers thereof), dixylyl carbonate (and isomers thereof), tolyl phenyl carbonate (and isomers thereof), xylyl phenyl carbonate (and isomers thereof), xylyl tolyl carbonate (and isomers thereof), dinaphthyl carbonate, diethylphenyl carbonate (and isomers thereof), di(propylphenyl) carbonate (and isomers thereof), di(butylphenyl) carbonate, di(trimethylphenyl) carbonate (and isomers thereof), di(methoxyphenyl) carbonate (and isomers thereof), di(chlorophenyl) carbonate (and isomers thereof) and di(nitrophenyl) carbonate.

With respect to a method for producing an alkyl aryl carbonate and/or a diaryl carbonate from a dialkyl carbonate and an aromatic hydroxyl compound, there have been known a number of conventional methods. In the present invention, the production of an alkyl aryl carbonate and/or a diaryl carbonate can be performed by any of such conventional methods.

In the present invention, the reaction of formula (9) above performed in step (4) is a transesterification reaction between a dialkyl carbonate and an aromatic hydroxy compound. This reaction is an equilibrium reaction and, hence, for advancing the reaction (i.e., displacing the equilibrium of the reaction in the direction of the desired product formation), it is preferred that the reaction is performed while withdrawing a by-produced alcohol from the reaction system. From the viewpoint of efficiently withdrawing the by-produced alcohol, it is preferred that the aromatic hydroxy compound used in step (4) has a boiling point higher than that of the alcohol (i.e., first alcohol) used in step (3). Especially, when the cycle of steps (1) to (4) is repeated at least one time (that is, a cycle of steps (1) to (4) is performed at least two times), it is preferred that each of the first alcohol (which is used in step (3)), the second alcohol (which is used in step (1)) and the third alcohol (which is used in step (2)) has a boiling point lower than that of the aromatic hydroxy compound used in step (4). Specifically, it is preferred that each of the first alcohol, the second alcohol and the third alcohol has a boiling point which is at least 2° C. lower than that of the aromatic hydroxy compound. Further, from the viewpoint of ease in the withdrawal of the by-produced alcohol in step (4), it is more preferred that each of the first alcohol, the second alcohol and the third alcohol has a boiling point which is at least 10° C. lower than that of the aromatic hydroxy compound.

With respect to the first alcohol used in step (3), it is preferred that the boiling point of the first alcohol is higher than that of water. Among such alcohols having a boiling point higher than that of water, preferred are 1-butanol, 2-methyl-1-propanol, alkyl alcohols having a straight chain or branched $C_5$-$C_{12}$ alkyl group, alkenyl alcohols having a straight chain or branched $C_4$-$C_{12}$ alkenyl group, cycloalkyl alcohols and aralkyl alcohols. Further, from the viewpoint of withdrawing the by-produced alcohol from the reaction vessel in step (4) to thereby advance the reaction in step (4), it is more preferred that the boiling point of the first alcohol used in step (3) is lower than that of the aromatic hydroxy compound used in step (4). In step (4), the by-produced alcohol is withdrawn from the reaction vessel in a gaseous form, and the produced alkyl aryl carbonate and/or diaryl carbonate is withdrawn from the reaction vessel in a liquid form. Therefore, it is preferred that the dialkyl carbonate used in step (4) is an ester obtained from an alcohol having a boiling point higher than that of water but lower than that of the aromatic hydroxy compound, and that the dialkyl carbonate has a boiling point lower than those of the dialkyl carbonate and the diaryl carbonate.

Further, the same as explained above in connection with the first alcohol used in step (3) applies to the case of the second alcohol used in step (1). Specifically, it is preferred that the second alcohol has a boiling point higher than that of water but lower than that of the aromatic hydroxy compound used in step (4). Preferred examples of second alcohols include alcohols having a straight chain or branched alkyl group, such as n-butyl alcohol, 2-methyl-1-propanol, pentanol (and isomers thereof), hexanol (and isomers thereof), heptanol (and isomers thereof), octanol (and isomers thereof), nonyl alcohol (and isomers thereof), decyl alcohol (and isomers thereof), dodecyl alcohol (and isomers thereof); and alcohols having a cycloalkyl group, such as cyclobutanol, cyclopentanol and cyclohexanol. Further, when the removal of water in step (3) is performed by distillation, or when the reaction in step (4) is performed while withdrawing the by-produced alcohol from the reaction vessel, it is preferred that the second alcohol used in step (1) is selected from the group consisting of 1-butanol, 2-methyl-1-propanol, a straight chain or branched $C_5$-$C_8$ alkyl alcohol and a $C_5$-$C_8$ alicyclic alcohol. Most preferred examples of second alcohols include 1-butanol, 2-methyl-1-propanol, and a straight chain or branched $C_5$-$C_6$ alkyl alcohol.

With respect to the above-mentioned alcohols, dialkyl carbonate and aromatic hydroxy compound, it is most preferred that all of the first alcohol, the second alcohol, the third alcohol, the alcohols corresponding to the alkoxy groups of the organometal compound (having a metal-carbon-oxygen linkage) represented by formula (1) or (2) above, and the alcohols corresponding to the alkoxy groups of the dialkyl carbonate are primary alcohols selected from the group consisting of 1-butanol, 2-methyl-1-propanol, pentanol (and isomers thereof) and hexanol, (and isomers thereof); and that the aromatic hydroxy compound is selected from the group consisting of phenol and cresol.

In step (4), it is preferred that the aromatic hydroxy compound is used in an amount which is 0.1 to 10,000 times the stoichiometric amount relative to the amount of the dialkyl carbonate. The larger the amount of the aromatic hydroxy compound used, the larger the amount of an aromatic carbonate produced. However, when the amount of the aromatic hydroxy compound is too large, it becomes necessary to use a large reaction vessel. Further, since most of the reactions occurring in step (4) are equilibrium reactions (see, e.g., formula (9) above), the use of too large an amount of the aromatic dihydroxy compound is disadvantageous in that, for recovering the aromatic carbonate produced, the use of a large distillation column becomes necessary. Therefore, in step (4), the amount of the aromatic hydroxy compound is more preferably 0.5 to 100 times, most preferably 0.5 to 10 times, as large as the stoichiometric amount relative to the amount of the dialkyl carbonate.

In step (4), the dialkyl carbonate and the aromatic hydroxy compound are fed to the reaction vessel. If desired, a catalyst may also be used. An impurity may be present in the reaction system of step (4) so long as the impurity does not adversely affect the reactions in step (4).

Each of the dialkyl carbonate and the aromatic hydroxy compound which are used as raw materials in step (4) may contain an alcohol, an alkyl aryl carbonate and a diaryl carbonate, which are products formed in step (4). However, the reaction for producing an alkyl aryl carbonate from the dialkyl carbonate and the aromatic hydroxy compound is an equilibrium reaction (i.e., reversible reaction) (see formula (9) above), so that, when the amounts of the above-mentioned products in the raw materials are large, there is a danger that the conversions of the raw materials are lowered. The amount ratio of the aromatic hydroxy compound to the dialkyl carbonate varies depending on the type and amount of a catalyst used and the reaction conditions; however, the amount ratio is preferably from 0.01 to 1,000, in terms of the molar ratio of the aromatic hydroxy compound to the dialkyl carbonate. As a method for adding a catalyst, a conventional method can be preferably used. When the production of the aromatic carbonate is performed by repeating a cycle of steps (1) to (4) or a cycle of steps (1) to (5), a catalyst used in step (4) may be recycled. In this case, a supplemental amount of a fresh catalyst may be added in step (4).

The time for the reaction in step (4) varies depending on the reaction conditions and the type and inner structure of the reaction vessel. However, the reaction time is generally from 0.001 to 50 hours, preferably from 0.01 to 10 hours, more preferably from 0.05 to 5 hours. The reaction temperature (i.e., temperature in the reaction vessel) varies depending on the types of the dialkyl carbonate and aromatic hydroxy compound used as raw materials. However, the reaction temperature is generally from 50 to 350° C., preferably from 100 to 280° C. The reaction pressure may be reduced pressure, atmospheric pressure or superatmospheric pressure, depending on the types of the dialkyl carbonate and aromatic hydroxy compound used as raw materials and the reaction temperature. However, the reaction pressure is generally from 10 Pa to 20 MPa.

In step (4), it is not necessary to use a solvent. However, for facilitating the operations in step (4), there can be used an inert solvent. Examples of inert solvents include ethers, aliphatic hydrocarbons, aromatic hydrocarbons, halogenated aliphatic hydrocarbons and halogenated aromatic hydrocarbons. Further, the reaction in step (4) may be performed in the presence of a gas inert to the reaction in step (4). Examples of such inert gases include nitrogen, helium, argon, and gasified, low boiling point organic compounds which are inert to the reaction in step (4). When step (4) is performed using a continuous multi-stage distillation column, for the purpose of promoting the removal of a low boiling point by-product by distillation, the above-mentioned inert gas or gasified, low boiling point organic compound may be introduced into the distillation column from the lower portion thereof.

After completion of step (4), the aromatic carbonate is separated from the dialkyl carbonate, the aromatic hydroxy compound, the by-produced alcohol and the catalyst, if any, by a conventional method to thereby recover the aromatic carbonate (as mentioned above, a catalyst may be used in step (4)). Each of the reactions of formulae (9) and (10) above performed in step (4) is a transesterification reaction. By these transesterification reactions, an alkyl aryl carbonate and a diaryl carbonate are obtained from a dialkyl carbonate. However, with respect to each of the transesterification reactions of formulae (9) and (10), the equilibrium of the reaction is biased in the direction of the original system and the rate of the reaction is low. Therefore, for improving the method for producing an aromatic carbonate using the above-mentioned transesterification reactions, several methods have been proposed. Such improved methods can be preferably used in the present invention.

With respect to the transesterification reaction catalyst (i.e., catalyst for promoting the transesterification reactions of formulae (9) and (10) above), the amount thereof varies depending on the type of the catalyst, the type of the reaction vessel, the types and amounts of the dialkyl carbonate and aromatic hydroxy compound, and the reaction conditions (such as the reaction temperature and the reaction pressure). However, the amount of the transesterification reaction catalyst is generally from 0.0001 to 50% by weight, based on the total weight of the dialkyl carbonate and the aromatic hydroxy compound used as raw materials. When the transesterification reaction catalyst is used in a solid form, it is preferred that the amount of the catalyst is from 0.01 to 75% by volume, based on the inner volume of the empty reaction vessel.

As the transesterification reaction catalyst, there are conventionally known a number of metal-containing catalysts. Any of such conventional catalysts for the transesterification reaction can be used in the present invention. Examples of transesterification reaction catalysts include Lewis acids (such as transition metal halides) and compounds which generate Lewis acids (see Unexamined Japanese Patent Application Laid-Open Specification Nos. Sho 51-105032, Sho 56-123948 and Sho 56-123949 (corresponding to Unexamined West German Patent Application Laid-Open Specification No. 2528412, U.K. Patent No. 1499530 and U.S. Pat. No. 4,182,726)); tin compounds, such as organotin alkoxides and organotin oxides (see Unexamined Japanese Patent Application Laid-Open Specification Nos. Sho 54-48733 (corresponding to Unexamined West German Patent Application Laid-Open Specification No. 2736062), Sho 54-63023, Sho 60-169444 (corresponding to U.S. Pat. No. 4,554,110), Sho 60-169445 (corresponding to U.S. Pat. No. 4,552,704), Sho 62-277345 and Hei 1-265063)); salts and alkoxides of an alkali metal or alkaline earth metal (see Unexamined Japanese Patent Application Laid-Open Specification No. Sho 57-176932); lead compounds (see Unexamined Japanese Patent Application Laid-Open Specification No. Sho 57-176932); complexes of a metal, such as copper, iron or zirconium (see Unexamined Japanese Patent Application Laid-Open Specification No. Sho 57-183745); titanic esters (see Unexamined Japanese Patent Application Laid-Open Specification No. Sho 58-185536 (corresponding to U.S. Pat. No. 4,410,464)), mixtures of a Lewis acid and a protonic acid (see Unexamined Japanese Patent Application Laid-Open Specification No. Sho 60-173016 (corresponding to U.S. Pat. No. 4,609,501)); compounds of Sc, Mo, Mn, Bi or Te (see Unexamined Japanese Patent Application Laid-Open Specification No. Hei 1-265064); and ferric acetate (see Unexamined Japanese Patent Application Laid-Open Specification No. Sho 61-172852).

A disproportionation reaction catalyst (i.e., catalyst for promoting the reaction of formula (11) above) may be used in combination with a transesterification reaction catalyst. A number of disproportionation reaction catalysts are also known. Examples of disproportionation reaction catalysts include Lewis acids and transition metal compounds which generate Lewis acids (see Unexamined Japanese Patent Application Laid-Open Specification No. Sho 51-75044 (corresponding to Unexamined West German Patent Application Laid-Open Specification No. 2552907 and U.S. Pat. No. 4,045,464)); polymeric tin compounds (see Unexamined Japanese Patent Application Laid-Open Specification No. Sho 60-169444 (corresponding to U.S. Pat. No. 4,554,110)); compounds represented by the formula: R—X(=O)OH wherein X is Sn or Ti and R is a monovalent hydrocarbon group (see Unexamined Japanese Patent Application Laid-Open Specification No. Sho 60-169445 (corresponding to U.S. Pat. No. 4,552,704)); mixtures of a Lewis acid and a protonic acid (see Unexamined Japanese Patent Application Laid-Open Specification No. Sho 60-173016, (corresponding to U.S. Pat. No. 4,609,501)); lead compounds (see Unexamined Japanese Patent Application Laid-Open Specification No. Hei 1-93560); compounds of titanium or zirconium (see Unexamined Japanese Patent Application Laid-Open Specification No. Hei 1-265062); tin compounds (see Unexamined Japanese Patent Application Laid-Open Specification No. Hei 1-265063); and compounds of Sc, Mo, Mn, Bi or Te (see Unexamined Japanese Patent Application Laid-Open Specification No. Hei 1-265064).

With respect to the reaction performed in step (4) of the method of the present invention, it has been attempted to modify the reaction mode for displacing the equilibrium of the reaction in the direction of the desired product formation as much as possible, thereby improving the yield of the aromatic carbonate. For example, there have been proposed a method in which methanol by-produced by the reaction of dimethyl carbonate with phenol is distilled off in the form of an azeotropic mixture thereof with an azeotrope former (see Unexamined Japanese Patent Application Laid-Open Specification Nos. Sho 54-48732 (corresponding to Unexamined West German Patent Application Laid-Open Specification No. 736063 and U.S. Pat. No. 4,252,737) and Sho 61-291545); and a method in which methanol by-produced by the reaction of dimethyl carbonate with phenol is removed by adsorption thereof onto molecular sieves (see Unexamined Japanese Patent Application Laid-Open Specification No. Sho 58-185536 (corresponding to U.S. Pat. No. 4,410,464)).

Further, there has also been proposed a method in which an alcohol by-produced by a transesterification reaction is distilled off using a reaction vessel having attached to an upper potion thereof a distillation column (see working examples of Unexamined Japanese Patent Application Laid-Open Specification No. Sho 56-123948 (corresponding to U.S. Pat. No.

4,182,726), working examples of Unexamined Japanese Patent Application Laid-Open Specification No. Sho 56-25138, working examples of Unexamined Japanese Patent Application Laid-Open Specification No. Sho 60-169444 (corresponding to U.S. Pat. No. 4,554,110), working examples of Unexamined Japanese Patent Application Laid-Open Specification No. Sho 60-169445 (corresponding to U.S. Pat. No. 4,552,704), working examples of Unexamined Japanese Patent Application Laid-Open Specification No. Sho 60-173016 (corresponding to U.S. Pat. No. 4,609,501), working examples of Unexamined Japanese Patent Application Laid-Open Specification No. Sho 61-172852, working examples of Unexamined Japanese Patent Application Laid-Open Specification No. Sho 61-291545, and working examples of Unexamined Japanese Patent Application Laid-Open Specification No. Sho 62-277345)).

Moreover, there has also been known a method in which a dialkyl carbonate and an aromatic hydroxy compound are continuously fed to a multi-stage distillation column to perform a reaction in the distillation column, wherein the reaction is continuously performed while continuously withdrawing a low boiling point mixture containing the by-produced alcohol from an upper portion of the distillation column by distillation and continuously withdrawing a reaction mixture containing the produced alkyl aryl carbonate from a lower portion of the distillation column (see Unexamined Japanese Patent Application Laid-Open Specification No. Hei 3-291257). By any of the above-mentioned methods, a continuous production of an aromatic carbonate can be efficiently performed.

Further examples of methods for continuously producing an aromatic carbonate include a method in which a transesterification reaction is performed in the presence of a catalyst in a column type reaction vessel (see Unexamined Japanese Patent Application Laid-Open Specification Nos. Hei 6-41022, Hei 6-157424 and Hei 6-184058); a method in which a plurality of reaction vessels are connected in series (Unexamined Japanese Patent Application Laid-Open Specification Nos. Hei 6-234707 and Hei 6-263694); a method using a bubble column reaction vessel (Unexamined Japanese Patent Application Laid-Open Specification No. Hei 6-298700); and a method using a vertical reaction vessel (Unexamined Japanese Patent Application Laid-Open Specification No. Hei 6-345697).

In the commercial scale production of an aromatic carbonate, it has also been attempted to perform the production stably for a long period of time. For example, in an attempt to prevent the deposition of a catalyst in a distillation column, Unexamined Japanese Patent Application Laid-Open Specification No. Hei 6-157410 proposes a method in which, in the production of an aromatic carbonate from a dialkyl carbonate and an aromatic hydroxy compound using a reaction vessel having attached thereto a distillation column, an aliphatic alcohol by-produced is withdrawn from the distillation column so that the concentration of the aliphatic alcohol in the reaction mixture in the column is suppressed to 2% by weight or less. This patent document describes that the above-mentioned method enables a stable practice of a continuous production of an aromatic carbonate. Further, in an attempt to prevent the deposition of a catalyst in a distillation column for the purpose of stably producing an aromatic carbonate for a long period of time, Japanese Patent Application Prior-to-Examination Publication No. Hei 9-11049 discloses a method in which the amount of an aromatic polyhydroxy compound in the reaction mixture containing a catalyst is suppressed to 2 or less, in terms of the weight ratio of the aromatic polyhydroxy compound to the metal contained in the catalyst.

It is known that, in the production of an aromatic carbonate from a dialkyl carbonate and an aromatic hydroxy compound, a compound having a high boiling point is by-produced. For example, Unexamined Japanese Patent Application Laid-Open Specification No. Sho 61-172852 describes that, in the production of diphenyl carbonate by the transesterification reaction of dimethyl carbonate with phenol, an impurity having a boiling point close to that of diphenyl carbonate is by-produced, and that the impurity gets mixed with the produced diphenyl carbonate, thereby leading to discoloration of the final product (such as a polycarbonate) obtained using the diphenyl carbonate. As an example of the impurity having a boiling point close to that of a diaryl carbonate (e.g., diphenyl carbonate), there can be mentioned an aryloxycarbonyl hydroxy arene, which is an isomer of a diaryl carbonate and is formed by the Fries rearrangement of a diaryl carbonate (such an example of an impurity is not described in the above-mentioned Unexamined Japanese Patent Application Laid-Open Specification No. Sho 61-172852). When diphenyl carbonate is used as the diaryl carbonate, the above-mentioned aryloxycarbonyl hydroxyl arene is phenyl salicylate, which has a high boiling point which is higher than that of diphenyl carbonate by 4 to 5° C. When the reaction for producing an aromatic carbonate from a dialkyl carbonate and an aromatic hydroxy compound is performed for a long period of time, the above-mentioned high boiling point compound is gradually accumulated in the reaction system, so that the amount of the high boiling point compound contained in the aromatic carbonate produced is increased, thereby lowering the purity of the aromatic carbonate. Further, as the amount of the high boiling point compound contained in the reaction mixture increases, the boiling point of the reaction mixture is elevated, thereby posing a problem in that the by-production of the high boiling point compound is further promoted.

On the other hand, however, by a method described in Unexamined Japanese Patent Application Laid-Open Specification No. Hei 11-92429, a high purity aromatic carbonate can be stably produced without the need for a large amount of the catalyst.

Specific examples of transesterification reaction catalysts include the following compounds:

<lead compounds> lead oxides, such as PbO, $PbO_2$ and $Pb_3O_4$; lead sulfides, such as PbS and $Pb_2S$; lead hydroxides, such as $Pb(OH)_2$ and $Pb_2O_2(OH)_2$; plumbates, such as $Na_2PbO_2$, $K_2PbO_2$, $NaHPbO_2$ and $KHPbO_2$; plumbates, such as $Na_2PbO_3$, $Na_2H_2PbO_4$, $K_2PbO_3$, $K_2[Pb(OH)_6]$, $K_4PbO_4$, $Ca_2PbO_4$ and $CaPbO_3$; lead carbonates and basic salts thereof, such as $PbCO_3$ and $2PbCO_3 \cdot Pb(OH)_2$; lead salts of organic acids and basic salts of lead salts of organic acids, such as $Pb(OCOCH_3)_2$, $Pb(OCOCH_3)_4$, $Pb(OCOCH_3)_2 \cdot PbO \cdot 3H_2O$; organolead compounds, such as $Bu_4Pb$, $Ph_4Pb$, $Bu_3PbCl$, $Ph_3PbBr$, $Ph_3Pb$ (or $Ph_6Pb_2$), $Bu_3PbOH$ and $Ph_3PbO$ (wherein Bu represents a butyl group and Ph represents a phenyl group); lead alkoxides and lead aryloxides, such as $Pb(OCH_3)_2$, $(CH_3O)Pb(OPh)$ and $Pb(OPh)_2$; lead alloys, such as Pb—Na, Pb—Ca, Pb—Ba, Pb—Sn and Pb—Sb; lead minerals, such as galena and zinc blende; and hydration products of these lead compounds;

<copper family metal compounds> copper family metal salts and complexes, such as CuCl, $CuCl_2$, CuBr, $CuBr_2$, CuI, $CuI_2$, $Cu(OAc)_2$, $Cu(acac)_2$, copper oleate, $Bu_2Cu$, $(CH_3O)_2Cu$, $AgNO_3$, AgBr, silver picrate, $AgC_6H_6ClO_4$, Ag(bullvalene)$_3$NO$_3$, [AuC≡C—C(CH$_3$)$_3$]$_n$ and [Cu(C$_7$H$_8$)Cl]$_4$ (wherein "acac" represents an acetylacetone chelate ligand);

<alkali metal complexes> alkali metal complexes, such as Li(acac) and LiN(C$_4$H$_9$)$_2$;

<zinc complexes> zinc complexes, such as Zn(acac)$_2$;

<cadmium complexes> cadmium complexes, such as Cd(acac)$_2$;

<iron family metal compounds> iron family metal complexes, such as Fe(C$_{10}$H$_8$)(CO)$_5$, Fe(CO)$_5$, Fe(C$_4$H$_6$)(CO)$_3$, Co(mesitylene)$_2$(PEt$_2$Ph)$_2$, CoC$_5$F$_5$(CO)$_7$, Ni-π-C$_5$H$_5$NO and ferrocene;

<zirconium complexes> zirconium complexes, such as Zr(acac)$_4$ and zirconocene;

<Lewis acid compounds> Lewis acids and transition metal compounds which generate Lewis acids, such as AlX$_3$, TiX$_3$, TiX$_4$, VOX$_3$, VX$_5$, ZnX$_2$, FeX$_3$ and SnX$_4$ (wherein X represents a halogen atom, an acetoxy group, an alkoxy group or an aryloxy group); and <organotin compounds> organotin compounds, such as (CH$_3$)$_3$SnOCOCH$_3$, (C$_2$H$_5$)$_3$SnOCOC$_6$H$_5$, Bu$_3$SnOCOCH$_3$, Ph$_3$SnOCOCH$_3$, Bu$_2$Sn(OCOCH$_3$)$_2$, Bu$_2$Sn(OCOC$_{11}$H$_{23}$)$_2$, Ph$_3$SnOCH$_3$, (C$_2$H$_5$)$_3$SnOPh, Bu$_2$Sn(OCH$_3$)$_2$, Bu$_2$Sn(OC$_2$H$_5$)$_2$, Bu$_2$Sn(OPh)$_2$, Ph$_2$Sn(OCH$_3$)$_2$, (C$_2$H$_5$)$_3$SnOH, Ph$_3$SnOH, Bu$_2$SnO, (C$_8$H$_{17}$)$_2$SnO, Bu$_2$SnCl$_2$ and BuSnO(OH).

Needless to say, each of the above-mentioned transesterification reaction catalysts may be used in the form of a reaction product thereof with an organic compound which is present in the reaction system, such as an alcohol, an aromatic hydroxy compound, an alkyl aryl carbonate, a diaryl carbonate or a dialkyl carbonate. Further, each of the above-mentioned transesterification reaction catalysts may, before the use thereof, be subjected to a heat treatment with a raw material used in step (4) or with a product in step (4).

It is preferred that the transesterification reaction catalyst has a high solubility in the reaction mixture under the reaction conditions. Preferred examples of transesterification reaction catalysts include PbO, Pb(OH)$_2$ and Pb(OPh)$_2$; TiCl$_4$ and Ti(OPh)$_4$; SnCl$_4$ and Sn(OPh)$_4$; Bu$_2$SnO and Bu$_2$Sn(OPh)$_2$; FeCl$_3$, Fe(OH)$_3$ and Fe(OPh)$_3$; and compounds obtained by treating the above-mentioned compounds with phenol or the reaction mixture.

As mentioned above, in step (4), an aromatic carbonate is produced by the transesterification reaction (equilibrium reaction) of a dialkyl carbonate with an aromatic hydroxy compound. For increasing the amount of an aromatic carbonate produced, it is preferred that the reaction is performed while withdrawing a by-produced alcohol from the reaction system. Further, the disproportionation reaction of an alkyl aryl carbonate (in which reaction a diaryl carbonate and dialkyl carbonate is produced) is also an equilibrium reaction (see formula (11) above). Therefore, when it is intended to increase the amount of a diaryl carbonate among the aromatic carbonates produced, it is preferred to employ a method in which the disproportionation reaction is performed while withdrawing one of the dialkyl carbonate and diaryl carbonate (each produced by the disproportionation reaction) from the reaction system.

In step (4), it is preferred that the alkyl groups of the dialkyl carbonate produced and the aryl groups of the aromatic carbonates produced are so selected that the dialkyl carbonate has a boiling point lower than those of the aromatic carbonates, and it is also preferred that the reaction is performed while withdrawing the produced dialkyl carbonate from the reaction system.

As mentioned above, in step (4), the reaction may be performed in the presence of not only a transesterification reaction catalyst but also a disproportionation reaction catalyst (catalyst for promoting the reaction of formula (11) above). Examples of disproportionation reaction catalysts include Lewis acids and transition metal compounds which generate Lewis acids (see Unexamined Japanese Patent Application Laid-Open Specification No. Sho 51-75044 (corresponding to Unexamined West German Patent Application Laid-Open Specification No. 2552907 and U.S. Pat. No. 4,045,464)); polymeric tin compounds (see Unexamined Japanese Patent Application Laid-Open Specification No. Sho 60-169444 (corresponding to U.S. Pat. No. 4,554,110)); compounds represented by the formula: R—X(=O)OH (wherein X is Sn or Ti and R is a monovalent hydrocarbon group) (see Unexamined Japanese Patent Application Laid-Open Specification No. Sho 60-169445 (corresponding to U.S. Pat. No. 4,552,704)); mixtures of a Lewis acid and a protonic acid (see Unexamined Japanese Patent Application Laid-Open Specification No. Sho 60-173016 (corresponding to U.S. Pat. No. 4,609,501)); lead compounds (see Unexamined Japanese Patent Application Laid-Open Specification No. Hei 1-93560); compounds of titanium or zirconium (see Unexamined Japanese Patent Application Laid-Open Specification No. Hei 1-265062); tin compounds (see Unexamined Japanese Patent Application Laid-Open Specification No. Hei 1-265063)); and compounds of Sc, Mo, Mn, Bi or Te (see Unexamined Japanese Patent Application Laid-Open Specification No. Hei 1-265064).

Specific examples of disproportionation reaction catalysts include the same catalysts as enumerated above as specific examples of transesterification reaction catalysts.

Needless to say, each of the above-mentioned disproportionation reaction catalysts may be used in the form of a reaction product thereof with an organic compound which is present in the reaction system, such as an alcohol, an aromatic hydroxy compound, an alkyl aryl carbonate, a diaryl carbonate or a dialkyl carbonate. Further, each of the above-mentioned disproportionation reaction catalysts may, before the use thereof, be subjected to a heat treatment with a raw material used in step (4) or with a product in step (4).

It is preferred that the disproportionation reaction catalyst has a high solubility in the reaction mixture under the reaction condition. Preferred examples of disproportionation reaction catalysts include the same catalysts as enumerated as above as preferred examples transesterification reaction catalysts.

After completion of step (4), the aromatic carbonate(s) is separated from the catalyst(s), the aromatic hydroxy compound and the alcohol by a conventional method to thereby recover the aromatic carbonate(s).

With respect to the type of the reaction vessel used in step (4), there is no particular limitation, and any conventional reaction vessel can be used. Examples of conventional reaction vessels include a stirring vessel, a multi-stage stirring vessel and a continuous multi-stage distillation column. These reaction vessels can be used individually or in combination. Using at least one of the above-mentioned reaction vessels, step (4) may be performed in a batchwise or continuous manner. From the viewpoint of efficiently displacing the equilibrium of the reaction in the direction of the desired product formation, it is preferred to use a multi-stage distillation column. It is more preferred that step (4) is continuously performed using a multi-stage distillation column.

With respect to the multi-stage distillation column, there is no particular limitation so long as it is a distillation column which has two or more theoretical stages and which is capable of continuous distillation. As such a multi-stage distillation column, any conventional multi-stage distillation column which is generally used in the art can be used. Examples of such multi-stage distillation columns include plate type columns using a tray, such as a bubble-cap tray, a sieve tray, a valve tray or a counterflow tray; and packed type columns packed with any of various packings, such as a Raschig ring, a Lessing ring, a Pall ring, a Berl saddle, an Interlox saddle, a Dixon packing, a McMahon packing, a Heli pack, a Sulzer packing and Mellapak. Further, a mixed type of plate column and packed column, which comprises both a plate portion and a portion packed with packings, can also be preferably used.

When, in step (4), the production of an aromatic carbonate from a dialkyl carbonate and an aromatic hydroxy compound is continuously performed using a multi-stage distillation column, the production is performed, for example, as follows. A dialkyl carbonate as a starting material and an aromatic hydroxy compound as a reactant are continuously fed to a multi-stage distillation column to effect a transesterification reaction therebetween in a liquid phase or a gaseous-liquid phase in the presence of a metal-containing catalyst, thereby producing an aromatic carbonate and by-producing an alcohol, wherein a high boiling point mixture containing the produced aromatic carbonate is withdrawn in a liquid form from a lower portion of the distillation column while continuously withdrawing, by distillation, a low boiling point mixture containing the by-product alcohol in a gaseous form from an upper portion of the distillation column.

In step (5), the alkyl aryl carbonate obtained in step (4) is subjected to a disproportionation reaction, thereby producing a dialkyl carbonate and a diaryl carbonate (see formula (11) above). (As mentioned above, in step (4), not only the above-mentioned transesterification reactions (see formulae (9) and (10) above) but also the disproportionation reaction may be performed, in the presence of a disproportionation reaction catalyst.) Each of steps (4) and (5) may be performed in a continuous or batchwise manner. As mentioned above, in step (4), a diaryl carbonate is sometimes produced together with an alkyl aryl carbonate. Even in such a case, step (5) may be performed after step (4).

As mentioned above, in step (4), an alkyl aryl carbonate is produced by the transesterification reaction between a dialkyl carbonate and an aromatic hydroxy compound (this transesterification reaction is an equilibrium reaction). For displacing the equilibrium of the transesterification reaction in the direction of the desired product formation, it is preferred to perform the transesterification reaction while withdrawing a by-produced alcohol from the reaction system. The disproportionation reaction in step (5) is also an equilibrium reaction. Therefore, for displacing the equilibrium of the disproportionation reaction in the direction of the desired product formation, it is preferred to perform the disproportionation reaction while withdrawing one of the dialkyl carbonate and the diaryl carbonate (which are produced in the disproportionation reaction) from the reaction system.

In step (5), it is preferred that the alkoxy groups of the dialkyl carbonate produced and the aryl groups of the diaryl carbonate produced are so selected that the dialkyl carbonate has a boiling point lower than that of the diaryl carbonate, and it is also preferred that the disproportionation reaction is performed while withdrawing the produced dialkyl carbonate from the reaction system. It is more preferred that the by-produced dialkyl carbonate is withdrawn in a gaseous form while withdrawing the produced diaryl carbonate in a liquid form. The withdrawn dialkyl carbonate may be recycled to step (2). In some cases, a dialkyl carbonate is produced in step (4). Also in this case, the dialkyl carbonate may be recovered and recycled to step (4). For increasing the amount of the diaryl carbonate produced, it is preferred that the withdrawn dialkyl carbonate is recycled to step (4).

In step (5), the reaction may be performed in the presence of a disproportionation reaction catalyst. Examples of disproportionation reaction catalysts used in step (5) include the above-exemplified disproportionation reaction catalysts used in step (4).

Needless to say, each of the above-mentioned disproportionation reaction catalysts may be used in the form of a reaction product thereof with an organic compound which is present in the reaction system, such as an alcohol, an aromatic hydroxy compound, an alkyl aryl carbonate, a diaryl carbonate or a dialkyl carbonate. Further, each of the above-mentioned disproportionation reaction catalysts may, before the use thereof in step (5), be subjected to a heat treatment with a raw material used in step (5) or with a product in step (5).

As a method for adding a catalyst, any conventional method can be preferably used. When step (5) is performed after step (4), the catalyst (used in step (4)) as such may be used in step (5).

Examples of alkyl aryl carbonates used in step (5) include methyl phenyl carbonate, ethyl phenyl carbonate, propyl phenyl carbonate (and isomers thereof), allyl phenyl carbonate, butyl phenyl carbonate (and isomers thereof), pentyl phenyl carbonate (and isomers thereof), hexyl phenyl carbonate (and isomers thereof), heptyl phenyl carbonate (and isomers thereof), octyl tolyl carbonate (and isomers thereof), nonyl ethylphenyl carbonate (and isomers thereof), decyl butylphenyl carbonate (and isomers thereof), methyl tolyl carbonate (and isomers thereof), ethyl tolyl carbonate (and isomers thereof), propyl tolyl carbonate (and isomers thereof), butyl tolyl carbonate (and isomers thereof), allyl tolyl carbonate (and isomers thereof), methyl xylyl carbonate (and isomers thereof), methyl trimethylphenyl carbonate (and isomers thereof), methyl chlorophenyl carbonate (and isomers thereof), methyl nitrophenyl carbonate (and isomers thereof), methyl methoxyphenyl carbonate, methyl cumyl carbonate (and isomers thereof), methyl naphtyl carbonate (and isomers thereof), methyl pyridyl carbonate (and isomers thereof), ethyl cumyl carbonate (and isomers thereof), methyl benzoylphenyl carbonate (and isomers thereof), ethyl xylyl carbonate (and isomers thereof) and benzyl xylyl carbonate. These alkyl aryl carbonates may be used individually or in combination.

Among these alkyl aryl carbonates, it is preferred to use an alkyl aryl carbonate such that the alcohol corresponding to the alkoxy group of the alkyl aryl carbonate has a boiling point higher than that of water and lower than that of the aromatic hydroxy compound used in step (4). Specific examples of such alcohols include 1-butanol, 2-methyl-1-propanol, alkyl alcohols having a straight chain or branched $C_5$-$C_{12}$ alkyl group, alkenyl alcohols having a straight chain or branched $C_4$-$C_{12}$ alkenyl group, cycloalkyl alcohols and aralkyl alcohols. From the viewpoint of removing the dialkyl carbonate produced in step (5) for displacing the equilibrium of the disproportionation reaction in the direction of the desired production formation, it is more preferred to use an alkyl aryl carbonate having a boiling point lower than that of the diaryl carbonate produced in step (5). For obtaining such an alkyl aryl carbonate, it is most preferred that each of the first alcohol, the second alcohol, the third alcohol, the alcohols corresponding to the alkoxy groups contained in the organometal compounds of formulae (1) and (2) above, and the alcohols corresponding to the alkoxy groups contained in the dialkyl carbonate is a primary alcohol selected from the group consisting of 1-butanol, 2-methyl-1-propanol, pentanol (and isomers thereof) and hexanol (and isomers thereof), and that the aromatic hydroxy compound is phenol or cresol.

In step (5), an alkyl aryl carbonate is used as a raw material. If desired, a disproportionation reaction catalyst may also be used. An impurity may be present in the reaction system of step (5) so long as the impurity does not adversely affect the disproportionation reaction.

The amount of the disproportionation reaction catalyst used in step (5) varies depending on the type of the catalyst, the type of the reaction vessel used, the type and amount of the alkyl aryl carbonate as a raw material, and the reaction conditions (such as the reaction temperature and the reaction pressure). However, the amount of the disproportionation reaction catalyst is generally from 0.0001 to 50% by weight, based on the weight of the alkyl aryl carbonate as a raw material. When the disproportionation reaction catalyst is used in a solid form, it is preferred that the amount of the catalyst is from 0.01 to 75% by volume, based on the inner volume of the empty reaction vessel.

The alkyl aryl carbonate as a raw material may contain at least one compound selected from the group consisting of an alcohol, an aromatic hydroxy compound and a diaryl carbonate. However, the disproportionation reaction in step (5) is an equilibrium reaction (i.e., reversible reaction) (see formula (11) above), so that, when the amounts of the above-mentioned compounds in the alkyl aryl carbonate are large, there is a danger that the conversion of the alkyl aryl carbonate is lowered.

The time for the reaction in step (5) varies depending on the reaction conditions and the type and inner structure of the reaction vessel. However, the reaction time is generally from 0.001 to 50 hours, preferably from 0.01 to 10 hours, more preferably from 0.05 to 5 hours. The reaction temperature (i.e., temperature in the reaction vessel) varies depending on the type of the alkyl aryl carbonate as a raw material. However, the reaction temperature is generally from 50 to 350° C., preferably from 100 to 280° C. The reaction pressure may be reduced pressure, atmospheric pressure or super-atmospheric pressure, depending on the type of the alkyl aryl carbonate as a raw material and the reaction temperature. However, the reaction pressure is generally from 10 Pa to 20 MPa.

In step (5), it is not necessary to use a solvent. However, for facilitating the operations in step (5), there can be used an inert solvent. Examples of inert solvents include ethers, aliphatic hydrocarbons, aromatic hydrocarbons, halogenated aliphatic hydrocarbons and halogenated aromatic hydrocarbons. Further, the disproportionation reaction in step (5) may be performed in the presence of a gas inert to the disproportionation reaction in step (5). Examples of such inert gases include nitrogen, helium, argon and gasified, low boiling point organic compounds which are inert to the reaction in step (5). When step (5) is performed using a multi-stage distillation column, for the purpose of promoting the removal of a low boiling point by-product by distillation, the above-mentioned inert gas or gasified, low boiling point organic compound may be introduced into the distillation column from a lower portion thereof.

After completion of step (5), the diaryl carbonate is separated from the alkyl aryl carbonate, the aromatic hydroxy compound, the alcohol and the catalyst, if any, by a conventional method to thereby recover the diaryl carbonate.

With respect to the type of the reaction vessel used in step (5), there is no particular limitation, and any conventional reaction vessel can be used. Examples of conventional reaction vessels include a stirring vessel, a multi-stage stirring vessel, a multi-stage distillation column. These reaction vessels can be used individually or in combination. Using at least one of the above-mentioned reaction vessels, step (5) may be performed in a batchwise or continuous manner. From the viewpoint of efficiently displacing the equilibrium of the reaction in the direction of the desired product formation, it is preferred to use a multi-stage distillation vessel. It is more preferred that step (5) is continuously performed using a multi-stage distillation vessel.

With respect to the multi-stage distillation column used in step (5), there is no particular limitation so long as it is a distillation column which has two or more theoretical stages and which is capable of continuous distillation. As such a multistage distillation column, any conventional multi-stage distillation column which is generally used in the art can be used. Examples of such multistage distillation columns include a plate type column using a tray, such as a bubble-cap tray, a sieve tray, a valve tray or a counterflow tray; and packed type columns packed with various packings, such as a Raschig ring, a Lesshing ring, a Pall ring, a Berl saddle, an Interlox saddle, a Dixon packing, a McMahon packing, a Heli pack, a Sulzer packing and Mellapak. Further, a mixed type of a plate column and packed column, which comprises both a plate portion and a portion packed with packings, can also be preferably used.

When, in step (5), the production of a diaryl carbonate from an alkyl aryl carbonate is continuously performed using a multi-stage distillation column, the production is performed, for example, as follows. An alkyl aryl carbonate as a starting material is continuously fed to a multi-stage distillation column to effect a disproportionation reaction of the alkyl aryl carbonate in a liquid phase or a gaseous-liquid phase in the presence of a metal-containing catalyst, thereby producing a diaryl carbonate and by-producing a dialkyl carbonate, wherein a high boiling point mixture containing the produced diaryl carbonate is withdrawn in a liquid form from a lower portion of the distillation column while continuously withdrawing, by distillation, a low boiling point mixture containing the by-produced dialkyl carbonate in a gaseous form from an upper portion of the distillation column.

With respect to the material of the apparatuses used in the method of the present invention, there is no particular limitation; however, the material is generally selected from the group consisting of stainless steel and glass lined material.

The accompanying drawings show flow charts of examples of the method of the present inventions. However, these examples should not be construed as limiting the scope of the present invention. For example, the apparatuses and equipment (such as the reaction vessel, conduits and tanks) used in the present invention are not limited to those which are shown in the accompanying drawings, and can be appropriately chosen, based on the conventional knowledge and technique. If desired, an additional step may be performed in the method of the present invention. For example, it is possible to perform an additional step for removing a compound by-produced during the production of the desired aromatic carbonate. Also, a blowdown step for removing, for example, the above-mentioned degraded compound may be added. Further, any of various conventional treatment steps may be performed. The apparatuses used in the present invention may be provided with any conventional equipment, such as a meter (e.g., a flowmeter or a thermometer), a reboiler, a pump, a condenser or a distillation column. In the method of the present invention, heating, if necessary, can be performed by a conventional method, such as a heating using steam or a heater, and cooling, if necessary, can also be performed by a conventional method, such as natural cooling, water cooling or brine cooling. For improving the thermal efficiency, the operation in each step of the method of the present invention may be performed so as to achieve the heat balance in the step. The production apparatus may be designed so as to achieve a satisfactory recovery of the final and intermediate products for easy recycling thereof.

Figure 2:
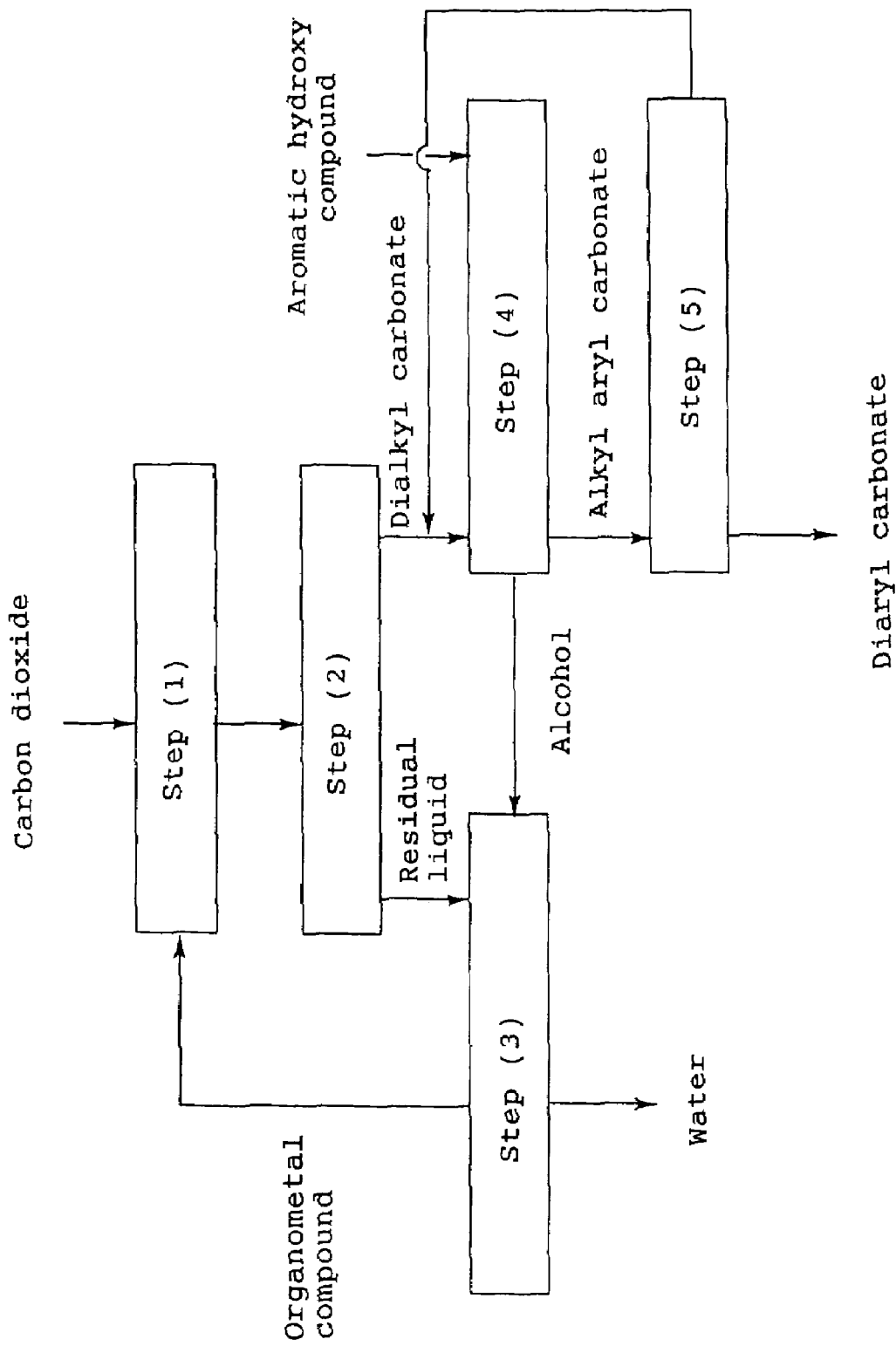
FIG. 2 is a flow chart showing an example of the method of the present invention for producing a diaryl carbonate.

In the method of the present invention for producing an aromatic carbonate, as shown in FIG. 1, the alcohol produced in step (4) can be recycled to step (3), and the dialkyl carbonate produced in step (4) can be recycled to step (4) as a raw material. As shown in FIG. 2, the alcohol produced in step (4) can be recycled to step (3), and the dialkyl carbonate produced in step (5) can be recycled to step (4) as a raw material. When a cycle of steps (1) to (4) or a cycle of steps (1) to (5) is repeated at least one time, an aromatic carbonate can be continuously obtained, wherein substantially no substance other than water is wasted.

In some cases, the alcohol recovered in step (4) as such can be recycled to step (3). However, when the alcohol recovered in step (4) contains a large amount of an aromatic hydroxy compound and/or a large amount of a carboxyl group-containing compound, the alcohol is purified by a conventional separation method so that the total amount of the aromatic hydroxy compound and the carboxyl group-containing compound in the alcohol becomes 1,000 ppm or less, preferably 100 ppm or less. As a separation method, it is preferred to employ a separation by distillation. It is preferred to perform step (4) by a reactive distillation method using a distillation column, because the purification of the alcohol by distillation can be performed simultaneously with the production of an aromatic carbonate.

In some cases, the dialkyl carbonate recovered in step (4) and/or step (5) as such can be recycled to step (4). However, when the recovered dialkyl carbonate contains an impurity, it is preferred that the purification or concentration adjustment of the dialkyl carbonate is performed before the recycle thereof to step (4). Examples of impurities contained in the dialkyl carbonate include an aromatic hydroxy compound, and by-products formed during the above-mentioned transesterification reaction and disproportionation reaction. Examples of such by-products include a dialkyl ether and an alkyl aryl ether, which are formed by the decarboxylation of a carbonic ester. As a method for the purification or concentration adjustment of the dialkyl carbonate, a conventional method can be used. Among conventional methods, a method using distillation is preferred.

As mentioned above, as a conventional method for producing an aromatic carbonate (e.g., a diaryl carbonate), a phosgene method using phosgene and an oxidative carbonylation method using carbon monoxide are known. However, each of these conventional methods is disadvantageous in that a chlorine-containing compound is used as a raw material or a catalyst, so that the aromatic carbonate produced by the conventional method inevitably contains a large amount of a chlorine-containing compound. The use of such an aromatic carbonate in the production of a polycarbonate poses serious problems, such as deactivation of a polymerization catalyst, discoloration and degradation of the polycarbonate produced. Further, when such an aromatic carbonate containing a large amount of a chlorine-containing compound is used as an additive for gasoline or diesel fuel, the aromatic carbonate causes the corrosion of an engine or a pipe. In their previous applications WO 03/055840 and WO 04/014840, the present inventors have disclosed a method for producing a carbonic ester, in which a carbonic ester and water are produced from carbon dioxide, an alcohol and a dialkyltin alkoxide, wherein the amount of a by-product is very small. The present inventors have succeeded in improving the technique of the above-mentioned previous applications and arrived at the present invention. By the method of the present invention, a high purity aromatic carbonate containing substantially no impurity (such as a chlorine-containing compound) can be simply and efficiently produced.

The high purity aromatic carbonate produced by the method of the present invention can be advantageously used as a raw material for a polycarbonate, an isocyanate, a polycarbonate diol and the like. As the aromatic carbonate used for producing each of the above-mentioned polymers, a diaryl carbonate is preferred.

With respect to each of the polycarbonate, isocyanate and polycarbonate diol, explanations are given below.

First, with respect to the polycarbonate, explanation is given below. A diaryl carbonate is known as a raw material used in the production of a polycarbonate by the conventional melt method which generally involves a transesterification reaction of the diaryl carbonate with bisphenol A. However, as mentioned above, a conventional diaryl carbonate contains a large amount of a chlorine-containing compound. The chlorine-containing compound contained in the diaryl carbonate deactivates a catalyst used in the transesterification reaction of the diaryl carbonate with bisphenol A. For avoiding this disadvantage, it is conceivable to use the catalyst in a large amount. However, the use of a large amount of the catalyst harmfully affects various properties of the polycarbonate produced, such as weatherability and color. Therefore, in such conventional melt method, it is necessary to perform an additional step for removing the chlorine-containing compound from the diaryl carbonate.

As a conventional method for removing a chlorine-containing compound from a diaryl carbonate, there can be mentioned a method in which a diaryl carbonate is washed with an alkali or is purified by distillation. However, such a conventional method has the following fatal problem. The washing of the diaryl carbonate is performed at a temperature at which the diaryl carbonate is in a molten state. However, the melting point of the diaryl carbonate is relatively high and, hence, the washing of the diaryl carbonate with the alkali needs to be performed at a relatively high temperature. As a result, the diaryl carbonate suffers a hydrolysis during the washing with the alkali. On the other hand, when the diaryl carbonate is purified by distillation, it is very difficult to remove the chlorine-containing compound satisfactorily from the diaryl carbonate since the diaryl carbonate contains various chlorine-containing compounds having different boiling points ranging from a low temperature to a high temperature. Therefore, when it is intended to obtain a polycarbonate which has a sufficiently high purity for commercial use, the cost for purification becomes very high.

In another conventional method for producing a diaryl carbonate (e.g., diphenyl carbonate), dimethyl carbonate is first produced from ethylene carbonate (which is produced using carbon dioxide as a raw material) and methanol, and methyl phenyl carbonate is produced from the dimethyl carbonate, and, then, diphenyl carbonate is produced from the methyl phenyl carbonate. In this method, it is necessary that dimethyl carbonate be formed as an intermediate product, and that methanol (which has the lowest boiling point in the reaction system) be distilled in the form of an azeotropic mixture thereof with the dimethyl carbonate in order to displace the equilibrium of the reaction (for producing dimethyl carbonate from ethylene carbonate and methanol) in the direction of the desired product formation. In this method, methyl phenyl carbonate is necessarily by-produced. The methyl phenyl carbonate is susceptible to a side reaction, such as a decarboxylation reaction, thereby forming methyl group-containing by-products, such as anisole. The methyl group-containing by-products get mixed with the desired diphenyl carbonate, and it is impossible to completely remove such by-products from the diphenyl carbonate even if the purification of the diphenyl carbonate is attempted. The presence of the methyl group-containing by-products in the diphenyl carbonate causes the following problems. The rate of the polymerization reaction for producing a polycarbonate from the diphenyl carbonate is lowered. Further, a polycarbonate having a uniform molecular weight cannot be obtained. Moreover, the polycarbonate produced becomes discolored.

On the other hand, in the method of the present invention, a diaryl carbonate can be produced without generation of such unfavorable by-products. It is difficult to confirm the absence of the methyl group-containing by-products in the diaryl carbonate produced by the method of the present invention. However, in the production of a diaryl carbonate by the method of the present invention, an intermediate of the aromatic carbonate is not limited to dimethyl carbonate. Therefore, in the method of the present invention, by using an intermediate other than dimethyl carbonate, it is possible to obtain an aromatic carbonate containing substantially no methyl group-containing by-product which adversely affects the polymerization reaction for producing a polycarbonate. Preferred examples of diaryl carbonates used as a raw material for producing a polycarbonate include a diaryl carbonate in which a methyl group-containing by-product is present in an amount of not more than 100 ppm by weight, more advantageously not more than 10 ppm by weight, based on the weight of the diaryl carbonate.

With respect to the isocyanate, explanation is given below. A high purity isocyanate can be produced by using the aromatic carbonate (especially, a diaryl carbonate) of the present invention. Specifically, for example, the diaryl carbonate is reacted with a polyamine to obtain a polyaryl carbamate (such as a hexamethylene diaryl carbamate), and the obtained polyaryl carbamate is subjected to thermal decomposition, thereby producing an isocyanate having a high purity. Conventionally, as a method for synthesizing an isocyanate at a low cost, only a method using phosgene (chloride-containing compound) as a raw material is known. On the other hand, the diaryl carbonate produced by the method of the present invention is inexpensive, and contains only a very small amount of a chlorine-containing compound, if any. Therefore, the isocyanate obtained from the diaryl carbonate of the present invention is very advantageous, as compared to a conventional isocyanate, which is produced by a method using phosgene and, hence, contains a chlorine-containing compound. An isocyanate is used mainly for producing a urethane. The production of a urethane from a conventional isocyanate has a problem in that a urethanation catalyst is easily deactivated and modified in the presence of chlorine. However, the isocyanate produced from the diphenyl carbonate obtained by the method of the present invention contains substantially no chlorine-containing compound and, hence, is free from the above-mentioned problem.

With respect to the polycarbonate diol, explanation is given below. Using the aromatic carbonate of the present invention, a high purity polycarbonate diol can be produced.

The polycarbonate, isocyanate and polycarbonate diol of the present invention, each of which is produced using the aromatic carbonate produced by the method of the present invention, have the following advantages over the conventional polycarbonate, isocyanate and polycarbonate diol. The polycarbonate, isocyanate and polycarbonate diol of the present invention have high purities and can be simply (and, hence, inexpensively) produced without causing the problem of the generation of a co-product. Therefore, the polycarbonate, isocyanate and polycarbonate diol of the present invention have a high commercial value.

BEST MODE FOR CARRYING THE INVENTION

Hereinbelow, the present invention will be described in more detail with reference to the following Examples and Comparative Examples, which should not be construed as limiting the scope of the present invention.

In the following Examples and Comparative Examples, various measurements and analyses were conducted by the following methods.

1) Nuclear Magnetic Resonance (NMR) Analysis of an Organometal Compound

Apparatus: JNM-A400 FT-NMR system (manufactured and sold by JEOL Ltd., Japan)

(1) Preparation of Sample Solutions for $^1$H- and $^{13}$C-NMR Analyses

About 0.1 to 0.5 g of an organometal compound was weighed and, then, about 0.9 g of deuterated chloroform was added thereto, thereby obtaining a sample solution for an NMR analysis.

(2) Preparation of a Sample Solution for a $^{119}$Sn-NMR Analysis

About 0.1 to 1 g of a liquid containing an organometal compound was weighed and, then, 0.05 g of tetramethyltin and about 0.85 g of deuterated chloroform were added thereto, thereby obtaining a sample solution for an NMR analysis.

2) Gas Chromatography (GC) Analysis of a Carbonic Ester

Apparatus: GC-2010 system (manufactured and sold by Shimadzu Corporation, Japan).

(1) Preparation of a Sample Solution 0.4 g of a liquid to be measured with respect to the carbonic ester content thereof was weighed and, then, about 0.5 ml of dehydrated dimethylformamide or dehydrated acetonitrile was added thereto. Further, to the resultant was added about 0.04 g of toluene or diphenyl ether as an internal standard, thereby obtaining a sample solution for a GC analysis.

(2) Conditions for a GC Analysis

Column: DB-1 (manufactured and sold by J & W Scientific, U.S.A.)

Liquid phase: 100% dimethyl polysiloxane

Column length: 30 m

Column diameter: 0.25 mm

Film thickness: 1 μm

Column temperature: the temperature was elevated from 50° C. to 300° C. at a rate of 10° C./min.

Injection temperature: 300° C.

Detector temperature: 300° C.

Detector: FID (flame ionization detector)

(3) Quantitative Analysis

The quantitative analysis of a sample solution was conducted using a calibration curve obtained with respect to standard samples.

3) Calculation of the Yield of an Aromatic Carbonate

The yield of aromatic carbonate obtained in step (4) was expressed either in terms of % by weight, based on the weight of the reaction mixture obtained in step (4), or in terms of the mol % of the obtained alkyl aryl carbonate and diaryl carbonate, based on the total molar amount of the dialkyl carbonate used as a starting material in the reaction of step (4).

4) Number Average Molecular Weight of Aromatic Carbonate

The number average molecular weight of an aromatic carbonate was determined by gel permeation chromatography (GPC).

EXAMPLE 1

Production of Dibutyltin Dialkoxide

Figure 3:
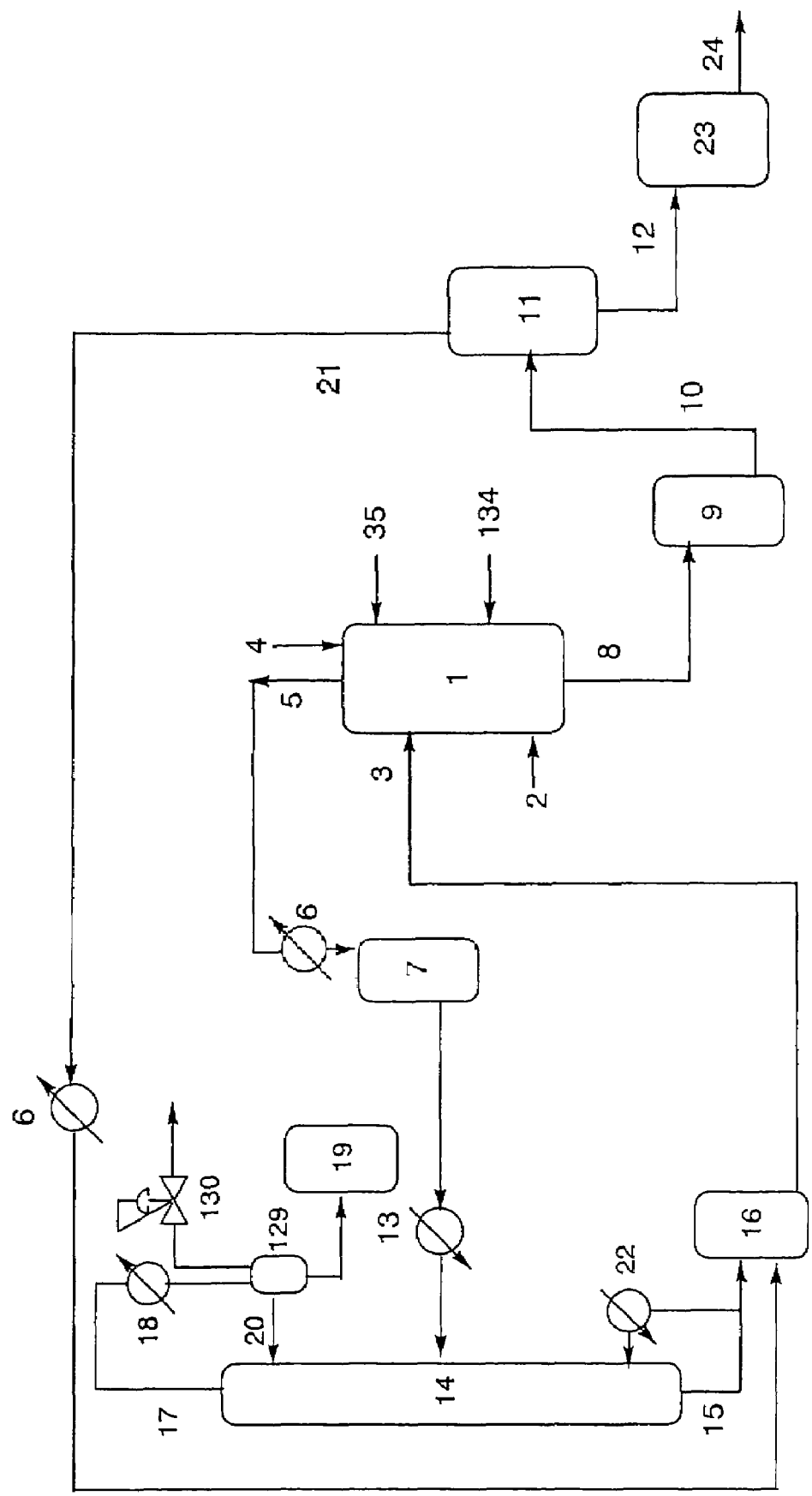
FIG. 3 is a flow chart showing examples of steps involved in the method of the present invention, i.e., step (3) of the method of the present invention, the step of producing a dibutyltin dialkoxide, the step of producing a dioctyltin dialkoxide, and the step of separating water from an alcohol by distillation.

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 2,224 g (30 mol) of 1-butanol (manufactured and sold by Aldrich, U.S.A.), wherein dibutyltin oxide was fed through conduit 4 provided at the top of reaction vessel 1, and 1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging the low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing 1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 320 g, and that the liquid contained about 0.54 mol of dibutyltin dibutoxide and about 0.18 mol of 1,1,3,3-tetrabutyl-1,3-dibutyloxydistannoxane.

(Step (1))

About 107 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.06 mol of dibutyl carbonate, and that the whole of the reaction mixture obtained 4 hours after the start of the reaction (i.e., the reaction mixture after the reaction) contained about 0.07 mol of dibutyl carbonate.

After the reaction, the inside of the autoclave was cooled, and carbon dioxide was purged therefrom.

(Step (2))

Figure 4:
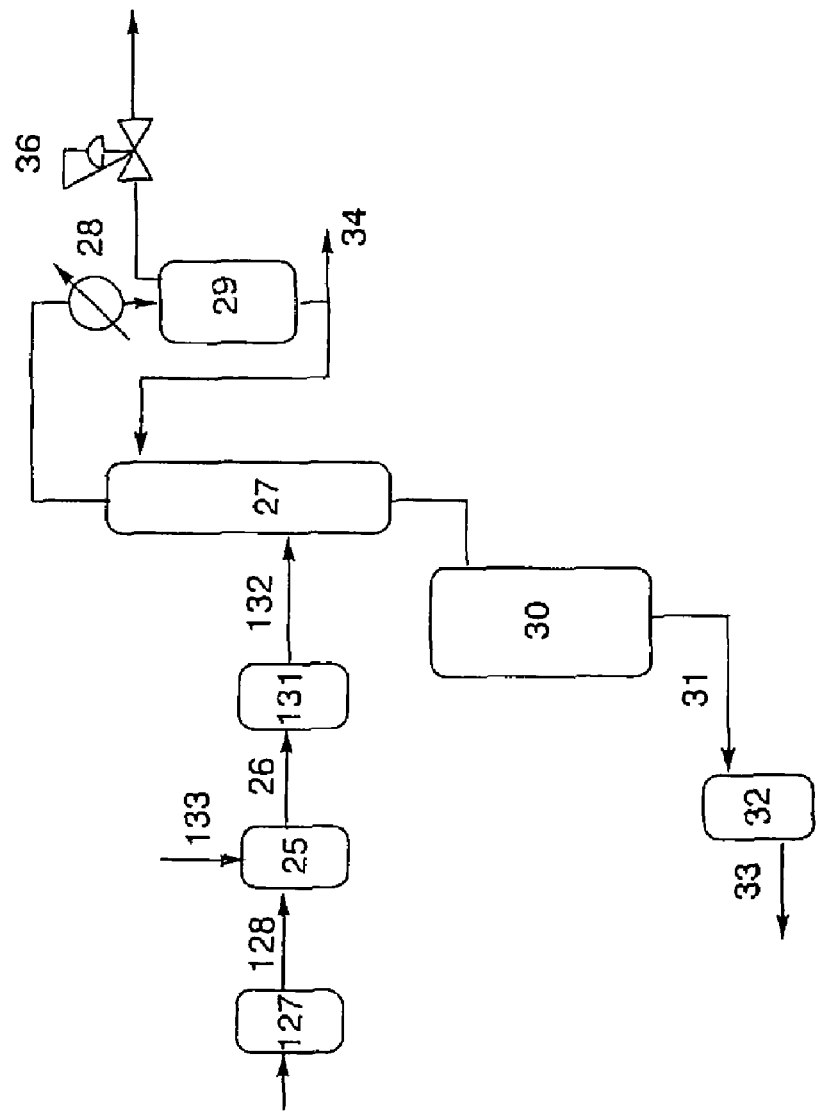
FIG. 4 is a flow chart showing a specific example of step (2) of the method of the present invention.

Using a device as shown in FIG. 4, step (2) was performed as follows.

After step (1), the resultant reaction mixture was withdrawn from the bottom of the autoclave, and transferred through conduit 133 to vessel 25 for removing carbon dioxide, wherein the atmosphere in vessel 25 had been purged with nitrogen. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 100 g/hr, and distillation was performed at a reflux ratio of about 0.2. Thin film distillation apparatus 30 was equipped with a heating jacket in which a heating medium having a temperature of 130° C. was circulated, and the internal pressure (column top pressure) was reduced to about 1.3 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from the top of distillation column 27, it was found that dibutyl carbonate was withdrawn and transferred to reservoir 29 at a rate of about 0.06 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 90 g/hr, and that no dibutyl carbonate was detected by gas chromatography (GC).

(Step (3))

Using a device as shown in FIG. 3, step (3) was performed as follows.

After step (2), the residual liquid collected in reservoir 32 and about 2,150 g (29 mol) of 1-butanol were fed to a 5-liter SUS reaction vessel 1, wherein the residual liquid and 1-butanol were fed through conduit 35 and conduit 3, respectively. Further, nitrogen gas was fed into reaction vessel 1 through a SUS tube connected to inert gas conduit 2 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing 1-butanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dibutyltin dibutoxide and 1,1,3,3-tetrabutyl-1,3-dibutyloxydistannoxane.

The liquid collected in reservoir 23 was recycled to step (1), and a cycle of steps (1) to (3) was repeatedly performed.

(Step (4))

(Preparation of Catalyst)

40 g of phenol and 8 g of lead monoxide were mixed together, and the resultant mixture was heated at 180° C. for 10 hours while distilling off the by-produced water with phenol, thereby obtaining catalyst A.

(Production of Aromatic Carbonate)

Figure 5:
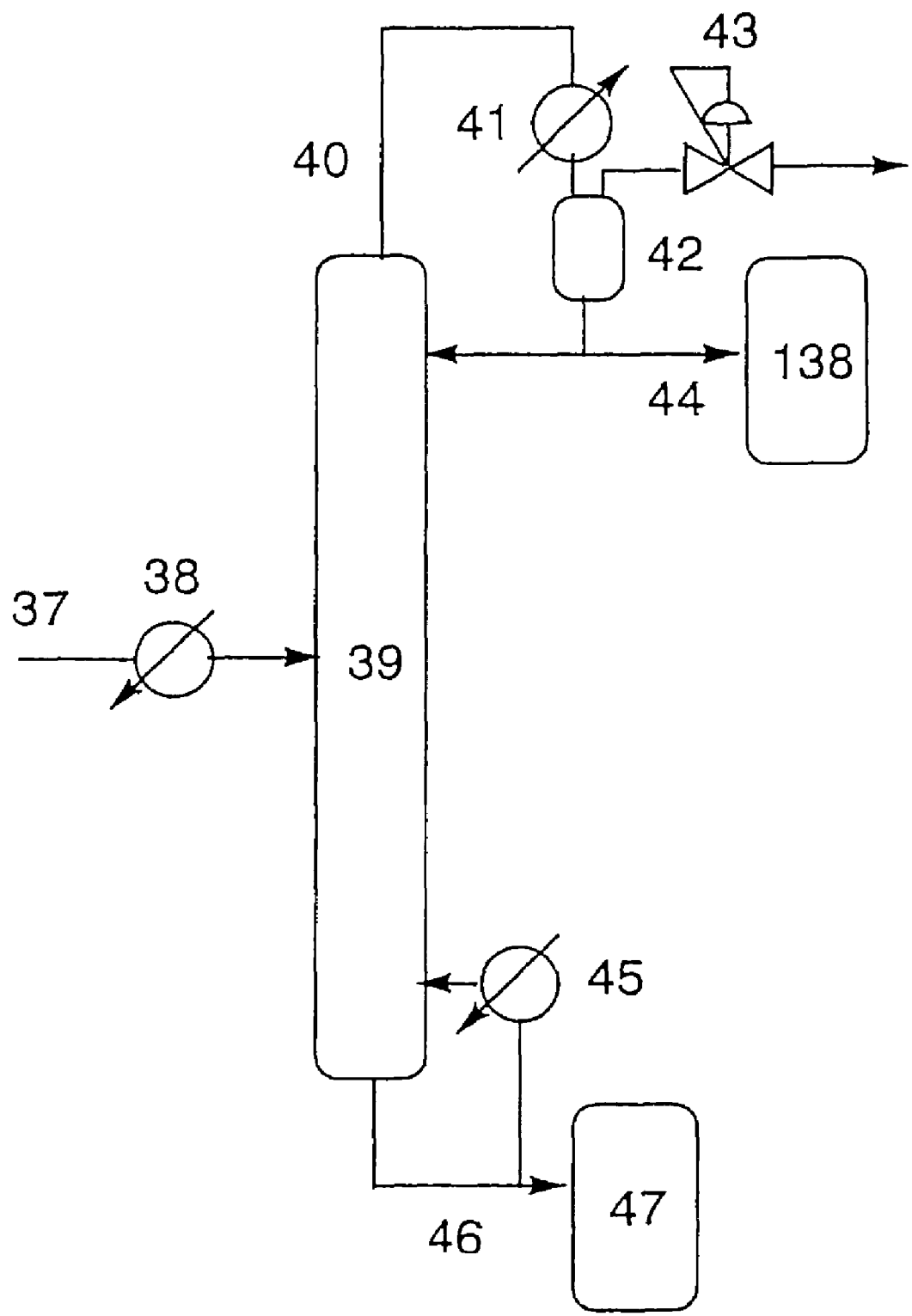
FIG. 5 is a flow chart showing a specific example of step (4) of the method of the present invention.

Using a device as shown in FIG. 5, step (4) was performed as follows.

The condensate (containing dibutyl carbonate) collected in reservoir 29 in step (2), phenol and catalyst A were mixed together to obtain a liquid mixture having a dibutyl carbonate/phenol weight ratio of 65/35 and a Pb content of about 1% by weight. The obtained liquid mixture was continuously fed through conduit 37 (equipped with preheater 38) to continuous multi-stage distillation column 39 (height: 4 m; inner diameter: about 5 cm) having 80 sieve trays at a middle portion thereof at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 231° C., the column top pressure was $1.2 \times 10^5$ Pa, and the reflux ratio was about 3. A gas discharged from the top of distillation column 39 was transferred through conduit 40 to condenser 41, to thereby condense the gas. The resultant condensate was withdrawn from condenser 41 and transferred through conduit 44 to reservoir 138 at a rate of about 240 g/hr. The liquid in distillation column 39 was withdrawn from the bottom thereof and transferred through conduit 46 to reservoir 47 at a rate of about 30 g/hr.

The condensate collected in reservoir 138 contained about 9% by weight of 1-butanol, about 30% by weight of phenol and about 61% by weight of dibutyl carbonate, based on the weight of the condensate. On the other hand, the liquid collected in reservoir 47 contained about 0.1% by weight of dibutyl carbonate, about 41% by weight of butyl phenyl carbonate, and about 50% by weight of diphenyl carbonate, based on the weight of the liquid collected in reservoir 47. Further, the liquid collected in reservoir 47 had a Pb content of about 9% by weight.

(Recycling of Alcohol)

Figure 7:
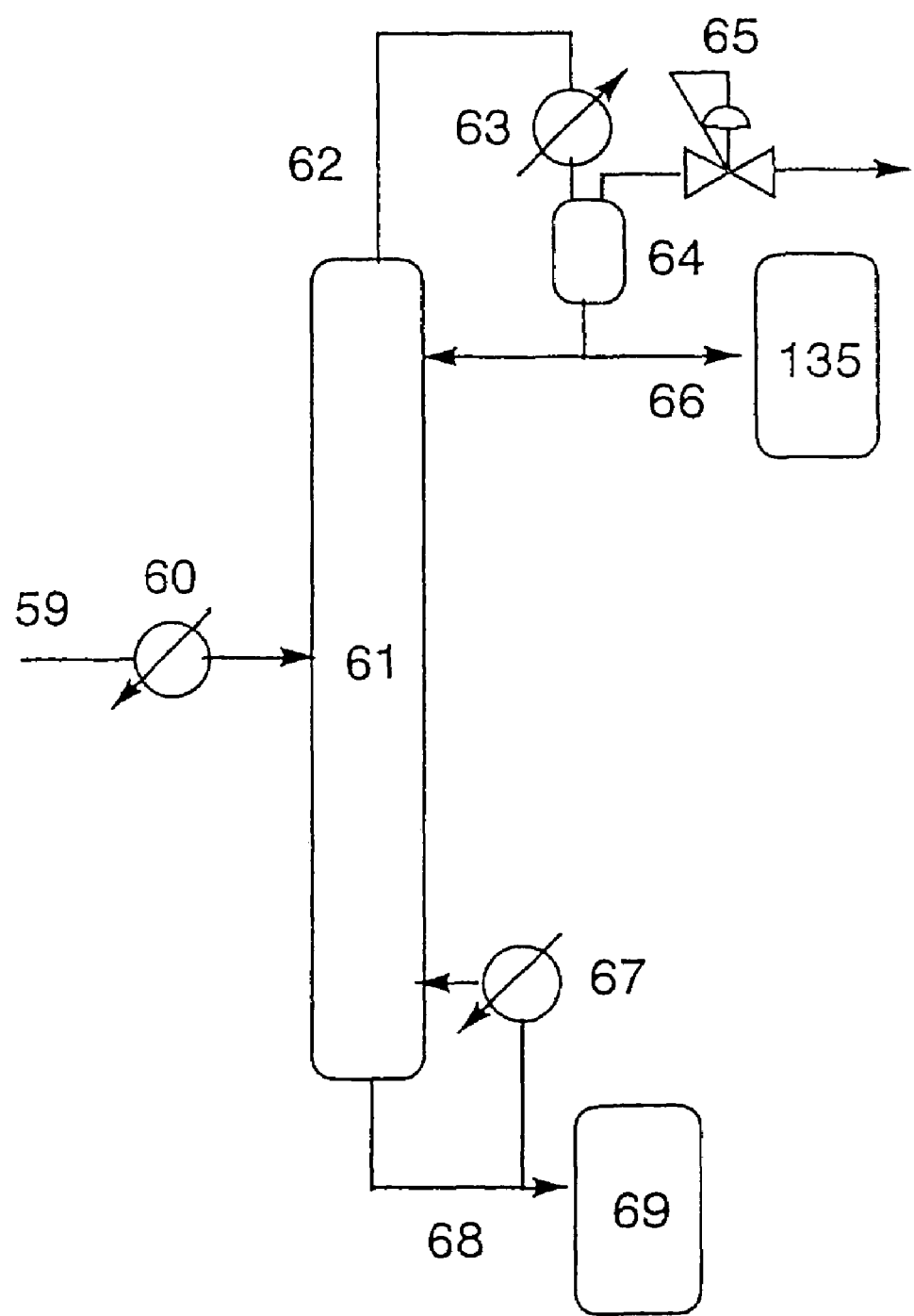
FIG. 7 is a flow chart showing a specific example of the step of recycling an alcohol, which is performed in the method of the present invention.

Using a device as shown in FIG. 7, recycling of the alcohol was performed as follows.

The condensate collected in reservoir 138 was fed through conduit 59 (equipped with preheater 60) to continuous multi-stage distillation column 61 (inner diameter: about 5 cm; height: 4 m) (which was filled with Dixon packing (6 mmφ)) at a portion thereof which is about 0.4 m above the bottom of distillation column 61 at a rate of about 240 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 189° C., the column top pressure was maintained at about 101.3 kPa (atmospheric pressure), and the reflux ratio was about 3.5. A gas distilled from the top of distillation column 61 was transferred through conduit 62 to condenser 63, to thereby condense the distilled gas. The resultant condensate was continuously withdrawn from condenser 63 and transferred through conduit 66 to alcohol reservoir 135 at a rate of about 16.3 g/hr. The residual liquid in distillation column 61 was continuously withdrawn from the bottom thereof and transferred through conduit 68 to reservoir 69 at a rate of about 223.7 g/hr.

The condensate collected in reservoir 135 contained about 99.99% by weight of 1-butanol and about 100 ppm by weight of phenol, based on the weight of the condensate. On the other hand, the residual liquid collected in reservoir 69 contained about 66% by weight of dibutyl carbonate, about 33% by weight of phenol and about 1% by weight of butyl phenyl carbonate, based on the weight of the residual liquid.

(Separation of Alcohol from Water by Distillation)

Using a device as shown in FIG. 3, the condensate in reservoir 7 was separated into alcohol and water by distillation as follows.

The condensate collected in reservoir 7 in the production of dibutyltin dialkoxides and step (3) was continuously fed through preheater 13 to continuous multi-stage distillation column 14 (inner diameter: about 5 cm; height: 2 m) (which was filled with Dixon packing (6 mmφ)) at a portion thereof which is about 0.4 m above the bottom of distillation column 14 at a rate of about 250 g/hr, and distillation was performed to thereby separate the condensate into an alcohol and water. During the distillation, the liquid in distillation column 14 was withdrawn from the bottom thereof. A portion of the withdrawn liquid was transferred through conduit 15 to reboiler 22 and, then, recycled to distillation column 14, so as to supply a sufficient amount of heat for performing the distillation. The distillation was performed under conditions wherein the temperature of the liquid at the bottom of distillation column 14 was 81° C., and the column top pressure thereof was reduced to about 20 kPa. A gas distilled from the top of distillation column 14 was transferred through conduit 17 to condenser 18, to thereby condense the gas. The resultant condensate was transferred to vapor-liquid separation apparatus 129, and was separated into two liquid phases. Then, the lower phase of the condensate was continuously withdrawn from vapor-liquid separation apparatus 129 and transferred to reservoir 19 at a rate of about 25 g/hr. On the other hand, the upper phase of the condensate was refluxed through conduit 20 to distillation column 14 at a reflux ratio of about 0.6. The residual liquid in distillation column 14 was continuously withdrawn from the bottom thereof and transferred through conduit 15 to reservoir 16 at a rate of about 225 g/hr.

The residual liquid collected in reservoir 16 contained almost 100% by weight, based on the weight of the residual liquid, of 1-butanol, and contained substantially no water (no water was detected in the analysis of the residual liquid). On the other hand, the liquid collected in reservoir 19 contained 75% by weight of 1-butanol and 25% by weight of water, based on the weight of the liquid in reservoir 19.

(Step (3))

Using a device as shown in FIG. 3, step (3) was performed after the separation of alcohol from water by distillation, as follows.

The residual liquid collected in reservoir 32 in the above-mentioned step (2) was fed through conduit 35 to a 5-liter SUS reaction vessel 1. Further, the 1-butanol product collected in reservoir 135 in the above-mentioned step of the recycling of the alcohol was fed through conduit 134 to reaction vessel 1, and the 1-butanol product in reservoir 16 (which is a mixture of fresh 1-butanol fed to reservoir 16 prior to the operation of the device of FIG. 3 and unreacted 1-butanol separated in apparatus 11) was fed through conduit 3 to reaction vessel 1, wherein the total amount of the 1-butanol products fed to reaction vessel 1 was about 2,224 g (30 mol). Furthermore, nitrogen gas was fed into reaction vessel 1 through a SUS tube connected to inert gas conduit 2 at a rate of 0.1 Nl/hr.

Subsequently, the contents of reaction vessel 1 were heated while stirring, so as to adjust the temperature thereof within the range of from 113° C. to the boiling point of 1-butanol, and a reaction was performed for about 6 hours while discharging low boiling point components in the form of a gas from gas discharging conduit 5 provided at the upper portion of reaction vessel 1, wherein the gas discharged from conduit 5 was transferred through condenser 6 to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, wherein apparatus 11 was equipped with a stirrer, a pressure-reducing device and a heater. Then, from the residual liquid collected in apparatus 11 was removed the unreacted alcohol in the same manner as mentioned above, and the residual liquid having the alcohol removed therefrom was discharged from conduit 12 and collected in reservoir 23.

The liquid collected in reservoir 23 was analyzed. As a result, it was found that the weight of the liquid was about 107 g, and that the liquid contained about 0.18 mol of dibutyltin dibutoxide and about 0.06 mol of 1,1,3,3-tetrabutyl-1,3-dibutyloxydistannoxane.

(Step (1))

After step (3) above, step (1) was performed as follows.

About 107 g of the liquid collected in reservoir 23 in step (3) was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.06 mol of dibutyl carbonate, and that the whole of the reaction mixture obtained 4 hours after the start of the reaction (i.e., the reaction mixture after the reaction) contained about 0.07 mol of dibutyl carbonate.

After the reaction, the inside of the autoclave was cooled, and carbon dioxide was purged therefrom.

EXAMPLE 2

Production of Dibutyltin Dialkoxide

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 2,224 g (30 mol) of 1-butanol (manufactured and sold by Aldrich, U.S.A.), wherein dibutyltin oxide was fed through conduit 4 provided at the top of reaction vessel 1, and 1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing 1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 320 g, and that the liquid contained about 0.54 mol of dibutyltin dibutoxide and about 0.18 mol of 1,1,3,3-tetrabutyl-1,3-dibutyloxydistannoxane.

(Step (1))

About 107 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.06 mol of dibutyl carbonate, and that the whole of the reaction mixture obtained 4 hours after the start of the reaction (i.e., the reaction mixture after the reaction) contained about 0.07 mol of dibutyl carbonate.

After the reaction, the inside of the autoclave was cooled, and carbon dioxide was purged therefrom.

(Step (2))

Using a device as shown in FIG. 4, step (2) was performed as follows.

After step (1), the resultant reaction mixture was withdrawn from the bottom of the autoclave, and transferred through conduit 133 to vessel 25 for removing carbon dioxide, wherein the atmosphere in vessel 25 had been purged with nitrogen. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 100 g/hr, and distillation was performed at a reflux ratio of about 0.2. Thin film distillation apparatus 30 was equipped with a heating jacket in which a heating medium having a temperature of 130° C. was circulated, and the internal pressure (column top pressure) was reduced to about 1.3 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from the top of distillation column 27, it was found that dibutyl carbonate was withdrawn and transferred to reservoir 29 at a rate of about 0.06 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 90 g/hr, and that no dibutyl carbonate was detected by gas chromatography (GC).

(Step (3))

Using a device as shown in FIG. 3, step (3) was performed as follows.

After step (2), the residual liquid collected in reservoir 32 and about 2,150 g (29 mol) of 1-butanol were fed to a 5-liter SUS reaction vessel 1, wherein the residual liquid and 1-butanol were fed through conduit 35 and conduit 3, respectively. Further, nitrogen gas was fed into reaction vessel 1 through a SUS tube connected to inert gas conduit 2 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing 1-butanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dibutyltin dibutoxide and 1,1,3,3-tetrabutyl-1,3-dibutyloxydistannoxane.

The liquid collected in reservoir 23 was recycled to step (1), and the cycle of steps (1) to (3) was repeatedly performed.

(Step (4))

(Preparation of Catalyst)

40 g of phenol and 8 g of lead monoxide were mixed together, and the resultant mixture was heated at 180° C. for 10 hours while distilling off the by-produced water with phenol, thereby obtaining catalyst A.

(Production of Aromatic Carbonate)

Using a device as shown in FIG. 5, step (4) was performed as follows.

The condensate (containing dibutyl carbonate) collected in reservoir 29 in step (2), phenol and catalyst A were mixed together to obtain a liquid mixture having a dibutyl carbonate/phenol weight ratio of 65/35 and a Pb content of about 1% by weight. The obtained liquid mixture was continuously fed through conduit 37 (equipped with preheater 38) to continuous multi-stage distillation column 39 (height: 2 m; inner diameter: about 5 cm) (which was filled with Dixon packing (6 mmφ)) at a middle portion thereof at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 231° C., the column top pressure was $2\times10^5$ Pa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 67 g/hr. The liquid in distillation column 39 was withdrawn from the bottom thereof and transferred through conduit 46 to reservoir 47 at a rate of about 203 g/hr.

The condensate collected in reservoir 138 contained about 28% by weight of 1-butanol, about 71% by weight of phenol and about 1% by weight of dibutyl carbonate, based on the weight of the condensate. On the other hand, the liquid collected in reservoir 47 contained about 11% by weight of phenol, 64% by weight of dibutyl carbonate, about 22% by weight of butyl phenyl carbonate, and about 1% by weight of diphenyl carbonate, based on the weight of the liquid collected in reservoir 47. Further, the liquid collected in reservoir 47 had a Pb content of about 1% by weight.

(Step (5))

Figure 6:
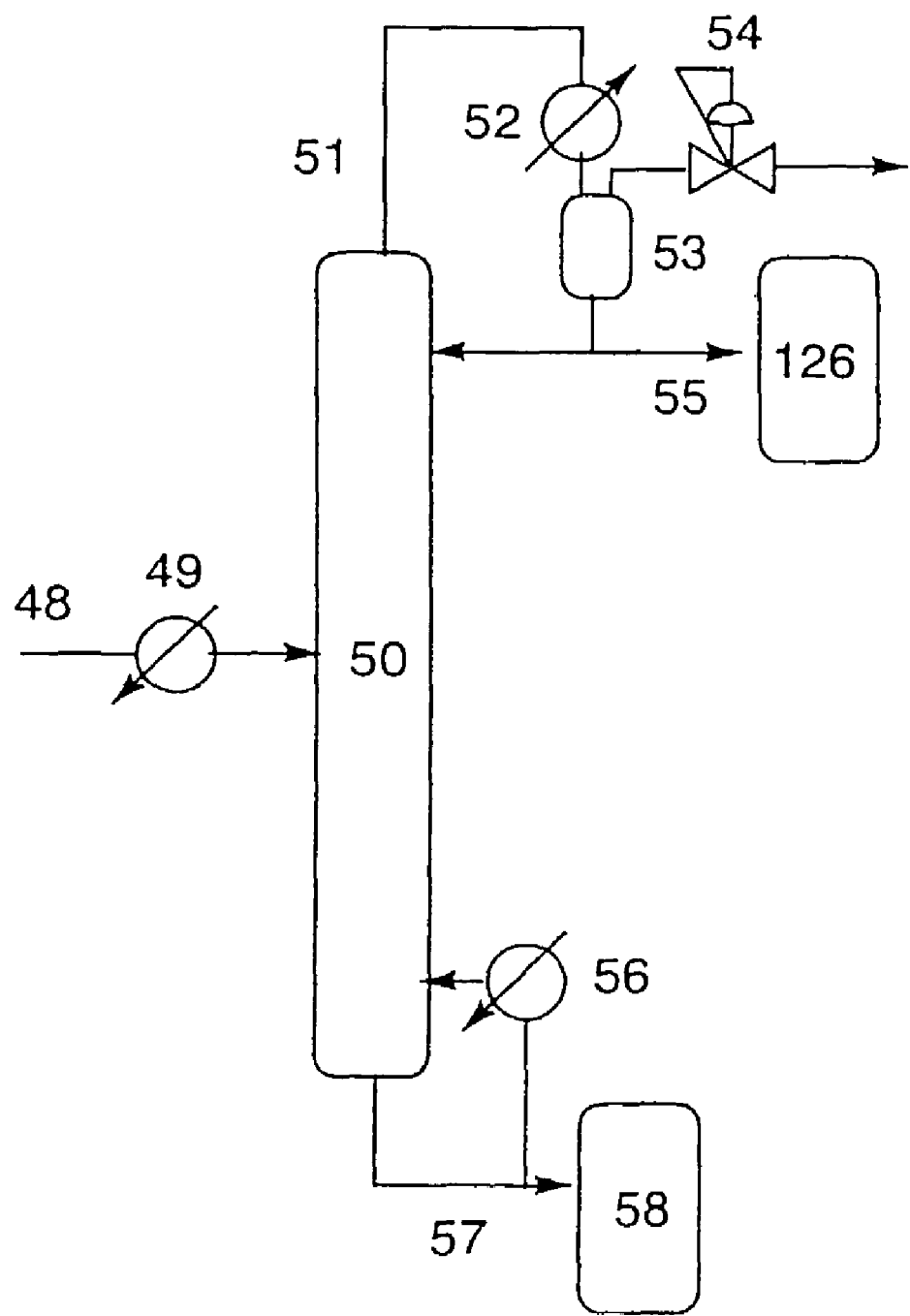
FIG. 6 is a flow chart showing a specific example of step (5) of the method of the present invention.

Using a device as shown in FIG. 6, step (5) was performed as follows.

The liquid collected in reservoir 47 was fed through conduit 48 (equipped with preheater 49) to continuous multi-stage distillation column 50 (inner diameter: about 5 cm; height: 2 m) (which was filled with Dixon packing (6 mmφ)) at a middle portion thereof at a rate of about 203 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The reactive distillation was performed under conditions wherein the temperature of the liquid at the bottom of distillation column 50 was 237° C., the column top pressure was about 26 kPa, and the reflux ratio was about 2. A gas distilled from the top of distillation column 50 was transferred through conduit 51 to condenser 52, to thereby condense the distilled gas. The resultant condensate was continuously withdrawn from condenser 52 through conduit 55 at a rate of about 172 g/hr. The residual liquid in distillation column 50 was continuously withdrawn from the bottom thereof and transferred through conduit 57 to reservoir 58 at a rate of about 31 g/hr.

The condensate withdrawn from distillation column 50 through conduit 55 contained about 400 ppm by weight of 1-butanol, about 13% by weight of phenol, about 84% by weight of dibutyl carbonate and about 3% by weight of butyl phenyl carbonate, based on the weight of the condensate. On the other hand, the residual liquid collected in reservoir 58 contained about 0.1% by weight of dibutyl carbonate, about 27% by weight of butyl phenyl carbonate, and about 64% by weight of diphenyl carbonate, based on the weight of the residual liquid. Further, the residual liquid collected in reservoir 58 had a Pb content of about 9% by weight.

(Recycling of Alcohol)

Using a device as shown in FIG. 7, recycling of the alcohol was performed as follows.

The condensate collected in reservoir 138 in step (4) was fed through conduit 59 (equipped with preheater 60) to continuous multi-stage distillation column 61 (inner diameter: about 5 cm; height: 2 m) (which was filled with Dixon packing (6 mmφ)) at a middle portion thereof at a rate of about 201 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 156° C., the column top pressure was about 40 kPa, and the reflux ratio was about 0.7. A gas distilled from the top of distillation column 61 was transferred through conduit 62 to condenser 63, to thereby condense the distilled gas. The resultant condensate was continuously withdrawn from condenser 63 and transferred through conduit 66 to alcohol reservoir 135 at a rate of about 55 g/hr. The residual liquid in distillation column 61 was continuously withdrawn from the bottom thereof and transferred through conduit 68 to reservoir 69 at a rate of about 146 g/hr.

The condensate collected in reservoir 135 contained almost 100% by weight of 1-butanol, based on the weight of the condensate, and contained substantially no phenol (no phenol was detected in the analysis of the condensate). On the other hand, the residual liquid collected in reservoir 69 contained about 1% by weight of dibutyl carbonate and about 99% by weight of phenol, based on the weight of the residual liquid, and contained substantially no 1-butanol (no 1-butanol was detected in the analysis of the residual liquid).

(Purification of Diaryl Carbonate)

Figure 8:
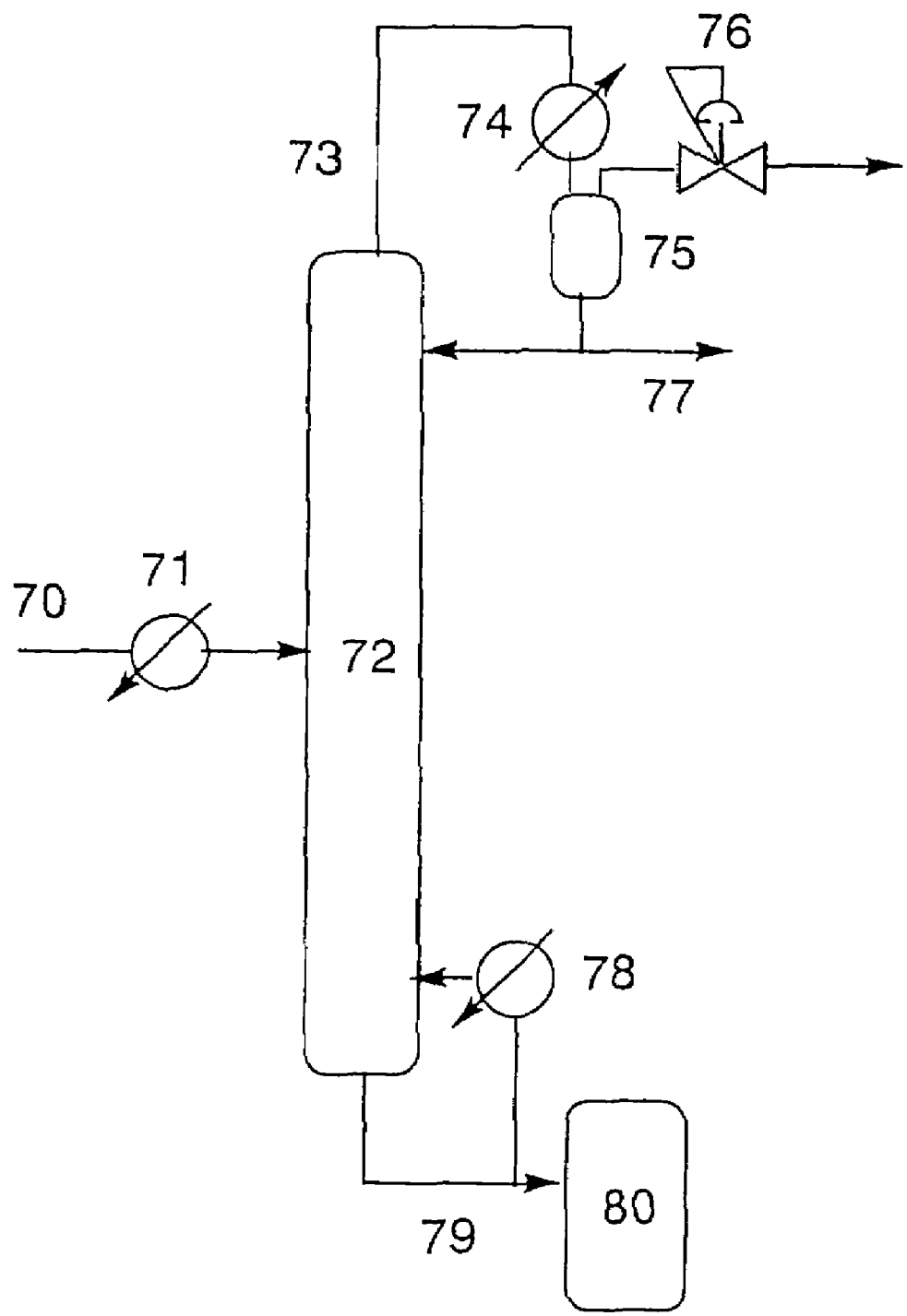
FIG. 8 is a flow chart showing a specific example of the step of purifying a diaryl carbonate, which is performed in the method of the present invention.
Figure 9:
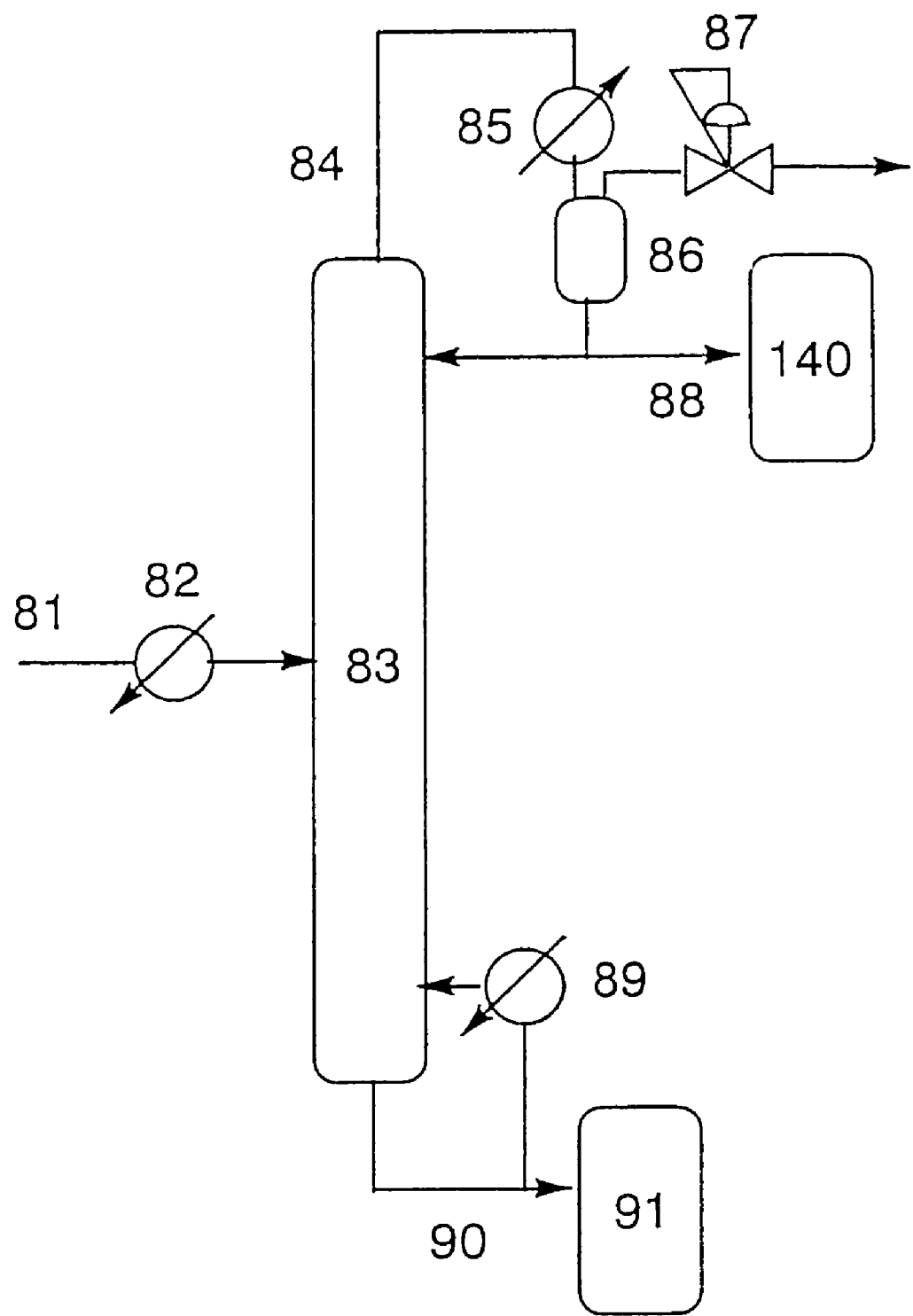
FIG. 9 is a flow chart showing another specific example of the step of purifying a diaryl carbonate, which is performed in the method of the present invention.

Using devices as shown in FIGS. 8 and 9, purification of a diaryl carbonate was performed as follows.

The residual liquid collected in reservoir 58 was fed through conduit 70 (equipped with preheater 71) to continuous multi-stage distillation column 72 (inner diameter: about 5 cm; height: 2 m) (which was filled with Dixon packing (6 mmφ)) at a middle portion thereof at a rate of about 310 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the distilled gas. The resultant condensate was continuously withdrawn from condenser 74 through conduit 77. The residual liquid in distillation column 72 was continuously withdrawn from the bottom thereof and transferred through conduit 79 to reservoir 80 at a rate of about 27 g/hr.

The condensate withdrawn from condenser 74 through conduit 77 contained about 0.1% by weight of dibutyl carbonate, about 30% by weight of butyl phenyl carbonate and about 70% by weight of diphenyl carbonate, based on the weight of the condensate.

Subsequently, the condensate withdrawn from condenser 74 through conduit 77 was fed through conduit 81 (equipped with preheater 82) to continuous multi-stage distillation column 83 (inner diameter: about 5 cm; height: 2 m) (which was filled with Dixon packing (6 mmφ)) at a middle portion thereof at a rate of about 283 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing the distillation. The distillation was performed under conditions wherein the temperature of the liquid at the bottom of distillation column 83 was 248° C., the column top pressure was about 27 kPa, and the reflux ratio was about 4. A gas distilled from the top of distillation column 83 was transferred through conduit 84 to condenser 85, to thereby condense the distilled gas. The resultant condensate was continuously withdrawn from condenser 85 through conduit 88 at a rate of about 85 g/hr. The residual liquid in distillation column 83 was continuously withdrawn from the bottom thereof and transferred through conduit 90 to reservoir 91 at a rate of about 198 g/hr.

The condensate withdrawn from condenser 85 through conduit 88 contained about 0.4% by weight of dibutyl carbonate, about 99% by weight of butyl phenyl carbonate and about 0.2% by weight of diphenyl carbonate, based on the weight of the condensate. On the other hand, the residual liquid collected in reservoir 91 contained about 0.1% by weight of butyl phenyl carbonate and about 99% by weight of diphenyl carbonate, based on the weight of the residual liquid, and contained substantially no chlorine (no chlorine was detected in the analysis of the residual liquid).

EXAMPLE 3

Production of Dibutyltin Dialkoxide

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 2,075 g (28 mol) of 1-butanol (manufactured and sold by Aldrich, U.S.A.), wherein dibutyltin oxide was fed through conduit 4 provided at the top of reaction vessel 1, and 1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing 1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated 11 times (i.e., the above-mentioned operation was performed 12 times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 1,280 g, and that the liquid contained about 2.08 mol of dibutyltin dibutoxide and about 0.76 mol of 1,1,3,3-tetrabutyl-1,3-dibutyloxydistannoxane.

(Step (1))

The liquid obtained in reservoir 23 was fed through conduit 24 to a 1-liter autoclave (manufactured and sold by Toyo Koatsu Co., Ltd., Japan) (which had a carbon dioxide gas bomb connected thereto through a SUS tube and a valve) at a rate of about 500 g/hr. The autoclave was sealed, and the atmosphere in the autoclave was purged with nitrogen gas. Then, the internal temperature of the autoclave was elevated to 120° C., and the above-mentioned valve was opened to introduce carbon dioxide gas having the pressure thereof adjusted to 4 MPa into the autoclave. Then, a reaction was performed while maintaining the internal pressure of the autoclave at about 4 MPa.

During the reaction, a sample of the reaction mixture in the autoclave was taken and analyzed. As a result, it was found that the sample contained about 0.57 mol/kg of dibutyl carbonate.

The reaction mixture in the autoclave was continuously withdrawn from the bottom thereof and collected in reservoir 127.

(Step (2))

Using a device as shown in FIG. 4, step (2) was performed as follows.

After step (1), the reaction mixture collected in reservoir 127 was transferred to vessel 25 for removing carbon dioxide at a rate of about 515 g/hr. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 100 g/hr, and distillation was performed at a reflux ratio of about 0.2. Thin film distillation apparatus 30 was equipped with a heating jacket in which a heating medium having a temperature of 130° C. was circulated, and the internal pressure (column top pressure) was reduced to about 1.3 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from the top of distillation column 27, it was found that dibutyl carbonate was withdrawn and transferred to reservoir 29 at a rate of about 0.06 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 90 g/hr, and that no dibutyl carbonate was detected by gas chromatography (GC).

(Step (3))

Using a device as shown in FIG. 3, step (3) was performed as follows.

After step (2), the residual liquid collected in reservoir 32 was fed through conduit 33 and conduit 35 to a 60-liter SUS reaction vessel 1 at a rate of about 413 g/hr. Further, 1-butanol was fed from reservoir 16 through conduit 3 to reaction vessel 1 at a rate of about 7,412 g/hr (100 mol/hr), and nitrogen gas was fed into reaction vessel 1 through a SUS tube connected to inert gas conduit 2 at a rate of 1.5 Nl/hr.

Subsequently, the contents of reaction vessel 1 were heated while stirring, so as to adjust the temperature thereof within the range of from 113° C. to the boiling point of 1-butanol, thereby performing a reaction while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing 1-butanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dibutyltin dibutoxide and 1,1,3,3-tetrabutyl-1,3-dibutyloxydistannoxane.

The liquid collected in reservoir 23 was recycled to step (1), and a cycle of steps (1) to (3) was repeatedly performed.

(Step (4))

(Preparation of Catalyst)

79 g of phenol and 32 g of lead monoxide were mixed together, and the resultant mixture was charged into a reaction vessel. Then, the mixture was heated at 180° C. for 10 hours while distilling off the by-produced water with phenol at a rate of about 0.25 g/hr. Then, an excess amount of phenol was distilled from an upper portion of the reaction vessel, thereby obtaining catalyst B.

(Production of Aromatic Carbonate)

Using a device as shown in FIG. 5, step (4) was performed as follows.

The condensate (containing dibutyl carbonate) collected in reservoir 29 in step (2), phenol and catalyst B were mixed together to obtain a liquid mixture having a dibutyl carbonate/phenol weight ratio of 65/35 and a Pb content of about 1% by weight. The obtained liquid mixture was continuously fed through conduit 37 (equipped with preheater 38) to continuous multi-stage distillation column 39 (height: 2 m; inner diameter: about 5 cm) having 40 sieve trays at a middle portion thereof at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 231° C., the column top pressure was $2 \times 10^5$ Pa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 67 g/hr. The liquid in distillation column 39 was withdrawn from the bottom thereof and transferred through conduit 46 to reservoir 47 at a rate of about 203 g/hr.

The condensate collected in reservoir 138 contained about 27% by weight of 1-butanol, about 72% by weight of phenol and about 1% by weight of dibutyl carbonate, based on the weight of the condensate. On the other hand, the liquid collected in reservoir 47 contained 330 ppm by weight of 1-butanol, about 11% by weight of phenol, about 65% by weight of dibutyl carbonate, about 21% by weight of butyl phenyl carbonate, and about 1% by weight of diphenyl carbonate, based on the weight of the liquid collected in reservoir 47. Further, the liquid collected in reservoir 47 had a Pb content of about 1% by weight.

(Step (5))

Using a device as shown in FIG. 6, step (5) was performed as follows.

After step (4), the liquid collected in reservoir 47 was fed through conduit 48 (equipped with preheater 49) to continuous multi-stage distillation column 50 (inner diameter: about 5 cm; height: 2 m) having 40 sieve trays at a middle portion thereof at a rate of about 203 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The reactive distillation was performed under conditions wherein the temperature of the liquid at the bottom of distillation column 50 was 237° C., the column top pressure was about 27 kPa, and the reflux ratio was about 2. A gas distilled from the top of distillation column 50 was transferred through conduit 51 to condenser 52, to thereby condense the distilled gas. The resultant condensate was continuously withdrawn from condenser 52 through conduit 55 to reservoir 126 at a rate of about 172 g/hr. The residual liquid in distillation column 50 was continuously withdrawn from the bottom thereof and transferred through conduit 57 to reservoir 58 at a rate of about 31 g/hr.

The condensate collected in reservoir 126 contained about 390 ppm by weight of 1-butanol, about 13% by weight of phenol, about 86% by weight of dibutyl carbonate and about 1% by weight of butyl phenyl carbonate, based on the weight of the condensate. On the other hand, the residual liquid collected in reservoir 58 contained about 500 ppm by weight of dibutyl carbonate, about 26% by weight of butyl phenyl carbonate, and about 65% by weight of diphenyl carbonate, based on the weight of the residual liquid. Further, the residual liquid collected in reservoir 58 had a Pb content of about 8% by weight.

A cycle of the above-mentioned steps (1) to (5) was repeatedly performed.

(Purification of Diaryl Carbonate)

Using a device as shown in FIG. 8, purification of a diaryl carbonate was performed as follows.

The residual liquid collected in reservoir 58 was fed through conduit 70 (equipped with preheater 71) to continuous multi-stage distillation column 72 (inner diameter: about 5 cm; height: 2 m) (which was filled with Dixon packing (6 mmφ)) at a middle portion thereof at a rate of about 310 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the distilled gas. The resultant condensate was continuously withdrawn from condenser 74 through conduit 77. The residual liquid in distillation column 72 was continuously withdrawn from the bottom thereof and transferred through conduit 79 to reservoir 80 at a rate of about 27 g/hr.

EXAMPLE 4

After the operation of Example 3, a cycle of the following steps (1) to (5) was repeatedly performed.

(Step (1))

The liquid obtained in reservoir 23 in step (3) of Example 3 was fed through conduit 24 to a 1-liter autoclave (manufactured and sold by Toyo Koatsu Co., Ltd., Japan) (which had a carbon dioxide gas bomb connected thereto through a SUS tube and a valve) at a rate of 500 g/hr. The autoclave was sealed, and the atmosphere in the autoclave was purged with nitrogen gas. Then, the internal temperature of the autoclave was elevated to 120° C., and the above-mentioned valve was opened to introduce carbon dioxide gas having the pressure thereof adjusted to 4 MPa into the autoclave. Then, a reaction was performed while maintaining the internal pressure of the autoclave at about 4 MPa.

During the reaction, a sample of the reaction mixture in the autoclave was taken and analyzed. As a result, it was found that the sample contained about 0.57 mol/kg of dibutyl carbonate.

The reaction mixture in the autoclave was continuously withdrawn from the bottom thereof and collected in reservoir 127.

(Step (2))

Using a device as shown in FIG. 4, step (2) was performed as follows.

After step (1), the reaction mixture collected in reservoir 127 was transferred to vessel 25 for removing carbon dioxide at a rate of about 515 g/hr. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 100 g/hr, and distillation was performed at a reflux ratio of about 0.2. Thin film distillation apparatus 30 was equipped with a heating jacket in which a heating medium having a temperature of 130° C. was circulated, and the internal pressure (column top pressure) was reduced to about 1.3 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from the top of distillation column 27, it was found that dibutyl carbonate was withdrawn and transferred to reservoir 29 at a rate of about 0.06 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 90 g/hr, and that no dibutyl carbonate was detected by gas chromatography (GC).

(Step (3))

Using a device as shown in FIG. 3, step (3) was performed as follows.

After step (2), the residual liquid collected in reservoir 32 was fed through conduit 35 to a 60-liter SUS reaction vessel 1 at a rate of about 413 g/hr. Further, 1-butanol was fed from reservoir 16 through conduit 3 to reaction vessel 1 at a rate of about 7,412 g/hr (100 mol/hr), and nitrogen gas was fed into reaction vessel 1 through a SUS tube connected to inert gas conduit 2 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing 1-butanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dibutyltin dibutoxide and 1,1,3,3-tetrabutyl-1,3-dibutyloxydistannoxane.

The liquid collected in reservoir 23 was recycled to step (1), and a cycle of steps (1) to (3) was repeatedly performed.

(Step (4))

(Preparation of Catalyst)

79 g of phenol and 32 g of lead monoxide were mixed together, and the resultant mixture was charged into a reaction vessel. Then, the mixture was heated at 180° C. for 10 hours while distilling off the by-produced water with phenol at a rate of about 0.25 g/hr. Then, an excess amount of phenol was distilled from an upper portion of the reaction vessel, thereby obtaining catalyst B.

(Production of Aromatic Carbonate)

Using a device as shown in FIG. 5, step (4) was performed as follows.

The condensate (containing dibutyl carbonate) collected in reservoir 29 in step (2), the condensate (containing dibutyl carbonate) collected in reservoir 126 in step (5) of Example 3, phenol, catalyst B and the liquid (containing Pb) collected in reservoir 80 in the step of the purification of a diaryl carbonate in Example 3 were mixed together to obtain a liquid mixture having a dibutyl carbonate/phenol weight ratio of 65/35 and a Pb content of about 1% by weight. The obtained liquid mixture was continuously fed through conduit 37 (equipped with preheater 38) to continuous multi-stage distillation column 39 (height: 2 m; inner diameter: about 5 cm) having 40 sieve trays at a middle portion thereof at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 231° C., the column top pressure was $2 \times 10^5$ Pa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 67 g/hr. The liquid in distillation column 39 was withdrawn from the bottom thereof and transferred through conduit 46 to reservoir 47 at a rate of about 203 g/hr.

The condensate collected in reservoir 138 contained about 27% by weight of 1-butanol, about 72% by weight of phenol and about 1% by weight of dibutyl carbonate, based on the weight of the condensate. On the other hand, the liquid collected in reservoir 47 contained 330 ppm by weight of 1-butanol, about 11% by weight of phenol, about 65% by weight of dibutyl carbonate, about 21% by weight of butyl phenyl carbonate, and about 1% by weight of diphenyl carbonate, based on the weight of the liquid collected in reservoir 47. Further, the liquid collected in reservoir 47 had a Pb content of about 1% by weight.

(Step (5))

Using a device as shown in FIG. 6, step (5) was performed as follows.

After step (4), the liquid collected in reservoir 47 was fed through conduit 48 (equipped with preheater 49) to continuous multi-stage distillation column 50 (inner diameter: about 5 cm; height: 2 m) at a middle portion thereof at a rate of about 203 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The reactive distillation was performed under conditions wherein the temperature of the liquid at the bottom of distillation column 50 was 237° C., the column top pressure was about 27 kPa, and the reflux ratio was about 2. A gas distilled from the top of distillation column 50 was transferred through conduit 51 to condenser 52, to thereby condense the distilled gas. The resultant condensate was continuously withdrawn from condenser 52 through conduit 55 at a rate of about 172 g/hr. The residual liquid in distillation column 50 was continuously withdrawn from the bottom thereof and transferred through conduit 57 to reservoir 58 at a rate of about 31 g/hr.

The condensate withdrawn from condenser 52 through conduit 55 contained about 390 ppm by weight of 1-butanol, about 13% by weight of phenol, about 86% by weight of dibutyl carbonate and about 1% by weight of butyl phenyl carbonate, based on the weight of the condensate. On the other hand, the residual liquid collected in reservoir 58 contained about 500 ppm by weight of dibutyl carbonate, about 26% by weight of butyl phenyl carbonate, and about 65% by weight of diphenyl carbonate, based on the weight of the residual liquid. Further, the residual liquid collected in reservoir 58 had a Pb content of about 8% by weight.

(Recycling of Alcohol)

Using a device as shown in FIG. 7, recycling of the alcohol was performed as follows.

The condensate collected in reservoir 138 in the above-mentioned step (4) was fed through conduit 59 (equipped with preheater 60) to continuous multi-stage distillation column 61 (inner diameter: about 5 cm; height: 4 m) (which was filled with Dixon packing (6 mmφ)) at a portion thereof which is about 0.4 m above the bottom of distillation column 61 at a rate of about 67 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 164° C., the column top pressure was about 53 kPa, and the reflux ratio was about 0.5. A gas distilled from the top of distillation column 61 was transferred through conduit 62 to condenser 63, to thereby condense the distilled gas. The resultant condensate was continuously withdrawn from condenser 63 and transferred through conduit 66 to alcohol reservoir 135 at a rate of about 18.2 g/hr. The residual liquid in distillation column 61 was continuously withdrawn from the bottom thereof and transferred through conduit 68 to reservoir 69 at a rate of about 48.8 g/hr.

The condensate collected in reservoir 135 contained about 99.9% by weight of 1-butanol and about 150 ppm by weight of phenol, based on the weight of the condensate. On the other hand, the residual liquid collected in reservoir 69 contained about 1% by weight of dibutyl carbonate, about 100 ppm by weight of 1-butanol and about 98% by weight of phenol, based on the weight of the residual liquid.

(Purification of Diaryl Carbonate)

Using devices as shown in FIGS. 8 and 9, purification of a diaryl carbonate was performed as follows.

The residual liquid collected in reservoir 58 in the above-mentioned step (5) was fed through conduit 70 (equipped with preheater 71) to continuous multi-stage distillation column 72 (inner diameter: about 5 cm; height: 2 m) (which was filled with Dixon packing (6 mmφ)) at a middle portion thereof at a rate of about 315 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the distilled gas. The resultant condensate was continuously withdrawn from condenser 74 through conduit 77. The residual liquid in distillation column 72 was continuously withdrawn from the bottom thereof and transferred through conduit 79 to reservoir 80 at a rate of about 27 g/hr.

The condensate withdrawn from condenser 74 through conduit 77 contained about 200 ppm by weight of dibutyl carbonate, about 29% by weight of butyl phenyl carbonate and about 71% by weight of diphenyl carbonate, based on the weight of the condensate.

Subsequently, the condensate withdrawn from condenser 74 through conduit 77 was fed through conduit 81 (equipped with preheater 82) to continuous multi-stage distillation column 83 (inner diameter: about 5 cm; height: 4 m) (which was filled with Dixon packing (6 mmφ)) at a middle portion thereof at a rate of about 288 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing the distillation. The distillation was performed under conditions wherein the temperature of the liquid at the bottom of distillation column 83 was 198° C., the column top pressure was about 6 kPa, and the reflux ratio was about 6. A gas distilled from the top of distillation column 83 was transferred through conduit 84 to condenser 85, to thereby condense the distilled gas. The resultant condensate was continuously withdrawn from condenser 85 through conduit 88 at a rate of about 90 g/hr. The residual liquid in distillation column 83 was continuously withdrawn from the bottom thereof and transferred through conduit 90 to reservoir 91 at a rate of about 198 g/hr.

The condensate withdrawn from condenser 85 through conduit 88 contained about 700 ppm by weight of dibutyl carbonate, about 93% by weight of butyl phenyl carbonate, and about 7% by weight of diphenyl carbonate, based on the weight of the condensate. On the other hand, the residual liquid collected in reservoir 91 contained almost 100% by weight of diphenyl carbonate, based on the weight of the residual liquid, and contained substantially no butyl phenyl carbonate (no butyl phenyl carbonate was detected by the GC analysis of the residual liquid). Further, the residual liquid collected in reservoir 91 contained substantially no chlorine (no chlorine was detected in the analysis of the residual liquid).

EXAMPLE 5

Production of Dioctyltin Dialkoxide

Using a device as shown in FIG. 3, dioctyltin dialkoxides were produced as follows.

Into a 5-liter SUS reaction vessel 1 equipped with a stirrer, a heater and a baffle were charged 108 g (0.3 mol) of dioctyltin oxide and 2,223 g (30 mol) of 1-butanol (manufactured and sold by Aldrich, U.S.A.), wherein dioctyltin oxide was fed through conduit 4 provided at the top of reaction vessel 1, and 1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.5 Nl/hr.

Subsequently, the contents of reaction vessel 1 were heated while stirring, so as to adjust the temperature thereof within the range of from 113° C. to the boiling point of 1-butanol, thereby performing a reaction for about 12 hours while discharging low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing 1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 375 g, and that the liquid contained about 0.50 mol of dioctyltin dibutoxide and about 0.20 mol of 1,1,3,3-tetraoctyl-1,3-dibutyloxydistannoxane.

(Step (1))

About 125 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.05 mol of dibutyl carbonate, and that the whole of the reaction mixture obtained 4 hours after the start of the reaction (i.e., the reaction mixture after the reaction) contained about 0.06 mol of dibutyl carbonate.

After the reaction, the inside of the autoclave was cooled, and carbon dioxide was purged therefrom.

(Step (2))

Using a device as shown in FIG. 4, step (2) was performed as follows.

After step (1), the resultant reaction mixture was withdrawn from the bottom of the autoclave, and transferred through conduit 133 to vessel 25 for removing carbon dioxide, wherein the atmosphere in vessel 25 had been purged with nitrogen. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 90 g/hr, and distillation was performed at a reflux ratio of about 0.2. Thin film distillation apparatus 30 was equipped with a heating jacket in which a heating medium having a temperature of 180° C. was circulated, and the internal pressure (column top pressure) was reduced to about 3 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from the top of distillation column 27, it was found that dibutyl carbonate was withdrawn and transferred to reservoir 29 at a rate of about 0.04 mol/hr, and that substantially no dioctyltin dialkoxide was contained therein. Further, with respect to the residual liquid withdrawn from thin film distillation apparatus 30, it was found that the residual liquid was transferred to reservoir 32 at a rate of about 80 g/hr, and that no dibutyl carbonate was detected by gas chromatography (GC).

(Step (3))

Using a device as shown in FIG. 3, step (3) was performed as follows.

After step (2), the residual liquid collected in reservoir 32 and about 2,223 g (30 mol) of 1-butanol were fed to a 5-liter SUS reaction vessel 1, wherein the residual liquid and 1-butanol were fed through conduit 35 and conduit 3, respectively. Further, nitrogen gas was fed into reaction vessel 1 through a SUS tube connected to inert gas conduit 2 at a rate of 0.5 Nl/hr.

Subsequently, the contents of reaction vessel 1 were heated while stirring, so as to adjust the temperature thereof within the range of from 113° C. to the boiling point of 1-butanol, thereby performing a reaction for about 12 hours while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing 1-butanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dioctyltin dibutoxide and 1,1,3,3-tetraoctyl-1,3-dibutyloxydistannoxane.

The liquid collected in reservoir 23 was recycled to step (1), and a cycle of steps (1) to (3) was repeatedly performed.

(Step (4))

(Preparation of Catalyst)

79 g of phenol and 32 g of lead monoxide were mixed together, and the resultant mixture was charged into a reaction vessel. Then, the mixture was heated at 180° C. for 10 hours while distilling off the by-produced water with phenol, wherein the amount of water distilled off was about 2.5 g. Then, an excess amount of phenol was distilled and withdrawn from an upper portion of the reaction vessel, thereby obtaining catalyst B.

(Production of Aromatic Carbonate)

Using a device as shown in FIG. 5, step (4) was performed as follows.

The condensate (containing dibutyl carbonate) collected in reservoir 29 in step (2), phenol and catalyst B were mixed together to obtain a liquid mixture having a dibutyl carbonate/phenol weight ratio of 65/35 and a Pb content of about 1% by weight. The obtained liquid mixture was continuously fed through conduit 37 (equipped with preheater 38) to continuous multi-stage distillation column 39 (height: 2 m; inner diameter: about 5 cm) at a middle portion thereof at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 239° C., the column top pressure was 250 kPa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 67 g/hr. The liquid in distillation column 39 was withdrawn from the bottom thereof and transferred through conduit 46 to reservoir 47 at a rate of about 203 g/hr.

The condensate collected in reservoir 138 contained about 33% by weight of 1-butanol, about 65% by weight of phenol and about 2% by weight of dibutyl carbonate, based on the weight of the condensate. On the other hand, the liquid collected in reservoir 47 contained about 11% by weight of phenol, about 60% by weight of dibutyl carbonate, about 26% by weight of butyl phenyl carbonate, and about 1.6% by weight of diphenyl carbonate, based on the weight of the liquid collected in reservoir 47. Further, the liquid collected in reservoir 47 had a Pb content of about 1% by weight.

(Step (5))

Using a device as shown in FIG. 6, step (5) was performed as follows.

The liquid collected in reservoir 47 was fed through conduit 48 (equipped with preheater 49) to continuous multi-stage distillation column 50 (inner diameter: about 5 cm; height: 2 m) (which was filled with Dixon packing (6 mmφ)) at a middle portion thereof at a rate of about 203 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The reactive distillation was performed under conditions wherein the temperature of the liquid at the bottom of distillation column 50 was 240° C., the column top pressure was about 27 kPa, and the reflux ratio was about 2. A gas distilled from the top of distillation column 50 was transferred through conduit 51 to condenser 52, to thereby condense the distilled gas. The resultant condensate was continuously withdrawn from condenser 52 and transferred through conduit 55 to reservoir 126 at a rate of about 165 g/hr. The residual liquid in distillation column 50 was continuously withdrawn from the bottom thereof and transferred through conduit 57 to reservoir 58 at a rate of about 39 g/hr.

The condensate collected in reservoir 126 contained about 500 ppm by weight of 1-butanol, about 13% by weight of phenol, about 85% by weight of dibutyl carbonate and about 2% by weight of butyl phenyl carbonate, based on the weight of the condensate. On the other hand, the residual liquid collected in reservoir 58 contained about 0.3% by weight of dibutyl carbonate, about 32% by weight of butyl phenyl carbonate, and about 61% by weight of diphenyl carbonate, based on the weight of the residual liquid. Further, the residual liquid collected in reservoir 58 had a Pb content of about 7% by weight.

(Recycling of Alcohol)

Using a device as shown in FIG. 7, recycling of the alcohol was performed as follows.

The condensate collected in reservoir 138 in step (4) was fed through conduit 59 (equipped with preheater 60) to continuous multi-stage distillation column 61 (inner diameter: about 5 cm; height: 2 m) (which was filled with Dixon packing (6 mmφ)) at a portion thereof which is about 0.7 m above the bottom of distillation column 61 at a rate of about 201 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 145° C., the column top pressure was about 13 kPa, and the reflux ratio was about 0.3. A gas distilled from the top of distillation column 61 was transferred through conduit 62 to condenser 63, to thereby condense the distilled gas. The resultant condensate was continuously withdrawn from condenser 63 and transferred through conduit 66 to alcohol reservoir 135 at a rate of about 68 g/hr. The residual liquid in distillation column 61 was continuously withdrawn from the bottom thereof and transferred through conduit 68 to reservoir 69 at a rate of about 133 g/hr.

The condensate collected in reservoir 135 contained about 99.9% by weight of 1-butanol and about 100 ppm by weight of phenol, based on the weight of the condensate. On the other hand, the residual liquid collected in reservoir 69 contained about 2% by weight of dibutyl carbonate, and about 98% by weight of phenol, based on the weight of the residual liquid.

(Purification of Diaryl Carbonate)

Using devices as shown in FIGS. 8 and 9, purification of a diaryl carbonate was performed as follows.

The residual liquid collected in reservoir 58 in step (5) was fed through conduit 70 (equipped with preheater 71) to continuous multi-stage distillation column 72 (inner diameter: about 5 cm; height: 2 m) (which was filled with Dixon packing (6 mmφ)) at a middle portion thereof at a rate of about 195 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the distilled gas. The resultant condensate was continuously withdrawn from condenser 74 through conduit 77. The residual liquid in distillation column 72 was continuously withdrawn from the bottom thereof and transferred through conduit 79 to reservoir 80 at a rate of about 14 g/hr.

The condensate withdrawn from condenser 74 through conduit 77 contained about 0.3% by weight of dibutyl carbonate, about 34% by weight of butyl phenyl carbonate and about 66% by weight of diphenyl carbonate, based on the weight of the condensate.

Subsequently, the condensate withdrawn from condenser 74 through conduit 77 was fed through conduit 81 (equipped with preheater 82) to continuous multi-stage distillation column 83 (inner diameter: about 5 cm; height: 2 m) (which was filled with Dixon packing (6 mmφ)) at a middle portion thereof at a rate of about 181 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing the distillation. The distillation was performed under conditions wherein the temperature of the liquid at the bottom of distillation column 83 was 232° C., the column top pressure was about 16 kPa, and the reflux ratio was about 2. A gas distilled from the top of distillation column 83 was transferred through conduit 84 to condenser 85, to thereby condense the distilled gas. The resultant condensate was continuously withdrawn from condenser 85 through conduit 88 at a rate of about 62 g/hr. The residual liquid in distillation column 83 was continuously withdrawn from the bottom thereof and transferred through conduit 90 to reservoir 91 at a rate of about 119 g/hr.

The condensate withdrawn from condenser 85 through conduit 88 contained about 0.6% by weight of dibutyl carbonate, about 99% by weight of butyl phenyl carbonate and about 0.4% by weight of diphenyl carbonate, based on the weight of the condensate. On the other hand, the residual liquid collected in reservoir 91 contained about 0.3% by weight of butyl phenyl carbonate and about 99.7% by weight of diphenyl carbonate, based on the weight of the residual liquid.

EXAMPLE 6

Production of Dibutyltin Dialkoxide

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 889 g (12 mol) of 1-butanol (manufactured and sold by Aldrich, U.S.A.), wherein dibutyltin oxide was fed through conduit 4 provided at the top of reaction vessel 1, and 1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing 1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 300 g, and that the liquid contained about 0.24 mol of dibutyltin dibutoxide and about 0.33 mol of 1,1,3,3-tetrabutyl-1,3-dibutyloxydistannoxane.

(Step (1))

About 100 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.02 mol of dibutyl carbonate, and that the whole of the reaction mixture obtained 4 hours after the start of the reaction (i.e., the reaction mixture after the reaction) contained about 0.03 mol of dibutyl carbonate.

After the reaction, the inside of the autoclave was cooled, and carbon dioxide was purged therefrom.

(Step (2))

Using a device as shown in FIG. 4, step (2) was performed as follows.

After step (1), the resultant reaction mixture was withdrawn from the bottom of the autoclave, and transferred through conduit 133 to vessel 25 for removing carbon dioxide, wherein the atmosphere in vessel 25 had been purged with nitrogen. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 80 g/hr, and distillation was performed at a reflux ratio of about 0.2. Thin film distillation apparatus 30 was equipped with a heating jacket in which a heating medium having a temperature of 100° C. was circulated, and the internal pressure (column top pressure) was reduced to about 1.3 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from the top of distillation column 27, it was found that dibutyl carbonate was withdrawn and transferred to reservoir 29 at a rate of about 0.02 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 77 g/hr, and that no dibutyl carbonate was detected by gas chromatography (GC).

(Step (3))

Using a device as shown in FIG. 3, step (3) was performed as follows.

After step (2), the residual liquid collected in reservoir 32 and about 889 g (12 mol) of 1-butanol were fed to a 5-liter SUS reaction vessel 1, wherein the residual liquid and 1-butanol were fed through conduit 35 and conduit 3, respectively. Further, nitrogen gas was fed into reaction vessel 1 through a SUS tube connected to inert gas conduit 2 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing 1-butanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dibutyltin dibutoxide and 1,1,3,3-tetrabutyl-1,3-dibutyloxydistannoxane.

The liquid collected in reservoir 23 was recycled to step (1), and a cycle of steps (1) to (3) was repeatedly performed.

(Step (4))

(Preparation of Catalyst)

79 g of phenol and 32 g of lead monoxide were mixed together, and the resultant mixture was charged into a reaction vessel. Then, the mixture was heated at 180° C. for 10 hours while distilling off the by-produced water with phenol, wherein the amount of water distilled off was about 2.5 g. Then, an excess amount of phenol was distilled from an upper portion of the reaction vessel, thereby obtaining catalyst B.

(Production of Aromatic Carbonate)

Using a device as shown in FIG. 5, step (4) was performed as follows.

The condensate (containing dibutyl carbonate) collected in reservoir 29 in step (2), phenol and catalyst B were mixed together to obtain a liquid mixture having a dibutyl carbonate/phenol weight ratio of 65/35 and a Pb content of about 1% by weight. The obtained liquid mixture was continuously fed through conduit 37 (equipped with preheater 38) to continuous multi-stage distillation column 39 (height: 2 m; inner diameter: about 5 cm) at a middle portion thereof at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 215° C., the column top pressure was about 150 kPa, and the reflux ratio was about 2. A gas discharged from the top of distillation column 39 was transferred through conduit 40 to condenser 41, to thereby condense the gas. The resultant condensate was withdrawn from condenser 41 and transferred through conduit 44 to reservoir 138 at a rate of about 16 g/hr. The liquid in distillation column 39 was withdrawn from the bottom thereof and transferred through conduit 46 to reservoir 47 at a rate of about 254 g/hr.

The condensate collected in reservoir 138 contained about 53% by weight of 1-butanol, and about 47% by weight of phenol, based on the weight of the condensate. On the other hand, the liquid collected in reservoir 47 contained about 29% by weight of phenol, about 60% by weight of dibutyl carbonate, about 9% by weight of butyl phenyl carbonate, and about 0.5% by weight of diphenyl carbonate, based on the weight of the liquid collected in reservoir 47. Further, the liquid collected in reservoir 47 had a Pb content of about 1% by weight.

(Step (5))

Using a device as shown in FIG. 6, step (5) was performed as follows.

The liquid collected in reservoir 47 in step (4) was fed through conduit 48 (equipped with preheater 49) to a middle portion of a continuous multi-stage distillation column 50 (inner diameter: about 5 cm; height: 2 m) (which was filled with Dixon packing (6 mmφ)) at a rate of about 254 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The reactive distillation was performed under conditions wherein the temperature of the liquid at the bottom of distillation column 50 was 235° C., the column top pressure was about 26 kPa, and the reflux ratio was about 2. A gas distilled from the top of distillation column 50 was transferred through conduit 51 to condenser 52, to thereby condense the distilled gas. The resultant condensate was continuously withdrawn from condenser 52 and transferred through conduit 55 to reservoir 126 at a rate of about 238 g/hr. The residual liquid in distillation column 50 was continuously withdrawn from the bottom thereof and transferred through conduit 57 to reservoir 58 at a rate of about 16 g/hr.

The condensate withdrawn from distillation column 50 through conduit 55 contained about 0.1% by weight of 1-butanol, about 31% by weight of phenol, about 67% by weight of dibutyl carbonate and about 1% by weight of butyl phenyl carbonate, based on the weight of the condensate. On the other hand, the residual liquid collected in reservoir 58 contained about 0.1% by weight of dibutyl carbonate, about 25% by weight of butyl phenyl carbonate, and about 58% by weight of diphenyl carbonate, based on the weight of the residual liquid. Further, the residual liquid collected in reservoir 58 had a Pb content of about 17% by weight.

(Recycling of Alcohol)

Using a device as shown in FIG. 7, recycling of the alcohol was performed as follows.

The condensate collected in reservoir 138 in step (4) was fed through conduit 59 (equipped with preheater 60) to continuous multi-stage distillation column 61 (inner diameter: about 5 cm; height: 2 m) (which was filled with Dixon packing (6 mmφ)) at a portion thereof which is about 0.8 m above the bottom of distillation column 61 at a rate of about 168 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 145° C., the column top pressure was about 27 kPa, and the reflux ratio was about 0.3. A gas distilled from the top of distillation column 61 was transferred through conduit 62 to condenser 63, to thereby condense the distilled gas. The resultant condensate was continuously withdrawn from condenser 63 and transferred through conduit 66 to alcohol reservoir 135 at a rate of about 90 g/hr. The residual liquid in distillation column 61 was continuously withdrawn from the bottom thereof and transferred through conduit 68 to reservoir 69 at a rate of about 78 g/hr.

The condensate collected in reservoir 135 contained about 99.9% by weight of 1-butanol and about 150 ppm by weight of phenol, based on the weight of the condensate. On the other hand, the residual liquid collected in reservoir 69 contained about 0.2% by weight of dibutyl carbonate, about 100 ppm by weight of 1-butanol, and about 99% by weight of phenol, based on the weight of the residual liquid.

(Purification of Diaryl Carbonate)

Using devices as shown in FIGS. 8 and 9, purification of a diaryl carbonate was performed as follows.

The residual liquid collected in reservoir 58 in step (5) was fed through conduit 70 (equipped with preheater 71) to continuous multi-stage distillation column 72 (inner diameter: about 5 cm; height: 2 m) (which was filled with Dixon packing (6 mmφ)) at a middle portion thereof at a rate of about 163 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the distilled gas. The resultant condensate was continuously withdrawn from condenser 74 through conduit 77. The residual liquid in distillation column 72 was continuously withdrawn from the bottom thereof and transferred through conduit 79 to reservoir 80 at a rate of about 27 g/hr.

The condensate withdrawn from condenser 74 through conduit 77 contained about 0.1% by weight of dibutyl carbonate, about 30% by weight of butyl phenyl carbonate and about 70% by weight of diphenyl carbonate, based on the weight of the condensate.

Subsequently, the condensate withdrawn from condenser 74 through conduit 77 was fed through conduit 81 (equipped with preheater 82) to continuous multi-stage distillation column 83 (inner diameter: about 5 cm; height: 2 m) (which was filled with Dixon packing (6 mmφ)) at a middle portion thereof at a rate of about 136 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing the distillation. The distillation was performed under conditions wherein the temperature of the liquid at the bottom of distillation column 83 was 233° C., the column top pressure was about 17 kPa, and the reflux ratio was about 3. A gas distilled from the top of distillation column 83 was transferred through conduit 84 to condenser 85, to thereby condense the distilled gas. The resultant condensate was continuously withdrawn from condenser 85 through conduit 88 at a rate of about 41 g/hr. The residual liquid in distillation column 83 was continuously withdrawn from the bottom thereof and transferred through conduit 90 to reservoir 91 at a rate of about 95 g/hr.

The condensate withdrawn from condenser 85 through conduit 88 contained about 0.3% by weight of dibutyl carbonate, about 99% by weight of butyl phenyl carbonate and about 0.3% by weight of diphenyl carbonate, based on the weight of the condensate. On the other hand, the residual liquid collected in reservoir 91 contained about 0.1% by weight of butyl phenyl carbonate and about 99% by weight of diphenyl carbonate, based on the weight of the residual liquid.

EXAMPLE 7

Production of Dibutyltin Dialkoxide

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 2,223 g (30 mol) of 1-butanol (manufactured and sold by Aldrich, U.S.A.), wherein dibutyltin oxide was fed through conduit 4 provided at the top of reaction vessel 1, and 1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing 1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 320 g, and that the liquid contained about 0.54 mol of dibutyltin dibutoxide and about 0.18 mol of 1,1,3,3-tetrabutyl-1,3-dibutyloxydistannoxane.

(Step (1))

About 107 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture 1 hour after the start of the reaction contained 0.06 mol of dibutyl carbonate, and that the whole of the reaction mixture obtained 4 hours after the start of the reaction (i.e., the reaction mixture after the reaction) contained about 0.07 mol of dibutyl carbonate.

After the reaction, the inside of the autoclave was cooled, and carbon dioxide was purged therefrom.

(Step (2))

Figure 11:
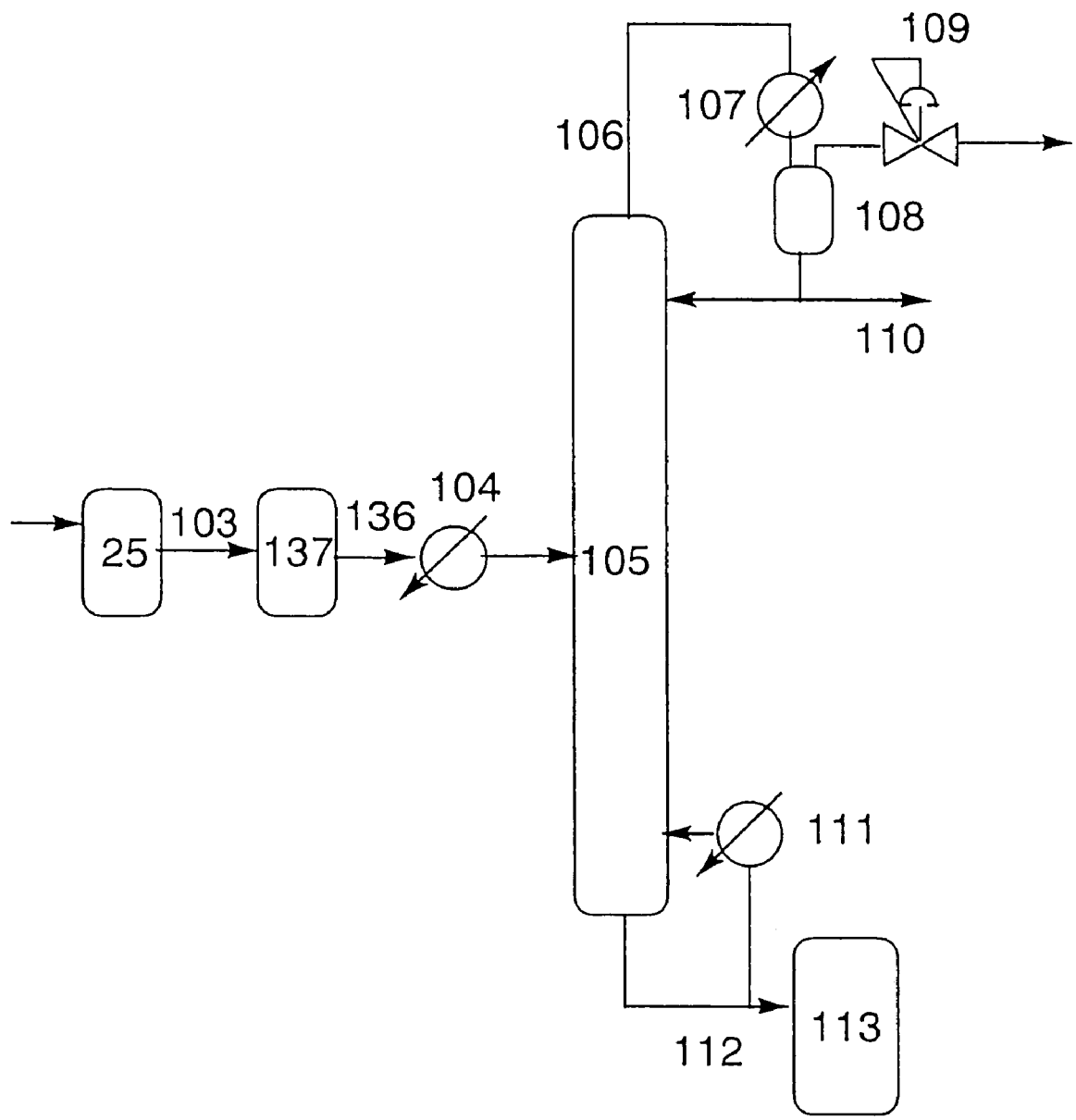
FIG. 11 is a flow chart showing a specific example of the step of purifying a dialkyl carbonate, which is performed in the method of the present invention.

Using a device as shown in FIG. 11, step (2) was performed as follows.

After step (1), the resultant reaction mixture was withdrawn from the bottom of the autoclave, and transferred to vessel 25 for removing carbon dioxide, wherein the atmosphere in vessel 25 had been purged with nitrogen. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 103 and collected in reservoir 137.

Subsequently, the liquid collected in reservoir 137 was fed through conduit 136 (equipped with preheater 104) to multistage distillation column 105 (inner diameter: 5 cm; height: 2 m) at a middle portion thereof at a rate of about 106 g/hr, to thereby perform a distillation. During the distillation, the liquid in distillation column 105 was withdrawn from the bottom thereof. A portion of the withdrawn liquid was transferred through conduit 112 to reboiler 111 and, then, recycled to distillation column 105, so as to supply a sufficient amount of heat for performing the distillation. The distillation was performed under conditions wherein the temperature of the liquid at the bottom of distillation column 105 was 170° C., the column top pressure was about 1 kPa, and the reflux ratio was about 1. A gas distilled from the top of distillation column 105 was transferred through conduit 106 to condenser 107, to thereby condense the distilled gas. The resultant condensate was continuously withdrawn from condenser 107 through conduit 110. The residual liquid in distillation column 105 was continuously withdrawn from the bottom thereof and transferred through conduit 112 to reservoir 113. With respect to the resultant condensate withdrawn from condenser 107 through conduit 110, it was found that the condensate was withdrawn from condenser 107 at a rate of about 12 g/hr, and that substantially no dibutyltin dialkoxide was contained therein. Further, with respect to the residual liquid withdrawn from distillation column 105, it was found that the residual liquid was transferred to reservoir 113 at a rate of about 94 g/hr, and that no dibutyl carbonate was detected by gas chromatography (GC).

(Step (3))

Using a device as shown in FIG. 3, step (3) was performed as follows.

After step (2), the residual liquid collected in reservoir 113 and about 2,223 g (30 mol) of 1-butanol were fed to a 5-liter SUS reaction vessel 1, wherein the residual liquid and 1-butanol were fed through conduit 35 and conduit 3, respectively. Further, nitrogen gas was fed into reaction vessel 1 through a SUS tube connected to inert gas conduit 2 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing 1-butanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dibutyltin dibutoxide and 1,1,3,3-tetrabutyl-1,3-dibutyloxydistannoxane.

The liquid collected in reservoir 23 was recycled to step (1), and a cycle of steps (1) to (3) was repeatedly performed.

(Step (4))

(Preparation of Catalyst)

79 g of phenol and 32 g of lead monoxide were mixed together, and the resultant mixture was charged into a reaction vessel. Then, the mixture was heated at 180° C. for 10 hours while distilling off the by-produced water with phenol, wherein the amount of water distilled off was about 2.5 g. Then, an excess amount of phenol was distilled from an upper portion of the reaction vessel, thereby obtaining catalyst B.

(Production of Aromatic Carbonate)

Using a device as shown in FIG. 5, step (4) was performed as follows.

The condensate (containing dibutyl carbonate) obtained in step (2), phenol and catalyst B were mixed together to obtain a liquid mixture having a dibutyl carbonate/phenol weight ratio of 65/35 and a Pb content of about 1% by weight. The obtained liquid mixture was continuously fed through conduit 37 (equipped with preheater 38) to a middle portion of continuous multi-stage distillation column 39 (height: 2 m; inner diameter: about 5 cm) (which had 40 sieve trays) at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 230° C., the column top pressure was about 150 kPa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 67 g/hr. The liquid in distillation column 39 was withdrawn from the bottom thereof and transferred through conduit 46 to reservoir 47 at a rate of about 203 g/hr.

The condensate collected in reservoir 138 contained about 22% by weight of 1-butanol, about 75% by weight of phenol and about 3% by weight of dibutyl carbonate, based on the weight of the condensate. On the other hand, the liquid collected in reservoir 47 contained about 12% by weight of phenol, about 68% by weight of dibutyl carbonate, about 17% by weight of butyl phenyl carbonate, and about 1% by weight of diphenyl carbonate, based on the weight of the liquid collected in reservoir 47. Further, the liquid collected in reservoir 47 had a Pb content of about 1% by weight.

(Step (5))

Using a device as shown in FIG. 6, step (5) was performed as follows.

The liquid collected in reservoir 47 in step (4) was fed through conduit 48 (equipped with preheater 49) to a continuous multi-stage distillation column 50 (inner diameter: about 5 cm; height: 2 m) (which was filled with Dixon packing (6 mmφ)) at a middle portion thereof at a rate of about 203 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The reactive distillation was performed under conditions wherein the temperature of the liquid at the bottom of distillation column 50 was 237° C., the column top pressure was about 26 kPa, and the reflux ratio was about 2. A gas distilled from the top of distillation column 50 was transferred through conduit 51 to condenser 52, to thereby condense the distilled gas. The resultant condensate was continuously withdrawn from condenser 52 and transferred through conduit 55 to reservoir 126 at a rate of about 178 g/hr. The residual liquid in distillation column 50 was continuously withdrawn from the bottom thereof and transferred through conduit 57 to reservoir 58 at a rate of about 25 g/hr.

The condensate collected in reservoir 126 contained about 400 ppm by weight of 1-butanol, about 14% by weight of phenol, about 83% by weight of dibutyl carbonate and about 3% by weight of butyl phenyl carbonate, based on the weight of the condensate. On the other hand, the residual liquid collected in reservoir 58 contained about 0.1% by weight of dibutyl carbonate, about 34% by weight of butyl phenyl carbonate, and about 55% by weight of diphenyl carbonate, based on the weight of the residual liquid. Further, the residual liquid collected in reservoir 58 had a Pb content of about 11% by weight.

(Recycling of Alcohol)

Using a device as shown in FIG. 7, recycling of the alcohol was performed as follows.

The condensate collected in reservoir 138 in step (4) was fed through conduit 59 (equipped with preheater 60) to a continuous multi-stage distillation column 61 (inner diameter: about 5 cm; height: 2 m) (which was filled with Dixon packing (6 mmφ)) at a middle portion thereof at a rate of about 201 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 124° C., the column top pressure was about 9 kPa, and the reflux ratio was about 0.5. A gas distilled from the top of distillation column 61 was transferred through conduit 62 to condenser 63, to thereby condense the distilled gas. The resultant condensate was continuously withdrawn from condenser 63 and transferred through conduit 66 to alcohol reservoir 135 at a rate of about 44 g/hr. The residual liquid in distillation column 61 was continuously withdrawn from the bottom thereof and transferred through conduit 68 to reservoir 69 at a rate of about 157 g/hr.

The condensate collected in reservoir 135 contained almost 100% by weight of 1-butanol, based on the weight of the condensate, and contained substantially no phenol (no phenol was detected in the analysis of the condensate). On the other hand, the residual liquid collected in reservoir 69 contained about 4% by weight of dibutyl carbonate and about 96% by weight of phenol, based on the weight of the residual liquid.

(Purification of Diaryl Carbonate)

Using devices as shown in FIGS. 8 and 9, purification of a diaryl carbonate was performed as follows.

The residual liquid collected in reservoir 58 in step (5) was fed through conduit 70 (equipped with preheater 71) to a middle portion of a continuous multi-stage distillation column 72 (inner diameter: about 5 cm; height: 2 m) (which was filled with Dixon packing (6 mmφ)) at a rate of about 252 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the distilled gas. The resultant condensate was continuously withdrawn from condenser 74 through conduit 77. The residual liquid in distillation column 72 was continuously withdrawn from the bottom thereof and transferred through conduit 79 to reservoir 80 at a rate of about 27 g/hr.

The condensate withdrawn from condenser 74 through conduit 77 contained about 0.1% by weight of dibutyl carbonate, about 38% by weight of butyl phenyl carbonate and about 62% by weight of diphenyl carbonate, based on the weight of the condensate.

Subsequently, the condensate withdrawn from condenser 74 through conduit 77 was fed through conduit 81 (equipped with preheater 82) to a middle portion of a continuous multi-stage distillation column 83 (inner diameter: about 5 cm; height: 2 m) (which was filled with Dixon packing (6 mmφ)) at a rate of about 225 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing the distillation. The distillation was performed under conditions wherein the temperature of the liquid at the bottom of distillation column 83 was 227° C., the column top pressure was about 13 kPa, and the reflux ratio was about 4. A gas distilled from the top of distillation column 83 was transferred through conduit 84 to condenser 85, to thereby condense the distilled gas. The resultant condensate was continuously withdrawn from condenser 85 through conduit 88 at a rate of about 87 g/hr. The residual liquid in distillation column 83 was continuously withdrawn from the bottom thereof and transferred through conduit 90 to reservoir 91 at a rate of about 138 g/hr.

The condensate withdrawn from condenser 85 through conduit 88 contained about 0.3% by weight of dibutyl carbonate, about 99% by weight of butyl phenyl carbonate and about 0.1% by weight of diphenyl carbonate, based on the weight of the condensate. On the other hand, the residual liquid collected in reservoir 91 contained about 400 ppm by weight of butyl phenyl carbonate and almost 100% by weight of diphenyl carbonate, based on the weight of the residual liquid.

EXAMPLE 8

Production of Dibutyltin Dialkoxide

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 2,333 g (30 mol) of isobutanol (manufactured and sold by Aldrich, U.S.A.), wherein dibutyltin oxide was fed through conduit 4 provided at the top of reaction vessel 1, and isobutanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr.

Subsequently, the contents of reaction vessel 1 were heated while stirring, so as to adjust the temperature thereof within the range of from 107° C. to the boiling point of isobutanol, thereby performing a reaction for about 6 hours while discharging low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing isobutanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 320 g, and that the liquid contained about 0.56 mol of dibutyltin diisobutoxide and about 0.17 mol of 1,1,3,3-tetrabutyl-1,3-diisobutyloxydistannoxane.

(Step (1))

About 107 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.06 mol of diisobutyl carbonate, and that the whole of the reaction mixture obtained 4 hours after the start of the reaction (i.e., the reaction mixture after the reaction) contained about 0.07 mol of diisobutyl carbonate.

After the reaction, the inside of the autoclave was cooled, and carbon dioxide was purged therefrom.

(Step (2))

Using a device as shown in FIG. 4, step (2) was performed as follows.

After step (1), the resultant reaction mixture was withdrawn from the bottom of the autoclave, and transferred through conduit 133 to vessel 25 for removing carbon dioxide, wherein the atmosphere in vessel 25 had been purged with nitrogen. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 100 g/hr, and distillation was performed at a reflux ratio of about 0.2. Thin film distillation apparatus 30 was equipped with a heating jacket in which a heating medium having a temperature of 130° C. was circulated, and the internal pressure (column top pressure) was reduced to about 2.7 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from the top of distillation column 27, it was found that diisobutyl carbonate was withdrawn and transferred to reservoir 29 at a rate of about 0.07 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 90 g/hr, and that no diisobutyl carbonate was detected by gas chromatography (GC).

(Step (3))

Using a device as shown in FIG. 3, step (3) was performed as follows.

After step (2), the residual liquid collected in reservoir 32 and about 2,150 g (29 mol) of isobutanol were fed to a 5-liter SUS reaction vessel 1, wherein the residual liquid and isobutanol were fed through conduit 35 and conduit 3, respectively. Further, nitrogen gas was fed into reaction vessel 1 through a SUS tube connected to inert gas conduit 2 at a rate of 0.1 Nl/hr.

Subsequently, the contents of reaction vessel 1 were heated while stirring, so as to adjust the temperature thereof within the range of from 107° C. to the boiling point of isobutanol, thereby performing a reaction for about 6 hours while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing isobutanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dibutyltin diisobutoxide and 1,1,3,3-tetrabutyl-1,3-diisobutyloxydistannoxane.

The liquid collected in reservoir 23 was recycled to step (1), and a cycle of steps (1) to (3) was repeatedly performed.

(Step (4))

(Preparation of Catalyst)

40 g of phenol and 8 g of lead monoxide were mixed together, and the resultant mixture was heated at 180° C. for 10 hours while distilling off the by-produced water with phenol, thereby obtaining catalyst A.

(Production of Aromatic Carbonate)

Using a device as shown in FIG. 5, step (4) was performed as follows.

The condensate (containing diisobutyl carbonate) collected in reservoir 29 in step (2), phenol and catalyst A were mixed together to obtain a liquid mixture having a diisobutyl carbonate/phenol weight ratio of 65/35 and a Pb content of about 1% by weight. The obtained liquid mixture was continuously fed through conduit 37 (equipped with preheater 38) to continuous multi-stage distillation column 39 (height: 2 m; inner diameter: about 5 cm) (which had 40 sieve trays) at a middle portion thereof at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 231° C., the column top pressure was $2 \times 10^5$ Pa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 42 g/hr. The liquid in distillation column 39 was withdrawn from the bottom thereof and transferred through conduit 46 to reservoir 47 at a rate of about 228 g/hr.

The condensate collected in reservoir 138 contained about 33% by weight of isobutanol, about 66.5% by weight of phenol and about 0.5% by weight of diisobutyl carbonate, based on the weight of the condensate. On the other hand, the liquid collected in reservoir 47 contained about 21% by weight of phenol, about 62% by weight of diisobutyl carbonate, about 15% by weight of isobutyl phenyl carbonate, and about 1% by weight of diphenyl carbonate, based on the weight of the liquid collected in reservoir 47. Further, the liquid collected in reservoir 47 had a Pb content of about 1% by weight.

(Step (5))

Using a device as shown in FIG. 6, step (5) was performed as follows.

The liquid collected in reservoir 47 in step (4) was fed through conduit 48 (equipped with preheater 49) to a continuous multi-stage distillation column 50 (inner diameter: about 5 cm; height: 2 m) (which was filled with Dixon packing (6 mmφ)) at a middle portion thereof at a rate of about 228 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The reactive distillation was performed under conditions wherein the temperature of the liquid at the bottom of distillation column 50 was 239° C., the column top pressure was about 30 kPa, and the reflux ratio was about 2. A gas distilled from the top of distillation column 50 was transferred through conduit 51 to condenser 52, to thereby condense the distilled gas. The resultant condensate was continuously withdrawn from condenser 52 through conduit 55 at a rate of about 206 g/hr. The residual liquid in distillation column 50 was continuously withdrawn from the bottom thereof and transferred through conduit 57 to reservoir 58 at a rate of about 22 g/hr.

The condensate withdrawn from condenser 52 through conduit 55 contained about 0.2% by weight of isobutanol, about 23% by weight of phenol, about 73% by weight of diisobutyl carbonate and about 4% by weight of isobutyl phenyl carbonate, based on the weight of the condensate. On the other hand, the residual liquid collected in reservoir 58 contained about 0.1% by weight of diisobutyl carbonate, about 28% by weight of isobutyl phenyl carbonate and about 60% by weight of diphenyl carbonate, based on the weight of the residual liquid. Further, the residual liquid collected in reservoir 58 had a Pb content of about 12% by weight.

(Recycling of Alcohol)

Using a device as shown in FIG. 7, recycling of the alcohol was performed as follows.

The condensate collected in reservoir 138 in step (4) was fed through conduit 59 (equipped with preheater 60) to a continuous multi-stage distillation column 61 (inner diameter: about 5 cm; height: 2 m) (which was filled with Dixon packing (6 mmφ)) at a middle portion thereof at a rate of about 210 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 175° C., the column top pressure was about 80 kPa, and the reflux ratio was about 0.3. A gas distilled from the top of distillation column 61 was transferred through conduit 62 to condenser 63, to thereby condense the distilled gas. The resultant condensate was continuously withdrawn from condenser 63 and transferred through conduit 66 to alcohol reservoir 135 at a rate of about 69 g/hr. The residual liquid in distillation column 61 was continuously withdrawn from the bottom thereof and transferred through conduit 68 to reservoir 69 at a rate of about 141 g/hr.

The condensate collected in reservoir 135 contained about 99.9% by weight of isobutanol and about 400 ppm by weight of phenol, based on the weight of the condensate. On the other hand, the residual liquid collected in reservoir 69 contained about 0.7% by weight of diisobutyl carbonate, about 300 ppm by weight of isobutanol, and about 99% by weight of phenol, based on the weight of the residual liquid.

(Purification of Diaryl Carbonate)

Using devices as shown in FIGS. 8 and 9, purification of a diaryl carbonate was performed as follows.

The residual liquid collected in reservoir 58 in step (5) was fed through conduit 70 (equipped with preheater 71) to a continuous multi-stage distillation column 72 (inner diameter: about 5 cm; height: 2 m) (which was filled with Dixon packing (6 mm$\phi$)) at a middle portion thereof at a rate of about 220 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the distilled gas. The resultant condensate was continuously withdrawn from condenser 74 through conduit 77. The residual liquid in distillation column 72 was continuously withdrawn from the bottom thereof and transferred through conduit 79 to reservoir 80 at a rate of about 27 g/hr.

The condensate withdrawn from condenser 74 through conduit 77 contained about 1,000 ppm by weight of diisobutyl carbonate, about 32% by weight of isobutyl phenyl carbonate and about 68% by weight of diphenyl carbonate, based on the weight of the condensate.

Subsequently, the condensate withdrawn from condenser 74 through conduit 77 was fed through conduit 81 (equipped with preheater 82) to a continuous multi-stage distillation column 83 (inner diameter: about 5 cm; height: 4 m) (which was filled with Dixon packing (6 mm$\phi$)) at a middle portion thereof at a rate of about 193 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing the distillation. The distillation was performed under conditions wherein the temperature of the liquid at the bottom of distillation column 83 was 211° C., the column top pressure was about 7 kPa, and the reflux ratio was about 2. A gas distilled from the top of distillation column 83 was transferred through conduit 84 to condenser 85, to thereby condense the distilled gas. The resultant condensate was continuously withdrawn from condenser 85 through conduit 88 at a rate of about 61 g/hr. The residual liquid in distillation column 83 was continuously withdrawn from the bottom thereof and transferred through conduit 90 to reservoir 91 at a rate of about 132 g/hr.

The condensate withdrawn from condenser 85 through conduit 88 contained about 0.3% by weight of diisobutyl carbonate, about 99% by weight of butyl phenyl carbonate and about 0.1% by weight of diphenyl carbonate, based on the weight of the condensate. On the other hand, the residual liquid collected in reservoir 91 contained about 500 ppm by weight of butyl phenyl carbonate and almost 100% by weight of diphenyl carbonate, based on the weight of the residual liquid.

EXAMPLE 9

Production of Dibutyltin Dialkoxide

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 4,837 g (21 mol) of 2-ethyl-1-butanol (manufactured and sold by Aldrich, U.S.A.), wherein dibutyltin oxide was fed through conduit 4 provided at the top of reaction vessel 1, and 2-ethyl-1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 1.0 Nl/hr.

Subsequently, the contents of reaction vessel 1 were heated while stirring, so as to adjust the temperature thereof at about 120° C., thereby performing a reaction for about 6 hours while discharging low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing 2-ethyl-1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 360 g, and that the liquid contained about 0.60 mol of dibutyltin bis(2-ethyl-1-butoxide) and about 0.15 mol of 1,1,3,3-tetrabutyl-1,3-bis(2-ethyl-1-butyloxy)distannoxane.

(Step (1))

About 120 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.07 mol of bis(2-ethylbutyl) carbonate, and that the whole of the reaction mixture obtained 4 hours after the start of the reaction (i.e., the reaction mixture after the reaction) contained about 0.08 mol of bis(2-ethylbutyl) carbonate.

After the reaction, the inside of the autoclave was cooled, and carbon dioxide was purged therefrom.

(Step (2))

Using a device as shown in FIG. 4, step (2) was performed as follows.

After step (1), the resultant reaction mixture was withdrawn from the bottom of the autoclave, and transferred through conduit 133 to vessel 25 for removing carbon dioxide, wherein the atmosphere in vessel 25 had been purged with nitrogen. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmϕ). The liquid collected in reservoir 131 was fed to multi-stage distillation column 27 through conduit 132 (which was provided at a middle portion of distillation column 27) at a rate of about 90 g/hr, and distillation was performed at a reflux ratio of about 0.2. Thin film distillation apparatus 30 was equipped with a heating jacket in which a heating medium having a temperature of 180° C. was circulated, and the internal pressure (column top pressure) was reduced to about 2.7 kPa. The volatilized components were withdrawn from distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from distillation column 27, it was found that bis(2-ethylbutyl) carbonate was withdrawn and transferred to reservoir 29 at a rate of about 0.06 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 80 g/hr, and that no bis(2-ethylbutyl) carbonate was detected by gas chromatography (GC).

(Step (3))

Using a device as shown in FIG. 3, step (3) was performed as follows.

After step (2), the residual liquid collected in reservoir 32 and about 4,837 g (21 mol) of 2-ethyl-1-butanol were fed to a 5-liter SUS reaction vessel 1, wherein the residual liquid and 2-ethyl-1-butanol were fed through conduit 35 and conduit 3, respectively. Further, nitrogen gas was fed into reaction vessel 1 through a SUS tube connected to inert gas conduit 2 at a rate of 1.0 Nl/hr.

Subsequently, the contents of reaction vessel 1 were heated while stirring, so as to adjust the temperature thereof to about 120° C., thereby performing a reaction for about 6 hours while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing 2-ethyl-1-butanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dibutyltin bis(2-ethylbutoxide) and 1,1,3,3-tetrabutyl-1,3-bis(2-ethylbutoxy)distannoxane.

The liquid collected in reservoir 23 was recycled to step (1), and a cycle of steps (1) to (3) was repeatedly performed.

(Step (4))

(Preparation of Catalyst)

40 g of phenol and 8 g of lead monoxide were mixed together, and the resultant mixture was heated at 180° C. for 10 hours while distilling off the by-produced water with phenol, thereby obtaining catalyst A.

(Production of Aromatic Carbonate)

Using a device as shown in FIG. 5, step (4) was performed as follows.

The condensate (containing bis(2-ethylbutyl) carbonate) collected in reservoir 29 in step (2), phenol and catalyst A were mixed together to obtain a liquid mixture having a bis(2-ethylbutyl) carbonate/phenol weight ratio of 71/29 and a Pb content of about 1% by weight. The obtained liquid mixture was continuously fed through conduit 37 (equipped with preheater 38) to continuous multi-stage distillation column 39 (height: 2 m; inner diameter: about 5 cm) (which had 40 sieve trays) at a middle portion thereof at a rate of about 200 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 237° C., the column top pressure was 13 kPa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 34 g/hr. The liquid in distillation column 39 was withdrawn from the bottom thereof and transferred through conduit 46 to reservoir 47 at a rate of about 166 g/hr.

The condensate collected in reservoir 138 contained about 29% by weight of 2-ethyl-1-butanol, about 70.7% by weight of phenol and about 0.3% by weight of bis(2-ethylbutyl) carbonate, based on the weight of the condensate. On the other hand, the liquid collected in reservoir 47 contained about 14% by weight of phenol, about 70% by weight of bis(2-ethylbutyl) carbonate, about 13% by weight of 2-ethylbutyl phenyl carbonate, and about 0.7% by weight of diphenyl carbonate, based on the weight of the liquid collected in reservoir 47. Further, the liquid collected in reservoir 47 had a Pb content of about 1% by weight.

(Step (5))

Using a device as shown in FIG. 6, step (5) was performed as follows.

The liquid collected in reservoir 47 in step (4) was fed through conduit 48 (equipped with preheater 49) to continuous multi-stage distillation column 50 (inner diameter: about 5 cm; height: 2 m) (which had 40 sieve trays) at a middle portion thereof at a rate of about 166 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The reactive distillation was performed under conditions wherein the temperature of the liquid at the bottom of distillation column 50 was 239° C., the column top pressure was about 19 kPa, and the reflux ratio was about 2. A gas distilled from the top of distillation column 50 was transferred through conduit 51 to condenser 52, to thereby condense the distilled gas. The resultant condensate was continuously withdrawn from condenser 52 through conduit 55 at a rate of about 157 g/hr. The residual liquid in distillation column 50 was continuously withdrawn from the bottom thereof and transferred through conduit 57 to reservoir 58 at a rate of about 9 g/hr.

The condensate withdrawn from condenser 52 through conduit 55 contained about 500 ppm by weight of 2-ethyl-1-butanol, about 15% by weight of phenol, about 78% by weight of bis(2-ethylbutyl) carbonate and about 7% by weight of 2-ethylbutyl phenyl carbonate, based on the weight of the condensate. On the other hand, the residual liquid collected in reservoir 58 contained about 0.1% by weight of bis(2-ethylbutyl) carbonate, about 26% by weight of 2-ethylbutyl phenyl carbonate, and about 53% by weight of diphenyl carbonate, based on the weight of the residual liquid. Further, the residual liquid collected in reservoir 58 had a Pb content of about 21% by weight.

(Recycling of Alcohol)

Using a device as shown in FIG. 7, recycling of the alcohol was performed as follows.

The condensate collected in reservoir 138 in step (4) was fed through conduit 59 (equipped with preheater 60) to a continuous multi-stage distillation column 61 (inner diameter: about 5 cm; height: 2 m) (which was filled with Dixon packing (6 mmφ)) at a portion thereof which is about 0.4 m above the bottom of distillation column 61 at a rate of about 170 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 138° C., the column top pressure was about 20 kPa, and the reflux ratio was about 2. A gas distilled from the top of distillation column 61 was transferred through conduit 62 to condenser 63, to thereby condense the distilled gas. The resultant condensate was continuously withdrawn from condenser 63 and transferred through conduit 66 to alcohol reservoir 135 at a rate of about 49 g/hr. The residual liquid in distillation column 61 was continuously withdrawn from the bottom thereof and transferred through conduit 68 to reservoir 69 at a rate of about 121 g/hr.

The condensate collected in reservoir 135 contained about 99.7% by weight of 2-ethyl-1-butanol and about 0.3% by weight of phenol, based on the weight of the condensate. On the other hand, the residual liquid collected in reservoir 69 contained about 0.4% by weight of bis(2-ethylbutyl) carbonate, about 0.1% by weight of 2-ethyl-1-butanol, and about 99.5% by weight of phenol, based on the weight of the residual liquid.

(Purification of Diaryl Carbonate)

Using devices as shown in FIGS. 8 and 9, purification of a diaryl carbonate was performed as follows.

The residual liquid collected in reservoir 58 in step (5) was fed through conduit 70 (equipped with preheater 71) to a continuous multi-stage distillation column 72 (inner diameter: about 5 cm; height: 2 m) (which was filled with Dixon packing (6 mmφ)) at a middle portion thereof at a rate of about 193 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 230° C., the column top pressure was about 1.5 kPa, and the reflux ratio was about 1.5. A gas distilled from the top of distillation column 72 was transferred through conduit 73 to condenser 74, to thereby condense the distilled gas. The resultant condensate was continuously withdrawn from condenser 74 through conduit 77. The residual liquid in distillation column 72 was continuously withdrawn from the bottom thereof and transferred through conduit 79 to reservoir 80 at a rate of about 40 g/hr.

The condensate withdrawn from condenser 74 through conduit 77 contained about 0.1% by weight of bis(2-ethylbutyl) carbonate, about 33% by weight of 2-ethylbutyl phenyl carbonate and about 67% by weight of diphenyl carbonate, based on the weight of the condensate.

Subsequently, the condensate withdrawn from condenser 74 through conduit 77 was fed through conduit 81 (equipped with preheater 82) to a continuous multi-stage distillation column 83 (inner diameter: about 5 cm; height: 4 m) (which was filled with Dixon packing (6 mmφ)) at a portion thereof which is about 0.2 m above the bottom of distillation column 83 at a rate of about 229 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing the distillation. The distillation was performed under conditions wherein the temperature of the liquid at the bottom of distillation column 83 was 241° C., the column top pressure was about 33 kPa, and the reflux ratio was about 5. A gas distilled from the top of distillation column 83 was transferred through conduit 84 to condenser 85, to thereby condense the distilled gas. The resultant condensate was continuously withdrawn from condenser 85 through conduit 88 at a rate of about 120 g/hr. The residual liquid in distillation column 83 was continuously withdrawn from the bottom thereof and transferred through conduit 90 to reservoir 91 at a rate of about 109 g/hr.

The condensate withdrawn from condenser 85 through conduit 88 contained about 0.2% by weight of bis(2-ethylbutyl) carbonate, about 61% by weight of 2-ethylbutyl phenyl carbonate and about 39% by weight of diphenyl carbonate, based on the weight of the condensate. On the other hand, the residual liquid collected in reservoir 91 contained about 2% by weight of 2-ethylbutyl phenyl carbonate and about 98% by weight of diphenyl carbonate, based on the weight of the residual liquid.

EXAMPLE 10

Production of Dibutyltin Dialkoxide

Using a device as shown in FIG. 3, dibutyltin dialkoxide were produced as follows.

Into a 5-liter SUS reaction vessel 1 equipped with a stirrer, a heater and a baffle were charged 75 g (0.3 mol) of dibutyltin oxide and 2,223 g (30 mol) of 1-butanol (manufactured and sold by Aldrich, U.S.A.), wherein dibutyltin oxide was fed through conduit 4 provided at the top of reaction vessel 1, and 1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing 1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 320 g, and that the liquid contained about 0.54 mol of dibutyltin dibutoxide and about 0.18 mol of 1,1,3,3-tetrabutyl-1,3-dibutyloxydistannoxane.

(Step (1))

About 107 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 100° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.05 mol of dibutyl carbonate, and that the whole of the reaction mixture obtained 4 hours after the start of the reaction (i.e., the reaction mixture after the reaction) contained about 0.06 mol of dibutyl carbonate.

After the reaction, the inside of the autoclave was cooled, and carbon dioxide was purged therefrom.

(Step (2))

Using a device as shown in FIG. 4, step (2) was performed as follows.

After step (1), the resultant reaction mixture was withdrawn from the bottom of the autoclave, and transferred through conduit 133 to vessel 25 for removing carbon dioxide, wherein the atmosphere in vessel 25 was purged with nitrogen. Then, the reaction mixture in vessel 25 was heated at 80° C. in nitrogen atmosphere for about 5 minutes while stirring, and the carbon dioxide released therefrom was purged from the vessel. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 90 g/hr, and distillation was performed at a reflux ratio of about 0.2. Thin film distillation apparatus 30 was equipped with a heating jacket in which a heating medium having a temperature of 120° C. was circulated, and the internal pressure (column top pressure) was reduced to about 1.3 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from the top of distillation column 27, it was found that dibutyl carbonate was withdrawn and transferred to reservoir 29 at a rate of about 0.05 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 80 g/hr, and that no dibutyl carbonate was detected by gas chromatography (GC).

(Step (3))

Using a device as shown in FIG. 3, step (3) was performed as follows.

After step (2), the residual liquid collected in reservoir 32 and about 2,223 g (30 mol) of 1-butanol were fed to a 5-liter SUS reaction vessel 1, wherein the residual liquid and 1-butanol were fed through conduit 35 and conduit 3, respectively. Further, nitrogen gas was fed into reaction vessel 1 through a SUS tube connected to inert gas conduit 2 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing 1-butanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dibutyltin dibutoxide and 1,1,3,3-tetrabutyl-1,3-dibutyloxydistannoxane.

The liquid collected in reservoir 23 was recycled to step (1), and a cycle of steps (1) to (3) was repeatedly performed.

(Step (4))

(Preparation of Catalyst)

79 g of phenol and 32 g of lead monoxide were mixed together, and the resultant mixture was charged into a reaction vessel. Then, the mixture was heated at 180° C. for 10 hours while distilling off the by-produced water with phenol, wherein the amount of water distilled off was about 2.5 g. Then, an excess amount of phenol was distilled from an upper portion of the reaction vessel, thereby obtaining catalyst B.

(Production of Aromatic Carbonate)

Using a device as shown in FIG. 5, step (4) was performed as follows.

The condensate (containing dibutyl carbonate) collected in reservoir 29 in step (2), phenol and catalyst B were mixed together to obtain a liquid mixture having a dibutyl carbonate/phenol weight ratio of 65/35 and a Pb content of about 1% by weight. The obtained liquid mixture was continuously fed through conduit 37 (equipped with preheater 38) to a continuous multi-stage distillation column 39 (height: 2 m; inner diameter: about 5 cm) (which had 40 sieve trays) at a portion which is about 0.5 m above the bottom of distillation column 39 at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 221° C., the column top pressure was 150 kPa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 42 g/hr. The liquid in distillation column 39 was withdrawn from the bottom thereof and transferred through conduit 46 to reservoir 47 at a rate of about 203 g/hr.

The condensate collected in reservoir 138 contained about 23% by weight of 1-butanol, about 73% by weight of phenol and about 4% by weight of dibutyl carbonate, based on the weight of the condensate. On the other hand, the liquid collected in reservoir 47 contained about 12% by weight of phenol, about 67% by weight of dibutyl carbonate, about 18% by weight of butyl phenyl carbonate, and about 1% by weight of diphenyl carbonate, based on the weight of the liquid collected in reservoir 47. Further, the liquid collected in reservoir 47 had a Pb content of about 1% by weight.

(Step (5))

Using a device as shown in FIG. 6, step (5) was performed as follows.

The liquid collected in reservoir 47 was fed through conduit 48 (equipped with preheater 49) to a continuous multi-stage distillation column 50 (inner diameter: about 5 cm; height: 2 m) (which was filled with Dixon packing (6 mmφ)) at a middle portion thereof at a rate of about 203 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The reactive distillation was performed under conditions wherein the temperature of the liquid at the bottom of distillation column 50 was 235° C., the column top pressure was about 26 kPa, and the reflux ratio was about 2. A gas distilled from the top of distillation column 50 was transferred through conduit 51 to condenser 52, to thereby condense the distilled gas. The resultant condensate was continuously withdrawn from condenser 52 and transferred through conduit 55 to reservoir 126 at a rate of about 176 g/hr. The residual liquid in distillation column 50 was continuously withdrawn from the bottom thereof and transferred through conduit 57 to reservoir 58 at a rate of about 27 g/hr.

The condensate collected in reservoir 126 contained about 300 ppm by weight of 1-butanol, about 14% by weight of phenol, about 84% by weight of dibutyl carbonate and about 1% by weight of butyl phenyl carbonate, based on the weight of the condensate. On the other hand, the residual liquid collected in reservoir 58 contained about 0.5% by weight of dibutyl carbonate, about 31% by weight of butyl phenyl carbonate, and about 59% by weight of diphenyl carbonate, based on the weight of the residual liquid. Further, the residual liquid collected in reservoir 58 had a Pb content of about 10% by weight.

(Recycling of Alcohol)

Using a device as shown in FIG. 7, recycling of the alcohol was performed as follows.

The condensate collected in reservoir 138 in step (4) was fed through conduit 59 (equipped with preheater 60) to a continuous multi-stage distillation column 61 (inner diameter: about 5 cm; height: 2 m) (which was filled with Dixon packing (6 mmφ)) at a middle portion thereof at a rate of about 201 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 116° C., the column top pressure was about 13 kPa, and the reflux ratio was about 0.5. A gas distilled from the top of distillation column 61 was transferred through conduit 62 to condenser 63, to thereby condense the distilled gas. The resultant condensate was continuously withdrawn from condenser 63 and transferred through conduit 66 to reservoir 135 at a rate of about 46 g/hr. The residual liquid in distillation column 61 was continuously withdrawn from the bottom thereof and transferred through conduit 68 to reservoir 69 at a rate of about 155 g/hr.

The condensate withdrawn from condenser 63 through conduit 66 contained almost 100% by weight of 1-butanol, based on the weight of the condensate, and contained substantially no phenol (no phenol was detected in the analysis of the condensate). On the other hand, the residual liquid collected in reservoir 69 contained about 5% by weight of dibutyl carbonate and about 95% by weight of phenol, based on the weight of the residual liquid.

(Purification of Diaryl Carbonate)

Using devices as shown in FIGS. 8 and 9, purification of a diaryl carbonate was performed as follows.

The residual liquid collected in reservoir 58 in step (5) was fed through conduit 70 (equipped with preheater 71) to a continuous multi-stage distillation column 72 (inner diameter: about 5 cm; height: 2 m) (which was filled with Dixon packing (6 mmφ)) at a middle portion thereof at a rate of about 273 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the distilled gas. The resultant condensate was continuously withdrawn from condenser 74 through conduit 77. The residual liquid in distillation column 72 was continuously withdrawn from the bottom thereof and transferred through conduit 79 to reservoir 80 at a rate of about 27 g/hr.

The condensate withdrawn from condenser 74 through conduit 77 contained about 0.6% by weight of dibutyl carbonate, about 34% by weight of butyl phenyl carbonate and about 65% by weight of diphenyl carbonate, based on the weight of the condensate.

Subsequently, the condensate withdrawn from condenser 74 through conduit 77 was fed through conduit 81 (equipped with preheater 82) to a continuous multi-stage distillation column 83 (inner diameter: about 5 cm; height: 2 m) (which was filled with Dixon packing (6 mmφ)) at a middle portion thereof at a rate of about 246 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing the distillation. The distillation was performed under conditions wherein the temperature of the liquid at the bottom of distillation column 83 was 211° C., the column top pressure was about 7 kPa, and the reflux ratio was about 2. A gas distilled from the top of distillation column 83 was transferred through conduit 84 to condenser 85, to thereby condense the distilled gas. The resultant condensate was continuously withdrawn from condenser 85 through conduit 88 at a rate of about 85 g/hr. The residual liquid in distillation column 83 was continuously withdrawn from the bottom thereof and transferred through conduit 90 to reservoir 91 at a rate of about 161 g/hr.

The condensate withdrawn from condenser 85 through conduit 88 contained about 1.6% by weight of dibutyl carbonate, about 98% by weight of butyl phenyl carbonate and about 0.4% by weight of diphenyl carbonate, based on the weight of the condensate. On the other hand, the residual liquid collected in reservoir 91 contained about 0.2% by weight of butyl phenyl carbonate and about 99% by weight of diphenyl carbonate, based on the weight of the residual liquid.

EXAMPLE 11

Production of Dibutyltin Dialkoxide

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 2,223 g (30 mol) of 1-butanol (manufactured and sold by Aldrich, U.S.A.), wherein dibutyltin oxide was fed through conduit 4 provided at the top of reaction vessel 1, and 1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing 1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, whole of the liquid reaction mixture collected in apparatus 11 for removing alcohol was transferred through conduit 12 to reservoir 23.

The liquid obtained in reservoir 23 was analyzed. As a result, it was found that the weight of the liquid was about 1,170 g, and that the liquid contained about 0.54 mol of dibutyltin dibutoxide and about 0.18 mol of 1,1,3,3-tetrabutyl-1,3-dibutyloxydistannoxane.

(Step (1))

About 130 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.01 mol of dibutyl carbonate, and that the whole of the reaction mixture obtained 4 hours after the start of the reaction (i.e., the reaction mixture after the reaction) contained about 0.02 mol of dibutyl carbonate.

After the reaction, the inside of the autoclave was cooled, and carbon dioxide was purged therefrom. Then, the resultant mixture was withdrawn from the bottom of the autoclave and transferred to reservoir 127 of a device as shown in FIG. 4.

The above-mentioned operation was repeated two times (i.e., the above-mentioned operation was performed three times in total). After the third operation, a sample of the resultant reaction mixture in reservoir 127 was analyzed. As a result, it was found that the resultant reaction mixture contained 0.07 mol of dibutyl carbonate.

(Step (2))

Using a device as shown in FIG. 4, step (2) was performed as follows.

The reaction mixture collected in reservoir 127 in step (1) was transferred through conduit 128 to vessel 25 for removing carbon dioxide. Then, the reaction mixture in vessel 25 was heated at 80° C. in nitrogen atmosphere for about 15 minutes while stirring, and the carbon dioxide released therefrom was purged from the vessel. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 26 g/hr, and distillation was performed at a reflux ratio of about 0.2. Thin film distillation apparatus 30 was equipped with a heating jacket in which a heating medium having a temperature of 120° C. was circulated, and the internal pressure (column top pressure) was reduced to about 1.3 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32.

With respect to the volatilized components withdrawn from the top of distillation column 27, it was found that dibutyl carbonate and 1-butanol were withdrawn and transferred to reservoir 29 at a rate of about 0.02 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 22 g/hr, and that no dibutyl carbonate was detected by gas chromatography (GC).

(Step (3))

Using a device as shown in FIG. 3, step (3) was performed as follows.

After step (2), the residual liquid collected in reservoir 32 and about 2,223 g (30 mol) of 1-butanol were fed to a 5-liter SUS reaction vessel 1, wherein the residual liquid and 1-butanol were fed through conduit 35 and conduit 3, respectively. Further, nitrogen gas was fed into reaction vessel 1 through a SUS tube connected to inert gas conduit 2 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing 1-butanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dibutyltin dibutoxide and 1,1,3,3-tetrabutyl-1,3-dibutyloxydistannoxane.

The liquid collected in reservoir 23 was recycled to step (1), and a cycle of steps (1) to (3) was repeatedly performed.

(Step (4))

(Preparation of Catalyst)

79 g of phenol and 32 g of lead monoxide were mixed together, and the resultant mixture was charged into a reaction vessel. Then, the mixture was heated at 180° C. for 10 hours while distilling off the by-produced water with phenol, wherein the amount of water distilled off was about 2.5 g. Then, an excess amount of phenol was distilled from an upper portion of the reaction vessel, thereby obtaining catalyst B.

(Separation of Alcohol from Dialkyl Carbonate)

Figure 10:
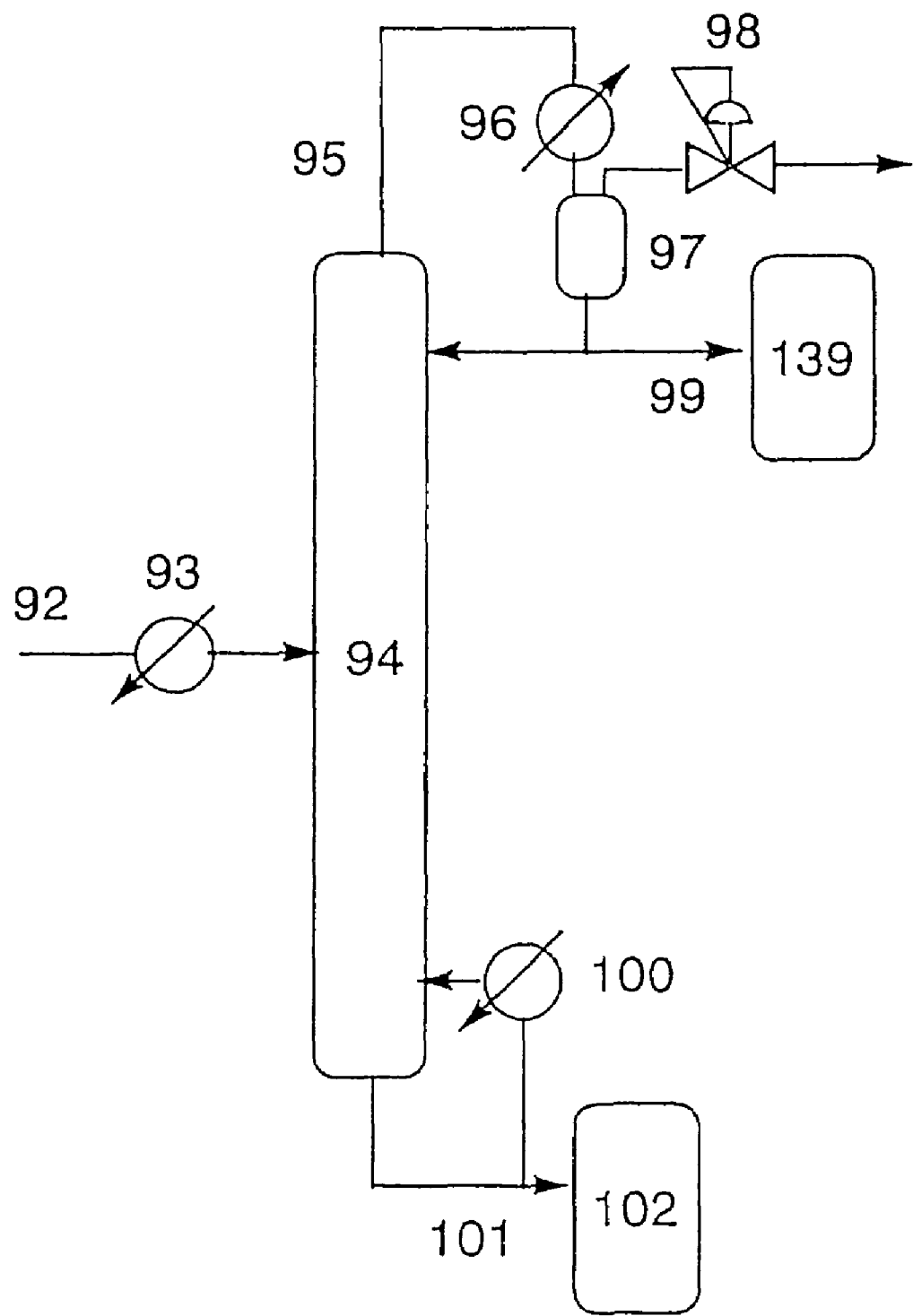
FIG. 10 is a flow chart showing a specific example of the step of separating an alcohol from a dialkyl carbonate, which is performed in the method of the present invention.

Using a device as shown in FIG. 10, the condensate in reservoir 29 in step (2) was separated into alcohol and dialkyl carbonate as follows.

The condensate collected in reservoir 29 in step (2) was continuously fed through conduit 92 (equipped with preheater 93) to a continuous multi-stage distillation column 94 (inner diameter: about 5 cm; height: 2 m) (which was filled with Dixon packing (6 mmφ)) at a portion thereof which is about 0.6 m above the bottom of distillation column 94 at a rate of about 295 g/hr, and distillation was performed to thereby separate the condensate into an alcohol and a dialkyl carbonate, namely, 1-butanol and dibutyl carbonate. During the distillation, the liquid in distillation column 94 was withdrawn from the bottom thereof. A portion of the withdrawn liquid was transferred through conduit 101 to reboiler 100 and, then, recycled to distillation column 94, so as to supply a sufficient amount of heat for performing the distillation. The distillation was performed under conditions wherein the temperature of the liquid at the bottom of distillation column 94 was 150° C., the column top pressure thereof was reduced to about 19 kPa, and the reflux ratio was about 0.1. A gas distilled from the top of distillation column 94 was transferred through conduit 95 to condenser 96, to thereby condense the gas. The resultant condensate was transferred through conduit 99 to reservoir 139 at a rate of about 283 g/hr. The residual liquid in distillation column 94 was continuously withdrawn from the bottom thereof and transferred through conduit 101 to reservoir 102 at a rate of about 12 g/hr.

The residual liquid collected in reservoir 139 contained almost 100% by weight, based on the weight of the residual liquid, of 1-butanol, and contained substantially no dibutyl carbonate (no dibutyl carbonate was detected by GC analysis of the residual liquid). On the other hand, the liquid collected in reservoir 102 contained about 99.6% by weight of dibutyl carbonate and about 0.4% by weight of 1-butanol, based on the weight of the liquid in reservoir 102.

(Production of Aromatic Carbonate)

Using a device as shown in FIG. 5, step (4) was performed as follows.

The condensate (containing dibutyl carbonate) collected in reservoir 29 in step (2), phenol and catalyst B were mixed together to obtain a liquid mixture having a dibutyl carbonate/phenol weight ratio of 65/35 and a Pb content of about 1% by weight. The obtained liquid mixture was continuously fed through conduit 37 (equipped with preheater 38) to a middle portion of continuous multi-stage distillation column 39 (height: 2 m; inner diameter: about 5 cm) (which had 40 sieve trays) at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 220° C., the column top pressure was 150 kPa, and the reflux ratio was about 1. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 67 g/hr. The liquid in distillation column 39 was withdrawn from the bottom thereof and transferred through conduit 46 to reservoir 47 at a rate of about 203 g/hr.

The condensate collected in reservoir 138 contained about 18% by weight of 1-butanol, about 74% by weight of phenol and about 8% by weight of dibutyl carbonate, based on the weight of the condensate. On the other hand, the liquid collected in reservoir 47 contained about 14% by weight of phenol, about 69% by weight of dibutyl carbonate, about 14% by weight of butyl phenyl carbonate and about 1% by weight of diphenyl carbonate, based on the weight of the liquid collected in reservoir 47. Further, the liquid collected in reservoir 47 had a Pb content of about 1% by weight.

(Step (5))

Using a device as shown in FIG. 6, step (5) was performed as follows.

The liquid collected in reservoir 47 was fed through conduit 48 (equipped with preheater 49) to a continuous multi-stage distillation column 50 (inner diameter: about 5 cm; height: 2 m) (which was filled with Dixon packing (6 mmφ)) at a middle portion thereof at a rate of about 203 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation The reactive distillation was performed under conditions wherein the temperature of the liquid at the bottom of distillation column 50 was 231° C., the column top pressure was about 26 kPa, and the reflux ratio was about 1. A gas distilled from the top of distillation column 50 was transferred through conduit 51 to condenser 52, to thereby condense the distilled gas. The resultant condensate was continuously withdrawn from condenser 52 and transferred through conduit 55 to reservoir 126 at a rate of about 181 g/hr. The residual liquid in distillation column 50 was continuously withdrawn from the bottom thereof and transferred through conduit 57 to reservoir 58 at a rate of about 22 g/hr.

The condensate collected in reservoir 126 contained about 500 ppm by weight of 1-butanol, about 16% by weight of phenol, about 82% by weight of dibutyl carbonate and about 2% by weight of butyl phenyl carbonate, based on the weight of the condensate. On the other hand, the residual liquid collected in reservoir 58 contained about 0.1% by weight of dibutyl carbonate, about 38% by weight of butyl phenyl carbonate and about 50% by weight of diphenyl carbonate, based on the weight of the residual liquid. Further, the residual liquid collected in reservoir 58 had a Pb content of about 12% by weight.

The condensate collected in reservoir 29 contained about 500 ppm by weight of 1-butanol, about 16% by weight of phenol, about 82% by weight of dibutyl carbonate and about 2% by weight of butyl phenyl carbonate, based on the weight of the condensate. On the other hand, the residual liquid collected in reservoir 58 contained about 0.1% by weight of dibutyl carbonate, about 38% by weight of butyl phenyl carbonate and about 50% by weight of diphenyl carbonate, based on the weight of the residual liquid. Further, the residual liquid collected in reservoir 58 had a Pb content of about 12% by weight.

(Recycling of Alcohol)

Using a device as shown in FIG. 7, recycling of the alcohol was performed as follows.

The condensate collected in reservoir 138 in step (4) was fed through conduit 59 (equipped with preheater 60) to a continuous multi-stage distillation column 61 (inner diameter: about 5 cm; height: 2 m) (which was filled with Dixon packing (6 mmφ)) at a middle portion thereof at a rate of about 201 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 134° C., the column top pressure was about 16 kPa, and the reflux ratio was about 0.5. A gas distilled from the top of distillation column 61 was transferred through conduit 62 to condenser 63, to thereby condense the distilled gas. The resultant condensate was continuously withdrawn from condenser 63 and transferred through conduit 66 to alcohol reservoir 135 at a rate of about 38 g/hr. The residual liquid in distillation column 61 was continuously withdrawn from the bottom thereof and transferred through conduit 68 to reservoir 69 at a rate of about 163 g/hr.

The condensate collected in reservoir 135 contained almost 100% by weight of 1-butanol, based on the weight of the condensate, and contained substantially no phenol (no phenol was detected in the analysis of the condensate). On the other hand, the residual liquid collected in reservoir 69 contained about 10% by weight of dibutyl carbonate and about 90% by weight of phenol, based on the weight of the residual liquid.

(Purification of Diaryl Carbonate)

Using devices as shown in FIGS. 8 and 9, purification of a diaryl carbonate was performed as follows.

The residual liquid collected in reservoir 58 in step (5) was fed through conduit 70 (equipped with preheater 71) to a continuous multi-stage distillation column 72 (inner diameter: about 5 cm; height: 2 m) (which was filled with Dixon packing (6 mmφ)) at a middle portion thereof at a rate of about 225 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the distilled gas. The resultant condensate was continuously withdrawn from condenser 74 through conduit 77. The residual liquid in distillation column 72 was continuously withdrawn from the bottom thereof and transferred through conduit 79 to reservoir 80 at a rate of about 27 g/hr.

The condensate withdrawn from condenser 74 through conduit 77 contained about 0.1% by weight of dibutyl carbonate, about 43% by weight of butyl phenyl carbonate and about 57% by weight of diphenyl carbonate, based on the weight of the condensate.

Subsequently, the condensate withdrawn from condenser 74 through conduit 77 was fed through conduit 81 (equipped with preheater 82) to a continuous multi-stage distillation column 83 (inner diameter: about 5 cm; height: 2 m) (which was filled with Dixon packing (6 mmφ)) at a middle portion thereof at a rate of about 198 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing the distillation. The distillation was performed under conditions wherein the temperature of the liquid at the bottom of distillation column 83 was 211° C., the column top pressure was about 7 kPa, and the reflux ratio was about 2. A gas distilled from the top of distillation column 83 was transferred through conduit 84 to condenser 85, to thereby condense the distilled gas. The resultant condensate was continuously withdrawn from condenser 85 through conduit 88 at a rate of about 86 g/hr. The residual liquid in distillation column 83 was continuously withdrawn from the bottom thereof and transferred through conduit 90 to reservoir 91 at a rate of about 112 g/hr.

The condensate withdrawn from condenser 85 through conduit 88 contained about 0.3% by weight of dibutyl carbonate, about 99% by weight of butyl phenyl carbonate and about 0.2% by weight of diphenyl carbonate, based on the weight of the condensate. On the other hand, the residual liquid collected in reservoir 91 contained about 0.1% by weight of butyl phenyl carbonate and about 99% by weight of diphenyl carbonate, based on the weight of the residual liquid.

EXAMPLE 12

Production of Dibutyltin Dialkoxide

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 2,223 g (30 mol) of 1-butanol (manufactured and sold by Aldrich, U.S.A.), wherein dibutyltin oxide was fed through conduit 4 provided at the top of reaction vessel 1, and 1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas through gas discharging conduit 5 provided at an upper portion of reaction vessel 1. During the reaction, the gas distilled from conduit 5 was transferred through condenser 6 to reservoir 7 in which a liquid mixture containing 1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 320 g, and that the liquid contained about 0.54 mol of dibutyltin dibutoxide and about 0.18 mol of 1,1,3,3-tetrabutyl-1,3-dibutyloxydistannoxane.

(Step (1))

About 107 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.06 mol of dibutyl carbonate, and that the whole of the reaction mixture obtained 4 hours after the start of the reaction (i.e., the reaction mixture after the reaction) contained about 0.07 mol of dibutyl carbonate.

After the reaction, the inside of the autoclave was cooled, and carbon dioxide was purged therefrom.

(Step (2))

Using a device as shown in FIG. 4, step (2) was performed as follows.

After step (1), the resultant reaction mixture was withdrawn from the bottom of the autoclave, and transferred through conduit 133 to vessel 25 for removing carbon dioxide, wherein the atmosphere in vessel 25 had been purged with nitrogen. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 120 g/hr, and distillation was performed at a reflux ratio of about 0.5. Thin film distillation apparatus 30 was equipped with a heating jacket in which a heating medium having a temperature of 130° C. was circulated, and the internal pressure (column top pressure) was reduced to about 1 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from the top of distillation column 27, it was found that dibutyl carbonate was withdrawn and transferred to reservoir 29 at a rate of about 0.08 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 110 g/hr, and that no dibutyl carbonate was detected by gas chromatography (GC).

(Step (3))

Using a device as shown in FIG. 3, step (3) was performed as follows.

After step (2), the residual liquid collected in reservoir 32 and about 2,223 g (30 mol) of 1-butanol were fed to a 5-liter SUS reaction vessel 1, wherein the residual liquid and 1-butanol were fed through conduit 35 and conduit 3, respectively. Further, nitrogen gas was fed into reaction vessel 1 through a SUS tube connected to inert gas conduit 2 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas from gas discharging conduit 5 provided at an upper portion of reaction vessel 1. During the reaction, the gas distilled from conduit 5 was transferred through condenser 6 and the resultant condensate, namely, a liquid mixture containing 1-butanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dibutyltin dibutoxide and 1,1,3,3-tetrabutyl-1,3-dibutyloxydistannoxane.

The liquid collected in reservoir 23 was recycled to step (1), and a cycle of steps (1) to (3) was repeatedly performed.

(Step (4))

(Preparation of Catalyst)

79 g of phenol and 32 g of lead monoxide were mixed together, and the resultant mixture was charged into a reaction vessel. Then, the mixture was heated at 180° C. for 10 hours while distilling off the by-produced water with phenol, wherein the amount of water distilled off was about 2.5 g. Then, an excess amount of phenol was distilled from an upper portion of the reaction vessel, thereby obtaining catalyst B.

(Production of Aromatic Carbonate)

Using a device as shown in FIG. 5, step (4) was performed as follows.

The condensate (containing dibutyl carbonate) collected in reservoir 29 in step (2), phenol and catalyst B were mixed together to obtain a liquid mixture having a dibutyl carbonate/phenol weight ratio of about 48/52 and a Pb content of about 1% by weight. The obtained liquid mixture was continuously fed through conduit 37 (equipped with preheater 38) to continuous multi-stage distillation column 39 (height: 2 m; inner diameter: about 5 cm) having 40 sieve trays at a middle portion thereof at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 221° C., the column top pressure was about 150 kPa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 60 g/hr. The liquid in distillation column 39 was withdrawn from the bottom thereof and transferred through conduit 46 to reservoir 47 at a rate of about 210 g/hr.

The condensate collected in reservoir 138 contained about 10% by weight of 1-butanol, about 90% by weight of phenol and about 0.3% by weight of dibutyl carbonate, based on the weight of the condensate. On the other hand, the liquid collected in reservoir 47 contained about 36% by weight of phenol, about 54% by weight of dibutyl carbonate, about 8% by weight of butyl phenyl carbonate, and about 0.5% by weight of diphenyl carbonate, based on the weight of the liquid collected in reservoir 47. Further, the liquid collected in reservoir 47 had a Pb content of about 1% by weight.

(Step (5))

Using a device as shown in FIG. 6, step (5) was performed as follows.

The liquid collected in reservoir 47 was fed through conduit 48 (equipped with preheater 49) to continuous multi-stage distillation column 50 (inner diameter: about 5 cm; height: 2 m) (which was filled with Dixon packing (6 mmφ)) at a middle portion thereof at a rate of about 210 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The distillation was performed under conditions wherein the temperature of the liquid at the bottom of distillation column 50 was 237° C., the column top pressure was about 26 kPa, and the reflux ratio was about 2. A gas distilled from the top of distillation column 50 was transferred through conduit 51 to condenser 52, to thereby condense the gas. The resultant condensate was continuously withdrawn from condenser 52 and transferred through conduit 55 to reservoir 126 at a rate of about 198 g/hr. The residual liquid in distillation column 50 was continuously withdrawn from the bottom thereof and transferred through conduit 57 to reservoir 58 at a rate of about 12 g/hr.

The condensate collected in reservoir 126 contained about 0.4% by weight of 1-butanol, about 38.% by weight of phenol, about 60% by weight of dibutyl carbonate and about 1% by weight of butyl phenyl carbonate, based on the weight of the condensate. On the other hand, the residual liquid collected in reservoir 58 contained about 1% by weight of dibutyl carbonate, about 11% by weight of butyl phenyl carbonate and about 65% by weight of diphenyl carbonate, based on the weight of the residual liquid. Further, the liquid collected in reservoir 58 had a Pb content of about 23% by weight.

(Recycling of Alcohol)

Using a device as shown in FIG. 7, recycling of the alcohol was performed as follows.

The condensate collected in reservoir 138 was fed through conduit 59 (equipped with preheater 60) to continuous multi-stage distillation column 61 (inner diameter: about 5 cm; height: 2 m) (which was filled with Dixon packing (6 mmφ)) at a middle portion thereof at a rate of about 300 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 134° C., the column top pressure was about 16 kPa, and the reflux ratio was about 0.7. A gas distilled from the top of distillation column 61 was transferred through conduit 62 to condenser 63, to thereby condense the gas. The resultant condensate was continuously withdrawn from condenser 63 and transferred through conduit 66 to alcohol reservoir 135 at a rate of about 30 g/hr. The residual liquid in distillation column 61 was continuously withdrawn from the bottom thereof and transferred through conduit 68 to reservoir 69 at a rate of about 270 g/hr.

The condensate collected in reservoir 135 contained almost 100% by weight of 1-butanol, based on the weight of the condensate, and contained substantially no phenol (no phenol was detected in the analysis of the condensate). On the other hand, the residual liquid collected in reservoir 69 contained about 0.3% by weight of dibutyl carbonate and about 99% by weight of phenol, based on the weight of the residual liquid.

(Purification of Diaryl Carbonate)

Using devices as shown in FIGS. 8 and 9, purification of a diaryl carbonate was performed as follows.

The condensate collected in reservoir 58 was fed through conduit 70 (equipped with preheater 71) to continuous multi-stage distillation column 72 (inner diameter: about 5 cm; height: 2 m) (which was filled with Dixon packing (6 mmφ)) at a middle portion thereof at a rate of about 118 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the gas. The resultant condensate was continuously withdrawn from condenser 74 and transferred through conduit 77. The residual liquid in distillation column 72 was continuously withdrawn from the bottom thereof and transferred through conduit 79 to reservoir 80 at a rate of about 27 g/hr.

The condensate withdrawn from condenser 74 through conduit 77 contained about 1% by weight of dibutyl carbonate, about 15% by weight of butyl phenyl carbonate and about 84% by weight of diphenyl carbonate, based on the weight of the condensate.

Subsequently, the condensate withdrawn from condenser 74 through conduit 77 was fed through conduit 81 (equipped with preheater 82) to continuous multi-stage distillation column 83 (inner diameter: about 5 cm; height: 2 m) (which was filled with Dixon packing (6 mmφ)) at a middle portion thereof at a rate of about 91 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing the distillation. The distillation was performed under conditions wherein the temperature of the liquid at the bottom of distillation column 83 was 207° C., the column top pressure was about 5 kPa, and the reflux ratio was about 3.5. A gas distilled from the top of distillation column 83 was transferred through conduit 84 to condenser 85, to thereby condense the distilled gas. The resultant condensate was continuously withdrawn from condenser 85 and transferred through conduit 88 at a rate of about 14 g/hr. The residual liquid in distillation column 83 was continuously withdrawn from the bottom thereof and transferred through conduit 90 to reservoir 91 at a rate of about 77 g/hr.

The condensate withdrawn from condenser 85 through conduit 88 contained about 8% by weight of dibutyl carbonate, about 90% by weight of butyl phenyl carbonate and about 2% by weight of diphenyl carbonate, based on the weight of the condensate. On the other hand, the residual liquid collected in reservoir 91 contained about 0.2% by weight of butyl phenyl carbonate and about 99% by weight of diphenyl carbonate, based on the weight of the residual liquid.

EXAMPLE 13

Production of Dibutyltin Dialkoxide

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 2,224 g (30 mol) of 1-butanol (manufactured and sold by Aldrich, U.S.A.), wherein dibutyltin oxide was fed through conduit 4 provided at the top of reaction vessel 1, and 1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas through gas discharging conduit 5 provided at an upper portion of reaction vessel 1. During the reaction, the gas distilled from conduit 5 was transferred through condenser 6 to reservoir 7 in which a liquid mixture containing 1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 320 g, and that the liquid contained about 0.54 mol of dibutyltin dibutoxide and about 0.18 mol of 1,1,3,3-tetrabutyl-1,3-butyloxydistannoxane.

(Step (1))

About 107 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.06 mol of dibutyl carbonate, and that the whole of the reaction mixture obtained 4 hours after the start of the reaction (i.e., the reaction mixture after the reaction) contained about 0.07 mol of dibutyl carbonate.

After the reaction, the inside of the autoclave was cooled, and carbon dioxide was purged therefrom.

(Step (2))

Using a device as shown in FIG. 4, step (2) was performed as follows.

After step (1), the resultant reaction mixture was withdrawn from the bottom of the autoclave, and transferred through conduit 133 to vessel 25 for removing carbon dioxide, wherein the atmosphere in vessel 25 had been purged with nitrogen. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 100 g/hr, and distillation was performed at a reflux ratio of about 0.2. Thin film distillation apparatus 30 was equipped with a heating jacket in which a heating medium having a temperature of 150° C. was circulated, and the internal pressure (column top pressure) was reduced to about 1.3 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from the top of distillation column 27, it was found that dibutyl carbonate was withdrawn and transferred to reservoir 29 at a rate of about 0.07 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 90 g/hr, and that no dibutyl carbonate was detected by gas chromatography (GC).

(Step (3))

Using a device as shown in FIG. 3, step (3) was performed as follows.

After step (2), the residual liquid collected in reservoir 32 and about 2,150 g (29 mol) of 1-butanol were fed to a 5-liter SUS reaction vessel 1, wherein the residual liquid and 1-butanol were fed through conduit 35 and conduit 3, respectively. Further, nitrogen gas was fed into reaction vessel 1 through a SUS tube connected to inert gas conduit 2 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing 1-butanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dibutyltin dibutoxide and 1,1,3,3-tetrabutyl-1,3-dibutyloxydistannoxane.

The liquid collected in reservoir 23 was recycled to step (1), and a cycle of steps (1) to (3) was repeatedly performed.

(Step (4))

(Production of Aromatic Carbonate)

Using a device as shown in FIG. 5, step (4) was performed as follows.

The condensate (containing dibutyl carbonate) collected in reservoir 29 in step (2), phenol and hafnium ethoxide (manufactured and sold by Gelest Inc., U.S.A.) were mixed together to obtain a liquid mixture having a dibutyl carbonate/phenol weight ratio of 65/35 and an Hf content of about 1% by weight. The obtained liquid mixture was continuously fed through conduit 37 (equipped with preheater 38) to continuous multistage distillation column 39 (height: 2 m; inner diameter: about 5 cm) having 40 sieve trays at a middle portion thereof at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 231° C., the column top pressure was $2 \times 10^5$ Pa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 40 g/hr. The liquid in distillation column 39 was withdrawn from the bottom thereof and transferred through conduit 46 to reservoir 47 at a rate of about 230 g/hr.

The condensate collected in reservoir 138 contained about 27% by weight of 1-butanol, about 70% by weight of phenol and about 1% by weight of dibutyl carbonate, based on the weight of the condensate. On the other hand, the liquid collected in reservoir 47 contained about 21% by weight of phenol, about 62% by weight of dibutyl carbonate, about 11% by weight of butyl phenyl carbonate, and about 1% by weight of diphenyl carbonate, based on the weight of the liquid collected in reservoir 47. Further, the liquid collected in reservoir 47 had an Hf content of about 1% by weight.

(Step (5))

Using a device as shown in FIG. 6, step (5) was performed as follows.

The liquid collected in reservoir 47 was fed through conduit 48 (equipped with preheater 49) to continuous multistage distillation column 50 (inner diameter: about 5 cm; height: 2 m) having 40 sieve trays at a middle portion thereof at a rate of about 230 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The distillation was performed under conditions wherein the temperature of the liquid at the bottom of distillation column 50 was 239° C., the column top pressure was about 20 kPa, and the reflux ratio was about 2. A gas distilled from the top of distillation column 50 was transferred through conduit 51 to condenser 52, to thereby condense the distilled gas. The resultant condensate was continuously withdrawn from condenser 52 and transferred through conduit 55 at a rate of about 220 g/hr. The residual liquid in distillation column 50 was continuously withdrawn from the bottom thereof and transferred through conduit 57 to reservoir 58 at a rate of about 15 g/hr.

The condensate withdrawn from condenser 52 through conduit 55 contained about 1% by weight of 1-butanol, about 22% by weight of phenol, about 68% by weight of dibutyl carbonate and about 2% by weight of butyl phenyl carbonate, based on the weight of the condensate. On the other hand, the residual liquid collected in reservoir 58 contained about 0.1% by weight of dibutyl carbonate, about 50% by weight of diphenyl carbonate and about 31% by weight of butyl phenyl carbonate, based on the weight of the residual liquid. Further, the liquid collected in reservoir 58 had an Hf content of about 18% by weight.

(Recycling of Alcohol)

Using a device as shown in FIG. 7, recycling of the alcohol was performed as follows.

The condensate collected in reservoir 138 in step (4) was fed through conduit 59 (equipped with preheater 60) to continuous multi-stage distillation column 61 (inner diameter: about 5 cm; height: 2 m) (which was filled with Dixon packing (6 mmφ)) at a middle portion thereof at a rate of about 200 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 121° C., the column top pressure was about 9 kPa, and the reflux ratio was about 0.5. A gas distilled from the top of distillation column 61 was transferred through conduit 62 to condenser 63, to thereby condense the distilled gas. The resultant condensate was continuously withdrawn from condenser 63 and transferred through conduit 66 to alcohol reservoir 135 at a rate of about 54 g/hr. The residual liquid in distillation column 61 was continuously withdrawn from the bottom thereof and transferred through conduit 68 to reservoir 69 at a rate of about 146 g/hr.

The condensate collected in reservoir 135 contained almost 100% by weight of 1-butanol, based on the weight of the condensate, and contained substantially no phenol (no phenol was detected in the analysis of the condensate). On the other hand, the residual liquid collected in reservoir 69 contained about 1% by weight of dibutyl carbonate and about 96% by weight of phenol, based on the weight of the residual liquid, and contained substantially no 1-butanol (no 1-butanol was detected in the analysis of the residual liquid).

(Purification of Diaryl Carbonate)

Using devices as shown in FIGS. 8 and 9, purification of a diaryl carbonate was performed as follows.

The condensate collected in reservoir 58 was fed through conduit 70 (equipped with preheater 71) to continuous multi-stage distillation column 72 (inner diameter: about 5 cm; height: 2 m) (which was filled with Dixon packing (6 mmφ)) at a middle portion thereof at a rate of about 149 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the distilled gas. The resultant condensate was continuously withdrawn from condenser 74 and transferred through conduit 77. The residual liquid in distillation column 72 was continuously withdrawn from the bottom thereof and transferred through conduit 79 to reservoir 80 at a rate of about 27 g/hr.

The condensate withdrawn from condenser 74 through conduit 77 contained about 0.1% by weight of dibutyl carbonate, about 50% by weight of butyl phenyl carbonate and about 50% by weight of diphenyl carbonate, based on the weight of the condensate.

Subsequently, the condensate withdrawn from condenser 74 through conduit 77 was fed through conduit 81 (equipped with preheater 82) to continuous multi-stage distillation column 83 (inner diameter: about 5 cm; height: 2 m) (which was filled with Dixon packing (6 mmφ)) at a middle portion thereof at a rate of about 122 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing the distillation. The distillation was performed under conditions wherein the temperature of the liquid at the bottom of distillation column 83 was 227° C., the column top pressure was about 13 kPa, and the reflux ratio was about 4. A gas distilled from the top of distillation column 83 was transferred through conduit 84 to condenser 85, to thereby condense the distilled gas. The resultant condensate was continuously withdrawn from condenser 85 and transferred through conduit 88 at a rate of about 61 g/hr. The residual liquid in distillation column 83 was continuously withdrawn from the bottom thereof and transferred through conduit 90 to reservoir 91 at a rate of about 61 g/hr.

The condensate withdrawn from condenser 85 through conduit 88 contained about 0.2% by weight of dibutyl carbonate, about 99% by weight of butyl phenyl carbonate and about 300 ppm by weight of diphenyl carbonate, based on the weight of the condensate. On the other hand, the residual liquid collected in reservoir 91 contained about 400 ppm by weight of butyl phenyl carbonate and almost 100% by weight of diphenyl carbonate, based on the weight of the residual liquid.

EXAMPLE 14

Production of Dibutyltin Dialkoxide

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 2,223 g (30 mol) of 1-butanol (manufactured and sold by Aldrich, U.S.A.), wherein dibutyltin oxide was fed through conduit 4 provided at the top of reaction vessel 1, and 1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr. Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing 1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 320 g, and that the liquid contained about 0.54 mol of dibutyltin dibutoxide and about 0.18 mol of 1,1,3,3-tetrabutyl-1,3-butyloxydistannoxane.

(Step (1))

About 107 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.06 mol of dibutyl carbonate, and that the whole of the reaction mixture obtained 4 hours after the start of the reaction (i.e., the reaction mixture after the reaction) contained about 0.07 mol of dibutyl carbonate.

After the reaction, the inside of the autoclave was cooled, and carbon dioxide was purged therefrom.

(Step (2))

Using a device as shown in FIG. 4, step (2) was performed as follows.

After step (1), the resultant reaction mixture was withdrawn from the bottom of the autoclave, and transferred through conduit 133 to vessel 25 for removing carbon dioxide, wherein the atmosphere in vessel 25 had been purged with nitrogen. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 60 g/hr, and distillation was performed at a reflux ratio of about 0.1. Thin film distillation apparatus 30 was equipped with a heating jacket in which a heating medium having a temperature of 140° C. was circulated, and the internal pressure (column top pressure) was reduced to about 2 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from the top of distillation column 27, it was found that dibutyl carbonate was withdrawn and transferred to reservoir 29 at a rate of about 0.04 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 55 g/hr, and that no dibutyl carbonate was detected by gas chromatography (GC).

(Step (3))

Using a device as shown in FIG. 3, step (3) was performed as follows.

After step (2), the residual liquid collected in reservoir 32 and about 2,223 g (30 mol) of 1-butanol were fed to a 5-liter SUS reaction vessel 1, wherein the residual liquid and 1-butanol were fed through conduit 35 and conduit 3, respectively. Further, nitrogen gas was fed into reaction vessel 1 through a SUS tube connected to inert gas conduit 2 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing 1-butanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dibutyltin dibutoxide and 1,1,3,3-tetrabutyl-1,3-dibutyloxydistannoxane.

The liquid collected in reservoir 23 was recycled to step (1), and a cycle of steps (1) to (3) was repeatedly performed.

(Step (4))

(Production of Aromatic Carbonate)

Using a device as shown in FIG. 5, step (4) was performed as follows.

The condensate (containing dibutyl carbonate) collected in reservoir 29 in step (2), phenol and diphenyltin oxide (manufactured and sold by Azmax Co. Ltd., Japan) were mixed together to obtain a liquid mixture having a dibutyl carbonate/phenol weight ratio of about 65/35 and an Sn content of about 1% by weight. The obtained liquid mixture was continuously fed through conduit 37 (equipped with preheater 38) to continuous multi-stage distillation column 39 (height: 2 m; inner diameter: about 5 cm) having 40 sieve trays at a middle portion thereof at a rate of about 135 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 231° C., the column top pressure was about 150 kPa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 31 g/hr. The liquid in distillation column 39 was withdrawn from the bottom thereof and transferred through conduit 46 to reservoir 47 at a rate of about 105 g/hr.

The condensate collected in reservoir 138 contained about 8% by weight of 1-butanol, about 84% by weight of phenol and about 8% by weight of dibutyl carbonate, based on the weight of the condensate. On the other hand, the liquid collected in reservoir 47 contained about 17% by weight of phenol, about 75% by weight of dibutyl carbonate, about 6% by weight of butyl phenyl carbonate, and about 0.3% by weight of diphenyl carbonate, based on the weight of the liquid collected in reservoir 47. Further, the liquid collected in reservoir 47 had an Sn content of about 1% by weight.

(Step (5))

Using a device as shown in FIG. 6, step (5) was performed as follows.

The liquid collected in reservoir 47 was fed through conduit 48 (equipped with preheater 49) to continuous multi-stage distillation column 50 (inner diameter: about 5 cm; height: 2 m) (which was filled with Dixon packing (6 mm$\phi$)) at a middle portion thereof at a rate of about 316 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The distillation was performed under conditions wherein the temperature of the liquid at the bottom of distillation column 50 was 240° C., the column top pressure was about 26 kPa, and the reflux ratio was about 2. A gas distilled from the top of distillation column 50 was transferred through conduit 51 to condenser 52, to thereby condense the distilled gas. The resultant condensate was continuously withdrawn from condenser 52 and transferred through conduit 55 into reservoir 126 at a rate of about 304 g/hr. The residual liquid in distillation column 50 was continuously withdrawn from the bottom thereof and transferred through conduit 57 to reservoir 58 at a rate of about 12 g/hr.

The condensate collected in reservoir 126 contained about 0.1% by weight of 1-butanol, about 18% by weight of phenol, about 79% by weight of dibutyl carbonate and about 3% by weight of butyl phenyl carbonate, based on the weight of the condensate. On the other hand, the residual liquid collected in reservoir 58 contained about 0.5% by weight of dibutyl carbonate, about 40% by weight of butyl phenyl carbonate and about 25% by weight of diphenyl carbonate, based on the weight of the residual liquid. Further, the liquid collected in reservoir 58 had an Sn content of about 34% by weight.

(Recycling of Alcohol)

Using a device as shown in FIG. 7, recycling of the alcohol was performed as follows.

The condensate collected in reservoir 138 in step (4) was fed through conduit 59 (equipped with preheater 60) to continuous multi-stage distillation column 61 (inner diameter: about 5 cm; height: 2 m) (which was filled with Dixon packing (6 mm$\phi$)) at a middle portion thereof at a rate of about 310 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 110° C., the column top pressure was about 9 kPa, and the reflux ratio was about 0.7. A gas distilled from the top of distillation column 61 was transferred through conduit 62 to condenser 63, to thereby condense the distilled gas. The resultant condensate was continuously withdrawn from condenser 63 and transferred through conduit 66 to alcohol reservoir 135 at a rate of about 25 g/hr. The residual liquid in distillation column 61 was continuously withdrawn from the bottom thereof and transferred through conduit 68 to reservoir 69 at a rate of about 285 g/hr.

The condensate collected in reservoir 135 contained almost 100% by weight of 1-butanol, based on the weight of the condensate, and contained substantially no phenol (no phenol was detected in the analysis of the condensate). On the other hand, the residual liquid collected in reservoir 69 contained about 9% by weight of dibutyl carbonate and about 91% by weight of phenol, based on the weight of the residual liquid.

(Purification of Diaryl Carbonate)

Using devices as shown in FIGS. 8 and 9, purification of a diaryl carbonate was performed as follows.

The condensate collected in reservoir 58 was fed through conduit 70 (equipped with preheater 71) to continuous multi-stage distillation column 72 (inner diameter: about 5 cm; height: 2 m) (which was filled with Dixon packing (6 mm$\phi$)) at a middle portion thereof at a rate of about 200 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the distilled gas. The resultant condensate was continuously withdrawn from condenser 74 and transferred through conduit 77. The residual liquid in distillation column 72 was continuously withdrawn from the bottom thereof and transferred through conduit 79 to reservoir 80 at a rate of about 70 g/hr.

The condensate transferred through conduit 77 contained about 1% by weight of dibutyl carbonate, about 61% by weight of butyl phenyl carbonate and about 38% by weight of diphenyl carbonate, based on the weight of the condensate.

Subsequently, the condensate withdrawn from condenser 74 through conduit 77 was fed through conduit 81 (equipped with preheater 82) to continuous multi-stage distillation column 83 (inner diameter: about 5 cm; height: 2 m) (which was filled with Dixon packing (6 mm$\phi$)) at a middle portion thereof at a rate of about 130 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing the distillation. The distillation was performed under conditions wherein the temperature of the liquid at the bottom of distillation column 83 was 227° C., the column top pressure was about 13 kPa, and the reflux ratio was about 4. A gas distilled from the top of distillation column 83 was transferred through conduit 84 to condenser 85, to thereby condense the distilled gas. The resultant condensate was continuously withdrawn from condenser 85 and transferred through conduit 88 at a rate of about 81 g/hr. The residual liquid in distillation column 83 was continuously withdrawn from the bottom thereof and transferred through conduit 90 to reservoir 91 at a rate of about 49 g/hr.

The condensate transferred through conduit 88 contained about 2% by weight of dibutyl carbonate, about 98% by weight of butyl phenyl carbonate and about 0.1% by weight of diphenyl carbonate, based on the weight of the condensate. On the other hand, the residual liquid collected in reservoir 91 contained almost 100% by weight of diphenyl carbonate, based on the weight of the residual liquid, and contained substantially no butyl phenyl carbonate (no butyl phenyl carbonate was detected in the analysis of the residual liquid).

EXAMPLE 15

Production of Dibutyltin Dialkoxide

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 3,486 g (30 mol) of 5-methyl-1-hexanol (manufactured and sold by Aldrich, U.S.A.), wherein dibutyltin oxide was fed through conduit 4 provided at the top of reaction vessel 1, and 5-methyl-1-hexanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr.

Subsequently, the contents of reaction vessel 1 were heated while stirring, so as to adjust the temperature thereof to about 120° C., thereby performing a reaction for about 6 hours while discharging low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing 5-methyl-1-hexanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 380 g, and that the liquid contained about 0.56 mol of dibutylin di(5-methylhexyloxide) and about 0.17 mol of 1,1,3,3-tetrabutyl-1,3-di (5-methylhexyloxy) di-stannoxane.

(Step (1))

About 127 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.07 mol of di(5-methylhexyl) carbonate, and that the whole of the reaction mixture obtained 4 hours after the start of the reaction (i.e., the reaction mixture after the reaction) contained about 0.08 mol of di(5-methylhexyl) carbonate.

After the reaction, the inside of the autoclave was cooled, and carbon dioxide was purged therefrom.

(Step (2))

Using a device as shown in FIG. 4, step (2) was performed as follows.

After step (1), the resultant reaction mixture was withdrawn from the bottom of the autoclave, and transferred through conduit 133 to vessel 25 for removing carbon dioxide, wherein the atmosphere in vessel 25 had been purged with nitrogen. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 60 g/hr, and distillation was performed at a reflux ratio of about 0.5. Thin film distillation apparatus 30 was equipped with a heating jacket in which a heating medium having a temperature of 100° C. was circulated, and the internal pressure (column top pressure) was reduced to about 1.3 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from the top of distillation column 27, it was found that di(5-methylhexyl) carbonate was withdrawn and transferred to reservoir 29 at a rate of about 0.04 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 55 g/hr, and that no di(5-methylhexyl) carbonate was detected by gas chromatography (GC).

(Step (3))

Using a device as shown in FIG. 3, step (3) was performed as follows.

After step (2), the residual liquid collected in reservoir 32 and about 3,486 g (30 mol) of 5-methyl-1-hexanol were fed to a 5-liter SUS reaction vessel 1, wherein the residual liquid and 5-methyl-1-hexanol were fed through conduit 35 and conduit 3, respectively. Further, nitrogen gas was fed into reaction vessel 1 through a SUS tube connected to inert gas conduit 2 at a rate of 0.1 Nl/hr.

Subsequently, the contents of reaction vessel 1 were heated while stirring, so as to adjust the temperature thereof to about 120° C., thereby performing a reaction for about 6 hours while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing 5-methyl-1-hexanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained di (5-methylhexyloxide) and 1,1,3,3-tetrabutyl-1,3-di (5-methylhexyloxy) distannoxane.

The liquid collected in reservoir 23 was recycled to step (1), and a cycle of steps (1) to (3) was repeatedly performed.

(Step (4))

(Preparation of Catalyst)

79 g of phenol and 32 g of lead monoxide were mixed together, and the resultant mixture was charged into a reaction vessel. Then, the mixture was heated at 180° C. for 10 hours while distilling off the by-produced water with phenol, wherein the amount of water distilled off was about 2.5 g. Then, an excess amount of phenol was distilled from an upper portion of the reaction vessel, thereby obtaining catalyst B.

(Production of Aromatic Carbonate)

Using a device as shown in FIG. 5, step (4) was performed as follows.

The condensate (containing di(5-methylhexyl) carbonate) collected in reservoir 29 in step (2), phenol and catalyst B were mixed together to obtain a liquid mixture having a di(5-methylhexyl) carbonate/phenol weight ratio of about 65/35 and a Pb content of about 1% by weight. The obtained liquid mixture was continuously fed through conduit 37 (equipped with preheater 38) to continuous multi-stage distillation column 39 (height: 2 m; inner diameter: about 5 cm) (which was filled with Dixon packing (6 mmϕ)) at a middle portion thereof at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 23° C., the column top pressure was about 150 kPa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 58 g/hr. The liquid in distillation column 39 was withdrawn from the bottom thereof and transferred through conduit 46 to reservoir 47 at a rate of about 212 g/hr.

The condensate collected in reservoir 138 contained about 21% by weight of 5-methyl-1-hexanol, about 79% by weight of phenol and about 0.3% by weight of di(5-methylhexyl) carbonate, based on the weight of the condensate. On the other hand, the liquid collected in reservoir 47 contained about 29% by weight of phenol, about 60% by weight of di(5-methylhexyl) carbonate, about 9% by weight of 5-methylhexyl phenyl carbonate, and about 0.5% by weight of diphenyl carbonate, based on the weight of the liquid collected in reservoir 47. Further, the liquid collected in reservoir 47 had a Pb content of about 1% by weight.

(Step (5))

Using a device as shown in FIG. 6, step (5) was performed as follows.

The liquid collected in reservoir 47 was fed through conduit 48 (equipped with preheater 49) to continuous multi-stage distillation column 50 (inner diameter: about 5 cm; height: 2 m) (which was filled with Dixon packing (6 mmϕ)) at a middle portion thereof at a rate of about 212 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The distillation was performed under conditions wherein the temperature of the liquid at the bottom of distillation column 50 was 237° C., the column top pressure was about 26 kPa, and the reflux ratio was about 2. A gas distilled from the top of distillation column 50 was transferred through conduit 51 to condenser 63, to thereby condense the distilled gas. The resultant condensate was continuously withdrawn from condenser 52 and transferred through conduit 55 to reservoir 126 at a rate of about 200 g/hr. The residual liquid in distillation column 50 was continuously withdrawn from the bottom thereof and transferred through conduit 57 to reservoir 58 at a rate of about 12 g/hr.

The condensate withdrawn from distillation column 50 through conduit 55 contained about 0.1% by weight of 5-methyl-1-hexanol, about 7% by weight of phenol, about 89% by weight of di(5-methylhexyl) carbonate and about 4% by weight of 5-methylhexyl phenyl carbonate, based on the weight of the condensate. On the other hand, the residual liquid collected in reservoir 58 contained about 3% by weight of di(5-methylhexyl) carbonate about 15% by weight of 5-methylhexyl phenyl carbonate and about 60% by weight of diphenyl carbonate, based on the weight of the residual liquid. Further, the liquid collected in reservoir 58 had a Pb content of about 2% by weight.

(Recycling of Alcohol)

Using a device as shown in FIG. 7, recycling of the alcohol was performed as follows.

The condensate collected in reservoir 138 in step (4) was fed through conduit 59 (equipped with preheater 60) to continuous multi-stage distillation column 61 (inner diameter: about 5 cm; height: 2 m) (which was filled with Dixon packing (6 mm$\phi$)) at a portion thereof which is about 0.4 m above the bottom of distillation column 61 at a rate of about 174 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 112° C., the column top pressure was about 4 kPa, and the reflux ratio was about 6. A gas distilled from the top of distillation column 61 was transferred through conduit 62 to condenser 63, to thereby condense the distilled gas. The resultant condensate was continuously withdrawn from condenser 63 and transferred through conduit 66 to alcohol reservoir 135 at a rate of about 36 g/hr. The residual liquid in distillation column 61 was continuously withdrawn from the bottom thereof and transferred through conduit 68 to reservoir 69 at a rate of about 138 g/hr.

The condensate collected in reservoir 135 contained almost 100% by weight of 5-methyl-1-hexanol and about 400 ppm by weight of phenol, based on the weight of the condensate. On the other hand, the residual liquid collected in reservoir 69 contained about 0.4% by weight of di(5-methylhexyl) carbonate, about 0.5% by weight of 5-methyl-1-hexanol and about 99% by weight of phenol, based on the weight of the residual liquid.

(Purification of Diaryl Carbonate)

Using devices as shown in FIGS. 8 and 9, purification of a diaryl carbonate was performed as follows.

The condensate collected in reservoir 58 was fed through conduit 70 (equipped with preheater 71) to continuous multi-stage distillation column 72 (inner diameter: about 5 cm; height: 2 m) (which was filled with Dixon packing (6 mm$\phi$)) at a middle portion thereof at a rate of about 244 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the distilled gas. The resultant condensate was continuously withdrawn from condenser 74 and transferred through conduit 77. The residual liquid in distillation column 72 was continuously withdrawn from the bottom thereof and transferred through conduit 79 to reservoir 80 at a rate of about 54 g/hr.

The condensate withdrawn from condenser 74 through conduit 77 contained about 4% by weight of di(5-methylhexyl) carbonate, about 19% by weight of (5-methylhexyl) phenyl carbonate and about 70% by weight of diphenyl carbonate, based on the weight of the condensate.

The condensate withdrawn from condenser 74 through conduit 77 was fed through conduit 81 (equipped with preheater 82) to continuous multi-stage distillation column 83 (inner diameter: about 5 cm; height: 2 m) (which was filled with Dixon packing (6 mm$\phi$)) at a middle portion thereof at a rate of about 190 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing the distillation. The distillation was performed under conditions wherein the temperature of the liquid at the bottom of distillation column 83 was 300° C., the column top pressure was about 101.3 kPa (atmospheric pressure), and the reflux ratio was about 6. A gas distilled from the top of distillation column 83 was transferred through conduit 84 to condenser 85, to thereby condense the distilled gas. The resultant condensate was continuously withdrawn from condenser 85 and transferred through conduit 88 at a rate of about 87 g/hr. The residual liquid in distillation column 83 was continuously withdrawn from the bottom thereof and transferred through conduit 90 to reservoir 91 at a rate of about 103 g/hr.

The condensate from condenser 85 through conduit 88 contained about 8% by weight of di(5-methylhexyl) carbonate, about 37% by weight of 5-methylhexyl phenyl carbonate and about 55% by weight of diphenyl carbonate, based on the weight of the condensate. On the other hand, the residual liquid collected in reservoir 91 contained about 4% by weight of (5-methylhexyl) phenyl carbonate and about 96% by weight of diphenyl carbonate, based on the weight of the residual liquid.

EXAMPLE 16

Production of Dibutyltin Dialkoxide

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 2,224 g (30 mol) of 1-butanol (manufactured and sold by Aldrich, U.S.A.), wherein dibutyltin oxide was fed through conduit 4 provided at the top of reaction vessel 1, and 1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing 1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 320 g, and that the liquid contained about 0.54 mol of dibutyltin dibutoxide and about 0.18 mol of 1,1,3,3-tetrabutyl-1,3-dibutyloxydistannoxane.

(Step (1))

About 107 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.06 mol of dibutyl carbonate, and that the whole of the reaction mixture obtained 4 hours after the start of the reaction (i.e., the reaction mixture after the reaction) contained about 0.07 mol of dibutyl carbonate.

After the reaction, the inside of the autoclave was cooled, and carbon dioxide was purged therefrom.

(Step (2))

Using a device as shown in FIG. 4, step (2) was performed as follows.

After step (1), the resultant reaction mixture was withdrawn from the bottom of the autoclave, and transferred through conduit 133 to vessel 25 for removing carbon dioxide, wherein the atmosphere in vessel 25 had been purged with nitrogen. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 100 g/hr, and distillation was performed at a reflux ratio of about 0.2. Thin film distillation apparatus 30 was equipped with a heating jacket in which a heating medium having a temperature of 130° C. was circulated, and the internal pressure (column top pressure) was reduced to about 1.3 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from the top of distillation column 27, it was found that dibutyl carbonate was withdrawn and transferred to reservoir 29 at a rate of about 0.06 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 90 g/hr, and that no dibutyl carbonate was detected by gas chromatography (GC).

(Step (3))

Using a device as shown in FIG. 3, step (3) was performed as follows.

After step (2), the residual liquid collected in reservoir 32 and about 2,150 g (29 mol) of 1-butanol were fed to a 5-liter SUS reaction vessel 1, wherein the residual liquid and 1-butanol were fed through conduit 35 and conduit 3, respectively. Further, nitrogen gas was fed into reaction vessel 1 through a SUS tube connected to inert gas conduit 2 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas from gas discharging conduit 5 provided at an upper portion of reaction vessel 1. During the reaction, the gas discharged from conduit 5 was transferred through condenser 6 and the resultant condensate, namely, a liquid mixture containing 1-butanol and water, was transferred to reservoir 7. After the reaction, the residual liquid in reaction vessel 1 was withdrawn from withdrawal conduit 8 and transferred to reservoir 9. From reservoir 9, the residual liquid was transferred through conduit 10 to apparatus 11 for removing alcohol, which was equipped with a stirrer, a pressure-reduction device and a heater. Then, the residual liquid collected in apparatus 11 for removing alcohol was heated under reduced pressure to thereby gasify the unreacted alcohol contained in the residual liquid. The gasified alcohol was discharged from conduit 21, and transferred through condenser 6 to reservoir 16. The residual liquid (having the alcohol removed therefrom) in apparatus 11 was discharged therefrom, and transferred through conduit 12 to reservoir 23.

The liquid collected in reservoir 23 was analyzed. As a result, it was found that the liquid contained dibutyltin dibutoxide and 1,1,3,3-tetrabutyl-1,3-dibutyloxydistannoxane.

The liquid collected in reservoir 23 was recycled to step (1), and a cycle of steps (1) to (3) was repeatedly performed.

(Step (4))

(Preparation of Catalyst)

40 g of phenol and 8 g of lead monoxide were mixed together, and the resultant mixture was charged into a reaction vessel. Then, the mixture was heated at 180° C. for 10 hours while distilling off the by-produced water with phenol, thereby obtaining catalyst A.

(Production of Aromatic Carbonate)

Using a device as shown in FIG. 5, step (4) was performed as follows.

The condensate (containing dibutyl carbonate) collected in reservoir 29 in step (2), phenol and catalyst A were mixed together to obtain a liquid mixture having a dibutyl carbonate/ phenol weight ratio of 65/35 and a Pb content of about 10% by weight. The obtained liquid mixture was continuously fed through conduit 37 (equipped with preheater 38) to continuous multi-stage distillation column 39 (height: 2 m; inner diameter: about 5 cm) (which was filled with Dixon packing (6 mmφ)) at a middle portion thereof at a rate of about 180 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 240° C., the column top pressure was $1.5 \times 10^5$ Pa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 35 g/hr. The liquid in distillation column 39 was withdrawn from the bottom thereof and transferred through conduit 46 to reservoir 47 at a rate of about 145 g/hr.

The condensate collected in reservoir 138 contained about 29% by weight of 1-butanol, about 71% by weight of phenol and about 0.2% by weight of dibutyl carbonate, based on the weight of the condensate. On the other hand, the liquid collected in reservoir 47 contained about 13% by weight of phenol, about 56% by weight of dibutyl carbonate, about 17% by weight of butyl phenyl carbonate, about 1% by weight of diphenyl carbonate and 0.7% by weight of butyl phenyl ether, based on the weight of the liquid collected in reservoir 47. Further, the liquid collected in reservoir 47 had a Pb content of about 12% by weight.

(Step (5))

Using a device as shown in FIG. 6, step (5) was performed as follows.

The liquid collected in reservoir 47 was fed through conduit 48 (equipped with preheater 49) to continuous multi-stage distillation column 50 (inner diameter: about 5 cm; height: 2 m) (which was filled with Dixon packing (6 mmφ)) at a middle portion thereof at a rate of about 219 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The distillation was performed under conditions wherein the temperature of the liquid at the bottom of distillation column 50 was 235° C., the column top pressure was about 26 kPa, and the reflux ratio was about 2. A gas distilled from the top of distillation column 50 was transferred through conduit 51 to condenser 52, to thereby condense the distilled gas. The resultant condensate was continuously withdrawn from condenser 52 and transferred through conduit 55 to reservoir 126 at a rate of about 164 g/hr. The residual liquid in distillation column 50 was continuously withdrawn from the bottom thereof and transferred through conduit 57 to reservoir 58 at a rate of about 52 g/hr.

The condensate collected in reservoir 126 contained about 0.1% by weight of 1-butanol, about 17% by weight of phenol, about 80% by weight of dibutyl carbonate, about 1% by weight of butyl phenyl carbonate and about 1.5% by weight of butyl phenyl ether, based on the weight of the condensate. On the other hand, the residual liquid collected in reservoir 58 contained about 0.5% by weight of dibutyl carbonate, about 17% by weight of butyl phenyl carbonate, about 30% by weight of diphenyl carbonate and about 0.2% by weight of butyl phenyl ether, based on the weight of the residual liquid. Further, the liquid collected in reservoir 58 had a Pb content of about 52% by weight.

(Recycling of Alcohol)

Using a device as shown in FIG. 7, recycling of the alcohol was performed as follows.

The condensate collected in reservoir 138 in step (4) was fed through conduit 59 (equipped with preheater 60) to continuous multi-stage distillation column 61 (inner diameter: about 5 cm; height: 2 m) (which was filled with Dixon packing (6 mmφ)) at a middle portion thereof at a rate of about 210 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 130° C., the column top pressure was about 9 kPa, and the reflux ratio was about 0.7. A gas distilled from the top of distillation column 61 was transferred through conduit 62 to condenser 63, to thereby condense the distilled gas. The resultant condensate was continuously withdrawn from condenser 63 and transferred through conduit 66 to alcohol reservoir 135 at a rate of about 61 g/hr. The residual liquid in distillation column 61 was continuously withdrawn from the bottom thereof and transferred through conduit 68 to reservoir 69 at a rate of about 149 g/hr.

The condensate collected in reservoir 135 contained almost 100% by weight of 1-butanol, based on the weight of the condensate, and contained substantially no phenol (no phenol was detected in the analysis of the condensate). On the other hand, the residual liquid collected in reservoir 69 contained about 0.3% by weight of dibutyl carbonate and about 99% by weight of phenol, based on the weight of the residual liquid, and contained substantially no 1-butanol (no 1-butanol was detected in the analysis of the residual liquid).

(Purification of Diaryl Carbonate)

Using devices as shown in FIGS. 8 and 9, purification of a diaryl carbonate was performed as follows.

The condensate collected in reservoir 58 was fed through conduit 70 (equipped with preheater 71) to a continuous multi-stage distillation column 72 (inner diameter: about 5 cm; height: 2 m) (which was filled with Dixon packing (6 mmφ)) at a middle portion thereof at a rate of about 346 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the distilled gas. The resultant condensate was continuously withdrawn from condenser 74 and transferred through conduit 77. The residual liquid in distillation column 72 was continuously withdrawn from the bottom thereof and transferred through conduit 79 to reservoir 80 at a rate of about 180 g/hr.

The condensate withdrawn from condenser 74 through conduit 77 contained about 1% by weight of dibutyl carbonate, about 36% by weight of butyl phenyl carbonate, about 62% by weight of diphenyl carbonate and 0.4% by weight of butyl phenyl ether, based on the weight of the condensate.

Subsequently, the condensate withdrawn from conduit 74 through conduit 77 was fed through conduit 81 (equipped with preheater 82) to continuous multi-stage distillation column 83 (inner diameter: about 5 cm; height: 2 m) (which was filled with Dixon packing (6 mm$\phi$)) at a middle portion thereof at a rate of about 167 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing the distillation. The distillation was performed under conditions wherein the temperature of the liquid at the bottom of distillation column 83 was 218° C., the column top pressure was about 9 kPa, and the reflux ratio was about 5. A gas distilled from the top of distillation column 83 was transferred through conduit 84 to condenser 85, to thereby condense the distilled gas. The resultant condensate was continuously withdrawn from condenser 85 and transferred through conduit 88 to reservoir 140 at a rate of about 63 g/hr. The residual liquid in distillation column 83 was continuously withdrawn from the bottom thereof and transferred through conduit 90 to reservoir 91 at a rate of about 104 g/hr.

The condensate withdrawn from condenser 85 through conduit 88 contained about 3% by weight of dibutyl carbonate, about 96% by weight of butyl phenyl carbonate, about 400 ppm by weight of diphenyl carbonate and about 1% by weight of butyl phenyl ether, based on the weight of the condensate. On the other hand, the residual liquid collected in reservoir 91 contained about 300 ppm by weight of butyl phenyl carbonate and almost 100% by weight of diphenyl carbonate, based on the weight of the residual liquid.

(Recycling of Dialkyl Carbonate)

Figure 12:
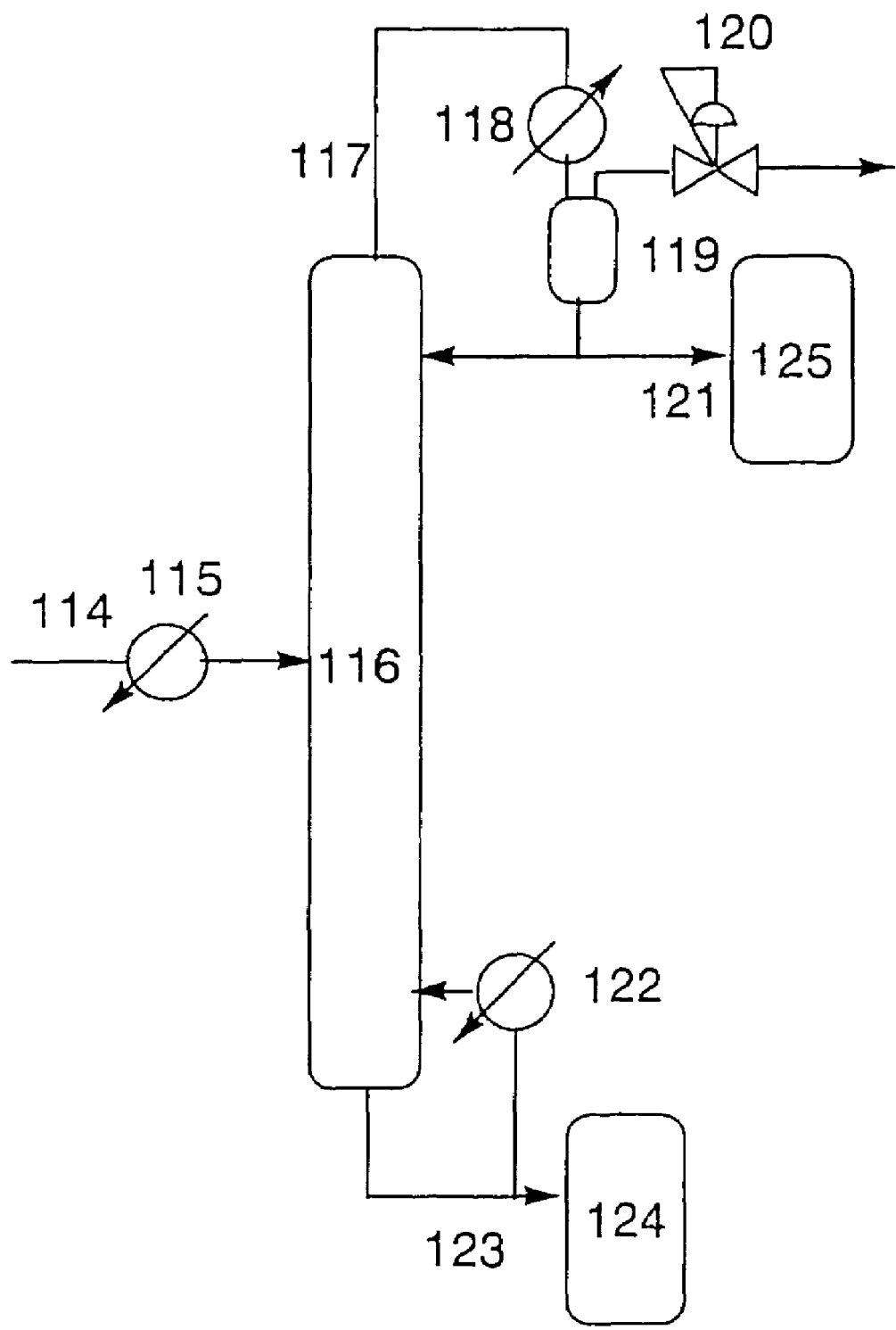
FIG. 12 is a flow chart showing a specific example of the step of recycling a dialkyl carbonate, which is performed in the method of the present invention.

Using a device as shown in FIG. 12, recycling of the dialkyl carbonate was performed as follows.

The condensate (withdrawn from the top of distillation column 83 through conduit 88 to reservoir 140 in the above-mentioned diaryl carbonate purification step) was continuously fed through conduit 114 (equipped with preheater 115) to continuous multi-stage distillation column 116 (inner diameter: about 5 cm; height: 2 m) (which was filled with Dixon packing (6 mm$\phi$)) at a middle portion thereof at a rate of about 189 g/hr, to thereby perform a distillation. During the distillation, the liquid in distillation column 116 was withdrawn from the bottom thereof. A portion of the withdrawn liquid was transferred through conduit 123 to reboiler 122 and, then, recycled to distillation column 116, so as to supply a sufficient amount of heat for performing the distillation. The distillation was performed under conditions wherein the temperature of the liquid at the bottom of distillation column 116 was 165° C., the column top pressure was about 9 kPa, and the reflux ratio was about 6. A gas distilled from the top of distillation column 116 was transferred through conduit 117 to condenser 118, to thereby condense the distilled gas. The resultant condensate was continuously withdrawn from condenser 118 and transferred through conduit 121 to reservoir 125 for dialkyl carbonate at a rate of about 4.5 g/hr. The residual liquid in distillation column 116 was continuously withdrawn from the bottom thereof and transferred through conduit 123 to reservoir 124 at a rate of about 184.5 g/hr.

The condensate withdrawn through conduit 121 to reservoir 125 contained about 96% by weight of dibutyl carbonate, about 2.5% of butyl phenyl ether and about 1.5% by weight of butyl phenyl carbonate, based on the weight of the condensate. On the other hand, the residual liquid collected in reservoir 124 contained about 0.5% by weight of dibutyl carbonate, about 1% of butyl phenyl ether, about 98% by weight of butyl phenyl carbonate and about 400 ppm by weight of diphenyl carbonate, based on the weight of the residual liquid.

(Production of Aromatic Carbonate)

Using a device as shown in FIG. 5, step (4) was performed as follows.

The condensate (containing dibutyl carbonate) collected to reservoir 125 in the above-mentioned dialkyl carbonate recycling step, phenol and catalyst A were mixed together to obtain a liquid mixture having a dibutyl carbonate/phenol weight ratio of 65/35 and a Pb content of about 1% by weight. The obtained liquid mixture was continuously fed through conduit 37 (equipped with preheater 38) to multi-stage distillation column 39 (height: 2 m; inner diameter: about 5 cm) (which was filled with Dixon packing (6 mm$\phi$)) at a middle portion thereof at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 240° C., the column top pressure was $1.5 \times 10^5$ Pa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 51 g/hr. The liquid in distillation column 39 was withdrawn from the bottom thereof and transferred through conduit 46 to reservoir 47 at a rate of about 219 g/hr.

The condensate collected in reservoir 138 contained about 29% by weight of 1-butanol, about 71% by weight of phenol and about 0.2% by weight of dibutyl carbonate, based on the weight of the condensate. On the other hand, the liquid collected in reservoir 47 contained about 13% by weight of phenol, about 55% by weight of dibutyl carbonate, about 17% by weight of butyl phenyl carbonate, about 1% by weight of diphenyl carbonate, and 3.5% by weight of butyl phenyl ether, based on the weight of the liquid collected in reservoir 47. Further, the liquid collected in reservoir 47 had a Pb content of about 11% by weight.

COMPARATIVE EXAMPLE 1

An aromatic carbonate is produced without performing step (2) or (3), as follows.

(Production of Dibutyltin Dialkoxide)

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 2,223 g (30 mol) of 1-butanol (manufactured and sold by Aldrich, U.S.A.), wherein dibutyltin oxide was fed through conduit 4 provided at the top of reaction vessel 1, and 1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing 1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 320 g, and that the liquid contained about 0.54 mol of dibutyltin dibutoxide and about 0.18 mol of 1,1,3,3-tetrabutyl-1,3-dibutyloxydistannoxane.

(Step (1))

About 107 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having the pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.06 mol of dibutyl carbonate, and that the whole of the reaction mixture obtained 4 hours after the start of the reaction (i.e., the reaction mixture after the reaction) contained about 0.07 mol of dibutyl carbonate.

After the reaction, the inside of the autoclave was cooled, and carbon dioxide was purged therefrom. The reaction mixture after the reaction was withdrawn from a lower portion of the autoclave and transferred to a reservoir.

The above-mentioned dibutyltin dialkoxide production step and step (1) were repeatedly performed.

(Step (4))

(Preparation of Catalyst)

79 g of phenol and 32 g of lead monoxide were mixed together, and the resultant mixture was charged into a reaction vessel. Then, the mixture was heated at 180° C. for 10 hours while distilling off the by-produced water with phenol, wherein the amount of water distilled off was about 2.5 g. Then, an excess amount of phenol was distilled from an upper portion of the reaction vessel, thereby obtaining catalyst B.

(Production of Aromatic Carbonate)

Using a device as shown in FIG. 5, step (4) was performed as follows.

The condensate (containing dibutyl carbonate) collected in the reservoir in step (1), phenol and catalyst B were mixed together to obtain a liquid mixture having a dibutyl carbonate/phenol weight ratio of about 65/35 and a Pb content of about 1% by weight. The obtained liquid mixture was continuously fed through conduit 37 (equipped with preheater 38) to continuous multi-stage distillation column 39 (height: 2 m; inner diameter: about 5 cm) having 40 sieve trays at a middle portion thereof at a rate of about 300 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 230° C., the column top pressure was about 150 KPa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 76 g/hr. The liquid in distillation column 39 was withdrawn from the bottom thereof and transferred through conduit 46 to reservoir 47 at a rate of about 224 g/hr.

The condensate collected in reservoir 138 contained about 98% by weight of 1-butanol and about 2% by weight of dibutyl carbonate, based on the weight of the condensate. On the other hand, the liquid collected in reservoir 47 contained about 13% by weight of dibutyl carbonate and about 3% by weight of butyl phenyl carbonate, based on the weight of the liquid collected in reservoir 47. Further, the liquid collected in reservoir 47 had a Pb content of about 1% by weight.

(Recycling of Alcohol and Aromatic Carbonate)

Using a device as shown in FIG. 10, recycling of the alcohol and the aromatic carbonate was performed as follows.

The condensate (withdrawn from condenser 41 through conduit 44 to reservoir 138 in step (4)) was fed through conduit 92 (equipped with preheater 93) to continuous multi-stage distillation column 94 (inner diameter: about 5 cm; height: 2 m) (which was filled with Dixon packing (6 mmφ)) at a middle portion thereof at a rate of about 220 g/hr, to thereby perform a distillation. During the distillation, the liquid in distillation column 94 was withdrawn from the bottom thereof. A portion of the withdrawn liquid was transferred through conduit 101 to reboiler 100 and, then, recycled to distillation column 94, so as to supply a sufficient amount of heat for performing the distillation. The distillation was performed under conditions wherein the temperature of the liquid at the bottom of distillation column 94 was 207° C., the column top pressure was about 101.3 kPa (atmospheric pressure), and the reflux ratio was about 0.5. A gas distilled from the top of distillation column 94 was transferred through conduit 95 to condenser 96, to thereby condense the distilled gas. The resultant condensate was continuously withdrawn from condenser 96 and transferred through conduit 99 to alcohol reservoir 139 at a rate of about 216 g/hr. The residual liquid in distillation column 94 was continuously withdrawn from the bottom thereof and transferred through conduit 99 to an alcohol reservoir 135 at a rate of about 216 g/hr.

The condensate collected in alcohol reservoir 139 contained almost 100% by weight of 1-butanol, based on the weight of the condensate, and contained substantially no phenol and substantially no dibutyl carbonate (neither phenol nor dibutyl carbonate was detected in the analysis of the condensate. On the other hand, the residual liquid collected in reservoir 102 contained almost 100% by weight of dibutyl carbonate, based on the weight of the residual liquid, and contained substantially no butanol and contained substantially no phenol (neither butanol nor phenol was detected in the analysis of the residual liquid).

COMPARATIVE EXAMPLE 2

An aromatic carbonate is produced without performing step (3), as follows.

(Production of Dibutyltin Dialkoxide)

Using a device as shown in FIG. 3, dibutyltin dialkoxides were produced as follows.

Into a 5-liter SUS reaction vessel 1 equipped with a stirrer, a heater and a baffle were charged 75 g (0.3 mol) of dibutyltin oxide and 2,223 g (30 mol) of 1-butanol (manufactured and sold by Aldrich, U.S.A.), wherein dibutyltin oxide was fed through conduit 4 provided at the top of reaction vessel 1, and 1-butanol was fed from alcohol reservoir 16 through conduit 3 provided at an upper portion of reaction vessel 1. Further, nitrogen gas was fed to reaction vessel 1 through a SUS tube connected to inert gas conduit 2 provided at a lower portion of reaction vessel 1 at a rate of 0.1 Nl/hr.

Subsequently, the contents of reaction vessel 1 were heated while stirring, so as to adjust the temperature thereof within the range of from 113° C. to the boiling point of 1-butanol, thereby performing a reaction for about 6 hours while discharging low boiling point components in the form of a gas through gas discharging conduit 5 provided at an upper portion of reaction vessel 1. During the reaction, the gas discharged from conduit 5 was transferred through condenser 6 to reservoir 7 in which a liquid mixture containing 1-butanol and water was obtained. After the reaction, the resultant liquid reaction mixture in reaction vessel 1 was withdrawn from withdrawal conduit 8 and transferred to reservoir 9. From reservoir 9, the liquid reaction mixture was transferred through conduit 10 to apparatus 11 for removing alcohol, which was equipped with a stirrer, a pressure-reduction device and a heater.

The above-mentioned operation was repeated two times (i.e., the above-mentioned operation was performed three times in total). Then, the liquid reaction mixture collected in apparatus 11 for removing alcohol was heated under reduced pressure to thereby gasify the unreacted alcohol contained in the liquid reaction mixture. The gasified alcohol was discharged from conduit 21, and transferred through condenser 6 to reservoir 16. The residual liquid having the alcohol removed therefrom was discharged from apparatus 11 and transferred through conduit 12 to reservoir 23.

The liquid obtained in reservoir 23 was analyzed. As a result, it was found that the weight of the liquid was about 320 g, and that the liquid contained about 0.54 mol of dibutyltin dibutoxide and about 0.18 mol of 1,1,3,3-tetrabutyl-1,3-dibutyloxydistannoxane.

(Step (1))

About 107 g of the liquid obtained in reservoir 23 was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having a pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.06 mol of dibutyl carbonate, and that the whole of the reaction mixture obtained 4 hours after the start of the reaction (i.e., the reaction mixture after the reaction) contained about 0.07 mol of dibutyl carbonate.

After the reaction, the inside of the autoclave was cooled, and carbon dioxide was purged therefrom.

(Step (2))

Using a device as shown in FIG. 4, step (2) was performed as follows.

After step (1), the resultant reaction mixture was withdrawn from the bottom of the autoclave, and transferred through conduit 133 to vessel 25 for removing carbon dioxide, wherein the atmosphere in vessel 25 had been purged with nitrogen. Then, the reaction mixture in vessel 25 was heated at 80° C. in nitrogen atmosphere for about 5 minutes while stirring, and the carbon dioxide released therefrom was purged from vessel 25. The resultant mixture was withdrawn from vessel 25 through conduit 26 and collected in reservoir 131.

To thin film distillation apparatus 30 (E-420; manufactured and sold by Sibata Scientific Technology Ltd., Japan) was connected multi-stage distillation column 27 (inner diameter: 5 cm) which was filled with Dixon packing (6 mmφ). The liquid collected in reservoir 131 was fed to multi-stage distillation column 27 through conduit 132 (which was provided at a middle portion of distillation column 27) at a rate of about 90 g/hr, and distillation was performed at a reflux ratio of about 0.2. Thin film distillation apparatus 30 was equipped with a heating jacket in which a heating medium having a temperature of 145° C. was circulated, and the internal pressure (column top pressure) was reduced to about 1.3 kPa. The volatilized components were withdrawn from the top of distillation column 27 and transferred to condenser 28 to condense the volatilized components, and the resultant condensate was collected in reservoir 29. The residual liquid in thin film distillation apparatus 30 was withdrawn by means of a pump, and transferred through conduit 31 to reservoir 32. With respect to the volatilized components withdrawn from the top of distillation column 27, it was found that dibutyl carbonate was withdrawn and transferred to reservoir 29 at a rate of about 0.06 mol/hr, and that substantially no dibutyltin dialkoxide was contained therein. Further, with respect to the residual liquid withdrawn from thin film distillation apparatus 30, it was found that the residual liquid was transferred to reservoir 32 at a rate of about 90 g/hr, and that no dibutyl carbonate was detected by gas chromatography (GC).

The above-mentioned dibutyltin dialkoxide step, step (1) and step (2) were repeatedly performed.

(Step (4))

(Preparation of Catalyst)

79 g of phenol and 32 g of lead monoxide were mixed together, and the resultant mixture was charged into a reaction vessel. Then, the mixture was heated at 180° C. for 10 hours while distilling off the by-produced water with phenol, wherein the amount of water distilled off was about 2.5 g. Then, an excess amount of phenol was distilled from an upper portion of the reaction vessel, thereby obtaining catalyst B.

(Production of Aromatic Carbonate)

Using a device as shown in FIG. 5, step (4) was performed as follows.

The condensate (containing dibutyl carbonate) collected in reservoir 29 in step (2), phenol and catalyst B were mixed together to obtain a liquid mixture having a dibutyl carbonate/phenol weight ratio of about 65/35 and a Pb content of about 1% by weight. The obtained liquid mixture was continuously fed through conduit 37 (equipped with preheater 38) to continuous multi-stage distillation column 39 (height: 2 m; inner diameter: about 5 cm) having 40 sieve trays at a middle portion thereof at a rate of about 270 g/hr, to thereby simultaneously perform a reaction and a distillation (i.e., reactive distillation). During the reactive distillation, the liquid in distillation column 39 was withdrawn from the bottom thereof. A portion of the withdrawn liquid was transferred through conduit 46 to reboiler 45 and, then, recycled to distillation column 39, so as to supply a sufficient amount of heat for performing the reaction and the distillation. The reactive distillation was performed under conditions wherein the temperature of the liquid collected at the bottom of distillation column 39 was 221° C., the column top pressure was about 150 kPa, and the reflux ratio was about 2. A gas distilled from the top of distillation column 39 was transferred through conduit 40 to condenser 41, to thereby condense the gas. The resultant condensate was withdrawn from condenser 41 and transferred through conduit 44 to reservoir 138 at a rate of about 67 g/hr. The liquid in distillation column 39 was withdrawn from the bottom thereof and transferred through conduit 46 to reservoir 47 at a rate of about 201 g/hr.

The condensate collected in reservoir 138 contained about 23% by weight of 1-butanol, about 73% by weight of phenol and about 4% by weight of dibutyl carbonate, based on the weight of the condensate. On the other hand, the liquid collected in reservoir 47 contained about 12% by weight of phenol, about 67% by weight of dibutyl carbonate, about 18% by weight of butyl phenyl carbonate and about 1% by weight of diphenyl carbonate, based on the weight of the liquid collected in reservoir 47. Further, the liquid collected in reservoir 47 had a Pb content of about 1% by weight.

(Step (5))

Using a device as shown in FIG. 6, step (5) was performed as follows.

The liquid collected in reservoir 47 was fed through conduit 48 (equipped with preheater 49) to continuous multi-stage distillation column 50 (inner diameter: about 5 cm; height: 2 m) (which was filled with Dixon packing (6 mm$\phi$)) at a middle portion thereof at a rate of about 201 g/hr, to thereby simultaneously perform a reaction and a distillation (i.e., reactive distillation). During the reactive distillation, the liquid in distillation column 50 was withdrawn from the bottom thereof. A portion of the withdrawn liquid was transferred through conduit 57 to reboiler 56 and, then, recycled to distillation column 50, so as to supply a sufficient amount of heat for performing the reaction and the distillation. The distillation was performed under conditions wherein the temperature of the liquid at the bottom of distillation column 50 was 235° C., the column top pressure was about 26 kPa, and the reflux ratio was about 2. A gas distilled from the top of distillation column 50 was transferred through conduit 51 to condenser 52, to thereby condense the distilled gas. The resultant condensate was continuously withdrawn from condenser 52 and transferred through conduit 55 to reservoir 126 at a rate of about 176 g/hr. The residual liquid in distillation column 50 was continuously withdrawn from the bottom thereof and transferred through conduit 57 to reservoir 58 at a rate of about 27 g/hr.

The condensate collected in reservoir 126 contained about 300 ppm by weight of 1-butanol, about 14% by weight of phenol, about 84% by weight of dibutyl carbonate and about 1% by weight of butyl phenyl carbonate, based on the weight of the condensate. On the other hand, the residual liquid collected in reservoir 58 contained about 0.5% by weight of dibutyl carbonate, about 31% by weight of butyl phenyl carbonate and about 59% by weight of diphenyl carbonate, based on the weight of the residual liquid. Further, the liquid collected in reservoir 58 had a Pb content of about 10% by weight.

(Recycling of Alcohol)

Using a device as shown in FIG. 7, recycling of the alcohol was performed as follows.

The condensate collected in reservoir 138 in step (4) was fed through conduit 59 (equipped with preheater 60) to continuous multi-stage distillation column 61 (inner diameter: about 5 cm; height: 2 m) (which was filled with Dixon packing (6 mm$\phi$)) at a middle portion thereof at a rate of about 201 g/hr, to thereby perform a distillation. During the distillation, the liquid in distillation column 61 was withdrawn from the bottom thereof. A portion of the withdrawn liquid was transferred through conduit 68 to reboiler 67 and, then, recycled to distillation column 61, so as to supply a sufficient amount of heat for performing the distillation. The distillation was performed under conditions wherein the temperature of the liquid at the bottom of distillation column 61 was 116° C., the column top pressure was about 13 kPa, and the reflux ratio was about 0.5. A gas distilled from the top of distillation column 61 was transferred through conduit 62 to condenser 63, to thereby condense the distilled gas. The resultant condensate was continuously withdrawn from condenser 63 and transferred through conduit 66 to alcohol reservoir 135 at a rate of about 46 g/hr. The residual liquid in distillation column 61 was continuously withdrawn from the bottom thereof and transferred through conduit 68 to reservoir 69 at a rate of about 155 g/hr.

The condensate collected in reservoir 135 contained almost 100% by weight of 1-butanol, based on the weight of the condensate, and contained substantially no phenol (no phenol was detected in the analysis of the condensate). On the other hand, the residual liquid collected in reservoir 69 contained about 5% by weight of dibutyl carbonate and about 95% by weight of phenol, based on the weight of the residual liquid.

(Purification of Diaryl Carbonate)

Using devices as shown in FIGS. 8 and 9, purification of a diaryl carbonate was performed as follows.

The residual liquid collected in reservoir 58 in step (5) was fed through conduit 70 (equipped with preheater 71) to continuous multi-stage distillation column 72 (inner diameter: about 5 cm; height: 2 m) (which was filled with Dixon packing (6 mmφ)) at a middle portion thereof at a rate of about 273 g/hr, to thereby perform a distillation. During the distillation, the liquid in distillation column 72 was withdrawn from the bottom thereof. A portion of the withdrawn liquid was transferred through conduit 79 to reboiler 78 and, then, recycled to distillation column 72, so as to supply a sufficient amount of heat for performing the distillation. The distillation was performed under conditions wherein the temperature of the liquid at the bottom of distillation column 72 was 210° C., the column top pressure was about 1.5 kPa, and the reflux ratio was about 1. A gas distilled from the top of distillation column 72 was transferred through conduit 73 to condenser 74, to thereby condense the distilled gas. The resultant condensate was continuously withdrawn from condenser 74 and transferred through conduit 77. The residual liquid in distillation column 72 was continuously withdrawn from the bottom thereof and transferred through conduit 79 to reservoir 80 at a rate of about 27 g/hr.

The condensate withdrawn from conduit 77 contained about 0.6% by weight of dibutyl carbonate, about 34% by weight of butyl phenyl carbonate and about 65% by weight of diphenyl carbonate, based on the weight of the condensate.

Subsequently, the condensate withdrawn through conduit 77 was continuously fed through conduit 81 (equipped with preheater 82) to continuous multi-stage distillation column 83 (inner diameter: about 5 cm; height: 2 m) (which was filled with Dixon packing (6 mmφ)) at a middle portion thereof at a rate of about 246 g/hr, to thereby perform a distillation. During the distillation, the liquid in distillation column 83 was withdrawn from the bottom thereof. A portion of the withdrawn liquid was transferred through conduit 90 to reboiler 89 and, then, recycled to distillation column 83, so as to supply a sufficient amount of heat for performing distillation. The distillation was performed under conditions wherein the temperature of the liquid at the bottom of distillation column 83 was 211° C., the column top pressure was about 7 kPa, and the reflux ratio was about 2. A gas distilled from the top of distillation column 83 was transferred through conduit 84 to condenser 85, to thereby condense the distilled gas. The resultant condensate was continuously withdrawn from condenser 85 and transferred through conduit 88 to reservoir 140 at a rate of about 85 g/hr. The residual liquid in distillation column 83 was continuously withdrawn from the bottom thereof and transferred through conduit 90 to reservoir 91 at a rate of about 161 g/hr.

The condensate transferred through conduit 88 to reservoir 140 contained about 1.6% by weight of dibutyl carbonate, about 98% by weight of butyl phenyl carbonate and about 0.4% by weight of diphenyl carbonate, based on the weight of the condensate. On the other hand, the residual liquid collected in reservoir 91 contained about 0.2% by weight of butyl phenyl carbonate and about 99% by weight of diphenyl carbonate, based on the weight of the residual liquid.

(Step (1))

About 94 g of the liquid (containing a metal) collected in reservoir 32 in step (2) was fed through conduit 24 to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having a pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the whole of the reaction mixture obtained 1 hour after the start of the reaction contained 0.003 mol of dibutyl carbonate, and the whole of the reaction mixture obtained 4 hours after the start of the reaction (i.e., the reaction mixture after the reaction) contained about 0.004 mol of dibutyl carbonate.

After the reaction, the inside of the autoclave was cooled, and carbon dioxide was purged therefrom.

EXAMPLE 17

Synthesis of Dibutyltin di(3-methylbutoxide)

Into a 1-liter four-neck flask equipped with a cooling tube (which was connected with a vacuum controller and a vacuum pump) and a Dean-Stark trap were charged 70.5 g (0.28 mol) of dibutyltin oxide (manufactured and sold by Aldrich, U.S.A.), 502 g (5.7 mol) of 3-methyl-1-butanol (manufactured and sold by Aldrich, U.S.A.). Further, a stirrer was placed in the flask.

The flask was immersed in an oil bath having a temperature of 140° C., and the pressure in the flask was gradually reduced to about 90 kPa while stirring the contents of the flask. Then, the pressure in the flask was further reduced to 85 kPa while stirring the contents of the flask and withdrawing a distillate from the flask, and a reaction was performed under 85 kPa for 12 hours while further withdrawing a distillate from the flask. Subsequently, unreacted components (such as an unreacted alcohol) in the flask were distilled off from the flask over 30 minutes while gradually reducing the pressure in the flask to about 200 Pa. The flask was taken out from the oil bath, and the inside of the flask was cooled. Then, nitrogen gas was introduced into the flask to elevate the pressure in the flask to atmospheric pressure. By this operation, 127 g of a viscous liquid was obtained.

The distillate withdrawn from the flask was analyzed. As a result, it was found that the distillate contained about 260 mmol of water. The above-obtained viscous liquid was analyzed by NMR. As a result, it was found that the viscous liquid contained dibutyltin di(3-methylbutoxide) and 1,1,3,3-tetrabutyl-1,3-di(3-methylbutoxy)distannoxane.

(Step (1))

114 g of the above-obtained viscous liquid was charged into a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the abovementioned valve was opened to introduce carbon dioxide gas having a pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the reaction mixture obtained 1 hour after the start of the reaction contained di(3-methylbutyl) carbonate in an amount of 18 mol %, in terms of the mol % of the di(3-methylbutyl) carbonate, based on the molar amount of the tin atom contained in the viscous liquid, and that the reaction mixture obtained 4 hours after the start of the reaction (i.e., the reaction mixture after the reaction) contained di(3-methylbutyl) carbonate in an amount of 20.4 mol %, in terms of the mol % of the di(3-methylbutyl) carbonate, based on the molar amount of the tin atom contained in the viscous liquid.

After the reaction, the inside of the autoclave was cooled, and carbon dioxide was purged therefrom.

(Step (2))

After step (1), the contents of the autoclave were cooled to room temperature (about 20° C.), and about 6 g of distilled water was charged into the autoclave, followed by stirring for 30 minutes, thereby performing a reaction. Then, the stirring was stopped and the autoclave was opened. It was found that a white slurry was obtained in the autoclave. The white slurry was subjected to filtration to thereby obtain white solids and a filtrate. The filtrate was charged into a 100-ml eggplant-shaped flask equipped with a cooling tube, a vacuum pump and a vacuum controller (manufactured and sold by Okano Works, Ltd., Japan). Further, a stirrer was placed in the flask. Then, the flask was immersed in an oil bath having a temperature of 140° C.

A distillation was performed at 140° C. while stirring the contents of the flask and gradually reducing the pressure in the flask. During the distillation, water and 3-methyl-1-butanol were first distilled from the flask and, then, di(3-methylbutyl) carbonate was distilled from the flask. The amount of the thus obtained di(3-methylbutyl) carbonate was about 11 g.

(Step (3))

Into a 1-liter four-neck flask equipped with a cooling tube (which was connected with a vacuum controller and a vacuum pump) and a Dean-Stark trap were charged the white solids obtained in step (2) above, 502 g (5.7 mol) of 3-methyl-1-butanol (manufactured and sold by Aldrich, U.S.A.). Further, a stirrer was placed in the flask.

The flask was immersed in an oil bath having a temperature of 140° C., and the pressure in the flask was gradually reduced to about 90 kPa while stirring the contents of the flask. Then, the pressure in the flask was further reduced to 85 kPa while stirring the contents of the flask and withdrawing a distillate from the flask, and a reaction was performed under 85 kPa for 12 hours while further withdrawing a distillate from the flask. Thereafter, unreacted components (such as an unreacted alcohol) in the flask were removed from the flask over 30 minutes while gradually reducing the pressure in the flask to about 200 Pa. The flask was taken out from the oil bath, and the inside of the flask was cooled. Then, nitrogen gas was introduced into the flask to elevate the pressure in the flask to atmospheric pressure. By this operation, 112 g of a viscous liquid was obtained.

The above-obtained viscous liquid was analyzed by NMR. As a result, it was found that the viscous liquid contained dibutyltin di(3-methylbutoxide) and 1,1,3,3-tetrabutyl-1,3-di(3-methylbutoxy)distannoxane.

(Step (4))

(Preparation of Catalyst)

40 g of phenol and 8 g of lead monoxide were mixed together, and the resultant mixture was charged into a reaction vessel. Then, the mixture was heated at 180° C. for 10 hours while distilling off by-produced water with phenol, thereby obtaining catalyst A.

(Production of Aromatic Carbonate)

Into a 100-ml autoclave (manufactured and sold by Toyo Koatsu Co., Ltd., Japan) were charged about 11 g of the di(3-methylbutyl) carbonate obtained in step (2) above, 49 g of phenol (manufactured and sold by Aldrich, U.S.A.) (which had been purified by distillation) and catalyst A obtained above, wherein the amount of catalyst A was such that the Pb content of the resultant mixture in the autoclave became 0.4% by weight. Then, the autoclave was sealed, and a reaction between the di(3-methylbutyl) carbonate and the phenol was performed as follows. The atmosphere in the autoclave was purged with nitrogen gas. Then, all valves of the autoclave were closed, and stirring of the contents of the autoclave was started. In the autoclave, a reaction was performed as follows. The internal temperature of the autoclave was elevated to 230° C. while stirring the contents of the autoclave. Nitrogen gas was introduced into the autoclave from the bottom thereof at a rate of 50 ml/min while controlling the internal pressure of the autoclave in the range of from 100 to 200 kPa by appropriately operating a valve provided at an upper portion of the autoclave, to thereby perform a distillation for about 4 hours to distill of a gaseous component from the autoclave. Subsequently, the introduction of nitrogen into the autoclave was stopped, and the resultant reaction mixture in the autoclave were allowed to cool.

The reaction mixture in the autoclave was analyzed. As a result, it was found that the reaction mixture contained about 28 mmol of di(3-methylbutyl) carbonate, about 21 mmol of 3-methylbutyl phenyl carbonate and about 2.6 mmol of diphenyl carbonate.

The reaction mixture in the autoclave was charged into a 100-ml three-neck flask equipped with a cooling tube (which was connected with a vacuum controller and a vacuum pump) and a Dean-Stark trap. Further, a stirrer was placed in the flask. Then, the flask was immersed in an oil bath having a temperature of 150° C. The pressure in the flask was gradually reduced to about 100 kPa while stirring the contents of the flask, thereby performing a reaction. During the reaction, unreacted phenol and di(3-methy-1-butyl) carbonate were distilled from the flask. The resultant liquid reaction mixture was comprised mainly of 3-methylbutyl phenyl carbonate and diphenyl carbonate.

(Step (1) Performed for the Second Time)

110 g of the viscous liquid obtained in step (3) above was charged into a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having a pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the reaction mixture obtained 1 hour after the start of the reaction contained di(3-methylbutyl) carbonate in an amount of 18 mol %, in terms of the mol % of the di(3-methylbutyl) carbonate, based on the molar amount of the tin atom contained in the viscous liquid, and that the reaction mixture obtained 4 hours after the start of the reaction (i.e., the reaction mixture after the reaction) contained di(3-methylbutyl) carbonate in an amount of 21 mol %, in terms of the mol % of the di(3-methylbutyl) carbonate, based on the molar amount of the tin atom contained in the viscous liquid.

After the reaction, the inside of the autoclave was cooled, and carbon dioxide was purged therefrom.

EXAMPLE 18

Synthesis of Dibutyltin di(3-methylbutoxide)

Into a 1-liter four-neck flask equipped with a cooling tube (which was connected with a vacuum controller and a vacuum pump) and a Dean-Stark trap were charged 70.5 g (0.28 mol) of dibutyltin oxide (manufactured and sold by Aldrich, U.S.A.), 502 g (5.7 mol) of 3-methyl-1-butanol (manufactured and sold by Aldrich, U.S.A.). Further, a stirrer was placed in the flask.

The flask was immersed in an oil bath having a temperature of 140° C., and the pressure in the flask was gradually reduced to about 90 kPa while stirring the contents of the flask. Then, the pressure in the flask was further reduced to 85 kPa while stirring the contents of the flask and withdrawing a distillate from the flask. Then, a reaction was performed under 85 kPa for 12 hours while further withdrawing a distillate from the flask. Subsequently, unreacted components (such as an unreacted alcohol) in the flask were removed from the flask over 30 minutes while gradually reducing the pressure in the flask to about 200 Pa. The flask was taken out from the oil bath, and the inside of the flask was cooled. Then, nitrogen gas was introduced into the flask to elevate the pressure in the flask to atmospheric pressure. By this operation, 127 g of a viscous liquid was obtained.

The distillate was analyzed. As a result, it was found that the distillate contained about 260 mmol of water. The above-obtained viscous liquid was analyzed by NMR. As a result, it was found that the viscous liquid contained dibutyltin di(3-methylbutoxide) and 1,1,3,3-tetrabutyl-1,3-di(3-methylbutoxy)distannoxane.

(Step (1))

114 g of the above-obtained viscous liquid was charged into a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having a pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the reaction mixture obtained 1 hour after the start of the reaction contained di(3-methylbutyl) carbonate in an amount of 18 mol %, in terms of the mol % of the di(3-methylbutyl) carbonate, based on the molar amount of the tin atom contained in the viscous liquid, and that the reaction mixture obtained 4 hours after the start of the reaction (i.e., the reaction mixture after the reaction) contained di(3-methylbutyl) carbonate in an amount of 20.4 mol %, in terms of the mol % of the di(3-methylbutyl) carbonate, based on the molar amount of the tin atom contained in the viscous liquid.

After the reaction, the inside of the autoclave was cooled, and carbon dioxide was purged therefrom.

(Step (2))

After step (1), the contents of the autoclave were cooled to room temperature (about 20° C.), and about 6 g of distilled water was charged into the autoclave, followed by stirring for 30 minutes, thereby performing a reaction. Then, the stirring was stopped and the autoclave was opened. It was found that a white slurry was obtained in the autoclave. The white slurry was subjected to filtration to thereby obtain white solids and a filtrate. The filtrate was charged into a 100-ml eggplant-shaped flask equipped with a cooling tube, a vacuum pump and a vacuum controller (manufactured and sold by Okano Works, Ltd., Japan). Further, a stirrer was placed in the flask. Then, the flask was immersed in an oil bath having a temperature of 140° C.

A distillation was performed at 140° C. while stirring the contents of the flask while gradually reducing the pressure in the flask. During the distillation, water and 3-methyl-1-butanol were first distilled from the flask and, then, di(3-methylbutyl) carbonate was distilled from the flask. The amount of the thus obtained di(3-methylbutyl) carbonate was about 11 g.

(Step (3))

Into a 1-liter four-neck flask equipped with a cooling tube (which was connected with a vacuum controller and a vacuum pump) and a Dean-Stark trap were charged the white solids obtained in step (2), 502 g (5.7 mol) of 3-methyl-1-butanol (manufactured and sold by Aldrich, U.S.A.). Further, a stirrer was placed in the flask.

The flask was immersed in an oil bath having a temperature of 140° C., and the pressure in the flask was gradually reduced to about 90 kPa while stirring the contents of the flask. Then, the pressure in the flask was further reduced to 85 kPa while stirring the contents of the flask and withdrawing a distillate from the flask, and a reaction was performed under 85 kPa for 12 hours while further withdrawing a distillate from the flask. Subsequently, unreacted components (such as an unreacted alcohol) in the flask were removed from the flask over 30 minutes while gradually reducing the pressure in the flask to about 200 Pa. The flask was taken out from the oil bath, and the inside of the flask was cooled. Then, nitrogen gas was introduced into the flask to elevate the pressure in the flask to atmospheric pressure. By this operation, 112 g of a viscous liquid was obtained.

The above-obtained viscous liquid was analyzed by NMR. As a result, it was found that the viscous liquid contained dibutyltin di(3-methylbutoxide) and 1,1,3,3-tetrabutyl-1,3-di(3-methylbutoxy)distannoxane.

(Step (4))

(Preparation of Catalyst)

40 g of phenol and 8 g of lead monoxide were mixed together, and the resultant mixture was charged into a reaction vessel. Then, the mixture was heated at 180° C. for 10 hours while distilling off by-produced water with phenol, thereby obtaining catalyst A.

(Production of Aromatic Carbonate)

Into a 100-ml autoclave (manufactured and sold by Toyo Koatsu Co., Ltd., Japan) were charged about 11 g of the di(3-methylbutyl) carbonate obtained in step (2) above, 49 g of phenol (manufactured and sold by Aldrich, U.S.A.) (which had been purified by distillation) and catalyst A obtained above, wherein the amount of catalyst A was such that the Pb content of the resultant mixture in the autoclave became 0.4% by weight. Then, the autoclave was sealed, and a reaction between the di(3-methylbutyl) carbonate and the phenol was performed as follows. The atmosphere in the autoclave was purged with nitrogen gas. Then, all valves of the autoclave were closed, and stirring of the contents of the autoclave was started. The internal temperature of the autoclave was elevated to 230° C. while stirring the contents of the autoclave. Nitrogen gas was introduced into the autoclave from the bottom thereof at a rate of 50 ml/min while controlling the internal pressure of the autoclave in the range of from 100 to 200 kPa by appropriately operating the valves at an upper portion of the autoclave, to thereby perform a distillation for about 4 hours to distil of a gaseous component from the autoclave. Subsequently, the introduction of nitrogen into the autoclave was stopped, and the resultant reaction mixture in the autoclave were allowed to cool.

The reaction mixture in the autoclave was analyzed. As a result, it was found that the reaction mixture contained about 28 mmol of di(3-methylbutyl) carbonate, about 21 mmol of 3-methylbutyl phenyl carbonate and about 2.6 mmol of diphenyl carbonate.

The reaction mixture in the autoclave was charged into a 100-ml three-neck flask equipped with a cooling tube (which was connected with a vacuum controller and a vacuum pump) and a Dean-Stark trap. Further, a stirrer was placed in the flask. Then, the flask was immersed in an oil bath having a temperature of 150° C. The pressure in the flask was gradually reduced to about 100 kPa while stirring the contents of the flask, thereby performing a reaction. During the reaction, unreacted phenol and di(3-methy-1-butyl) carbonate were distilled from the flask. The resultant liquid reaction mixture was comprised mainly of 3-methylbutyl phenyl carbonate and diphenyl carbonate.

(Step (5))

After step (4), the internal pressure of the flask and the temperature of the oil bath were adjusted to about 50 kPa and 220° C., respectively, and a reaction was performed for 6 hours while stirring. During the reaction, di(3-methylbutyl) carbonate was distilled from the flask. The resultant reaction mixture obtained in the flask was analyzed. As a result, it was found that the reaction mixture contained diphenyl carbonate in an amount of about 26 mmol.

(Step (1) Performed for the Second Time)

110 g of the viscous liquid obtained in step (3) above was fed to a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having a pressure thereof adjusted to 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken and analyzed. As a result, it was found that the reaction mixture obtained 1 hour after the start of the reaction contained di(3-methylbutyl) carbonate in an amount of 18 mol %, in terms of the mol % of the di(3-methylbutyl) carbonate, based on the molar amount of the tin atom contained in the viscous liquid, and that the reaction mixture obtained 4 hours after the start of the reaction (i.e., the reaction mixture after the reaction) contained di(3-methylbutyl) carbonate in an amount of 21 mol %, in terms of the mol t of the di(3-methylbutyl) carbonate, based on the molar amount of the tin atom contained in the viscous liquid.

After the reaction, the inside of the autoclave was cooled, and carbon dioxide was purged therefrom.

EXAMPLE 19

Production of Hexamethylene Diisocyanate from the Diphenyl Carbonate Obtained in Example 4

Into a 500-ml flask equipped with a stirrer, a thermometer and a dropping funnel were charged 161 g (0.75 mol) of diphenyl carbonate produced in substantially the same manner as in Example 4, and 142 g (1.5 mol) of phenol (manufactured and sold by Aldrich, U.S.A.) (which had been purified by distillation). The atmosphere in the flask was purged with dried nitrogen gas. The flask was immersed in a water bath having a temperature of 50° C., and the contents of the flask were stirred.

After confirming that the solids in the flask had been dissolved, the temperature of the water bath was adjusted to 45° C. The above-mentioned dropping funnel contained 35 g (0.3 mol) of 1,6-hexamethylene diamine (manufactured and sold by Aldrich, U.S.A.) (which had been purified by distillation and maintained at 45 to 50° C.). The 1,6-hexamethylene diamine in the dropping funnel was dripped into the flask over about 20 minutes to perform a reaction while adjusting the temperature of the contents of the flask in the range of from 50 to 60° C.

After completion of the dripping of the 1,6-hexamethylene diamine, a reaction was further performed for 1 hour while stirring the contents of the flask and maintaining the temperature of the contents of the flask at 50° C. by appropriately adjusting the temperature of the water bath, thereby obtaining a reaction mixture.

The obtained reaction mixture was analyzed by high performance liquid chromatography and gel permeation chromatography. As a result, it was found that the conversion of 1,6-hexamethylene diamine was 100 mol %, that N,N'-hexanediyl-bis-carbamic acid diphenyl ester was produced in a yield of 99.6 mol % and with a selectivity of 99.6 mol %, and that a urea compound was produced in an amount of about 0.4 mol %, based on the molar amount of the 1,6-hexamethylene diamine.

The above-obtained reaction mixture was continuously fed through a preheater to a continuous multi-stage distillation column (inner diameter: 2 inches; height: 4 m) (which was filled with Dixon packing (6 mmϕ)) at a middle portion thereof, thereby performing a distillation. During the distillation, an excess amount of phenol was withdrawn in the form of a gas from an upper portion of the column and a high boiling point mixture was continuously withdrawn in the form of a liquid from a lower portion of the column. During the distillation, the liquid withdrawn from a lower portion of the column was recycled to the column through a reboiler having a temperature of 130° C., and the column top pressure was maintained at about 20 kPa. The liquid mixture withdrawn from the bottom of the column was transferred through a conduit and a pump to another continuous multi-stage distillation column (inner diameter: 2 inches; height: 4 m) (which was filled with Dixon packing (6 mm$\phi$)) at a portion thereof which is 1 m above the bottom of the column, and thermal decomposition of the liquid mixture was performed. During the thermal decomposition, a liquid was withdrawn from a lower portion of the column, and the withdrawn liquid was recycled to the column through a reboiler having a temperature of 220° C., and the column top pressure was maintained at about 2.6 kPa.

During the thermal decomposition, a mixture containing hexamethylene diisocyanate was withdrawn in the form of a gas from a portion of the column, which is 2 m below the top of the column, while withdrawing phenol in the form of a gas from the top of the column. The mixture containing hexamethylene diisocyanate was fed to still another continuous multi-stage distillation column (inner diameter: 2 inches; height: 4 m) (which was filled with Dixon packing (6 mm$\phi$)) at a middle portion thereof, and a distillation was performed to purify the hexamethylene diisocyanate. During the distillation for purification, a liquid was withdrawn from a lower portion of the column, and the withdrawn liquid was recycled to the column through a reboiler having a temperature of 120° C., and the column top pressure was maintained at about 130 Pa. A gas withdrawn from the top of the column and a liquid withdrawn from the bottom of the column were analyzed. As a result, it was found that the gas withdrawn from the top of the column was a hexamethylene diisocyanate product having a purity of 99.9% by weight, and the liquid withdrawn from the bottom of the column was comprised mainly of diphenyl carbonate.

COMPARATIVE EXAMPLE 3

Production of Hexamethylene Diisocyanate from Diphenyl Carbonate Containing a Chlorine Compound Into a 500-ml flask equipped with a stirrer, a thermometer and a dropping funnel were charged 161 g (0.75 mol) of diphenyl carbonate (manufactured and sold by Bayer AG, Germany) (which contained 15 ppm by weight of a hydrolyzable chlorine compound), and 142 g (1.5 mol) of phenol (manufactured and sold by Aldrich, U.S.A.) (which had been purified by distillation). The atmosphere in the flask was purged with dried-nitrogen gas. Then, the flask was immersed in a water bath having a temperature of 50° C., and the contents of the flask were stirred.

After confirming that the solids in the flask had been dissolved, the temperature of the water bath was adjusted to 45° C. The above-mentioned dropping funnel contained 35 g (0.3 mol) of 1,6-hexamethylene diamine (manufactured and sold by Aldrich, U.S.A.) (which had been purified by distillation and maintained at 45 to 50° C.). The 1,6-hexamethylene diamine in the dropping funnel was dripped into the flask over about 20 minutes to perform a reaction while adjusting the temperature of the contents of the flask in the range of from 50 to 60° C.

After completion of the dripping of the 1,6-hexamethylene diamine, a reaction was further performed for 1 hour while stirring the contents of the flask and maintaining the temperature of the contents of the flask at 50° C. by appropriately adjusting the temperature of the water bath, thereby obtaining a reaction mixture.

The obtained reaction mixture was analyzed by high performance liquid chromatography and gel permeation chromatography. As a result, it was found that the conversion of 1,6-hexamethylene diamine was 99 mol %, that N,N'-hexanediyl-bis-carbamic acid diphenyl ester was produced in a yield of 99 mol % and with a selectivity of 99.6 mol %, and that a urea compound was produced in an amount of about 0.5 mol %, based on the molar amount of the 1,6-hexamethylene diamine.

The above-obtained reaction mixture was continuously fed through a preheater to a continuous multi-stage distillation column (inner diameter: 2 inches; height: 4 m) (which was filled with Dixon packing (6 mm$\phi$)) at a middle portion thereof, thereby performing a distillation. During the distillation, an excess amount of phenol was withdrawn in the form of a gas from an upper portion of the column while continuously withdrawing a high boiling point mixture in the form of a liquid from a lower portion of the column. During the distillation, the liquid withdrawn from a lower portion of the column was recycled to the column through a reboiler having a temperature of 130° C., and the column top pressure was maintained at about 20 kPa. The liquid mixture withdrawn from the bottom of the column was transferred through a conduit and a pump to a continuous multi-stage distillation column (inner diameter: 2 inches; height: 4 m) (which was filled with Dixon packing (6 mm$\phi$)) at a portion thereof which is 1 m above the bottom of the column, and thermal decomposition of the liquid mixture was performed. During the thermal decomposition, a liquid was withdrawn from a lower portion of the column, and the withdrawn liquid was recycled to the column through a reboiler having a temperature of 220° C., and the column top pressure was maintained at about 2.6 kPa.

A mixture containing hexamethylene diisocyanate was withdrawn in the form of a gas from a portion of the column which is 2 m below the top of the column while withdrawing phenol in the form of a gas from the top of the column. The mixture containing hexamethylene diisocyanate was fed to another continuous multi-stage distillation column (inner diameter: 2 inches; height: 4 m) (which was filled with Dixon packing (6 mm$\phi$)) at a middle portion, and a distillation was performed to purify the hexamethylene diisocyanate. During the distillation for purification, a liquid was withdrawn from a lower portion of the column, and the withdrawn liquid was recycled to the column through a reboiler having a temperature of 120° C., and the column top pressure was maintained at about 130 Pa. A gas withdrawn from the top of the column and a liquid withdrawn from the bottom of the column were analyzed. As a result, it was found that the gas withdrawn from the top of the column was a hexamethylene diisocyanate product having a purity of 99.3% and containing 5 ppm of a hydrolyzable chlorine compound, and the liquid withdrawn from the bottom of the column was comprised mainly of diphenyl carbonate.

EXAMPLE 20

Production of Polycarbonate from the Diphenyl Carbonate Obtained in Example 4

23.5 g of the diphenyl carbonate obtained in Example 4 and 22.8 g of bisphenol A were fed into a vacuum reaction device equipped with a stirrer. (The diphenyl carbonate was analyzed by NMR, and no impurity containing a methyl group (other than a methyl group present at the terminal of an alkyl group of any compound in the reaction system) was detected in the diphenyl carbonate.) Then, a polymerization reaction was performed under 8,000 Pa for 30 minutes and, then, under 4,000 Pa for 90 minutes, while purging the atmosphere in the vacuum reaction device with nitrogen gas. Thereafter, the temperature of the contents of the vacuum reaction device was elevated to 270° C., and a further polymerization reaction was performed at 270° C. under 70 Pa for one hour, thereby obtaining an aromatic polycarbonate. The obtained aromatic polycarbonate was excellent in color (i.e., colorless and transparent) and had a number average molecular weight of 10,500.

EXAMPLE 21

Production of Polycarbonate from Diphenyl Carbonate Containing an Impurity Having a Methyl Group A transesterification reaction was performed between dimethyl carbonate and phenol to obtain methyl phenyl carbonate. The obtained methyl phenyl carbonate was subjected to a disproportionation reaction to obtain a diphenyl carbonate product containing about 90 ppm by weight of methyl phenyl carbonate.

23.5 g of the obtained diphenyl carbonate product (containing methyl phenyl carbonate) and 22.8 g of bisphenol A were fed to a vacuum reaction device equipped with a stirrer. Then, a polymerization reaction was performed under 8,000 Pa for 30 minutes and, then, under 4,000 Pa for 90 minutes, while purging the atmosphere in the vacuum reaction device with nitrogen gas. Thereafter, the temperature of the contents of the vacuum reaction device was elevated to 270° C., and a further polymerization reaction was performed at 270° C. under 70 Pa for one hour, thereby obtaining an aromatic polycarbonate. The obtained aromatic polycarbonate was excellent in color (i.e., colorless and transparent) and had a number average molecular weight of 9,500.

COMPARATIVE EXAMPLE 4

Production of Polycarbonate from Diphenyl Carbonate Containing a Chlorine Compound 23.5 g of diphenyl carbonate (manufactured and sold by Bayer AG, Germany) (which contained 5 ppm by weight of chlorine) and 22.8 g of bisphenol A were fed to a vacuum reaction device equipped with a stirrer. Then, a reaction was performed under 8,000 Pa for 30 minutes and, then, under 4,000 Pa for 90 minutes, while purging the atmosphere in the vacuum reaction device with nitrogen gas. Thereafter, the temperature of the contents of the vacuum reaction device was elevated to 270° C., and a further reaction was performed at 270° C. under 70 Pa for one hour. However, by the above-mentioned reactions, it was impossible to obtain a polymer having a high molecular weight. Specifically, the reaction mixture obtained after the reaction at 270° C. under 70 Pa for one hour contained only a mixture containing unreacted raw material compounds and an oligomer having a number average molecular weight of 800 or less.

INDUSTRIAL APPLICABILITY

The method of the present invention is advantageous not only in that the method does not need the use of any toxic substance and is free from the generation of any corrosive substance, but also in that the amounts of by-products are very small and intermediate products generated during the production of the desired aromatic carbonate can be recycled. Therefore, the method of the present invention is favorable from the view point of environmental protection, and enables a simple and efficient production of a high purity aromatic carbonate.

The invention claimed is:

1. A method for producing an aromatic carbonate, comprising:
   (1) performing a reaction between an organometal compound and carbon dioxide to obtain a reaction mixture containing a dialkyl carbonate formed by the reaction,
   (2) separating said dialkyl carbonate from said reaction mixture to obtain a residual liquid, and
   performing the following steps (3) and (4) in either order, or partially or wholly simultaneously:
   (3) reacting said residual liquid with an alcohol to form at least one organometal compound and form water and removing said water from said organometal compound, and
   (4) reacting said dialkyl carbonate separated in step (2) with an aromatic hydroxy compound to obtain an aromatic carbonate.

2. The method according to claim 1, wherein said aromatic carbonate obtained in step (4) is at least one compound selected from the group consisting of an alkyl aryl carbonate and a diaryl carbonate.

3. The method according to claim 1 or 2, wherein, in step (3), said organometal compound having said water removed therefrom is recycled to step (1).

4. The method according to claim 1 or 2, wherein, in step (4), an alcohol which is generated together with said aromatic carbonate is recycled to step (3).

5. The method according to claim 1 or 2, wherein a dialkyl carbonate recovered in step (4) is recycled to step (4).

6. The method according to claim 1 or 2, wherein a cycle of steps (1) to (4) is repeated at least one time.

7. The method according to claim 2, wherein said aromatic carbonate obtained in step (4) is an alkyl aryl carbonate and which, after step (4), further comprises the following step (5):
   (5) subjecting said alkyl aryl carbonate to a disproportionation reaction to obtain a diaryl carbonate.

8. The method according to claim 7, wherein, in step (5), a dialkyl carbonate which is generated together with said diaryl carbonate is recycled to step (4).

9. The method according to claim 7 or 8, wherein a cycle of steps (1) to (5) is repeated at least one time.

10. The method according to claim 1 or 2, wherein, in step (1), said organometal compound is used in an amount which is 1/200 to 1 time the stoichiometric amount relative to the amount of said carbon dioxide.

11. The method according to claim 1 or 2, wherein said reaction in step (1) is performed at 20° C. or higher.

12. The method according to claim 1 or 2, wherein said organometal compound used in step (1) is an organometal compound having a metal-oxygen-carbon linkage.

13. The method according to claim 12, wherein said organometal compound having a metal-oxygen-carbon linkage comprises at least one compound selected from the group consisting of:
    an organometal compound represented by the formula (1):

wherein:

M¹ represents a metal atom selected from the group consisting of elements belonging to Groups 4 and 14 of the Periodic Table, exclusive of silicon;

each of R¹ and R² independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;

each of R³ and R⁴ independently represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and each of a and b is an integer of from 0 to 2, a+b=0 to 2, each of c and d is an integer of from 0 to 4, and a+b+c+d=4; and an organometal compound represented by the formula (2):

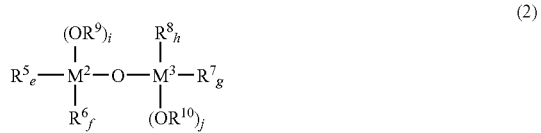

(2)

wherein:

each of M² and M³ independently represents a metal atom selected from the group consisting of elements belonging to Groups 4 and 14 of the Periodic Table, exclusive of silicon;

each of R⁵, R⁶, R⁷ and R⁸ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;

each of R⁹ and R¹⁰ independently represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and each of e, f, g and h is an integer of from 0 to 2, e+f=0 to 2, g+h=0 to 2, each of i and j is an integer of from 1 to 3, e+f+i=3, and g+h+j=3.

14. The method according to claim 1 or 2, wherein said separation of said dialkyl carbonate in step (2) is performed by at least one separation method selected from the group consisting of distillation, extraction and filtration.

15. The method according to claim 14, wherein said separation of said dialkyl carbonate in step (2) is performed by distillation.

16. The method according to claim 15, wherein said separation of said dialkyl carbonate in step (2) is performed by thin film distillation.

17. The method according to claim 1 or 2, wherein said removal of said water in step (3) is performed by membrane separation.

18. The method according to claim 17, wherein said membrane separation is pervaporation.

19. The method according to claim 1 or 2, wherein said removal of said water in step (3) is performed by distillation.

20. The method according to claim 1 or 2, wherein said alcohol used in step (3) is at least one alcohol selected from the group consisting of an alkyl alcohol having a straight chain or branched $C_1$-$C_{12}$ alkyl group, a cycloalkyl alcohol having a $C_5$-$C_{12}$ cycloalkyl group, an alkenyl alcohol having a straight chain or branched $C_2$-$C_{12}$ alkenyl group, and an aralkyl alcohol having a $C_7$-$C_{20}$ aralkyl group comprised of unsubstituted or substituted $C_6$-$C_{19}$ aryl and alkyl selected from the group consisting of a straight chain or branched $C_1$-$C_{14}$ alkyl and $C_5$-$C_{14}$ cycloalkyl.

21. The method according to claim 1 or 2, wherein the alcohol used in step (3) has a boiling point which is higher than the boiling point of water.

22. The method according to claim 21, wherein the alcohol used in step (3) is at least one alcohol selected from the group consisting of 1-butanol, 2-methyl-1-propanol, an alkyl alcohol having a straight chain or branched $C_5$-$C_{12}$ alkyl group, and an alkenyl alcohol having a straight chain or branched $C_4$-$C_{12}$ alkenyl group.

23. The method according to claim 21, wherein the alcohol used in step (3) has a boiling point which is lower than that of said aromatic hydroxy compound used in step (4).

24. The method according to claim 13, wherein each of R³ and R⁴ in formula (1) and R⁹ and R¹⁰ in formula (2) independently represents an n-butyl group, a 2-methylpropyl group, a straight chain or branched $C_5$-$C_{12}$ alkyl group, or a branched $C_4$-$C_{12}$ alkenyl group.

25. The method according to claim 1 or 2, wherein, in step (1), said organometal compound is used in at least one form selected from the group consisting of a monomeric form, an oligomeric form, a polymeric form and an associated form.

26. The method according to claim 13, wherein each of M¹ in formula (1) and M² and M³ in formula (2) represents a tin atom.

27. The method according to claim 1 or 2, wherein said organometal compound used in step (1) is produced from an organotin oxide and an alcohol.

28. The method according to claim 1 or 2, wherein, the amount of said aromatic hydroxy compound used in step (4) is 0.1 to 10,000 times the stoichiometric amount relative to the amount of said dialkyl carbonate used in step (4).

29. The method according to claim 1 or 2, wherein said reaction in step (4) is performed at a temperature in the range of from 50 to 350° C.

30. The method according to claim 1 or 2, wherein said reaction in step (4) is performed in the presence of a transesterification reaction catalyst.

31. The method according to claim 7 or 8, wherein said reaction in step (5) is performed in the presence of a disproportionation reaction catalyst.

32. The method according to claim 1 or 2, wherein said aromatic hydroxy compound is represented by the following formula (3):

ArOH     (3)

wherein Ar is a $C_5$-$C_{30}$ aromatic group.

33. The method according to claim 32, wherein said aromatic hydroxy compound represented by formula (3) is phenol.

34. The method according to claim 1 or 2, wherein the total content of an aromatic hydroxy compound and a carboxyl group-containing compound in said alcohol used in step (3) is 1,000 ppm or less.

35. A continuous method for producing an aromatic carbonate, comprising:
   (1) performing a reaction between an organometal compound and carbon dioxide to obtain a reaction mixture containing a dialkyl carbonate formed by the reaction;
   (2) separating said dialkyl carbonate from said reaction mixture to obtain a residual liquid;
   (3) reacting said residual liquid with an alcohol to form an organometal compound and water and removing said water from said organometal compound;
   (4) reacting said dialkyl carbonate separated in step (2) with an aromatic hydroxy compound to obtain an alkyl aryl carbonate and an alcohol; and
   (5) subjecting said alkyl aryl carbonate to a disproportionation reaction to obtain a diaryl carbonate and a dialkyl carbonate, wherein the organometal compound having said water removed therefrom in step (3) is recycled to step (1), the alcohol obtained in step (4) is recycled to step (3), and the dialkyl carbonate which is obtained in step (5) is recycled to step (4).

* * * * *